(12) United States Patent
Negoro et al.

(10) Patent No.: US 7,968,552 B2
(45) Date of Patent: Jun. 28, 2011

(54) OXADIAZOLIDINEDIONE COMPOUND

(75) Inventors: Kenji Negoro, Tokyo (JP); Fumiyoshi Iwasaki, Tokyo (JP); Kei Ohnuki, Tokyo (JP); Toshio Kurosaki, Tokyo (JP); Yasuhiro Yonetoku, Tokyo (JP); Norio Asai, Tokyo (JP); Shigeru Yoshida, Tokyo (JP); Takatoshi Soga, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 122 days.

(21) Appl. No.: 12/298,522

(22) PCT Filed: Apr. 23, 2007

(86) PCT No.: PCT/JP2007/058694
§ 371 (c)(1),
(2), (4) Date: Oct. 24, 2008

(87) PCT Pub. No.: WO2007/123225
PCT Pub. Date: Nov. 1, 2007

(65) Prior Publication Data
US 2009/0186909 A1    Jul. 23, 2009

(30) Foreign Application Priority Data

Apr. 24, 2006    (JP) .............................. P.2006-118630

(51) Int. Cl.
*A61K 31/506* (2006.01)
*A61K 31/4439* (2006.01)
*A61K 31/4245* (2006.01)
*C07D 413/12* (2006.01)
*C07D 271/07* (2006.01)

(52) U.S. Cl. ........ 514/256; 514/340; 514/364; 544/333; 546/269.1; 548/132

(58) Field of Classification Search .................. 514/256, 514/340, 364; 544/333; 546/269.1; 548/132
See application file for complete search history.

(56) References Cited

U.S. PATENT DOCUMENTS

| 5,480,896 A | 1/1996 | Malamas et al. | |
| 5,885,997 A * | 3/1999 | Lohray et al. | 514/256 |
| 6,288,096 B1 * | 9/2001 | Andersson et al. | 514/369 |
| 2005/0113428 A1 * | 5/2005 | Gopalsamy et al. | 514/364 |

FOREIGN PATENT DOCUMENTS

| EP | 0 696 585 A1 | 2/1996 |
| EP | 1 559 422 A1 | 8/2005 |
| EP | 1 726 580 A1 | 11/2006 |
| JP | 7-2848 | 1/1995 |
| JP | 8-59638 | 3/1996 |
| JP | H10-502907 A | 3/1998 |
| JP | 2000-212174 | 8/2000 |
| JP | 2002-503255 A | 1/2002 |
| JP | 2002-515874 A | 5/2002 |
| JP | 2005-015461 A | 1/2005 |
| RU | 2 135 487 C1 | 8/1999 |
| WO | WO 94/025448 A1 | 11/1994 |
| WO | WO 95/30664 | 11/1995 |
| WO | WO 97/41097 | 11/1997 |
| WO | WO 98/57941 | 12/1998 |
| WO | WO 2004041266 A1 * | 5/2004 |
| WO | WO 2005/030203 A1 | 4/2005 |
| WO | WO 2005/063725 A1 | 7/2005 |
| WO | WO 2005/063729 A1 | 7/2005 |
| WO | WO 2005/086661 | 9/2005 |

OTHER PUBLICATIONS

Preliminary STN search report__12298522__04242010.*
Padwal et al. Diabetes Care, vol. 28 (3), p. 736-744, (2005), at p. 736.*
Y. Itoh et al., "Free fatty acids regulate insulin secretion from pancreatic β cells through GPR40", Nature, vol. 422, pp. 173-176 (2003).
Michael S. Malamas, et al., "Antihyperglycemic activity of new 1,2,4-oxadiazolidine-3,5-diones", European Journal of Medicinal Chemistry, vol. 36, pp. 31-42 (2001).
Stuart W. Bright et al., "Monoclonal Antibodies as Surrogate Receptors in a high throughput screen for compounds that enhance insulin sensitivity", Life Sciences, vol. 61, pp. 2305-2315 (1997).
Guarram R. Madhavan et al., "Synthesis and Biological Actiity of Novel Pyrimidinone Containing Thiazolidinedione Derivatives", Bioorganic & Medicinal Chemistry, vol. 10, pp. 2671-2680 (2002).
Examination Report mailed Jun. 1, 2010, by the Intellectual Property Office of New Zealand in corresponding Application No. 572146.
Official Action in corresponding Indonesian Application No. W-00 2008 03450, dated Sep. 6, 2010.
Supplementary European Search Report mailed Sep. 9, 2010, in corresponding EP Application No. 07742129.5-2101.
Office Action mailed Dec. 9, 2010, in corresponding Chinese Patent Application No. 200780014661.8.
Official Action mailed Mar. 16, 2011, in corresponding Russian Patent Application No. 2008146088/04(060236), Russian Agency for Patents and Trademarks.

* cited by examiner

*Primary Examiner* — Yong Chu
(74) *Attorney, Agent, or Firm* — Finnegan, Henderson, Farabow, Garrett & Dunner, LLP

(57) ABSTRACT

A compound which can be used as a pharmaceutical, particularly a insulin secretion promoter or a agent for preventing/treating disease in which GPR40 is concerned such as diabetes or the like, is provided.
It was found that an oxadiazolidinedione compound which is characterized by the possession of a benzyl or the like substituent binding to the cyclic group via a linker at the 2-position of the oxadiazolidinedione ring, or a pharmaceutically acceptable salt thereof, has excellent GPR40 agonist action. In addition, since the oxadiazolidinedione compound of the present invention showed excellent insulin secretion promoting action and blood glucose level-lowering action, it is useful as an insulin secretion promoter or an agent for preventing/treating diabetes.

15 Claims, No Drawings

OXADIAZOLIDINEDIONE COMPOUND

CROSS REFERENCE TO RELATED APPLICATIONS

This application is a national phase application based on PCT/JP2007/058694, filed Apr. 23, 2007, which claims the priority of Japanese Patent Application No. 2006-118630, filed Apr. 24, 2006, the contents of both of which are incorporated herein by reference.

TECHNICAL FIELD

The present invention relates to a pharmaceutical, particularly a novel oxadiazolidinedione compound or a pharmaceutically acceptable salt thereof which is useful as an insulin secretion promoter or an agent for preventing/treating diabetes.

BACKGROUND OF THE INVENTION

Diabetes is a disease having a chronically high blood glucose level as the main symptom, which is generated by absolute or relative insufficiency of insulin action. Clinically, it is roughly divided into insulin dependent diabetes mellitus (IDDM) and non insulin dependent diabetes mellitus (NIDDM). In the non insulin dependent diabetes mellitus (NIDDM), lowering of insulin secretion from pancreatic β cells is one of the main causes of the onset of the disease, and particularly a high blood glucose level after meal is recognized due to an initial stage insulin secretion disorder.

Recently, it has been confirmed by large scale clinical tests that correction of high blood glucose level after meal is important for the onset and suppression of diabetic complications. In addition, it has been reported that arteriosclerosis is generated at a stage of only high blood glucose level after meal, and that continuation of slightly high blood glucose level after meal increases mortality rate caused by a vascular disease and the like. It shows that the high blood glucose level after meal is an independent risk factor of cardiovascular death even when it is slight. Based on the above information, necessity of a drug therapy for high blood glucose level after meal has been recognized.

Currently, sulfonylurea (SU) preparations are the main stream as the insulin secretion promoter, but it is known that it is apt to cause hypoglycemia and induces secondary invalidity due to exhaustion of the pancreas in the case of its long-time administration. In addition, the SU preparations are effective in controlling blood glucose level during meal, but it is difficult to suppress over blood glucose level after meal.

GPR40 is a G protein-coupled receptor which has been identified as a fatty acid receptor and is highly expressed in β cells of the pancreas, and it has been reported that it is concerned in the insulin secretory action of fatty acid (Non-patent Reference 1).

Accordingly, since correction of high blood glucose level after meal is expected based on its insulin secretion promoting action, the GPR40 receptor agonist is useful as an agent for preventing/treating insulin dependent diabetes mellitus (IDDM), non insulin dependent diabetes mellitus (MDDM) and a border type (abnormal glucose tolerance and fasting blood glucose level) mild case diabetes.

Patent Reference 1 reports that the compound represented by the formula (A) including a broad range of compounds has the GPR40 receptor-controlling action and is useful as an insulin secretion promoter or an agent for preventing/treating diabetes.

However, there is no illustrative disclosure on a compound having oxadiazolidinedione structure.

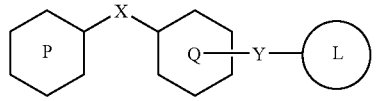

(A)

(In the formula, ring P represents an aromatic ring which may have a substituent, and ring Q an aromatic ring which may further have a substituent other than

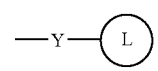

X and Y spacers, and

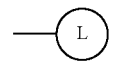

a group capable of releasing a cation.)

Patent Reference 2 reports that the compound represented by the formula (B) has the GPR40 receptor-controlling action and is useful as an insulin secretion promoter or an agent for preventing/treating of diabetes. However, there is no illustrative disclosure on a compound having oxadiazolidinedione structure.

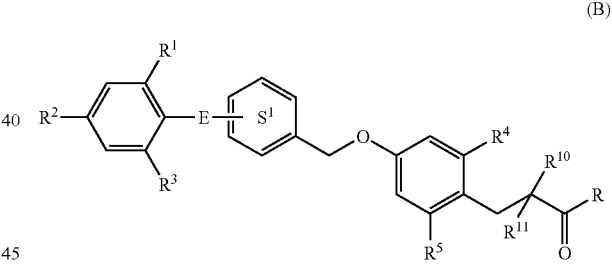

(B)

(See Said Official Gazette for Symbols in the Formula.)

Patent Reference 3 reports that the compound represented by the formula (C) has the GPR40 receptor-controlling action and is useful as an insulin secretion promoter or an agent for preventing/treating diabetes. However, there is no illustrative disclosure on a compound having oxadiazolidinedione structure.

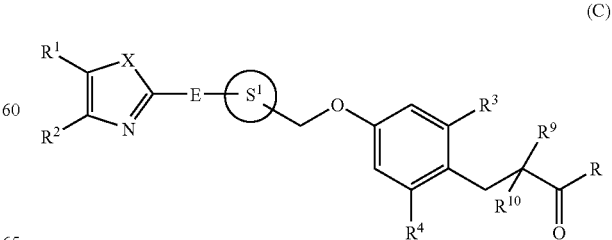

(C)

(See Said Official Gazette for Symbols in the Formula.)

Patent Reference 4 reports that the oxadiazolidinedione compound represented by the formula (D) has the plasminogen activation inhibitor (PAI)-1 inhibiting action and is useful in treating thrombus, atrial fibrillation, myocardial ischemia, diabetes and the like. However, there is no description on its action for the GPR40 receptor.

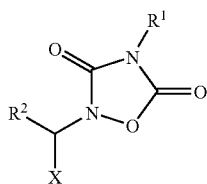

(D)

(In the formula, X represents

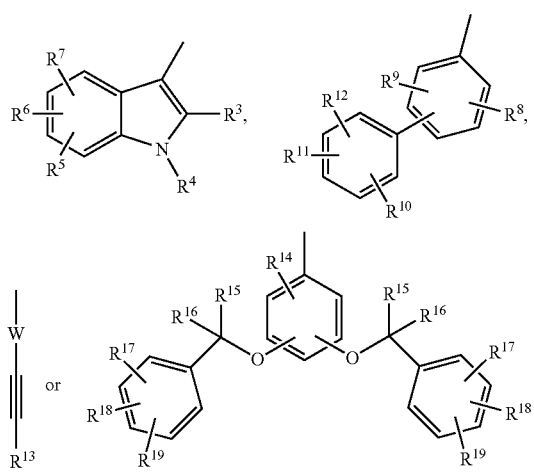

See said official gazette for other symbols.)

Patent Reference 5 reports that the compound having two oxadiazolidinedione structures, represented by the formula (E), has an action to enhance insulin sensitivity and is useful in treating diabetes. However, there is no description on its action on the GPR40 receptor.

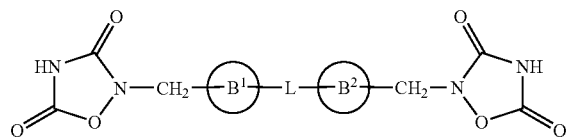

(E)

(See Said Official Gazette for Symbols in the Formula.)

Patent Reference 6 reports that the oxazolidinedione compound represented by the formula (F) has blood glucose level-lowering action and blood lipid-lowering action and is useful in treating diabetes. However, the ring which corresponds to the oxadiazolidinedione of the present invention is oxazolidinedione. In addition, there is no description on its action for the GPR40 receptor.

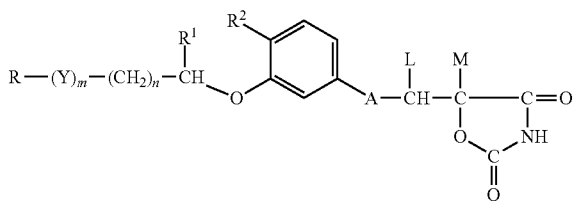

(F)

(See Said Official Gazette for Symbols in the Formula.)

Patent Reference 7 reports that the oxadiazolidinedione compound represented by formula (G) has the blood glucose level-lowering action and is useful in treating diabetes. However, the ring which corresponds to the ring A of the present invention is oxadiazole ring. In addition, there is no description on its action on the GPR40 receptor.

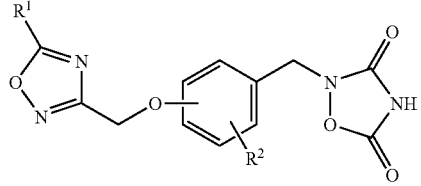

(G)

(See Said Official Gazette for Symbols in the Formula.)

Patent Reference 8 reports that the compound represented by formula (H) has the blood glucose level-lowering action and is useful in treating diabetes. However, there is no description on its action on the GPR40 receptor.

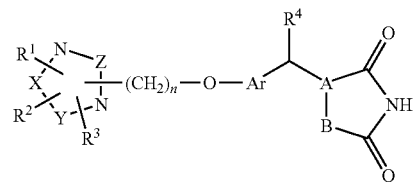

(H)

(See Said Official Gazette for Symbols in the Formula)

Patent Reference 9 reports that the oxadiazolidinedione compound represented by formula (J) has the blood glucose level-lowering action and is useful in treating diabetes. However, the ring which corresponds to the ring A of the compound of the present invention is oxazole or thiazole. In addition, there is no description on its action on the GPR40 receptor.

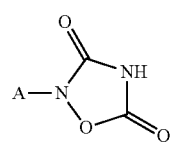

(J)

A:

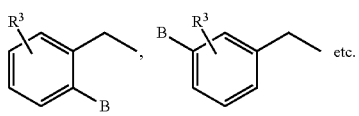

B:

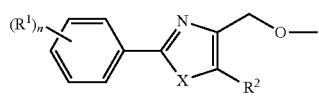

(X in the formula represents oxygen atom or sulfur atom. See said official gazette for other symbols.)

Patent Reference 10 reports that the compound represented by formula (K) is useful for hyperlipemia, hyperglycemia, obesity, and the like. However, the ring which corresponds to the ring A of the compound of the present invention is morpholine or thiomorpholine. In addition, there is no description on its action on the GPR40 receptor.

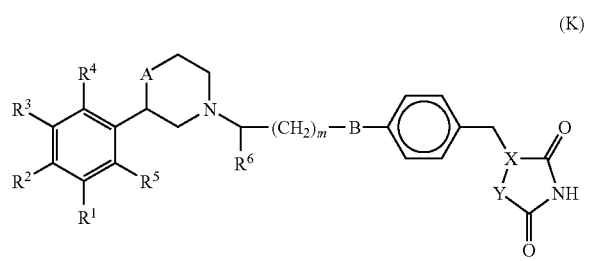

(K)

(A in the formula represents oxygen atom or sulfur atom. See said official gazette for other symbols.)

Non-patent Reference 2 reports that the oxadiazolidinedione compound represented by formula (L) has the blood glucose level-lowering action and is useful in treating diabetes. However, the ring which corresponds to the ring A of the compound of the present invention is (di)azole ring. In addition, there is no description on its action on the GPR40 receptor.

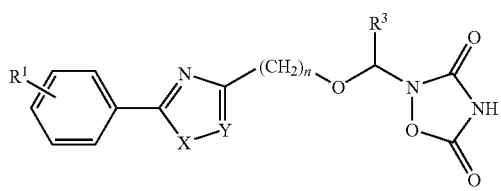

(L)

(In the formula, X represents O, S or N, Y represents C or N, and n is 1 or 2. See said reference for other symbols.)

Non-patent Reference 1: Nature, (England), 2003, vol. 422, p. 173-176
Non-patent Reference 2: European Journal of Medicinal Chemistry, (France), 2001, vol. 36, p. 31-42
Patent Reference 1: International Publication No. 2004/041266
Patent Reference 2: International Publication No. 2005/063729
Patent Reference 3: International Publication No. 2005/063725
Patent Reference 4: International Publication No. 2005/030203
Patent Reference 5: International Publication No. 94/25448
Patent Reference 6: JP-A-2000-212174
Patent Reference 7: International Publication No. 95/30664
Patent Reference 8: International Publication No. 97/41097
Patent Reference 9: U.S. Pat. No. 5,480,896
Patent Reference 10: JP-A-7-2848

DISCLOSURE OF THE INVENTION

Problems that the Invention is to Solve

The present invention aims at providing a novel compound which has a GPR40 receptor agonistic action and is useful as an insulin secretion promoter or an agent for preventing/treating diabetes.

Means for Solving the Problems

The present inventors have conducted extensive studies on compounds having a GPR40 receptor agonistic action and found that novel oxadiazolidinedione compounds or salts thereof have an excellent GPR40 receptor agonistic action. Thereafter, the present invention was accomplished by finding that these oxadiazolidinedione compounds have excellent insulin secretion-promoting action and strongly inhibit increase of blood glucose level after glucose loading.

That is, the present invention relates to an oxadiazolidinedione compound represented by the following formula (I) or a pharmaceutically acceptable salt thereof.

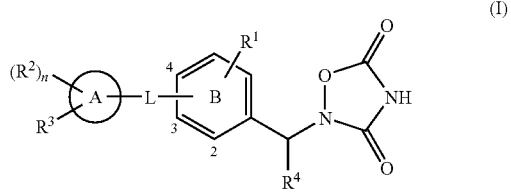

(I)

(Symbols in the formula represent the following meanings,
$R^1$: —H, halogen, —$R^0$, halogeno-lower alkyl, —$OR^z$, —S—$R^0$ or —O-halogeno-lower alkyl,
$R^0$: lower alkyl,
$R^z$: the same or different from each other and each represents —H or lower alkyl,
L: *-lower alkylene-O—, *-lower alkylene-N($R^z$)— or *—CON($R^z$)—, wherein the * in L represents binding to ring A,
ring A: benzene, pyridine, thiophene, piperidine, dihydropyridine, pyrimidine or tetrahydroquinoline,
ring B: benzene or pyridine,
$R^2$: respectively the same or different from one another and each represents -halogen,
—$R^0$, halogeno-lower alkyl, —$OR^z$, —S—$R^0$, —O-halogeno-lower alkyl, —O-lower alkylene-aryl or oxo,
n: 0, 1 or 2,
$R^3$: -halogen, —$R^0$, -halogeno-lower alkyl, —$OR^0$, —S—$R^0$, —O-halogeno-lower alkyl, —X-(phenyl which may be substituted) or —X-(heteroaryl which may be substituted),
X: single bond, O, S or N($R^z$),
$R^4$: —H or lower alkyl,
or $R^1$ and $R^4$ may together form a lower alkylene,
with the proviso that
2-{4-[2-(4-methyl-6-oxo-2-propylpyrimidin-1(6H)-yl)ethoxy]benzyl}-1,2,4-oxadiazolidine-3,5-dione, and 2-{4-[2-(2-ethyl-4-methyl-6-oxopylpyrimidin-1(6H)-yl)
ethoxy]benzyl}-1,2,4-oxadiazolidine-3,5-dione
are excluded. The same shall apply hereinafter.)

In addition, this application also relates to a pharmaceutical, particularly a GPR40 agonist, which uses the oxadiazolidinedione compound represented by the general formula (I) or a salt thereof as the active ingredient.

Further, this application also relates to the use of the compound represented by the formula (I) or a pharmaceutically acceptable salt thereof, for the manufacture of the GPR40 agonist, insulin secretion promoter or an agent for preventing and/or treating diabetes, and a method for preventing and/or treating diabetes, which comprises administering an effective amount of the compound represented by the formula (I) or a pharmaceutically acceptable salt thereof to a patient.
That is,
(1) a pharmaceutical composition, which comprises the compound represented by the formula (I) or a pharmaceutically acceptable salt thereof and a pharmaceutically acceptable carrier,
(2) the pharmaceutical composition described in (1), which is a GPR40 agonist,
(3) the pharmaceutical composition described in (1), which is an insulin secretion promoter,
(4) the pharmaceutical composition described in (1), which is an agent for preventing and/or treating diabetes,
(5) use of the compound described in the formula (I) or a pharmaceutically acceptable salt thereof, for the manufacture of a GPR40 agonist, an insulin secretion promoter or an agent for preventing and/or treating diabetes,
(6) a method for preventing and/or treating diabetes, which comprises administering an effective amount of the compound described in the formula (I) or a pharmaceutically acceptable salt thereof to a patient.

Effect of the Invention

Pharmacological activities of the compound of the present invention were confirmed by the test methods shown in the following.
Test Method 1: Measurement of GPR40 Agonist Action
i) Cloning of Human GPR40

Complete length sequence of GPR40 was obtained by carrying out a PCR method in accordance with the procedure shown below using a human genomic DNA (Clontech) as the template.

An oligonucleotide consisting of the nucleotide sequence represented by SEQ ID NO:1 was used as the forward primer, and an oligonucleotide consisting of the nucleotide sequence represented by SEQ ID NO:2 as the reverse primer. In this connection, a nucleotide sequence comprising a XbaI recognition region is added to the respective 5'-termini of the aforementioned forward primer and reverse primer. PCR was carried out in the presence of 5% dimethyl sulfoxide (DMSO) using a Taq DNA polymerase (Ex Taq DNA polymerase; Takara Bio), by repeating 30 times of a cycle consisting of 94° C. (15 seconds)/55° C. (30 seconds)/72° C. (1 minute). As a result, a DNA fragment of about 0.9 kbp was amplified. This DNA fragment was digested with XbaI and then inserted into the XbaI site of a plasmid pEF-BOS-dhfr (Nucleic acids Research, 18, 5322, 1990), thereby obtaining a plasmid pEF-BOS-dhfr-GPR40.

Nucleotide sequence of the GPR40 gene in the pEF-BOS-dhfr-GPR40 was determined by the dideoxy terminator method using a DNA sequencer (ABI 377 DNA Sequencer, Applied Biosystems). Nucleotide sequence of the GPR40 gene was as the nucleotide sequence represented by SEQ ID NO:3. The nucleotide sequence represented by SEQ ID NO:3 has an open reading frame (ORF) of 903 bases, and the amino acid sequence deduced from this ORF (300 amino acids) was as the amino acid sequence represented by SEQ ID NO:4.
ii) Preparation of GPR40 Stable Expression Cell As the cell for expressing GPR protein, CHO dhfr cell (a dihydrofolate reductase (dhfr)-deficient CHO cell) was used. Also, as the plasmid for expressing GPR40 protein, the plasmid pEF-BOS-dhfr-GPR40 obtained in the aforementioned i) was used. The CHO dhfr cell was inoculated into αMEM medium containing 10% fetal calf serum (FCS) using a 6 well plate (Asahi Techno Glass) and cultured overnight to an 80 to 90% confluence, and then 2 μg per well of the plasmid pEF-BOS-dhfr-GPR40 was gene-transferred using a transfection reagent (Lipofectamine 2000; Invitrogen). After 24 hours of culturing from the gene transfer, the cells were diluted and inoculated again. In this case, the αMEM medium containing 10% FCS was changed to an αMEM medium which contains 10% FCS but does not contain nucleic acid. After 20 days of culturing, the thus formed colonies of cells were individually recovered and cultured to obtain CHO cells stably expressing GPR40. From these, cells having high reactivity for intrinsic ligands oleic acid and linoleic acid were selected.
iii) Measurement of GPR40 Agonist Action This test was measured by FLIPR (registered trademark, Molecular Device) using a change in intracellular calcium concentration as the index. The test method is shown in the following.

A CHO cell strain in which human GPR40 was expressed was inoculated into a 384 well black plate (Becton Dickinson) in $6 \times 10^3$ cells per well portions and cultured overnight in a $CO_2$ incubator.

Using Calcium-3 assay kit (Molecular Device), one bottle of the phosphorescent pigment was dissolved in 10 ml of HBSS-HBEPES buffer (pH 7.4, 1×HBSS, 20 mM HEPES, Invitrogen). A 35.68 mg of probenecid (Sigma) was dissolved in 250 μl of 1M NaOH and adjusted by adding 250 μl of the HBSS-HEPES buffer. A phosphorescent pigment solution was prepared by mixing 16 ml of HBSS-HEPES buffer, 640 μl of the phosphorescent pigment and 32 μl of probenecid per one plate. The medium was discarded from the plate, and the phosphorescent pigment solution was dispensed in 40 μl per well portions and then incubated at room temperature for 2 hours. Each compound to be tested was dissolved in DMSO and then diluted with HBSS-HEPES buffer and dispensed in 10 μl portions into the plate, thereby starting the reaction, and changes in the intracellular calcium concentration were measured by FLIPR. The $EC_{50}$ value of each compound to be tested was calculated by a dose-response curve of changes in fluorescence intensity after 1 minute of the measurement.

The test results are shown in Table 1. Ex represents Example compound number which is described later.

TABLE 1

| Ex | $EC_{50}$ (μM) |
|---|---|
| 4 | 0.35 |
| 8 | 0.031 |
| 9 | 0.80 |
| 14 | 0.39 |
| 16 | 0.45 |
| 33 | 0.64 |
| 38 | 0.65 |
| 39 | 0.26 |
| 44 | 0.67 |
| 47 | 0.42 |
| 56 | 0.76 |
| 60 | 0.46 |

TABLE 1-continued

| Ex | EC$_{50}$ (μM) |
|---|---|
| 82 | 0.93 |
| 99 | 0.45 |
| 117 | 0.29 |
| 119 | 0.22 |
| 166 | 0.22 |
| 173 | 0.66 |
| 189 | 0.059 |
| 193 | 0.52 |
| 406 | 0.12 |

Test Method 2: Insulin Secretion-Promoting Action Using MIN6 Cell

This rest examined insulin acceleration action of compounds to be tested using a mouse pancreas β cell strain, MIN6 cell. The test method is shown in the following.

The MIN6 cell was dispensed in 5×10$^4$ cells/well (200 μl) portions into a 96 well plate. DMEM (25 mM glucose) containing 10% FBS, 55 μM 2-mercaptoethanol, 100 U/ml penicillin and 100 μg/ml streptomycin was used as the medium. The medium was discarded 2 days thereafter using an aspirator, followed by washing once with 200 μl of KRB-HEPES (116 mM NaCl, 4.7 mM KCl, 1.2 mM KH2PO4, 1.2 mM MgSO4, 0.25 mM CaCl2, 25 mM NaHCO3, 0.005% FFA Free BSA, 24 mM HEPES (pH 7.4)) containing 2.8 mM glucose, which was warmed up to 37° C., and subsequent incubation again at 37° C. for 1 hour by adding 200 μl of the same buffer. After discarding the above-mentioned buffer using an aspirator and again washing with the buffer (200 μl), a predetermined concentration of a compound to be tested was added to the KRB-HEPES containing 2.8 mM or 22.4 mM glucose and added to respective wells in 100 μl portions and incubated at 37° C. for 2 hours. The above-mentioned samples were fractioned and diluted 100 times, and the insulin concentration was determined using an insulin RIA kit (Amersham RI). The activity value was shown by a relative activity value (%) at the time of 1 μM of each compound, based on 100% control (DMSO).

The test results are shown in Table 2. As a result, it was confirmed that the compound of the present invention has excellent insulin secretion promoting action.

TABLE 2

| Ex | Insulin secretion-accelerating action (%) |
|---|---|
| 4 | 177 |
| 34 | 169 |
| 38 | 228 |
| 39 | 192 |
| 44 | 287 |

Test Method 3: Normal Mice Single Oral Glucose Tolerance Test

This test examined on the blood glucose suppression action of compounds to be tested after glucose loading, using normal mice. The test method is shown below.

Male ICR mice (6 weeks of age) after 1 week of preliminary rearing were subjected to overnight fasting and used as the animals to be tested. Each compound to be tested was made into a 0.5% methyl cellulose suspension and orally administered at a dose of 10 mg/kg 30 minutes before the glucose loading (2 g/kg). Administration of 0.5% methyl cellulose was used in the control group. Blood glucose lowering ratio (%) after 30 minutes of glucose loading was calculated based on the control group.

The test results are shown in Table 3. As a result, it was confirmed that the compound of the present invention has excellent blood glucose-lowering action.

TABLE 3

| Ex | Blood glucose lowering ratio (%) |
|---|---|
| 14 | 34 |
| 39 | 26 |
| 44 | 21 |
| 47 | 36 |
| 56 | 31 |
| 60 | 35 |
| 117 | 21 |
| 119 | 22 |
| 166 | 35 |
| 173 | 21 |
| 189 | 30 |
| 193 | 46 |
| 406 | 42 |

As a result of the above respective tests, it is evident that the compound of the present invention has excellent GPR40 agonistic action and therefore is useful as an insulin secretion promoter or an agent for preventing/treating a disease in which GPR40 is concerned, such as diabetes (insulin dependent diabetes mellitus (IDDM), non insulin dependent diabetes mellitus (NIDDM), a border type (abnormal glucose tolerance and fasting blood glucose level) mild case diabetes) and the like.

BEST MODE FOR CARRYING OUT THE INVENTION

The following describes the present invention in detail.

In this description, the "alkyl" and "alkylene" mean straight or branched hydrocarbon chains.

The "lower alkyl" is preferably an alkyl group having from 1 to 6 carbon atoms (to be referred to as $C_{1-6}$ hereinafter), more preferably a $C_{1-4}$ alkyl, and further preferably methyl and ethyl.

The "lower alkynyl" is preferably a straight or branched $C_{2-6}$ alkynyl and is illustratively ethynyl, propynyl, butynyl, pentynyl, 1-methyl-2-propynyl, 1,3-butadynyl, 1,3-pentadynyl or the like. More preferred is a $C_{2-4}$ alkynyl and particularly preferred is ethynyl or propynyl.

The "lower alkylene" means a divalent group ($C_{1-6}$ alkylene) in which one optional hydrogen is removed from the above-mentioned "lower alkyl", and is preferably a $C_{1-4}$ alkylene, more preferably methylene, ethylene, trimethylene, propylene or dimethylmethylene, and further preferably methylene or ethylene.

The "halogen" means F, Cl, Br and I.

The "halogeno-lower alkyl" is preferably a $C_{1-6}$ alkyl substituted with at least one halogen, more preferably a halogeno $C_{1-3}$ alkyl, further preferably fluoromethyl, difluoromethyl, trifluoromethyl, 1,1-difluoroethyl, 2,2,2-trifluoroethyl or 3,3,3-trifluoropropyl, further more preferably trifluoromethyl, 1,1-difluoroethyl or 2,2,2-trifluoroethyl.

The "cycloalkyl" is a $C_{3-10}$ saturated hydrocarbon ring group which may have a bridge. Illustratively, it is cyclopropyl, cyclobutyl, cyclopentyl, cyclohexyl, cycloheptyl, cyclooctyl, adamantyl or the like. Preferred is a $C_{3-6}$ cycloalkyl cyclopropyl and further preferred is cyclopropyl, cyclobutyl, cyclopentyl or cyclohexyl.

The "cycloalkenyl" is a $C_{3-15}$ cycloalkenyl which may have a bridge, and a ring group condensed with benzene ring at the double bond region is included therein. It is illustratively cyclopentenyl, cyclopentadienyl, cyclohexenyl, cyclohexadienyl, 1-tetrahydronaphthyl, 1-indenyl, 9-fluorenyl or the like. Preferred is a $C_{5-10}$ cycloalkenyl and more preferred is cyclopentenyl, cyclohexenyl, 1-indenyl or 1-tetrahydronaphthyl.

The "aryl" is a $C_{6-14}$ aromatic hydrocarbon radical, preferably phenyl, naphthyl or tetrahydronaphthyl and more preferably phenyl.

The "heteroaryl" means a group having a ring selected from i) a monocyclic 5- or 6-membered aromatic hetero ring having from 1 to 4 hetero atoms selected from O, S and N, ii) a bicyclic hetero ring in which the hetero rings shown in the above-mentioned i) are ring-condensed, wherein the condensing rings may be the same or different from each other, and iii) a bicyclic hetero ring in which a hetero ring shown in the above-mentioned i) is condensed with benzene ring or a 5- to 7-membered cycloalkane. As the ring which constitutes said group, for example, i) pyridine, pyrazine, pyrimidine, pyridazine, imidazole, pyrrole, thiophene, furan, triazine, triazole, thiazole, thiadiazole, oxadiazole, pyrazole, isothiazole, oxazole, isoxazole, ii) naphthyridine, imidazopyridine, pyrrolopyrimidine, thienopyridine, thienopyrroline, iii) quinoline, benzimidazole, benzofuran, benzothiophene, benzothiadiazole, benzothiazole, benzoisothiazole, benzoxazole, benzoisoxazole, quinoline, isoquinoline, 5,6,7,8-tetrahydroquinoline, 5,6,7,8-tetrahydroisoquinoline, quinazoline, quinoxaline, phthalazine, indole, isoindole, tetrahydrobenzimidazole, chroman and indazole may be exemplified. In addition, oxido may be formed through the oxidation of S or N of the ring. Preferred is the above-mentioned i) monocyclic aromatic hetero ring.

The "hetero ring" or "hetero ring group" means a group having a ring selected from i) a monocyclic 4- to 8-membered, preferably from 5- to 7-membered, saturated, unsaturated or partially unsaturated hetero ring having from 1 to 4 hetero atoms selected from O, S and N, ii) a bicyclic hetero ring in which the hetero rings shown in the above-mentioned i) are ring-condensed, wherein the condensing rings may be the same or different from each other, and iii) a bicyclic hetero ring in which a hetero ring shown in the above-mentioned i) is condensed with benzene ring or a 5- to 7-membered cycloalkane. As the ring which constitutes said group, for example, i) azetidine, piperidine, pyrrolidine, piperazine, azepan, diazepan, morpholine, thiomorpholine, dioxane, dioxolan, pyrazoline, piperidine, piperazine, oxetane, tetrahydrofuran, tetrahydrofuran, dihydropyridine, pyridine, pyrazine, pyrimidine, pyridazine, imidazole, pyrrole, thiophene, furan, triazine, triazole, thiazole, thiadiazole, oxadiazole, pyrazole, isothiazole, oxazole, isoxazole, ii) quinuclidine, naphthyridine, imidazopyridine, pyrrolopyrimidine, thienopyridine, thienopyrroline, iii) dihydrobenzofuran, 1,2,3,4-tetrahydroquinoline, 1,2,3,4-tetrahydroisoquinoline, dihydrobenzofuran benzodioxolan, indoline, indazoline, quinoline, benzimidazole, benzofuran, benzothiophene, benzothiadiazole, benzothiazole, benzoisothiazole, benzoxazole, benzoisoxazole, quinoline, isoquinoline, 5,6,7,8-tetrahydroquinoline, 5,6,7,8-tetrahydroisoquinoline, quinazoline, quinoxaline, phthalazine, indole, isoindole, tetrahydrobenzimidazole, chroman and indazole may be exemplified. In addition, oxido or dioxido may be formed through the oxidation of S or N of the ring. Preferred is the above-mentioned i) monocyclic hetero ring.

The term "may be substituted" means "not substituted" or "substituted with the same or different 1 to 5 substituents". The "substituted" means "has the same or different 1 to 5 substituents".

Preferred as the acceptable substituent of the "phenyl which may be substituted" and "heteroaryl which may be substituted" in $R^3$ is a group of the group G shown in the following.

Group G: halogen, —CN, —$R^0$, halogeno-lower alkyl, —$OR^z$, —O-halogeno-lower alkyl, —$N(R^z)CO$—$R^z$, —$CO_2R^z$, —$CON(R^z)_2$, —CO-hetero ring group, —CON($R^z$)-lower alkynyl, —CON($R^z$)-cycloalkyl, —CON($R^z$)-cycloalkenyl, —CON(cycloalkyl)(hetero ruing group), —CON($R^z$)-hetero ring group, —S—$R^0$, —$SO_2$—$R^0$, —O—$S(O)_2$—$R^0$, —O—$S(O)_2$-halogeno-lower alkyl, lower alkylene-$OR^z$, lower alkylene-O—$COR^z$, lower alkylene-N($R^z$)_2, lower alkylene-N($R^z$)CO—$R^z$, lower alkylene-$COR^z$, lower alkylene-$CO_2R^z$, lower alkylene-CON($R^z$)_2, —O-lower alkylene-$OR^z$, —O-lower alkylene-O—$COR^z$, —O-lower alkylene-N($R^z$)_2, —O-lower alkylene-N($R^z$)CO—$R^z$, —O-lower alkylene-N($R^z$)$CO_2$—$R^0$, —O-lower alkylene-CO—$R^z$, —O-lower alkylene-$CO_2$—$R^z$, —O-lower alkylene-CON(R)_2, —O-lower alkylene-CON($R^z$)-(lower alkyl which may be substituted with —$OR^z$), —O-lower alkylene-$SR^0$, —O-lower alkylene-cycloalkyl, —O-lower alkylene-CON($R^z$)— cycloalkyl, —O-hetero ring group, —O-lower alkylene-hetero ring group, —O-lower alkylene-CO-hetero ring group, —O-lower alkylene-CON($R^z$)-hetero ring group, —N($R^z$)CO-lower alkylene-$OR^z$, —CON($R^z$)-halogeno-lower alkyl, —CON($R^z$)-(lower alkyl substituted with —$OR^z$), —CON($R^z$)-lower alkylene-CN, —CON($R^z$)-lower alkylene-O-lower alkylene-$OR^z$, —CON(lower alkylene-$OR^z$)_2, —CON($R^z$)-lower alkylene-O—$COR^z$, —CON($R^z$)-lower alkylene-N($R^z$)_2, —CON($R^z$)-lower alkylene-N($R^z$)CO—$R^z$, —CON($R^z$)-lower alkylene-$COR^z$, —CON($R^z$)-lower alkylene-$CO_2R^z$, —CON($R^z$)-lower alkylene-CON($R^z$)_2, —CON($R^z$)-lower alkylene-$SO_2R^z$, —CON($R^z$)-lower alkylene-cycloalkyl, —CON($R^z$)-lower alkylene-O-cycloalkyl, —CON($R^z$)-lower alkylene-aryl, —CON($R^z$)-(lower alkylene substituted with —$N(R^z)_2$)-aryl, —CON($R^z$)-lower alkylene-O-aryl, —CON($R^z$)-lower alkylene-N($R^z$)-aryl, —CON($R^z$)-lower alkylene-CO-aryl, —CON(lower alkylene-$OR^z$)-lower alkylene-aryl, —CON($R^z$)-lower alkylene-hetero ring group, —CON($R^z$)-lower alkylene-O-hetero ring group, —CON($R^z$)-lower alkylene-N($R^z$)-hetero ring group, —CON($R^z$)-lower alkylene-CO-hetero ring group, —CON(lower alkylene-$OR^z$)-lower alkylene-hetero ring group, —CON(lower alkylene-CN)-lower alkylene-hetero ring group and —CON(lower alkylene-hetero ring group)_2.

In this regard, in the group G, lower alkylene may be substituted with halogen or —$OR^z$, and cycloalkyl, cycloalkenyl, aryl and hetero ring group may be substituted with a group selected from the following group $G^1$.

Group $G^1$: halogen, cyano, —$R^0$, halogeno-lower alkyl, —$OR^z$, —O-halogeno-lower alkyl, —$N(R^z)_2$, —S—$R^0$, —$SO_2$—$R^0$, —$SO_2N(R^z)_2$, —CO—$R^z$, —CON($R^z$)_2, —CON($R^z$)-lower alkylene-$OR^z$, —N($R^z$)CO—$R^z$, oxo, lower alkylene-CN, lower alkylene-$OR^z$, -aryl, -(lower alkylene which may be substituted with —$OR^z$)-aryl, lower alkylene-O-aryl, hetero ring group and lower alkylene-hetero ring group.

In this regard, aryl and hetero ring group in the group $G^1$ may be substituted with a group selected from the following group $G^2$.

Group $G^2$: halogen, cyano, halogeno-lower alkyl, —$OR^z$, —O-halogeno-lower alkyl and oxo.

Preferred as the acceptable substituent for the "phenyl which may be substituted" and "heteroaryl which may be substituted" in $R^3$ is more preferably a group of the following group $G^1$.

Group $G^3$: halogen, —$R^0$ halogeno-lower alkyl, —$OR^z$, —$CON(R^z)_2$, —$CON(R^z)$-hetero ring group, —O—S(O)$_2$—$R^z$, —O-lower alkylene-$OR^z$, —O-lower alkylene-O—$COR^z$, —O-lower alkylene-N($R^z$)$_2$, —O-lower alkylene-N($R^z$)CO—$R^z$, —O-lower alkylene-CO$_2R^z$, —O-lower alkylene-CON($R^z$)$_2$, —O-lower alkylene-CON($R^z$)-(lower alkyl substituted with —$OR^z$), —O-lower alkylene-$SR^0$, —O-lower alkylene-cycloalkyl, —O-lower alkylene-CON($R^z$)-cycloalkyl, —O-lower alkylene-hetero ring group and —O-lower alkylene-CON($R^z$)-hetero ring group.

In this regard, lower alkylene in the group $G^3$ may be substituted with halogen or —$OR^z$, and cycloalkyl and hetero ring group may be substituted with a group selected from the aforementioned group $G^1$.

Preferred as the acceptable substituent of the "phenyl which may be substituted" and "heteroaryl which may be substituted" in $R^3$ is further preferably a group selected from halogen, —$R^0$, —$OR^z$, —O-halogeno-lower alkyl, —O-lower alkylene-$OR^z$, —O-lower alkylene-CON($R^z$)$_2$ and —O-lower alkylene-(cycloalkyl which may be substituted with —$OR^z$).

Preferred as the acceptable substituent for the "phenyl which may be substituted" and "heteroaryl which may be substituted" in $R^3$ is further more preferably —O-lower alkylene-$OR^z$, O-lower alkylene-CON($R^z$)$_2$ or —O-lower alkylene-(cycloalkyl which may be substituted with —$OR^z$).

A preferred embodiment of the present invention is shown in the following.

(a) Preferred as $R^1$ is —H, -halogen or —$R^1$, more preferably —H.
(b) Preferred as $R^2$ is -halogen, —O—$R^0$, or —$R^0$, more preferably -halogen or —$R^0$.
(c) Preferred as n is 0 or 1.
(d) Preferred as $R^3$ is —X-(phenyl which may be substituted) or —X-(heteroaryl which may be substituted), more preferably phenyl or pyridyl which may respectively be substituted, further preferably phenyl which may be substituted, further more preferably phenyl which may be substituted with a group selected from the aforementioned group $G^3$, particularly preferably phenyl which is substituted with a group selected from the class consisting of —O-lower alkylene-$OR^z$, —O-lower alkylene-CON($R^z$)$_2$ and —O-lower alkylene-(cycloalkyl which may be substituted with —$OR^z$), and may further be substituted with $R^0$, halogen or —$OR^0$.
(e) Preferred as $R^4$ is —H.
(f) Preferred as ring A is benzene ring, pyridine ring or thiophene ring, more preferably benzene ring.
(g) Preferred as ring B is benzene ring.
(h) Preferred as L is *-lower alkylene-O— or *-lower alkylene-NH—, more preferably *—CH$_2$—O— or *—CH$_2$—NH— (wherein * represents binding to ring A). In addition, as the substituting position of L on the ring B, the 4-position to —CH($R^4$)-(3,5-dioxo-1,2,4-oxadiazolin-2-yl) is preferable.

As other preferred embodiment, a compound consisting of the combination of the preferred groups described in the above-mentioned (a) to (h) is preferable.

Also, another preferred embodiment of the compound of the present invention represented by the general formula (I) is shown in the following.

(1) The compound described in the general formula (I), wherein the substituting position of L on ring B is the 4-position.
(2) The compound described in (1), wherein the ring A is benzene ring.
(3) The compound of (2), wherein $R^3$ is phenyl or pyridyl which may respectively be substituted.
(4) The compound described in (3), wherein L is *—CH$_2$—O— or *—CH$_2$—NH— (wherein * represents binding to ring A).
(5) The compound of (4), wherein $R^4$ is —H.
(6) The compound described in (5), wherein $R^1$ is —H, halogen or $R^0$.
(7) The compound described in (6), wherein n is 0, or $R^2$ is halogen or $R^0$.
(8) The compound of (7), wherein $R^3$ is phenyl which is substituted with a group selected from the class consisting of —O-lower alkylene-$OR^z$, —O-lower alkylene-CON($R^z$)$_2$ and —O-lower alkylene-(cycloalkyl which may be substituted with —$OR^z$), and may further be substituted with 1 or 2 lower alkyl, halogen or —$OR^0$.
(9) The compound described in the formula (I), which is selected from the group consisting of 2-{[3'-({4-[(3,5-dioxo-1,2,4-oxadiazolidin-2-yl)methyl]phenoxy}methyl)-2,6-dimethylbiphenyl-4-yl]oxy}-N-methylacetamide, 2-(4-{[4'-(2-hydroxyethoxy)-2'-methylbiphenyl-3-yl]methoxy}benzyl)-1,2,4-oxadiazolidine-3,5-dione, 2-(4-{[4'-(3-hydroxy-3-methylbutoxy)-2',6'-dimethylbiphenyl-3-yl]methoxy}benzyl)-1,2,4-oxadiazolidine-3,5-dione, 2-(4-{[4'-(3-hydroxy-3-methylbutoxy)-2,2'-dimethylbiphenyl-3-yl]methoxy}benzyl)-1,2,4-oxadiazolidine-3,5-dione, 2-(4-{[4'-(3-hydroxy-3-methylbutoxy)-2,2',6'-trimethylbiphenyl-3-yl]methoxy}benzyl)-1,2,4-oxadiazolidine-3,5-dione, 2-{4-[(4'-{[(3R)-3-hydroxybutyl]oxy}-2,2'-dimethylbiphenyl-3-yl)methoxy]benzyl}-1,2,4-oxadiazolidine-3,5-dione, 2-{4-[(4'-{[(3S)-3-hydroxybutyl]oxy}-2,2'-dimethylbiphenyl-3-yl)methoxy]benzyl}-1,2,4-oxadiazolidine-3,5-dione, 2-[4-({[4'-(3-hydroxy-3-methylbutoxy)-2,2'-dimethylbiphenyl-3-yl]methyl}amino)benzyl]-1,2,4-oxadiazolidine-3,5-dione, 2-(4-{[4'-(3-hydroxy-3-methylbutoxy)-2'-methoxy-2-methylbiphenyl-3-yl]methoxy}benzyl)-1,2,4-oxadiazolidine-3,5-dione, 2-{4-[(4'-{[(3R)-3-hydroxybutyl]oxy}-2,2'6'-trimethylbiphenyl-3-yl)methoxy]benzyl}-1,2,4-oxadiazolidine-3,5-dione, 2-{4-[(4'-{[(3S)-3-hydroxybutyl]oxy}-2,2'6'-trimethylbiphenyl-3-yl)methoxy]benzyl}-1,2,4-oxadiazolidine-3,5-dione, 2-[(6-{[4'-(3-hydroxy-3-methylbutoxy)-2,2',6'-trimethylbiphenyl-3-yl]methoxy}pyridin-3-yl)methoxy]-1,2,4-oxadiazolidine-3,5-dione, and 2-[4-({4'-[2-(1-hydroxycyclopropyl)ethoxy]-2,2',6'-trimethylbiphenyl-3-yl}methoxy)benzyl]-1,2,4-oxadiazolidine-3,5-dione, or a pharmaceutically acceptable salt thereof.

There is a case in which the compound of the present invention represented by the formula (I) forms a salt, and such a salt is included in the compound of the present invention as long as it is a pharmaceutically acceptable salt. Illustratively, acid addition salts with inorganic acids such as hydrochloric acid, hydrobromic acid, hydriodic acid, sulfuric acid, nitric acid, phosphoric acid and the like, or organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like, salts with inorganic bases which contain metals (e.g., sodium, potassium, calcium, magnesium and the like) or with organic bases such as methylamine, ethylamine, ethanolamine, lysine, ornithine and the like, ammonium salts and the like may be exemplified.

In addition, the compound of the present invention may have an asymmetric carbon atom in some cases depending on the kind of substituents, and optical isomers based on this can be present. The present invention includes all of the mixtures and isolated forms of these optical isomers. Also, tautomers are present in the compound of the present invention in some cases, and the present invention includes separated forms of these isomers or mixtures thereof. In addition, a labeled substance, namely a compound in which at least one atom of the compound of the present invention is replaced by a radioisotope or non-radioactive isotope, is also included in the present invention.

In addition, various types of hydrate and solvate and polymorphism of the compound of the present invention are also included in the present invention. In this connection, as a matter of course, the compound of the present invention is not limited to the compounds described in Examples which are described later, and all of the compounds represented by the formula (I) and pharmaceutically acceptable salts thereof are included therein.

In this connection, all of the compounds which are converted into the compounds of the present invention in the living body, so-called prodrugs, are also included in the compound of the present invention. As the groups which form prodrugs of the compounds of the present invention, the groups described in "Progress in Medicine", Lifescience Medica, 1985, vol. 5, p. 2157-2161, and the groups described in "Iyakuhin no Kaihatsu (Development of Medicines)", vol. 7 Bunshi Sekkei (Molecular Design), pp. 163-198, published by Hirokawa Shoten in 1990, may be exemplified.

(Production Methods)

The compound of the present invention and a pharmaceutically acceptable salt thereof can be produced by employing various conventionally known synthesis methods making use of the characteristics based on its basic skeleton or kind of the substituents. Typical production methods are exemplified in the following. In this connection, depending on the kinds of functional group, there is an effective case from the production technology point of view to replace said functional group with an appropriate protecting group, namely a group which can be easily converted into said functional group, at the stage of starting material to intermediate. Thereafter, the desired compound can be obtained by removing the protecting group as occasion demands. As such a functional group, hydroxyl group, carboxyl group, amino group and the like can for example be cited, and as their protecting groups, the protecting groups described for example in "Protective Groups in Organic Synthesis" (USA) third edition, edited by Greene and Wuts, John Wiley & Sons, 1999, may be exemplified, which may be optionally used in response to the reaction conditions.

Production Method 1: Cyclization Reaction

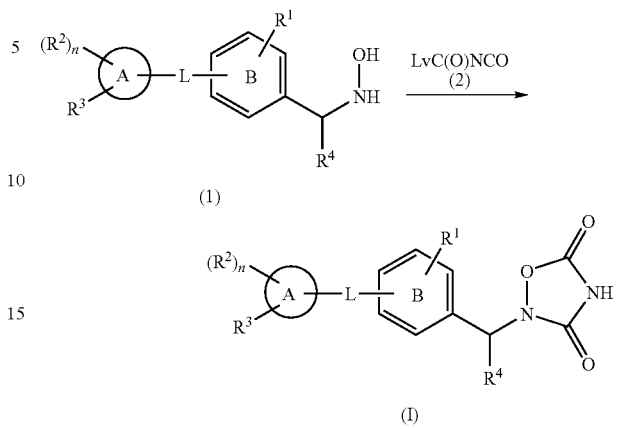

(In the Formula, Lv Represents a Leaving Group. The Same Shall Apply Hereinafter.)

This production method is a method in which the compound (I) of the present invention is produced by a cyclization reaction of a compound (1) and a compound (2). As the leaving group of Lv, halogen (e.g., chloro, bromo or the like) or alkoxy group (e.g., methoxy, ethoxy or the like) is preferable.

The reaction can be carried out using the compound (1) and compound (2) in equivalent amounts, or one of them in an excess amount, under cooling, under room temperature or under heating, in a solvent such as ethers (e.g., diethyl ether, tetrahydrofuran (THF), dioxane, dimethoxyethane (DME) or the like), halogenated hydrocarbons (e.g., dichloromethane, 1,2-dichloroethane, chloroform or the like), aromatic hydrocarbons (e.g., benzene, toluene, xylene or the like), or the like.

When the compound (1) has a hydroxyl group other than the hydroxyamino group, the hydroxyl group is carbamoylated in some cases. Removal of the carbamoyl group can be carried out a method generally used for de-carbamoylation by those skilled in the art. For example, it can be carried out in a solvent such as alcohols (e.g., methanol, ethanol or the like), water, or the like, under cooling, under room temperature or under heating, using a base such as sodium methoxide, sodium ethoxide, sodium hydroxide or the like.

Production Method 2: Coupling Reaction

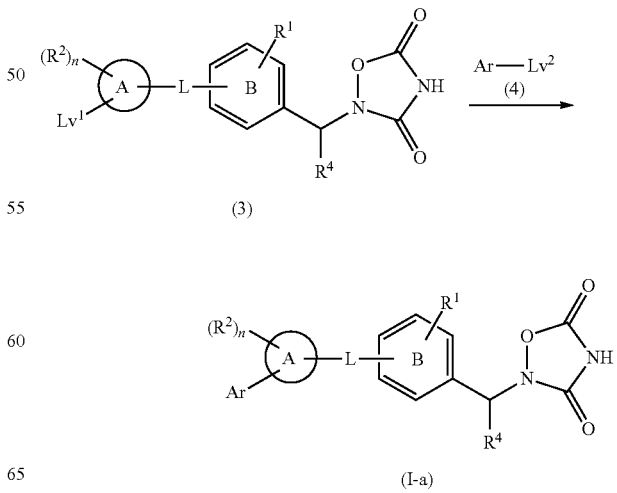

(In the formula, either one of $Lv^1$ and $Lv^2$ represents halogen or trifluoromethylsulfonyloxy group, and the other —B(OH)$_2$, —B(OR$^{00}$)$_2$ or —SnR$^0{}_3$, Ar represents phenyl or heteroaryl which may be respectively substituted, and $R^{00}$ represents lower alkyl, or two $R^{00}$ together form lower alkylene. The same shall apply hereinafter.

This production method is a method in which a compound (I-a) of the present invention is produced by a coupling reaction of a compound (3) and a compound (4).

The reaction can be carried out using palladium complex such as tetrakistriphenylphosphine palladium, palladium acetate or the like as the catalyst and using the compound (3) and compound (4) in equivalent amounts, or one of them in an excess amount, under cooling, under room temperature or under heating, in a solvent such as ethers, alcohols, halogenated hydrocarbons, aromatic hydrocarbons, water or the like. In addition, it is sometimes advantageous in smoothly advancing the reaction to carry out the reaction in the presence of a base such as sodium carbonate, cesium carbonate, sodium tert-butoxide or the like or a lithium salt such as lithium chloride, lithium bromide or the like.

Production Method 3: Reductive Amination

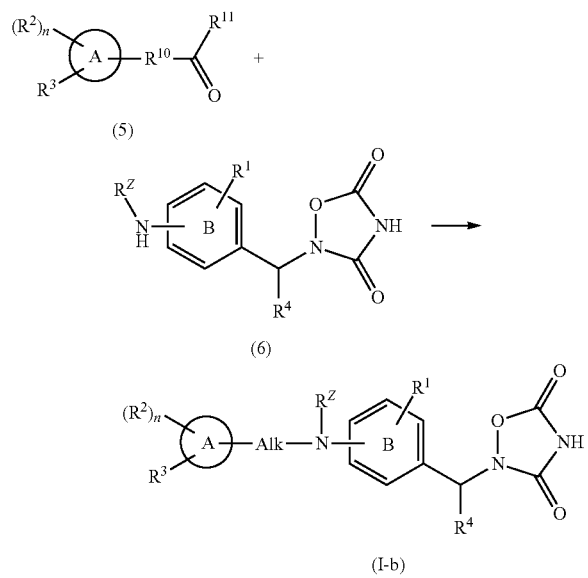

(In the formula, Alk represents lower alkylene, and $R^{10}$ a bond or $C_{1-5}$ alkylene and $R^{11}$—H or $C_{1-5}$ alkyl. However, the number of carbons of $R^{10}$ and $R^{11}$ is from 0 to 5 in total. The same shall apply hereinafter.)

This production method is a method in which a compound (1-b) of the present invention is produced by subjecting a compound (5) and a compound (6) to a reductive amination.

The reaction is carried out using the compound (5) and compound (6) in equivalent amounts, or one of them in an excess amount, and stirring, in the presence of a reducing agent and in a reaction inert solvent, at from −45° C. to under heating reflux, preferably at from 0° C. to room temperature, generally for from 0.1 hour to 5 days. As the solvent in this case, for example, alcohols, ethers or mixtures thereof may be exemplified. As the reducing agent, sodium cyanoborohydride, sodium triacetoxy borohydride, sodium borohydride and the like may be exemplified. It is preferable in some case to carry out the reaction in the presence of a dehydrating agent such as molecular sieve or the like or an acid such as acetic acid, hydrochloric acid, titanium(IV) isopropoxide complex or the like. Depending on the reaction, when the imine compound formed in the reaction system as an intermediate can be stably isolated, a reduction reaction may be separately carried out after obtaining said imine compound.

Production Method 4: Amidation

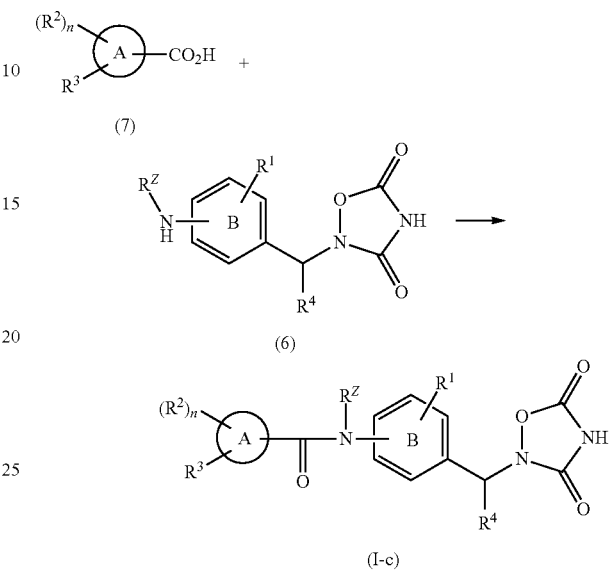

This production method is a method in which a compound (I-c) of the present invention is produced by subjecting a compound (7) and the compound (6) to amidation.

Instead of the carboxylic acid compound (7), a reactive derivative thereof can also be used. The reaction can be carried out using the carboxylic acid compound (7) or a reactive derivative thereof and the amino compound (6) in equivalent amounts, or one of them in an excess amount, under cooling, under room temperature or under heating, in a solvent such as aromatic hydrocarbons, halogenated hydrocarbons, ethers, N,N-dimethylformamide (DMF), N,N-dimethylacetamide (DMA), 1-methylpyrrolidin-2-one (NMP), dimethyl sulfoxide (DMSO), ethyl acetate, pyridine, acetonitrile or the like.

When the carboxylic acid compound (7) is used, it is preferable to use N,N'-dicyclohexylcarbodiimide (DCC), PS-carbodiimide (Argonaut, USA), 1-[3-(dimethylamino)propyl]-3-ethylcarbodiimide (WSC), 1,1'-carbonylbisimidazole (CDI), N,N'-disuccinimidyl carbonate, Bop reagent (Aldrich, USA), 2-(1H-benzotriazol-1-yl)-1,1,3,3-tetramethyluronium tetrafluoroborate(TBTU), 2-(1H-benzotriazol-1-yl)-1,1,3,3-tetramethyluronium hexafluorophosphate (HBTU), diphenylphosphoric acid azide (DPPA), 4-(4,6-dimethoxy-1,3,5-triazin-2-yl)-4-methylmorpholinium chloride (DMT-MM) or the like as the condensing agent, and in some cases, further 1-hydroxybenzotriazole ((HOBt), N-hydroxysuccinimide (HONSu), 1-hydroxy-7-azabenzotriazole ((HOAt) or the like as an additive agent.

As the reactive derivative of the carboxylic acid compound (7), an acid halide (acid chloride, acid bromide or the like), an acid anhydride (a mixed acid anhydride obtained by the reaction with ethyl chlorocarbonate, benzyl chlorocarbonate, phenyl chlorocarbonate, p-toluenesulfonic acid, isovaleric acid and the like, or a symmetric acid anhydride), an active ester (an ester prepared using phenol, HOBt, HONSu or the like which may be substituted with an electron attractive group such as a nitro group, a fluorine atom, or the like), a lower alkyl ester, an acid azide and the like may be exemplified. These reactive derivatives can be produced by general methods.

Depending on the kind of the reaction, it is sometimes advantageous in smoothly advancing the reaction to carry out the reaction in the presence of a base sch as triethylamine, diisopropylethylamine, N-methylmorpholine, pyridine, 4-(N,N-dimethylamino)pyridine (DMAP) or the like.

Production Method 5: Other Production Methods

In addition, several compounds represented by the formula (I) can also be produced from the compounds of the present invention obtained in the above manner, by optionally combining conventionally known amidation, oxidation, hydrolysis and the like processes which can be generally employed by those skilled in the art. For example, the following reactions can be employed.

5-1: Amidation

Amidation can be carried out in the same manner as in the production method 4.

5-2: Oxidation

A sulfoxide compound or sulfone compound can be produced by oxidizing the S atom of a sulfide compound with various oxidizing agents. The reaction can be carried out, for example, under cooling, under room temperature or under heating, by using an equivalent amount or excess amount of m-chloroperbenzoic acid, peracetic acid, a hydrogen peroxide aqueous solution, Dess-Martin reagent (1,1,1-triacetoxy-1,1-dihydro-1,2-benzoiodoxol-3(1H)-one) or the like as the oxidizing agent, in a solvent such as halogenated hydrocarbons, acetic acid, water or the like.

5-3: Hydrolysis

A compound having carboxyl group can be produced by hydrolyzing a compound having an ester group. For example, it can be carried out at from under cooling to under heating in a reaction inert solvent such as aromatic hydrocarbons, ethers, halogenated hydrocarbons, alcohols, DMF, DMA, NMP, DMSO, pyridine, water or the like, in the presence of a mineral acid such as sulfuric acid, hydrochloric acid, hydrobromic acid or the like or an organic acid such as formic acid, acetic acid or the like, or the like; or in the presence of a base such as lithium hydroxide, sodium hydroxide, potassium hydroxide, potassium carbonate, sodium carbonate, cesium carbonate, ammonia or the like.

(Production Methods of Starting Compounds)

The starting materials to be used in the production of the compounds of the present invention can be produced, for example, by employing the following methods, the methods described in the Production Examples which are described later, the conventionally known methods or methods obvious to those skilled in the art, or modified methods thereof.

Starting Material Syntheses

Starting Material Synthesis 1: O-alkylation

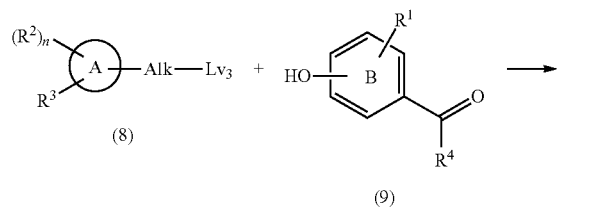

(8)  (9)

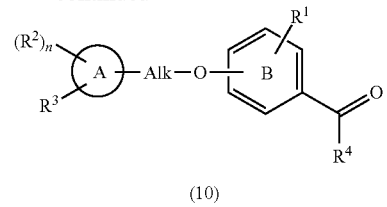

(10)

(In the formula, $Lv^3$ represents —OH, or a leaving group such as halogen, methanesulfonyloxy, p-toluenesulfonyloxy or the like. The same shall apply hereinafter.)

This production method is a method in which a compound (10) is obtained by O-alkylating a compound (8) with a compound (9).

When the compound (8) in which $Lv^3$ is —OH is used, it can be carried out using the general method of Mitsunobu reaction generally used by those skilled in the art.

For example, it can be carried out using an activating agent prepared from a phosphorus compound (e.g., tributylphosphine, triphenylphosphine or the like) and an azodicarbonyl compound (e.g., diethyl azodicarboxylate, 1,1'-(azodicarbonyl)dipiperidine or the like) or using cyanomethylenetributylphosphorane or the like reagent, in a solvent such as halogenated hydrocarbons, ethers, aromatic hydrocarbons or the like under cooling, under room temperature or under heating.

When the compound (8) in which $Lv^3$ is a leaving group such as halogen, methanesulfonyloxy, p-toluenesulfonyloxy or the like is used, for example, it can be carried out using the compound (8) and compound (9) in equivalent amounts, or one of them in an excess amount in the presence of a base such as potassium carbonate, cesium carbonate, sodium methoxide, sodium hydride or the like, in a solvent such as halogenated hydrocarbons, ethers, aromatic hydrocarbons or the like, DMF or the like, under cooling, under room temperature or under heating.

Starting Material Synthesis 2

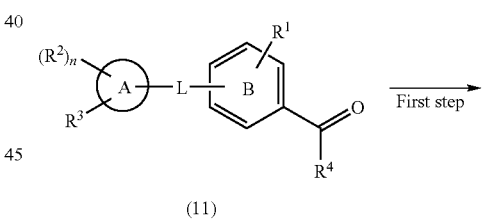

(11)

First step

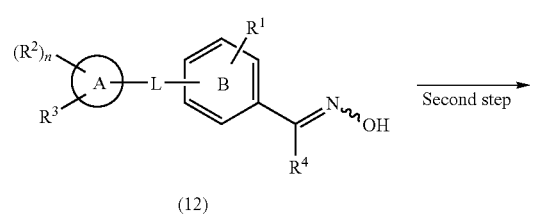

(12)

Second step

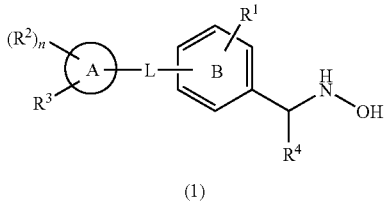

(1)

First Step: Oxime Formation

This step is a step in which a compound (12) is obtained by subjecting a compound (11) to oxime formation.

Regarding the oxime formation, an oxime formation method generally used by those skilled in the art can be employed. For example, it can be carried out using the compound (11) and hydroxylamine or a salt thereof in equivalent amounts, or one of them in an excess amount, in a solvent such as alcohols, acetic acid, pyridine, water or the like, under cooling, under room temperature or under heating. Depending on the kind of compound, it is sometimes advantageous for the progress of the reaction to add sodium acetate, p-toluenesulfonic acid or the like.

Second Step: Reduction

This step is a step in which the compound (1) is obtained by reducing the compound (12).

Regarding reducing reaction of the oxime, an oxime reducing method generally used by those skilled in the art can be employed. For example, it can be carried out using the compound (12) and a reducing agent such as a borane-pyridine complex, sodium cyanoborohydride or the like, in equivalent amounts, or one of them in an excess amount, in a solvent such as ethers, alcohols, aromatic hydrocarbons, acetic acid or the like, under cooling, under room temperature or under heating.

The compound of the present invention produced in this manner is isolated and purified directly as such or as a salt thereof by applying a salt formation treatment in the usual way. The isolation and purification are carried out by employing general chemical operations such as extraction, concentration, evaporation, crystallization, filtration, recrystallization, various types of chromatography and the like.

Various types of isomers can be isolated in the usual way making use of the difference in the physicochemical properties between isomers. For example, a racemic mixture can be converted into an optically pure isomer by a general racemic resolution such as, for example, a method in which these are converted into diastereomer salts with optically active acid such as a tartaric acid or the like and then subjected to optical resolution. Also, a diastereomer mixture can be separated, for example, by a fractional crystallization or various types of chromatography. In addition, an optically active compound can also be produced using an appropriate optically active compound as the starting material.

The pharmaceutical composition which contains one or more of the compounds of the present invention or pharmaceutically acceptable salts thereof as the active ingredient is prepared into tablets, powders, fine subtilaes, granules, capsules, pills, solutions, injections, suppositories, ointments, patches and the like using carriers, fillers and other additive agents generally used in preparing pharmaceuticals, and administered orally or parenterally.

Clinical dose of the compound of the present invention for human is optionally decided by taking symptom, age, sex and the like of each patient into consideration, but in the case of oral administration, its daily dose is generally from about 0.0001 to 50 mg/kg, preferably from about 0.001 to 10 mg/kg, further preferably from 0.01 to 1 mg/kg, and this is administered in one portion or by dividing into 2 to 4 portions. In the case of intravenous administration, its daily dose per body weight is from about 0.0001 to 1 mg/kg, preferably from about 0.0001 to 0.1 mg/kg, and this is administered once a day or dividing it into two or more times per day. Since the dose varies under various conditions, there is a case in which sufficient effect is obtained at a smaller amount than the above-mentioned range of dose.

As the solid composition for oral administration by the present invention, tablets, powders, granules and the like are used. In such a solid composition, one or more active substances are mixed with at least one inert diluent such as lactose, mannitol, glucose, hydroxypropylcellulose, microcrystalline cellulose, starch, polyvinyl pyrrolidone, aluminum magnesium silicate or the like. In accordance with the usual way, the composition may contain other additive agents than the inert diluent, such as lubricants (e.g., magnesium stearate or the like), disintegrating agent (e.g., calcium cellulose glycolate or the like,) a stabilizing agent, solubilizing agent and the like. When necessary, tablets or pills may be coated with a sugar coating or film of a gastric or enteric substance, such as of sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol (EtOH). In addition to the inert diluent, this composition may contain a moistening agent, a suspending agent and the like auxiliary agents, as well as sweeteners, flavors, aromatics and antiseptics.

As the injections for parenteral administration, aseptic aqueous or non-aqueous solutions, suspensions and emulsions are included. As the aqueous solutions and suspensions, for example, distilled water for injection and physiological saline are included. As the non-aqueous solutions and suspensions, for example, there are propylene glycol, polyethylene glycol, plant oil (e.g., olive oil or the like), alcohols (e.g., EtOH or the like), polysorbate 80 and the like. Such a composition may further contain auxiliary agents such as an antiseptic, a moistening agent, an emulsifying agent, a dispersing agent, a stabilizing agent, a solubilizing agent or the like. These are sterilized for example by filtration through a bacteria retaining filter, blending of a germicide or irradiation. These can also be used by producing sterile solid compositions and dissolving them in sterile water or a sterile solvent for injection prior to their use.

As the external preparations, ointments, hard cream preparations, creams, jellies, cataplasmas, sprays, lotions, eye drops, eye ointments and the like are included. Generally used ointment base, lotion base, aqueous or non-aqueous solutions, suspensions, emulsions and the like are contained therein. For example, polyethylene glycol, propylene glycol, white petrolatum, white beeswax, polyoxyethylene hydrogenated castor oil, glycerol monostearate, stearyl alcohol, cetyl alcohol, lauromacrogol, sorbitan sesquioleate and the like may be exemplified as the ointment or lotion base.

Inhalations, transmucosal preparations such as transnasal preparations and the like are used in a solid, liquid or semi-solid form and can be produced in accordance with conventionally known methods. For example, a conventionally known filler and, further, a pH adjusting agent, an antiseptic, a surfactant, a lubricant, a stabilizer, a thickener and the like may be optionally added thereto. An appropriate device for inhalation or blowing can be used for the administration. For example, using a measured administration inhalation device or the like conventionally known device or a sprayer, a compound can be administered alone or as a powder of a formulated mixture, or as a solution or suspension by a combination with a medicinally acceptable carrier. The dry powder inhaler or the like may be for single or multiple administration use, and a dry powder or a powder-containing capsule can be used. Alternatively, it may be a pressurized aerosol spray or the like form which uses chlorofluproalkane, hydrofluoroalkane or carbon dioxide or the like suitable gas.

EXAMPLES

The following illustratively describes the present invention based on examples, but the present invention is not restricted by these examples. In this connection, since novel substances are included in the starting material compounds to be used in the examples, production methods of such starting material compounds are described as production examples.

In this connection, the following abbreviations are used in the examples and tables. REx: production example number, Ex: Example number, No: compound number, Str: structural formula (When HCl is present in the structural formula, it means that the compound is hydrochloride.), Syn: production method (In the case of a numeral alone, it shows the Example number in which it is produced in the same manner, and when R is present before the numeral, a production example number in which it is produced in the same manner, respectively.), Dat: physicochemical data (NMR1: δ (ppm) of $^1$H NMR in DMSO-$d_6$, NMR2: δ (ppm) of $^1$H NMR in CDCl$_3$, FAB: FAB-MS (cation), FAB-N; FAB-MS (anion), ESI: ESI-MS (cation), ESI-N: ESI-MS (anion), EI: EI-MS (cation), CI: CI-MS (cation)), Me: methyl, Et: ethyl, Ac: acetyl, TBS: tert-butyldimethylsilyl, Boc: tert-butoxycarbonyl, Ts: p-toluenesulfonyl.

Production Example 1

By adding thionyl chloride and DMF to 1-(2,6-dimethylphenyl)-6-oxo-1,6-dihydropyrrolidine-3-carboxylic acid and stirring the reaction mixture at 60° C. for 2 hours, 1-(2,6-dimethylphenyl)-6-oxo-1,6-dihydropyrrolidine-3-carbonyl chloride was obtained. The resulting 1-(2,6-dimethylphenyl)-6-oxo-1,6-dihydropyrrolidine-3-carbonyl chloride was dissolved in DMF, and sodium borohydride was added under ice-cooling, followed by stirring for 0.5 hour, to obtain 1-(2,6-dimethylphenyl)-5-(hydroxymethyl)pyridine-2(1H)one.

Production Example 2

In an atmosphere of nitrogen, a 1.0 M diisobutylaluminum hydride THF solution was dropwise added at −78° C. to a THF solution of methyl 1-(2,6-dimethylphenyl)-6-oxo-1,6-dihydropyridine-3-carboxylate. After stirring at −78° C. for 2 hours, the temperature was risen to 0° C., followed by stirring at 0° C. for 1.5 hours. The reaction mixture was warmed up to room temperature, followed by stirring at room temperature for 2 hours. A 1.0 M diisobutylaluminum hydride THF solution was dropwise added to the reaction mixture at 0° C., followed by warming up to room temperature and stirring for 1 hour to obtain methyl 1-(2,6-dimethylphenyl)-6-oxo-1,4,5,6-tetrahydropyridine-3-carboxylate. In an atmosphere of nitrogen, lithium aluminum hydride was added to the resulting methyl 1-(2,6-dimethylphenyl)-6-oxo-1,4,5,6-tetrahydropyridine-3-carboxylate, while cooling on an ice-methanol bath. Thereafter, by stirring the reaction mixture for 2 hours while heating under reflux, [1-(2,6-dimethylphenyl)piperidin-3-yl]methanol was obtained.

Production Example 3

By adding tert-butyl(dimethyl)silyl chloride to a DMF solution of 4'-hydroxy-2',6'-dimethylbiphenyl-3-carbaldehyde and imidazole, and stirring at room temperature for 10 hours, 4'-{[tert-butyl(dimethyl)silyl]oxy}-2',6'-dimethylbiphenyl-3-carbaldehyde was obtained.

Production Example 4

In an atmosphere of nitrogen, n-butyl lithium (a hexane solution) was added at −75° C. to a THF solution of (4-bromo-3-methoxyphenoxy)(tert-butyl)dimethylsilane, followed by stirring at −75° C. for 1 hour. Triisopropyl borate was added to the reaction mixture, followed by stirring at room temperature for 30 minutes. The reaction mixture was treated with hydrochloric acid to obtain (4-{[tert-butyl(dimethyl)silyl]oxy}-2-methoxyphenyl)boronic acid.

Production Example 5

In an atmosphere of nitrogen, a mixture of methyl 3-bromo-2-methylbenzoate, bis(pinacolate)diboron, bis(triphenylphosphine)palladium(II) dichloride, triphenyl phosphine, tripotassium phosphate and dioxane was stirred at 100° C. for 3 days, thereby obtaining methyl 2-methyl-3-(4,4,5,5-tetramethyl-1,3,2-dioxaborolan-2-yl)benzoate.

Production Example 6

In an atmosphere of nitrogen, a mixture of (2,6-dimethylphenyl)boronic acid, ethyl 3-bromobenzoate, tetrakis(triphenylphosphine)palladium, a 1 M sodium carbonate aqueous solution, toluene and ethanol was stirred with heating at 80° C., thereby obtaining ethyl 2',6'-dimethylbiphenyl-3-carboxylate. A mixture of ethyl 2',6'-dimethylbiphenyl-3-carboxylate, a 1 M sodium hydroxide aqueous solution and ethanol was stirred with heating at 60° C., thereby obtaining 2',6'-dimethylbiphenyl-3-carboxylic acid.

Production Example 7

In an atmosphere of nitrogen, tetrakis(triphenylphosphine)palladium was added to a mixture of 2-bromo-1,3-dimethylbenzene, (5-formyl-2-methoxyphenyl)boronic acid, a 1 M sodium carbonate aqueous solution, ethanol and dimethoxyethane, followed by stirring at 80° C. for 25 hours to obtain 6-methoxy-2',6'-dimethylbiphenyl-3-carbaldehyde.

Production Example 8

Trifluoromethanesulfonic anhydride was dropwise added, under ice-cooling, to a mixture of 4-hydroxy-3,5-dimethylbenzonitrile, pyridine and dichloromethane, followed by stirring at room temperature for 2 hours to obtain 4-cyano-2,6-dimethylphenyl trifluoromethanesulfonate. In an atmosphere of nitrogen, a mixture of 4-cyano-2,6-dimethylphenyl trifluoromethanesulfonate, (3-formylphenyl)boronic acid, palladium acetate, dicyclohexyl(2',6'-dimethoxybiphenyl-2-yl)phosphine, tripotassium phosphate, toluene and water was stirred at room temperature for 6 hours to obtain 3'-formyl-2,6-dimethylbiphenyl-4-carbonitrile.

Production Example 9

In an atmosphere of nitrogen, a mixture of methyl 2-methyl-3-(4,4,5,5-tetramethyl-1,3,2-dioxaborolan-2-yl)benzoate, 4-bromo-3,5-dimethylphenol, palladium acetate, dicyclohexyl(2',6'-dimethoxybiphenyl-2-yl)phosphine, tripotassium phosphate, toluene and water was stirred for 14.5 hours with heating at 60° C. to obtain methyl 4'-hydroxy-2,2',6'-trimethylbiphenyl-3-carboxylate.

Production Example 10

In an atmosphere of nitrogen, a mixture of (4-{[tert-butyl(dimethyl)silyl]oxy}-2,6-dimethylphenyl)boronic acid, 6-bromopyridine-2-carbaldehyde, palladium acetate, 2'-(dicyclohexylphosphino)-N,N-dimethylbiphenyl-2-amine, tripotassium phosphate, toluene and water was stirred for 20 hours with heating at 60° C., thereby obtaining 6-(4-{[tert-butyl(dimethyl)silyl]oxy}-2,6-dimethylphenyl)pyridine-2-carbaldehyde.

Production Example 11

In an atmosphere of nitrogen, under ice-cooling, sodium borohydride was added to an ethanol solution of 4'-chloro-2'-methylbiphenyl-3-carbaldehyde, followed by stirring for 1 hour to obtain (4'-chloro-2'-methylbiphenyl-3-yl)methanol.

Production Example 12

In an atmosphere of nitrogen, under ice-cooling, methyl 4'-(methylsulfonyl)biphenyl-3-carboxylate was added to a THF suspension of lithium aluminum hydride, followed by stirring for 20 minute to obtain [4'-(methylsulfonyl)biphenyl-3-yl]methanol.

Production Example 13

In an atmosphere of nitrogen, a mixture of methyl 3-bromo-4-chlorobenzoate, (2,6-dimethylphenyl)boronic acid, lithium chloride, sodium carbonate, water, ethanol, dimethoxyethane and tetrakis(triphenylphosphine)palladium was stirred at 90° C. for 15 hours, thereby obtaining methyl 6-chloro-2',6'-dimethylbiphenyl-3-carboxylate. Lithium aluminum hydride was added under ice-cooling to a THF solution of the resulting methyl 6-chloro-2',6'-dimethylbiphenyl-3-carboxylate, followed by warming up to room temperature and stirring for 2 hours to obtain (6-chloro-2',6'-dimethylbiphenyl-3-yl)methanol.

Production Example 14

In an atmosphere of nitrogen, tetrakistriphenylphosphine palladium was added to a mixture of 2-bromo-1,3-dimethylbenzene, 2-fluoro-5-formylphenyl boronic acid, a 1 M sodium carbonate aqueous solution, ethanol and toluene, followed by stirring at 80° C. for 8 hours to obtain 6-fluoro-2',6'-dimethylbiphenyl-3-carbaldehyde. Under cooling on an ice-methanol bath, sodium borohydride was added in small portions to an ethanol solution of the resulting 6-fluoro-2',6'-dimethylbiphenyl-3-carbaldehyde, and the reaction mixture was stirred at the same temperature for 1 hour to obtain (6-fluoro-2',6'-dimethylbiphenyl-3-yl)methanol.

Production Example 15

Thionyl chloride was added to (4'-chloro-2'-methylbiphenyl-3-yl)methanol under cooing with ice-methanol, followed by stirring at room temperature for 1 hour to obtain 4-chloro-3'-(chloromethyl)-2-methylbiphenyl.

Production Example 16

Potassium carbonate was added to a DMF solution of 4-chloro-3'-(chloromethyl)-2-methylbiphenyl and 4-hydroxybenzaldehyde, followed by stirring at room temperature for 20 hours to obtain 4-[(4'-chloro-2'-methylbiphenyl-3-yl)methoxy]benzaldehyde.

Production Example 17

Tributylphosphine and 1,1'-(azodicarbonyl)dipiperidine were added to a THF solution of (4-{[tert-butyl(dimethyl)silyl]oxy}-2',6'-dimethylbiphenyl-3-yl)methanol and 4-hydroxybenzaldehyde, followed by stirring at room temperature for 14 hours to obtain 4-[(4-{[tert-butyl(dimethyl)silyl]oxy}-2',6'-dimethylbiphenyl-3-yl)methoxybenzaldehyde.

Production Example 18

In an atmosphere of nitrogen, sodium hydride was added under ice-cooling to a THF solution of (2',6'-dimethylbiphenyl-3-yl)methanol, followed by stirring at that temperature for 15 minutes. Thereafter, 6-chloronicotinonitrile was added to the reaction mixture under ice-cooling, followed by warming up to room temperature and stirring for 3 hours to obtain 6-[(2',6'-dimethylbiphenyl-3-yl)methoxy]nicotinonitrile.

Production Example 19

Under an atmosphere of nitrogen, a 1.0 M diisopropyl aluminum hydride toluene solution was dropwise added at −78° C. to a toluene solution of 6-[(2',6'-dimethylbiphenyl-3-yl)methoxy]nicotinonitrile, followed by stirring at −78° C. for 1.5 hours to obtain 6-[(2',6'-dimethylbiphenyl-3-yl)methoxy]nicotinaldehyde.

Production Example 20

In an atmosphere of nitrogen, a THF solution of methyl 4-[(4'-chloro-2'-methylbiphenyl-3-yl)methoxy]-2-fluorobenzoate was dropwise added to a THF suspension of lithium aluminum hydride under cooling on an ice-methanol bath, followed by stirring at room temperature for 1 hour to obtain 4-[(4'-chloro-2'-methylbiphenyl-3-yl)methoxy]-2-fluorobenzyl alcohol. By adding manganese dioxide to a THF solution of the resulting 4-[(4'-chloro-2'-methylbiphenyl-3-yl)methoxy]-2-fluorobenzyl alcohol and stirring at 40° C. for 17 hours, 4-[(4'-chloro-2'-methylbiphenyl-3-yl)methoxy]-2-fluorobenzaldehyde was obtained.

Production Example 21

In an atmosphere of nitrogen, sodium borohydride was added to a methanol solution of 4-{[2',6'-dimethyl-4'-(2-oxopropoxy)biphenyl-3-yl]methoxy}benzaldehyde under ice-cooling, followed by stirring at room temperature for 2 hours to obtain 1-[(-3'-{[4-(hydroxymethyl)phenoxy]methyl}-2,6-dimethylbiphenyl-4-yl)oxy]propan-2-ol. By adding chloroform and manganese dioxide to the resulting compound and stirring at 60° C. for 5 hours, 4-{[4'-(2-hydroxypropoxy)-2',6'-dimethylbiphenyl-3-yl]methoxy}benzaldehyde was obtained.

Production Example 22

Methanesulfonyl chloride was dropwise added under ice-cooling to a mixture of 4-[(4'-hydroxy-2',6'-dimethylbiphenyl-3-yl)methoxy]benzaldehyde, triethylamine and ethyl acetate, followed by stirring at 0° C. for 2 hours to obtain 3'-[(4-formylphenoxy)methyl]-2,6-dimethylbiphenyl-4-yl methanesulfonate.

Production Example 23

A mixture of 4-[(4'-hydroxy-2',6'-dimethylbiphenyl-3-yl)methoxy]benzaldehyde, 2-bromoethyl acetate, cesium carbonate and DMF was stirred at 60° C. for 21 hours to obtain 2-({3'-[(4-formylphenoxy)methyl]-2,6-dimethylbiphenyl-4-yl}oxy)ethyl acetate.

Production Example 24

In an atmosphere of nitrogen, a mixture of 2-hydroxyethyl acetate, sodium hydride and DMF was stirred at room temperature for 15 minutes and then 1-bromo-4-fluoro-2-(trifluoromethyl)benzene was added, followed by stirring at room temperature for 1.5 hours to obtain 2-[4-bromo-3-(trifluoromethyl)phenoxy]ethanol.

Production Example 25

Methanesulfonyl chloride was dropwise added to a mixture of 1-(3-hydroxypropyl)pyrrolidin-2-one, triethylamine and ethyl acetate under ice-cooling, followed by stirring at 0° C. for 2 hours to obtain a colorless oil. 4-[(4'-Hydroxy-2',6'-dimethylbiphenyl-3-yl)methoxy]benzaldehyde, cesium carbonate and DMF were added to the resulting oil, followed by stirring with heating at 60° C. for 19 hours to obtain 4-({2',6'-dimethyl-4'-[3-(2-oxopyrrolidin-1-yl)propoxy]biphenyl-3-yl}methoxy)benzaldehyde.

Production Example 26

In an atmosphere of nitrogen, a THF solution of methylmagnesium iodide was dropwise added under ice-cooling to a THF solution of 1-[(3'-{[4-(hydroxymethyl)phenoxy]methyl}-2,6-dimethylbiphenyl-4-yl)oxy]acetone, followed by stirring at room temperature for 30 minute to obtain 1-[(3'-{[4-(hydroxymethyl)phenoxy]methyl}-2,6-dimethylbiphenyl-4-yl)oxy]-2-methylpropan-2-ol.

Production Example 27

A mixture of 1-[(3'-{[4-(hydroxymethyl)phenoxy]methyl}-2,6-dimethylbiphenyl-4-yl)oxy]-2-methylpropan-2-ol, manganese dioxide and chloroform was stirred with heating at 50° C. for 20 hours to obtain 4-{[4'-(2-hydroxy-2-methylpropoxy)-2',6'-dimethylbiphenyl-3-yl]methoxy}benzaldehyde.

Production Example 28

A mixture of 4-{[4'-(3-hydroxypropoxy)-2,6'-dimethylbiphenyl-3-yl]methoxy}benzaldehyde, acetyl chloride, triethylamine and dichloromethane was stirred at room temperature for 3.5 hours to obtain 3-({3'-[(4-formylphenoxy)methyl]-2,6-dimethylbiphenyl-4-yl}oxy)propyl acetate.

Production Example 29

A mixture of 4-{[4'-(3-hydroxy-3-methylbutoxy)-2',6'-dimethylbiphenyl-3-yl]methoxy}benzaldehyde, acetic anhydride, pyridine, DMAP and chloroform was stirred at room temperature for 2 days to obtain 3-({3'-[(4-formylphenoxy)methyl]-2,6-dimethylbiphenyl-4-yl}oxy)-1,1-dimethylpropyl acetate.

Production Example 30

A 4 M hydrogen chloride ethyl acetate solution was dropwise added under ice-cooling to an ethyl acetate solution of tert-butyl [2-({3'-[(4-formylphenoxy)methyl]-2,6-dimethylbiphenyl-4-yl}oxy)ethyl]carbamate, followed by stirring at 0° C. for 2 hours. Dichloromethane, acetyl chloride and triethylamine were added to the resulting compound, followed by stirring at room temperature for 12 hours to obtain N-[2-({3'-[(4-formylphenoxy)methyl]-2,6-dimethylbiphenyl-4-yl}oxy)ethyl]acetamide.

Production Example 31

Trifluoromethanesulfonic anhydride was dropwise added under ice-cooling to a mixture of 4-[(4'-hydroxy-2,2'-dimethylbiphenyl-3-yl)methoxy]benzaldehyde, pyridine and dichloromethane; followed by stirring at 0° C. for 1 hour to obtain 3'-[(4-formylphenoxy)methyl]-2,2'-dimethylbiphenyl-4-yl trifluoromethanesulfonate.

Production Example 32

Hydroxylamine hydrochloride and a sodium acetate aqueous solution were added to an ethanol solution of 4-[(4'-chloro-2'-methylbiphenyl-3-yl)methoxy]benzaldehyde, followed by stirring at room temperature for 18 hours to obtain 4-[(4-{[tert-butyl(dimethyl)silyl]oxy}-2',6'-dimethylbiphenyl-3-yl)methoxy]benzaldehyde oxime. Sodium cyanoborohydride was added to a methanol-THF mixed solution of the resulting 4-[(4-{[tert-butyl(dimethyl)silyl]oxy}-2',6'-dimethylbiphenyl-3-yl)methoxy]benzaldehyde oxime, and then a 4 M hydrogen chloride dioxane solution was dropwise added thereto, followed by stirring at room temperature for 1 hour to obtain N-{4-[(4-{[tert-butyl(dimethyl)silyl]oxy}-2',6'-dimethylbiphenyl-3-yl)methoxy]benzyl}hydroxylamine.

Production Example 33

In an atmosphere of nitrogen, a sulfur trifluoride diethylamine complex was dropwise added at −75° C. to a dichloromethane solution of 4-(4-bromo-3-methylphenoxy)-2-methylbutan-2-ol, and the temperature was raised to room temperature to obtain 1-bromo-4-(3-fluoro-3-methylbutoxy)-2-methylbenzene.

Production Example 34

In an atmosphere of nitrogen, a mixture of 1-bromo-4-(3-fluoro-3-methylbutoxy)-2-methylbenzene, methyl 2-methyl-3-(4,4,5,5-tetramethyl-1,3,2-dioxaborolan-2-yl)benzoate, palladium acetate, dicyclohexyl(2',6'-dimethoxybiphenyl-2-yl)phosphine, tripotassium phosphate, toluene and water was stirred at 80° C. for 12 hours to obtain methyl 4'-(3-fluoro-3-methylbutoxy)-2,2'-dimethylbiphenyl-3-carboxylate.
Lithium aluminum hydride was added to a THF solution of the resulting methyl 4'-(3-fluoro-3-methylbutoxy)-2,2'-dimethylbiphenyl-3-carboxylate under ice-cooling, followed by warming up to room temperature and stirring for 1 hour to obtain [4'-(3-fluoro-3-methylbutoxy)-2,2'-dimethylbiphenyl-3-yl]methanol.

Production Example 35

In an atmosphere of nitrogen, sodium hydride was added under ice-cooling to a mixture of 5-bromo-4-methylpyridin-2-ol and DMF, followed by stirring at room temperature for 1 hour. Then, 3-hydroxy-3-methylbutyl 4-methylbenzenesulfonate was added thereto, followed by stirring at 40° C. for 14 hours to obtain 4-[(5-bromo-4-methylpyridin-2-yl)oxy]2-methylbutan-2-ol and 5-bromo-1-(3-hydroxy-3-methylbutyl)-4-methylpyridin-2(1H)-one.

Production Example 36

In an atmosphere of nitrogen, a mixture of (4-{[tert-butyl(dimethyl)silyl]oxy}-2-methylphenyl)boronic acid, 6-[(3- bromo-2-methylbenzyl)oxy]nicotinaldehyde, palladium acetate, dicyclohexyl(2',6'-dimethoxybiphenyl-2-yl)phosphine, tripotassium phosphate, toluene and water was stirred with heating at 60° C. for 2 days to obtain 6-[(4'-{[tert-butyl(dimethyl)silyl]oxy}-2,2'-dimethylbiphenyl-3-yl)methoxy]nicotinaldehyde.

Production Example 37

In an atmosphere of nitrogen, a mixture of tert-butyl [3,5-dimethyl-4-(4,4,5,5-tetramethyl-1,3,2-dioxaborolan-2-yl)phenoxy]dimethylsilane, 6-[(3-bromo-2-methylbenzyl)oxy]nicotinaldehyde, palladium acetate, dicyclohexyl(2',6'-dimethoxybiphenyl-2-yl)phosphine, tripotassium phosphate, toluene and water was stirred with heating at 60° C. for 3 days to obtain 6-[(4'-{[tert-butyl(dimethyl)silyl]oxy}-2,2',6'-trimethylbiphenyl-3-yl)methoxy]nicotinaldehyde.

Production Example 38

In an atmosphere of nitrogen, potassium tert-butoxide was added under ice-cooling to a mixture of cyclobutanone, ethyl chloroacetate and THF, spending 40 minutes, followed by stirring at 0° C. for 2 hours, raising the temperature to room temperature, and stirring at room temperature for 1 day, thereby obtaining ethyl 1-oxaspiro[2,3]hexane-2-carboxylate. A diethyl ether solution of the resulting ethyl 1-oxaspiro[2,3]hexane-2-carboxylate was added to a THF suspension of lithium aluminum hydride under ice-cooling in an atmosphere of nitrogen, followed by stirring at room temperature for 7 hours to obtain 1-(2-hydroxyethyl)cyclobutanol. A mixture of the resulting 1-(2-hydroxyethyl)cyclobutanol, 4-methylbenzenesulfonyl chloride, triethylamine and THF was stirred at room temperature for 16 hours to obtain 2-(1-hydroxycyclobutyl)ethyl 4-methylbenzenesulfonate.

In the same manner as in the above-mentioned methods of Production Examples 1 to 38, Production Example compounds 39 to 299 were produced using respectively corresponding starting materials. Structures of the production example compounds are shown in Tables 4 to 44, and the production methods and physicochemical data in Tables 45 to 52.

Example 1

Chlorocarbonyl isocyanate (0.10 ml) was dropwise added, under cooling on an ice-methanol bath, to a THF (10 ml) solution of N-{4-[(4'-chloro-2'-methylbiphenyl-3-yl)methoxy]benzyl}hydroxylamine (430 mg), and the temperature was raised to room temperature, followed by stirring for 1 hour. 1 M Hydrochloric acid (30 ml) was added to the reaction mixture, followed by extraction with chloroform. The organic layer was dried over anhydrous magnesium sulfate and then the solvent was evaporated under a reduced pressure. By purifying the resulting residue by silica gel column chromatography (chloroform-methanol), a colorless foamy substance was obtained. The resulting foamy substance was dissolved in ethanol (5 ml), and a 1 M sodium hydroxide aqueous solution (1.06 ml) was added thereto, followed by concentration under a reduced pressure. By recrystallizing the resulting residue from water-isopropanol, sodium 2-{4-[(4'-chloro-2'-methylbiphenyl-3-yl)methoxy]benzyl}-3,5-dixo-1,2,4-oxadiazolidin-4-ide (347 mg) as colorless crystals.

Example 2

Chlorocarbonyl isocyanate (0.14 ml) was dropwise added, under cooling on an ice-methanol bath, to a THF (15 ml) solution of 4-({[3'-({4-[(hydroxyamino)methyl]phenoxy}methyl)-2,6-dimethylbiphenyl-4-yl]oxy}methyl)tetrahydro-2H-thiopyran-4-ol (792 mg), followed by temperature rising to room temperature and subsequent 1 hour of stirring. A 1 M hydrochloric acid (40 ml) was added to the reaction mixture, followed by extraction with chloroform. The organic layer was dried over anhydrous magnesium sulfate and then the solvent was evaporated under a reduced pressure. By purifying the resulting residue by silica gel column chromatography (chloroform-methanol), a colorless foamy substance (777 mg) was obtained. Sodium methoxide (50 mg) was added to a methanol (10 ml) solution of the resulting foamy substance (116 mg), followed by stirring at room temperature for 30 minutes. Thereafter, sodium methoxide (200 mg) was added to the reaction mixture, followed by stirring at room temperature for 1 hour. The reaction mixture was warmed up to 60° C., stirred for 2 hours and then spontaneously cooled to room temperature. 1 M Hydrochloric acid (10 ml) and water (20 ml) were added to the reaction mixture, followed by extraction with chloroform. The organic layer was dried over anhydrous magnesium sulfate and then the solvent was evaporated under a reduced pressure. The resulting residue was dissolved in methanol (5 ml)-THF (10 ml), and a 1 M sodium hydroxide aqueous solution (0.20 ml) was added, followed by concentration under a reduced pressure. By washing the resulting residue with isopropanol-diethyl ether, sodium 2-[4-({4'-[(4-hydroxytetrahydro-2H-thiopyran-4-yl)methoxy]-2',6'-dimethylbiphenyl-3-yl}methoxy)benzyl]-3,5-dioxo-1,2,4-oxadiazolidin-4-ide (80 mg) was obtained as a pale yellow solid.

Example 3

Chlorocarbonyl isocyanate (0.14 ml) was added dropwise, under cooling on an ice-methanol bath, to a THF (15 ml) solution of 4-({[3'-({4-[(hydroxyamino)methyl]phenoxy}methyl)-2,6-dimethylbiphenyl-4-yl]oxy}methyl)tetrahydro-2H-thiopyran-4-ol (792 mg), followed by temperature rising to room temperature and subsequent 1 hour of stirring. A 1 M hydrochloric acid (40 ml) was added to the reaction mixture, followed by extraction with chloroform. The organic layer was dried over anhydrous magnesium sulfate and then the solvent was evaporated under a reduced pressure. By purifying the resulting residue by silica gel column chromatography (chloroform-methanol), a colorless foamy substance (777 mg) was obtained. Under cooling on an ice-methanol bath, m-chloroperbenzoic acid (630 mg) was added to a chloroform (20 ml) solution of the resulting foamy substance (600 mg), followed by stirring for 30 minutes. Water (20 ml) was added to the reaction mixture, followed by extraction with chloroform. The organic layer was dried over anhydrous magnesium sulfate and then the solvent was evaporated under a reduced pressure. By purifying the resulting residue by silica gel column chromatography (chloroform-methanol), a colorless foamy substance (510 mg) was obtained. The resulting foamy substance (510 mg) was washed with diisopropyl ether-ethyl acetate-hexane and dried under a reduced pressure to obtain a slightly yellow solid (432 mg).

Sodium methoxide (800 mg) was added to a methanol (30 ml) solution of the resulting slightly yellow solid (387 mg), followed by stirred at 60° C. for 2 hours and then spontaneously cooling to room temperature. 1 M Hydrochloric acid (30 ml) and water (50 ml) were added to the reaction mixture, followed by extraction with chloroform. The organic layer was dried over anhydrous magnesium sulfate and then the solvent was evaporated under a reduced pressure. The resulting residue was dissolved in methanol (5 ml)-THF (15 ml), a 1 M sodium hydroxide aqueous solution (0.63 ml) was added, followed by concentration under a reduced pressure. By washing the resulting residue with isopropanol-diethyl ether, sodium 2-[4-({4'-[(4-hydroxy-1,1-dioxotetrahydro-2H-thiopyran-4-yl)methoxy]-2',6'-dimethylbiphenyl-3-yl}methoxy)benzyl]-3,5-dioxo-1,2,4-oxadiazolidin-4-ide (252 mg) was obtained as a colorless solid.

Example 4

A mixture of 2-{4-[(3-bromobenzyl)oxy]benzyl}-1,2,4-oxadiazolidine-3,5-dione (500 mg), 2,6-difluoro-4-methoxyphenyl boronic acid (325 mg), tetrakistriphenylphosphine palladium (80 mg), lithium chloride (6 mg), a sodium carbonate aqueous solution (562 mg/5 ml), ethanol (5 ml) and 1,2-dimethoxyethane (25 ml) was stirred at 90° C. for 5 hours in an atmosphere of nitrogen. 2,6-Difluoro-4-methoxyphenyl boronic acid (325 mg) was further added thereto, followed by stirring at 90° C. for 13 hours. Further, 2,6-difluoro-4-methoxyphenyl boronic acid (325 mg) was added thereto, followed by stirring at 90° C. for 2 hours. Further, 2,6-difluoro-4-methoxyphenyl boronic acid (325 mg) was added thereto, followed by stirring at 90° C. for 5 hours and spontaneous cooling to room temperature. A 1 M hydrochloric acid (50 ml) was added to the reaction mixture, followed by extraction with ethyl acetate. The organic layer was washed with a saturated sodium chloride aqueous solution and then dried over anhydrous magnesium sulfate and filtered. Silica gel (3 g) was added to the filtrated, followed by concentration under a reduced pressure. The carrying product thus obtained was purified by silica gel column chromatography (chloroform-methanol) to obtain a light yellow foamy substance (614 mg). The resulting foamy substance (614 mg) was dissolved in THF (5 ml)-ethanol (5 ml), a 1 M sodium hydroxide aqueous solution (1.32 ml) was added, followed by concentration under a reduced pressure. By recrystallizing the resulting residue from isopropanol-water, sodium 2-{4-[(2',6'-difluoro-4'-methoxybiphenyl-3-yl)methoxy]benzyl}-3,5-dioxo-1,2,4-oxadiazolidin-4-ide (366 mg) was obtained as a colorless solid.

Example 5

A 1 M sodium hydroxide aqueous solution (5 ml) was added to a mixture of methyl 3'-({4-[(3,5-dioxo-1,2,4-oxadiazolidin-2-yl)methyl]phenoxy}methyl)-4-biphenylcarboxylate (196 mg), methanol (5 ml) and THF (5 ml), followed by stirring for 1 hour with heating at 60° C. A 1 M hydrochloric acid (7 ml) was added to the reaction mixture, followed by stirring at room temperature. The solid precipitated was collected by filtration and dried by heating under a reduced pressure to obtain 3'-({4-[(3,5-dioxo-1,2,4-oxadiazolidin-2-yl)methyl]phenoxy}methyl)-4-biphenylcarboxylic acid (176 mg) as a white solid.

Example 6

WSC hydrochloride (163 mg) was added to a mixture of 3'-({4-[(3,5-dioxo-1,2,4-oxadiazolidin-2-yl)methyl]phenoxy}methyl)-4-biphenylcarboxylic acid (293 mg), (2-ethoxyethyl)amine (0.11 ml), HOBt (142 mg) and DMF (10 ml), followed by stirring at room temperature for 27 hours. The solvent was evaporated under a reduced pressure, and chloroform/methanol (4/1) was added to the residue, followed by washing with water and a saturated ammonium chloride aqueous solution. The solvent was evaporated under a reduced pressure, and the residue was purified by silica gel column chromatography (chloroform/methanol), the resulting foamy substance was further crystallized by adding diethyl ether, and the resulting crystals were recrystallized from methanol to obtain 3'-({4-[(3,5-dioxo-1,2,4-oxadiazolidin-2-yl)methyl]phenoxy}methyl)-N-(2-ethoxyethyl)-4-biphenylcarboxamide (135 mg) as white crystals.

Example 7

DMT-MM (653 mg) was added to an ice-cooled mixture of 3'-({4-[(3,5-dioxo-1,2,4-oxadiazolidin-2-yl)methyl]phenoxy}methyl)-4-biphenylcarboxylic acid (329 mg), 2-aminoethanol (0.14 ml), THF (20 ml) and methanol (4 ml), followed by stirring at room temperature for 25 hours. The solvent was evaporated under a reduced pressure, and a saturated ammonium chloride aqueous solution was added to residue, followed by extraction with chloroform/methanol (4/1). The solvent was evaporated under a reduced pressure, and the residue was purified by silica gel column chromatography (chloroform-methanol). The resulting pale yellow solid (276 mg) was dissolved in THF (5 ml)-methanol (5 ml), and a 1 M sodium hydroxide aqueous solution (0.79 ml) was added, followed by stirring art room temperature for 10 minutes. The solid precipitated was collected by filtration and dried by heating under a reduced pressure to obtain sodium 2-{4-[(4'-{[(2-hydroxyethyl)amino]carbonyl}biphenyl-3-yl)methoxy]benzyl}-3,5-dioxo-1,2,4-oxadiazolidin-4-ide (188 mg) as a white solid.

Example 8

A 1.0 M tetrabutylammonium fluoride (TBAF) THF solution (1.94 ml) was dropwise added to an ice-cooled mixture of 2-(4-[4'-(2-{[tert -butyl(dimethyl)silyl]oxy}ethoxy)biphenyl-3-yl ]methoxy}benzyl-1,2,4-oxadiazolidine-3,5-dione (532 mg) and THF (10 ml), followed by gradual temperature rising to room temperature and subsequent stirring for 13 hours. The reaction mixture was diluted with chloroform/methanol (4/1) and washed with a saturated ammonium chloride aqueous solution and a saturated sodium chloride aqueous solution. Then, the solvent was evaporated under a reduced pressure. The residue was purified by silica gel column chromatography (chloroform-methanol), and the resulting solid was recrystallized from ethyl acetate-hexane-diethyl ether to obtain 2-(4-{[4'-(2-hydroxyethoxy)-3-biphenyl]methoxy}benzyl-1,2,4-oxadiazolidine-3,5-dione (171 mg) as white crystals.

Example 9

Hydroxylamine hydrochloride (12.85 g) and a sodium acetate aqueous solution (19.22 g/110 ml) were added to an ethanol (800 ml) suspension of 4-[(3-bromobenzyl)oxy]benzaldehyde (17.94 g), followed by stirring at room temperature for 18 hours. The reaction mixture was concentrated under a reduced pressure, and water (100 ml) was added to the residue, followed by extraction with chloroform. The organic layer was dried over anhydrous magnesium sulfate, and the solvent was evaporated under a reduced pressure to obtain a colorless solid (19.94 g). To a methanol (350 ml)-THF (350 ml) solution of the resulting colorless solid (19.94 g) was added sodium cyanoborohydride (19.36 g). Thereafter, a 4 M hydrogen chloride dioxane solution (160 ml) was slowly added dropwise under ice-cooling. The reaction mixture was stirred at room temperature for 2 hours. A 1 M sodium hydroxide aqueous solution (700 ml) was added to the reaction mixture under ice-cooling, followed by extraction with chloroform. The organic layer was washed with a saturated sodium chloride aqueous solution and then dried over anhydrous magnesium sulfate. The solvent was evaporated under a reduced pressure to obtain a light yellow solid (25.53 g). Chlorocarbonyl isocyanate (5.00 ml) was added dropwise to a THF (380 ml) solution of the resulting light yellow solid (25.53 g) under cooling on an ice-methanol bath, followed by stirring at room temperature for 2 hours. A 1 M hydrochloric acid (400 ml) was added to the reaction mixture, followed by extraction with chloroform. The organic layer was dried over anhydrous magnesium sulfate, and the solvent was evaporated under a reduced pressure. The resulting residue was washed with ethyl acetate and then dried at 50° C. under a reduced pressure to obtain 2-{4-[(3-bromobenzyl)oxy]benzyl}-1,2,4-oxadiazolidine-3,5-dione (6.08 g) as a colorless solid.

Example 10

A mixture of 2-(4-aminobenzyl)-1,2,4-oxadiazolidine-3,5-dione (500 mg), 4'-chloro-2'-methylbiphenyl-3-carbaldehyde (668 mg), acetic acid (0.33 ml) and THF (40 ml) was stirred at room temperature for 24 hours. Sodium triacetoxyborohydride (767 mg) was added to the reaction mixture, followed by stirring at room temperature for 15 minutes. The solvent was evaporated under a reduced pressure, and water was added to the residue, followed by extraction with chloroform. The organic layer was washed with a saturated sodium chloride aqueous solution, the solvent was evaporated under a reduced pressure, toluene was added to the residue, and the solvent was again evaporated under a reduced pressure. The residue was purified by silica gel column chromatography (hexane-ethyl acetate), and THF (5 ml), methanol (5 ml) and a 1 M sodium hydroxide aqueous solution (1.47 ml) were added to the resulting pale yellow foamy substance (620 mg), followed by stirring at room temperature for 5 minutes. The solvent was evaporated under a reduced pressure, the residue was purified by an ODS column chromatography (water-acetonitrile) and made into a solid by adding diethyl ether. The solid was collected by filtration and then dried by heating under a reduced pressure to obtain sodium 2-(4-{[(4'-chloro-2'-methylbiphenyl-3-yl)methyl]amino}benzyl)3,5-dioxo-1,2,4-oxadiazolidin-4-ide (160 mg) as a white solid.

Example 11

A mixture of 2-(4-aminobenzyl)-1,2,4-oxadiazolidine-3,5-dione (365 mg), 2-[(3'-formyl-2,6-dimethylbiphenyl-4-yl)oxy]ethyl acetate (660 mg), acetic acid (0.3 ml), THF (20 ml) and Molecular Sieves 4A (1 g) was stirred at room temperature for 22 hours. Sodium triacetoxyborohydride (560 mg) was added to the reaction mixture, followed by stirring at room temperature for 22 hours. Water was added to the reaction mixture, followed by extraction with ethyl acetate. The organic layer was washed with a saturated sodium chloride aqueous solution and then dried over anhydrous magnesium sulfate. The solvent was evaporated under a reduced pressure, toluene was added to the residue, the solvent was again evaporated under a reduced pressure, and then the residue was purified by silica gel column chromatography (hexane-ethyl acetate). Methanol (10 ml) and sodium methoxide (52 mg) were added to the resulting pale yellow foamy substance (406 mg), followed by stirring for 2 hours while heating at 60° C. The solvent was evaporated under a reduced pressure, and chloroform was added to the residue, followed by washing with water and a saturated sodium chloride aqueous solution and drying over anhydrous magnesium sulfate. The solvent was evaporated under a reduced pressure, and THF (5 ml), methanol (5 ml) and a 1 M sodium hydroxide aqueous solution (0.81 ml) were added to the resulting pale yellow foamy substance (373 mg), followed by stirring at room temperature for 5 minutes. The solvent was evaporated under a reduced pressure, the residue was purified by an ODS column chromatography (water-acetonitrile), the resulting pale yellow foamy substance was made into a solid by adding diethyl ether. The solid was collected by filtration and then dried by heating under a reduced pressure to obtain sodium 2-[4-({[4'-(2-hydroxyethoxy)-2',6'-dimethylbiphenyl-3-yl]methyl}amino)benzyl]-3,5-dioxo-1,2,4-oxadiazolidin-4-ide (226 mg) as a pale yellow solid.

Example 12

A mixture of 3-[(3'-formyl-2,2'-dimethylbiphenyl-4-yl)oxy]-1,1-dimethylpropyl acetate (479 mg), 2-(4-aminobenzyl)-1,2,4-oxadiazolidine-3,5-dione (340 mg) and acetic acid (6 ml) was stirred at room temperature for 20 hours. Sodium triacetoxyborohydride (573 mg) was added to the reaction solution, followed by stirring at room temperature for 2 hours. After evaporation of the solvent under a reduced pressure, water was added to the residue, followed by extraction with chloroform. The organic layer was dried over anhydrous magnesium sulfate and then the solvent was evaporated under a reduced pressure. The resulting residue was purified by silica gel column chromatography (hexane-ethyl acetate), and a mixture of the resulting pale yellow foamy substance (719 mg), THF (5 ml), methanol (5 ml) and a 1 M sodium hydroxide aqueous solution (4 ml) was stirred at 50° C. for 4 hours. The pH was made to 4 to 5 by adding 1 M hydrochloric acid, followed by extraction with chloroform. The organic layer was dried over anhydrous magnesium sulfate and then the solvent was evaporated under a reduced pressure. The resulting residue was purified by silica gel column chromatography (hexane-ethyl acetate), and a 1 M sodium hydroxide aqueous solution (0.89 ml) was added to a mixture of the resulting pale yellow oil (448 mg), THF (3 ml) and methanol (3 ml), followed by stirring for 10 minutes. After evaporation of the solvent under a reduced pressure, the resulting residue was washed with diethyl ether to obtain sodium 2-[4-({[4'-(3-hydroxy-3-methylbutoxy)-2,2'-dimethylbiphenyl-3-yl]methyl}amino)benzyl]-3,5-dioxo-1,2,4-oxadiazolidin-4-ide (398 mg) as a white solid.

Example 13

A mixture of 3-({3'-[(4-formylphenoxy)methyl]-2,6-dimethylbiphenyl-4-yl}oxy)propyl acetate (675 mg), hydroxylamine hydrochloride (217 mg), sodium acetate (307 mg), ethanol (15 ml) and water (4 ml) was stirred at room temperature for 18 hours. The solvent was evaporated under a reduced pressure, and water was added to the residue, followed by extraction with chloroform. The organic layer was washed with a saturated sodium chloride aqueous solution and dried over anhydrous magnesium sulfate. The solvent was evaporated under a reduced pressure, and acetic acid (5 ml) and sodium cyanoborohydride (196 mg) were added to the residue, followed by stirring at room temperature for 7 hours. The reaction system was alkalified by adding a saturated sodium carbonate aqueous solution, followed by extraction with chloroform. The organic layer was washed with a saturated sodium chloride aqueous solution, and then the solvent was evaporated under a reduced pressure. The residue was purified by silica gel column chromatography (chloroform-methanol), and THF (10 ml) was added to the resulting colorless oil (256 mg), followed by ice-cooling. Chlorocarbonyl isocyanate (0.05 ml) was added dropwise thereto, followed by 15.5 hours of stirring at room temperature. The solvent was evaporated under a reduced pressure, and chloroform was added to the residue, followed by washing with 1 M hydrochloric acid and a saturated sodium chloride aqueous solution. The solvent was evaporated under a reduced pressure, and the residue was purified by silica gel column chromatography (hexane-ethyl acetate), and methanol (10 ml) and sodium methoxide (92 mg) were added to the resulting colorless oil (242 mg), followed by stirring with heating at 60° C. for 2 hours. The solvent was evaporated under a reduced pressure, and water was added to the residue, followed by extraction with chloroform and washing with a saturated sodium chloride aqueous solution. The solvent was evaporated under a reduced pressure, the residue was purified by silica gel column chromatography (hexane-ethyl acetate), and THF (5 ml), methanol (5 ml) and a 1 M sodium hydroxide aqueous solution (0.33 ml) were added to the resulting colorless oil (152 mg), followed by stirring at room temperature for 5 minutes. The solvent was evaporated under a reduced pressure, the residue was purified by an ODS column chromatography (water-acetonitrile), the resulting colorless oil was made into a solid by adding diethyl ether, and the solid was collected by filtration and then dried by heating under a reduced pressure to obtain sodium 2-(4-{[4'-(3-hydroxypropoxy)-2',6'-dimethylbiphenyl-3-yl]methoxy}benzyl)-3,5-dioxo-1,2,4-oxadiazolidin-4-ide (126 mg) as a white solid.

Example 14

A mixture of 2-({3'-[(4-formylphenoxy)methyl]-2-methylbiphenyl-4-yl}oxy)ethyl acetate (935 mg), hydroxylamine hydrochloride (480 mg), a sodium acetate aqueous solution (760 mg/3 ml) and ethanol (15 ml) was stirred at room temperature for 1.5 hours. After evaporation of the solvent under a reduced pressure, water (20 ml) was added to the residue, followed by extraction with ethyl acetate. The organic layer was washed with a saturated sodium chloride aqueous solution and dried over anhydrous magnesium sulfate, and the solvent was evaporated under a reduced pressure to obtain a colorless oil (1.07 g). Sodium cyanoborohydride (430 mg) and acetic acid (1 ml) were added in that order under ice-cooling to a mixture of the resulting oil, methanol (10 ml) and THF (10 ml), followed by stirring for 5 minutes. While warming up the reaction liquid gradually to room temperature, a 4 M hydrogen chloride dioxane solution was properly added thereto (1 ml in total), followed by stirring for 5 hours. A saturated sodium bicarbonate aqueous solution (20 ml) was added to the reaction liquid, followed by extraction with chloroform. Then, the organic layer was dried over anhydrous magnesium sulfate and the solvent was evaporated under a reduced pressure. The resulting residue was purified by silica gel column chromatography (hexane-ethyl acetate) to obtain a colorless oil (0.50 g). Chlorocarbonyl isocyanate (190 mg) was added to a mixture of the resulting oil and THF (5 ml), followed by stirred at room temperature for 15 minutes and then allowing to stand overnight. Water (10 ml) was added to the reaction liquid, followed by extraction with ethyl acetate. The organic layer was washed with a saturated sodium chloride aqueous solution and dried over anhydrous magnesium sulfate. By evaporating the solvent under a reduced pressure, a colorless oil (413 mg) was obtained.

A mixture of this with a 1 M sodium hydroxide aqueous solution (3 ml), methanol (3 ml) and THF (6 ml) was stirred at 60° C. for 3 hours. 1 M hydrochloric acid (3.5 ml) was added to the reaction liquid, followed by extraction with ethyl acetate. The organic layer was washed with a saturated sodium chloride aqueous solution and then dried over anhydrous magnesium sulfate, and the solvent was evaporated under a reduced pressure. The resulting residue was purified by silica gel column chromatography (hexane-ethyl acetate) to obtain colorless oil (331 mg). THF (10 ml), methanol (1 ml) and a 1 M sodium hydroxide aqueous solution (0.7 ml) were added to the resulting oil, and the solvent was evaporated under a reduced pressure. Diethyl ether was added to the resulting residue, and the solid was collected by filtration and dried at 60° C. under a reduced pressure to obtain sodium 2-(4-{[4'-(2-hydroxyethoxy)-2'-methylbiphenyl-3-yl]methoxy}benzyl)-3,5-dioxo-1,2,4-oxadiazolidin-4-ide (243 mg) as a colorless solid.

Example 15

A mixture of {[3'-({4-[(3,5-dioxo-1,2,4-oxadiazolidin-2-yl)methyl]phenoxy}methyl)-2,6-dimethylbiphenyl-4-yl]oxy}acetic acid (482 mg), dimethylamine hydrochloride (165 mg), WSC hydrochloride (388 mg), triethylamine (0.56 ml) and DMF (10 ml) was stirred at room temperature for 22.5 hours. The solvent was evaporated under a reduced pressure, and 1 M hydrochloric acid was added to the residue, followed by extraction with chloroform/methanol (4/1). The organic layer was washed with a saturated sodium chloride aqueous solution and then dried over anhydrous magnesium sulfate. The solvent was evaporated under a reduced pressure, and the residue was purified by silica gel column chromatography (hexane-ethyl acetate and chloroform-methanol). Methanol (5 ml), THF (5 ml) and a 1 M sodium hydroxide aqueous solution (0.36 ml) were added to the resulting pale yellow oil (178 mg), followed by stirring at room temperature for 5 minutes. The solvent was evaporated under a reduced pressure, and the residue was purified by an ODS column chromatography (water-acetonitrile). The resulting colorless foamy substance was solidified by adding diethyl ether, and the solid was collected by filtration and then dried by heating under a reduced pressure to obtain sodium 2-[4-({4'-[2-(dimethylamino)-2-oxoethoxy]-2',6'-dimethylbiphenyl-3-yl}methoxy)benzyl]-3,5-dioxo-1,2,4-oxadiazolidin-4-ide (52 mg) as a white solid.

Example 16

Oxalyl dichloride (0.15 ml) was added to a THF (10 ml) solution of 2',6'-dimethylbiphenyl-3-carboxylic acid (277 mg), followed by stirring at room temperature for 5 minutes. Then, DMF (1 drop) was added, followed by stirring at the same temperature for 1 hour. The solvent was evaporated under a reduced pressure, and a THF (10 ml) solution of the resulting residue was added dropwise to a mixture of 2-(4-aminobenzyl-1,2,4-oxadiazolidine-3,5-dione (380 mg) and a saturated sodium bicarbonate aqueous solution (10 ml), followed by stirring at room temperature for 2 hours. 1 M hydrochloric acid (20 ml) was added to the reaction liquid, followed by extraction with ethyl acetate. The organic layer was washed with a saturated sodium chloride aqueous solution and then dried over anhydrous magnesium sulfate, and the solvent was evaporated under a reduced pressure. Methanol (5 ml), THF (5 ml) and a 1 M sodium hydroxide aqueous solution (1.2 ml) were added to the resulting residue, and the solvent was evaporated under a reduced pressure. THF-hexane was added to the resulting residue and the solvent was evaporated under a reduced pressure, followed by drying at 50° C. under a reduced pressure, thereby obtaining sodium 2-(4-{[(2',6'-dimethylbiphenyl-3-yl)carbonyl] amino}benzyl)-3,5-dioxo-1,2,4-oxadiazolidin-4-ide (530 mg) as a yellow solid.

Example 17

A mixture of {[3'-({4-[(3,5-dioxo-1,2,4-oxadiazolidin-2-yl)methyl]phenoxy}methyl)-2,6-dimethylbiphenyl-4-yl] oxy}acetic acid (500 mg), a 12 M ethylamine aqueous solution (0.175 ml), WSC hydrochloride (302 mg), HOAt (214 mg) and DMF (10 ml) was stirred at room temperature for 21.5 hours. 1 M hydrochloric acid and water were added to the reaction mixture, followed by extraction with ethyl acetate. The organic layer was washed with a saturated sodium chloride aqueous solution and then dried over anhydrous magnesium sulfate. The solvent was evaporated under a reduced pressure, and the residue was purified by silica gel column chromatography (chloroform-methanol and hexane-ethyl acetate). Methanol (3 ml), THF (3 ml) and a 1 M potassium hydroxide aqueous solution (0.611 ml) were added to the resulting colorless foamy substance (308 mg), followed by stirring at room temperature for 10 minutes. The solvent was evaporated under a reduced pressure, ethyl acetate was added to the residue, the solvent was again evaporated under a reduced pressure. The solid precipitated was collected by filtration and then dried by heating under a reduced pressure to obtain potassium 2-[4-({4'-[2-(ethylamino)-2-oxoethoxy]-2',6'-dimethylbiphenyl-3-yl}methoxy)benzyl]-3,5-dioxo-1,2,4-oxadiazolidin-4-ide (300 mg) as a white solid.

Example 18

A mixture of 2,2,2-trifluoro-1-[({3'-[(4-formylphenoxy)methyl]-2,6-dimethylbiphenyl-4-yl}oxy)methyl]ethyl acetate (590 mg), hydroxylamine hydrochloride (253 mg), sodium acetate (378 mg), ethanol (15 ml) and water (4 ml) was stirred at room temperature for 21 hours. The solvent was evaporated under a reduced pressure, and water was added to the residue, followed by extraction with chloroform. The organic layer was washed with a saturated sodium chloride aqueous solution and then dried over anhydrous magnesium sulfate. The solvent was evaporated under a reduced pressure, the residue was purified by silica gel column chromatography (hexane-ethyl acetate), and acetic acid (8 ml) and sodium cyanoborohydride (127 mg) were added to the resulting colorless oil (310 mg), followed by stirring at room temperature for 4 hours. The solvent was evaporated under a reduced pressure, and the residue was alkalified by adding a 1 M sodium hydroxide aqueous solution, followed by extraction with chloroform. The organic layer was washed with a saturated sodium chloride aqueous solution and then dried over anhydrous magnesium sulfate. The solvent was evaporated under a reduced pressure, the residue was purified by silica gel column chromatography (chloroform-methanol). THF (10 ml) was added to the resulting colorless foamy substance (266 mg), followed by ice-cooling. Then, ethoxycarbonyl isocyanate (0.065 ml) was added dropwise thereto, followed by stirring at 0° C. for a while and then stirring at room temperature for 4 days. Water was added to the reaction mixture, followed by extraction with ethyl acetate. The organic layer was washed with a saturated sodium chloride aqueous solution, and then the solvent was evaporated under a reduced pressure. The residue was purified by silica gel column chromatography (hexane-ethyl acetate), and THF (5 ml) and a 1 M sodium hydroxide aqueous solution (0.36 ml) were added to the resulting colorless foamy substance, followed by stirring at room temperature for 6 hours. The solvent was evaporated under a reduced pressure, and 1 M hydrochloric acid was added to the residue, followed by extraction with chloroform. The organic layer was washed with a saturated sodium chloride aqueous solution, and then dried over anhydrous magnesium sulfate. The solvent was evaporated under a reduced pressure and the residue was purified by silica gel column chromatography (hexane-ethyl acetate). Methanol (4 ml), THF (4 ml) and a 1 M potassium hydroxide aqueous solution (0.31 ml) were added to the resulting colorless foamy substance (164 mg), followed by stirring at room temperature for 10 minutes. The solvent was evaporated under a reduced pressure, ethyl acetate was added to the residue, and the solvent was again evaporated under a reduced pressure. Diethyl ether was added to the residue, followed by stirring at room temperature. The solid precipitated was collected by filtration and then dried by heating under a reduced pressure to obtain potassium 2-(4-{[2',6'-dimethyl-4'-(3,3,3-trifluoro-2-hydroxypropoxy)biphenyl-3-yl]methoxy}benzyl)-3,5-dioxo-1,2,4-oxadiazolidin-4-ide (163 mg) as a white solid.

Example 19

A mixture of 2-(4-{[4'-(2-hydroxypropoxy)-2',6'-dimethylbiphenyl-3-yl]methoxy}benzyl)-1,2,4-oxadiazolidine-3,5-dione (240 mg), 1,1,1-triacetoxy-1,1-dihydro-1,2-benzoiodoxol-3(1H)-one (320 mg) and dichloromethane (10 ml) was stirred at room temperature for 1.5 hours. Water was added to the reaction mixture, followed by extraction with chloroform. The organic layer was washed with a saturated sodium chloride aqueous solution and then dried over anhydrous magnesium sulfate, and the solvent was evaporated under a reduced pressure. The residue was purified by silica gel column chromatography (chloroform-methanol and hexane-ethyl acetate), and methanol (3 ml), THF (3 ml) and a 1 M sodium hydroxide aqueous solution (0.41 ml) were added to the resulting colorless foamy substance (196 mg), followed by stirring at room temperature for 10 minutes. The solvent was evaporated under a reduced pressure, and the residue was purified by an ODS column chromatography (water-acetonitrile). The resulting colorless foamy substance was solidified by adding diethyl ether, and the solid was collected by filtration and dried by heating under a reduced pressure to obtain sodium 2-(4-{[2',6'-dimethyl-4'-(2-oxopropoxy)biphenyl-3-yl]methoxy}benzyl)-3,5-dioxo-1,2,4-oxadiazolidin-4-ide (70 mg) as a white solid.

Example 20

A mixture of tert-butyl [2-({3'-[(4-formylphenoxy)methyl]-2,6-dimethylbiphenyl-4-yl}oxy)ethyl]carbamate (505 mg), hydroxylamine hydrochloride (221 mg), sodium acetate (331 mg), ethanol (15 ml) and water (4 ml) was stirred at room temperature for 24 hours. The solvent was evaporated under a reduced pressure, and water was added to the residue, followed by extraction with chloroform. The organic layer was washed with a saturated sodium chloride aqueous solution and then dried over anhydrous magnesium sulfate. The solvent was evaporated under a reduced pressure, and acetic acid (10 ml) and sodium cyanoborohydride (167 mg) were added to the residue, followed by stirring at room temperature for 4 hours. The reaction mixture was alkalified by adding a 1 M sodium hydroxide aqueous solution, followed by extraction with chloroform. The organic layer was washed with a saturated sodium chloride aqueous solution and then dried over anhydrous magnesium sulfate. The solvent was evaporated under a reduced pressure, and THF (8 ml) was added to the resulting colorless foamy substance (528 mg), followed by ice-cooling. Chlorocarbonyl isocyanate (0.094 ml) was added dropwise thereto, followed by stirring at room temperature for 14.5 hours. The solvent was evaporated under a reduced pressure, and a saturated ammonium chloride aqueous solution was added to the residue, followed by extraction with chloroform. The organic layer was washed with a saturated sodium chloride aqueous solution and then dried over anhydrous magnesium sulfate. The solvent was evaporated under a reduced pressure, and the residue was purified by silica gel column chromatography (hexane-ethyl acetate). Ethyl acetate (3 ml) was added to the resulting colorless foamy substance, followed by ice-cooling. A 4 M hydrogen chloride ethyl acetate solution (12 ml) was added dropwise thereto, followed by stirring at 0° C. for 2 hours. The solvent was evaporated under a reduced pressure, and diethyl ether-hexane was added to the resulting pale yellow foamy substance, followed by stirring at room temperature. The solid was collected by filtration and then dried by heating under a reduce pressure to obtain 2-(4-{[4'-(2-aminoethoxy)-2',6'-dimethylbiphenyl-3-yl]methoxy}benzyl)-1,2,4-oxadiazolidine-3,5-dione hydrochloride (200 mg) as a pale yellow solid.

Example 21

A mixture of ethyl 2-({3'-[(4-formylphenoxy)methyl]-2,2'-dimethylbiphenyl-4-yl}oxy)-2-methylpropanoate (1.87 g), hydroxylamine hydrochloride (378 mg), sodium acetate (515 mg), ethanol (36 ml) and water (9 ml) was stirred at room temperature for 3 hours. After evaporation of the solvent under a reduced pressure, water was added to the residue, followed by extraction with chloroform. The organic layer was dried over anhydrous magnesium sulfate and then the solvent was evaporated under a reduced pressure. Sodium cyanoborohydride (790 mg) was added to an acetic acid (20 ml) solution of the resulting pale yellow foamy substance (1.95 g), followed by stirring at room temperature for 3 hours. The reaction solution was alkalified by adding a saturated sodium bicarbonate aqueous solution and sodium carbonate, followed by extraction with chloroform. The organic layer was dried over anhydrous magnesium sulfate, and then the solvent was evaporated under a reduced pressure. The resulting residue was purified by silica gel column chromatography (chloroform-methanol), and chlorocarbonyl isocyanate (0.234 ml) was added to a THF (15 ml) solution of the resulting colorless foamy substance (1.17 g) under ice-cooling, followed by stirring at room temperature for 24 hours. 1 M Hydrochloric acid was added to the reaction mixture, followed by extraction with chloroform. The organic layer was dried over anhydrous magnesium sulfate, and then the solvent was evaporated under a reduced pressure. A mixture of the resulting colorless foamy substance (1.43 g), THF (15 ml), methanol (15 ml) and a 1 M sodium hydroxide aqueous solution (15 ml) was stirred at 60° C. for 1 hour. The solvent was evaporated under a reduced pressure, and 1 M hydrochloric acid was added to the resulting residue, followed by extraction with chloroform. The organic layer was dried over anhydrous magnesium sulfate, and then the solvent was evaporated under a reduced pressure to obtain 2-{[3'-({4-[(3,5-dioxo-1,2,4-oxadiazolidin-2-yl)methyl]-phenoxy}methyl)-2,2'-dimethylbiphenyl-4-yl]-oxy}-2-methylpropanoic acid (1.29 g) as a colorless foamy substance. To a mixture of the resulting 2-{[3'-({4-[(3,5-dioxo-1,2,4-oxadiazolidin-2-yl)methyl]phenoxy}methyl)-2,2'-dimethylbiphenyl-4-yl]oxy}-2-methylpropanoic acid (291 mg), THF (3 ml) and methanol (3 ml) was added a 1 M sodium hydroxide aqueous solution (1.15 ml), followed by stirring for 10 minutes. Then, the solvent was evaporated under a reduced pressure. By recrystallizing the resulting residue from ethanol-water, disodium 2-{[3'-({4-[(3,5-dioxo-1,2,4-oxadiazolidin-2-yl)methyl]phenoxy}methyl)-2,2'-dimethylbiphenyl-4-yl]oxy}-2-methylpropanoate (149 mg) was obtained as white crystals.

Example 22

Under ice-cooling, a 4 M hydrogen chloride dioxane solution (15 ml) was added dropwise to a mixture of tert-butyl (3-{[3'-({4-[(3,5-dioxo-1,2,4-oxadiazolidin-2-yl)methyl]phenoxy}methyl)-2,2'-dimethylbiphenyl-4-yl]oxy}propyl) carbamate (1.95 g) and ethyl acetate (5 ml), followed by stirring at 0° C. for a while and then stirring at room temperature for 1.5 hours. The solvent was evaporated under a reduced pressure, and the solid precipitated was collected by filtration and dried by heating under a reduced pressure to obtain 2-(4-{[4'-(3-aminopropoxy)-2,2'-dimethylbiphenyl-3-yl]methoxy}benzyl)-1,2,4-oxadiazolidine-3,5-dione hydrochloride (1.53 g) as a white solid.

Example 23

A mixture of sodium 2-{4-[(4'-{[(4R)-2,2-dimethyl-1,3-dioxolan-4-yl]methoxy}-2,2'-dimethylbiphenyl-3-yl)methoxy]benzyl}-3,5-dioxo-1,2,4-oxadiazolidin-4-ide (467 mg), 1 M hydrochloric acid (5 ml) and THF (5 ml) was stirred at 50° C. for 2 hours. After cooling down to room temperature, water (10 ml) was added to the reaction mixture, followed by extraction with chloroform. The organic layer was dried over anhydrous magnesium sulfate, and then the solvent was evaporated under a reduced pressure. A 1 M sodium hydroxide aqueous solution (0.977 ml) was added to a THF (5 ml) solution of the resulting residue, followed by concentration under a reduced pressure. By washing the resulting residue with diethyl ether, sodium 2-{[(4'-{[(2S)-2,2-dihydroxypropyl]oxy}-2,2'-dimethylbiphenyl-3-yl)methoxy]benzyl}-3,5-dioxo-1,2,4-oxadiazolidin-4-ide (392 mg) was obtained as a white solid.

Example 24

A mixture of 2,2-difluoro-2-({3'-[(4-formylphenoxy)methyl]-2,2'-dimethylbiphenyl-4-yl}oxy)-N-methylacetamide, hydroxylamine hydrochloride (122 mg), sodium acetate (167 mg), ethanol (12 ml) and water (3 ml) was stirred at room temperature for 16 hours. Water was added to the reaction mixture, followed by extraction with chloroform. After drying the organic layer over anhydrous magnesium sulfate, the solvent was evaporated under a reduced pressure. Sodium cyanoborohydride (257 mg) was added to a methanol (5 ml)-THF (5 ml) solution of the resulting colorless foamy substance (594 mg), and then a 4 M hydrogen chloride dioxane solution (2 ml) was slowly added dropwise thereto under ice-cooling. The reaction mixture was stirred at room temperature for 2 hours. A 1 M sodium hydroxide aqueous solution (7 ml) was added to the reaction mixture under ice-cooling, followed by extraction with chloroform. The organic layer was dried over anhydrous magnesium sulfate and then the solvent was evaporated under a reduced pressure. The resulting residue was purified by silica gel column chromatography (chloroform-methanol), THF (6 ml) was added to the resulting colorless oil (559 mg), followed by ice-cooling. Ethoxycarbonyl isocyanate (0.152 ml) was added dropwise thereto, followed by stirring at 0° C. for 30 minutes and then stirring at room temperature for 1 hour. A 1 M sodium hydroxide aqueous solution (3 ml) was added to the reaction mixture, followed by stirring at room temperature for 12 hours. A 1 M hydrochloric acid (4 ml) was added to the reaction mixture, followed by extraction with chloroform. The organic layer was dried over anhydrous magnesium sulfate and then the solvent was evaporated under a reduced pressure. By purifying the resulting residue by silica gel column chromatography (chloroform-methanol), 2-{[3'-({4-[(3,5-dioxo-1,2,3-oxadiazolidin-2-yl)methyl]phenoxy}-2-methyl)-2,2'-dimethylbiphenyl-4-yl]oxy}-2,2-difluoro-N-methylacetamide (76 mg) was obtained as a colorless foamy substance, and {[3'-({4-[(3,5-dioxo-1,2,4-oxadiazolidin-2-yl)methyl]phenoxy}methyl)-2,2-dimethylbiphenyl-4-yl]oxy}(difluoro)acetic acid (217 mg) as a colorless foamy substance. To a THF (5 ml) solution of the resulting {[3'-({4-[(3,5-dioxo-1,2,4-oxadiazolidin-2-yl)methyl]phenoxy}methyl)-2,2'-dimethylbiphenyl-4-yl]oxy}(difluoro)acetic acid was added a 1 M sodium hydroxide aqueous solution (0.847 ml), followed by concentration under a reduced pressure. By washing the resulting residue with diethyl ether, disodium {[3'-({4-[(3,5-dioxo-1,2,4-oxadiazolidin-4-id-2-yl)methyl]phenoxy}methyl)-2,2'-dimethylbiphenyl-4-yl]oxy}(difluoro)acetate (203 mg) was obtained as a white solid.

Example 25

3'-({4-[(3,5-Dioxo-1,2,4-oxadiazolidin-2-yl)methyl]phenoxy}methyl)-2-methylbiphenyl-4-carboxylic acid (10.8 mg) was dissolved in a THF-methanol [1 ml, 4:1 (v/v)] mixed solution, and the solution was added to pyrrolidine (3.2 mg). DMT-MM (12 mg) was added, followed by overnight stirring at room temperature. Thereafter, chloroform was added to the reaction liquid, and the organic layer was washed with 1 M hydrochloric acid. The organic layer was concentrated, and the residue was purified by a fractional HPLC (Waters, product name: Waters SunFire™ Prep C₁₈OBD™ (19×100 mm, 5 μm)) to obtain 2-(4-{[2'-methyl-4'-(pyrrolidin-1-ylcarbonyl)biphenyl-3-yl]methoxy}benzyl)-1,2,4-oxadiazolidine-3,5-dione (8.2 mg).

Example 26

3'-({4-[(3,5-Dioxo-1,2,4-oxadiazolidin-2-yl)methyl]phenoxy}methyl)-2-methylbiphenyl-4-carboxylic acid (10.8 mg) was dissolved in a THF-methanol [1 ml, 4:1 (v/v)] mixed solution, and the solution was added to 4-(methoxymethyl)piperidine hydrochloride (7.5 mg). DMT-MM (12 mg) and triethylamine (20 μl) were added, followed by overnight stirring at room temperature. Thereafter, chloroform was added to the reaction liquid, and the organic layer was washed with 1 M hydrochloric acid. The organic layer was concentrated, and the residue was purified by a fractional HPLC (Waters, product name: Waters SunFire™ Prep C₁₈OBD™ (19×100 mm, 5 μm)) to obtain 2-{4-[(4'-{[4-(methoxymethyl)piperidin-1-yl]carbonyl}-2'-methylbiphenyl-3-yl)methoxy]benzyl}-1,2,4-oxadiazolidine-3,5-dione (9.0 mg).

Example 27

3'-({4-[(3,5-Dioxo-1,2,4-oxadiazolidin-2-yl)methyl]phenoxy}methyl)-2-methylbiphenyl-4-carboxylic acid (10.8 mg) was dissolved in a THF-methanol [1 ml, 4:1 (v/v)] mixed solution, and the solution was added to 1-ethylpiperidine-3-amine (5.8 mg). DMT-MM (12 mg) was added, followed by overnight stirring at room temperature. Thereafter, chloroform was added to the reaction liquid, and the organic layer was washed with water. The organic layer was concentrated, and the residue was purified by a fractional HPLC (Waters, product name: Waters SunFire™ Prep C₁₈OBD™ (19×100 mm, 5 μm)) to obtain 3'-({4-[(3,5-dioxo-1,2,4-oxadiazolidin-2-yl)methyl]phenoxy}methyl)-N-(1-ethylpiperidin-3-yl)-2-methylbiphenyl-4-carboxamide (3.4 mg).

In the same manner as in the methods of Examples 1 to 27, Example compounds 28 to 407 shown in the following tables were produced using respectively corresponding starting materials. Structures of Example compounds are shown in Tables 53 to 113, and the production methods and physicochemical data in Tables 114 to 135.

In addition, structures of other compounds of the present invention are shown in Tables 136 to 138. These can be easily synthesized by the use of the above-mentioned production methods, the methods described in Examples and the methods which are obvious to those skilled in the art, or modified methods thereof.

TABLE 4

| REx | Str |
|---|---|
| 1 | |
| 2 | |
| 3 | |
| 39 | |
| 40 | |
| 41 | |
| 4 | |

TABLE 4-continued
| REx | Str |
|---|---|
| 42 | 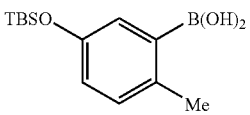 |
TABLE 5
| REx | Str |
|---|---|
| 5 | 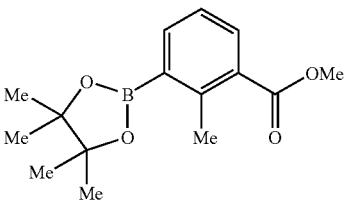 |
| 43 | 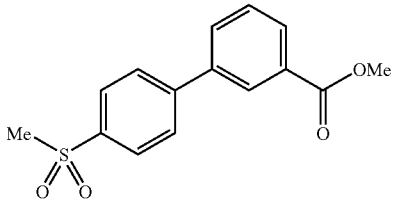 |
| 44 | 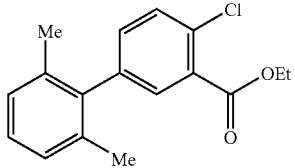 |
| 45 | 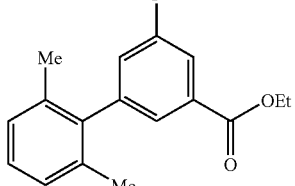 |
| 46 | 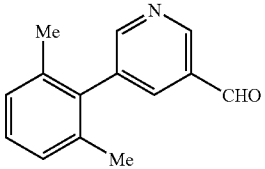 |
| 47 | 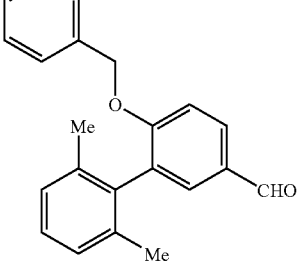 |
TABLE 6
| | |
|---|---|
| 48 | 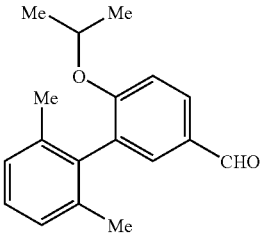 |
| 49 | 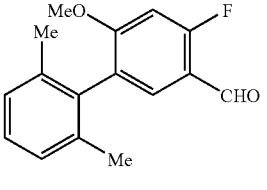 |
| 50 | 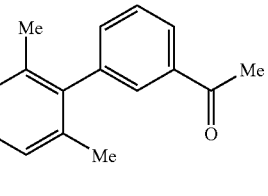 |
| 51 | 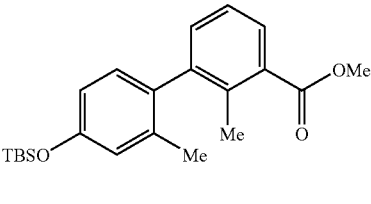 |
| 52 | 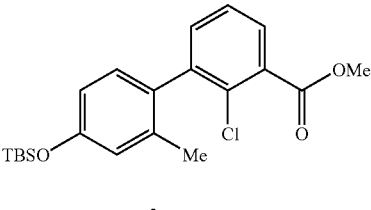 |
| 53 | 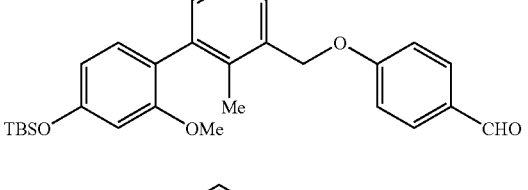 |
| 54 | 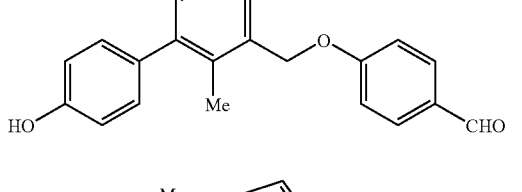 |
| 55 | 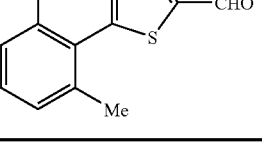 |

TABLE 7
| | |
|---|---|
| 56 | 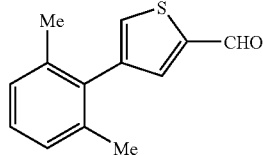 |
| 57 | 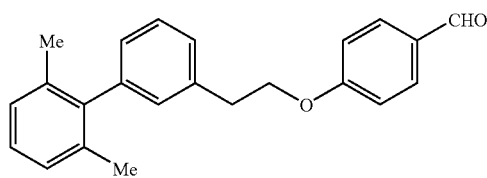 |
| 58 | 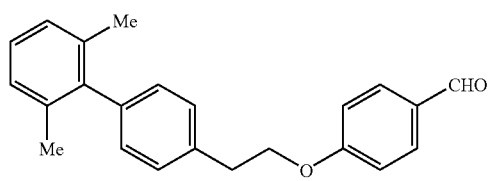 |
| 59 | 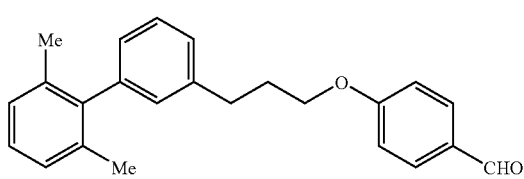 |
| 60 | 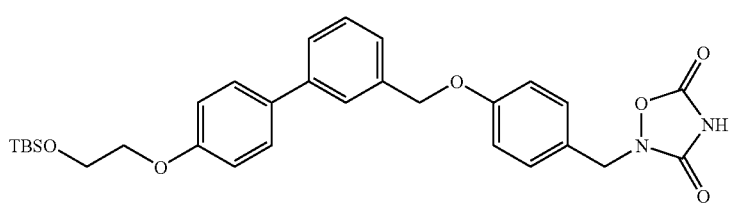 |
| 6 | 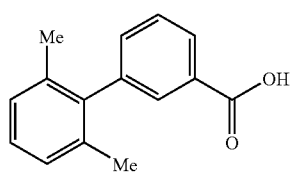 |
| 7 | 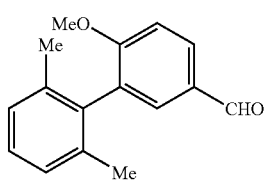 |
| 61 | 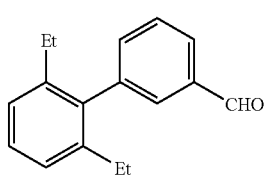 |

TABLE 8
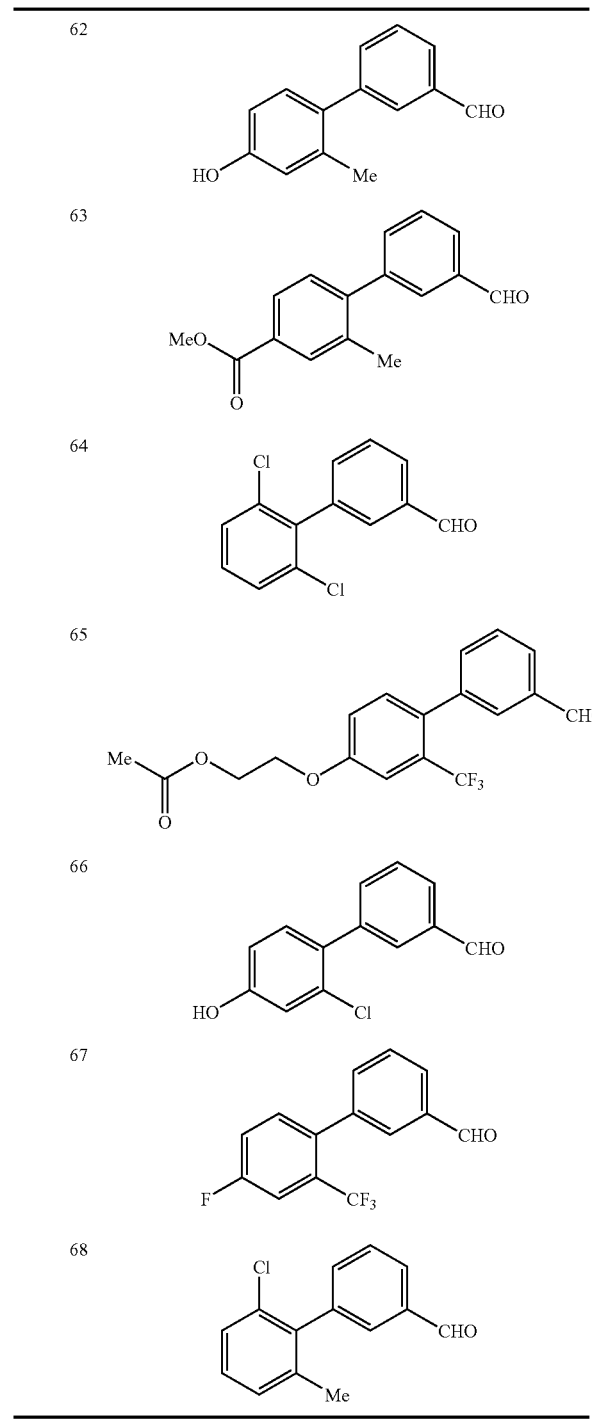
TABLE 9
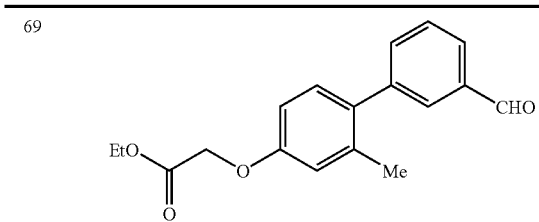
TABLE 9-continued
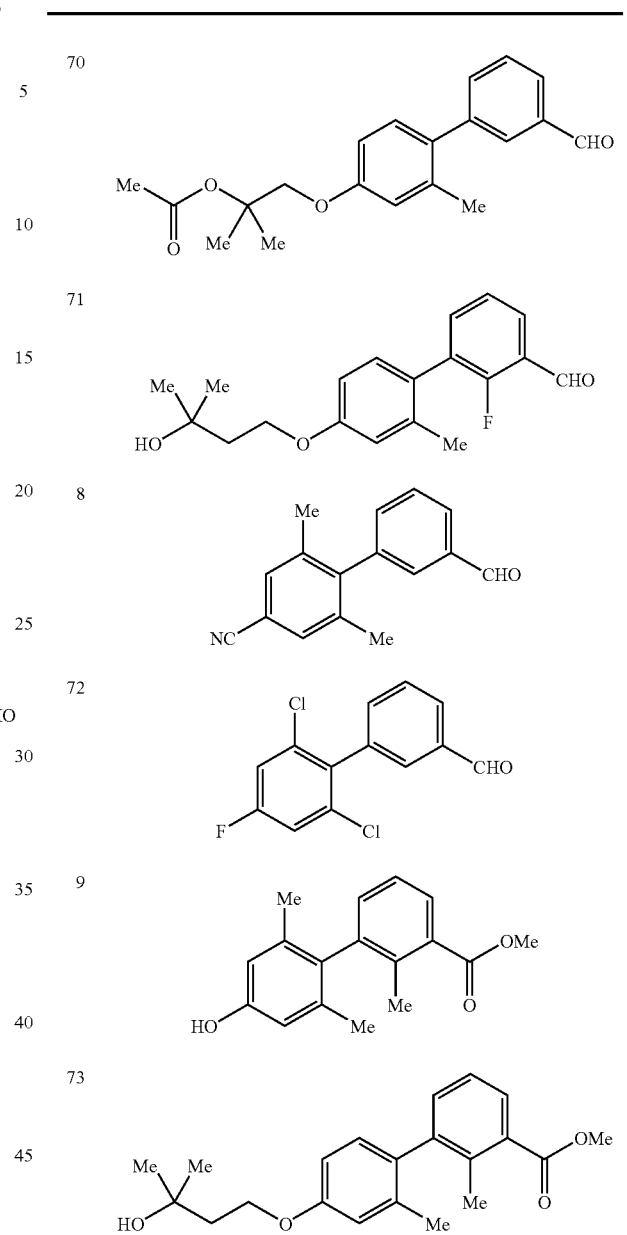
TABLE 10
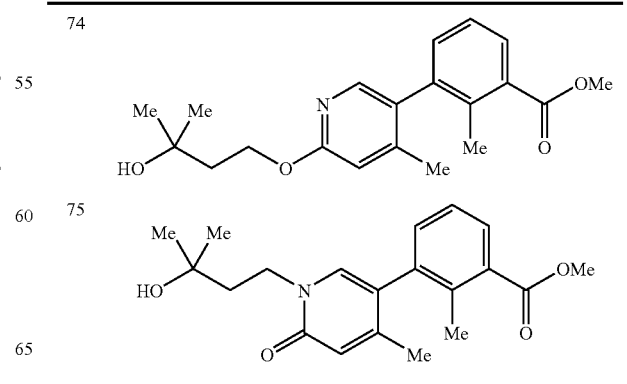

TABLE 10-continued
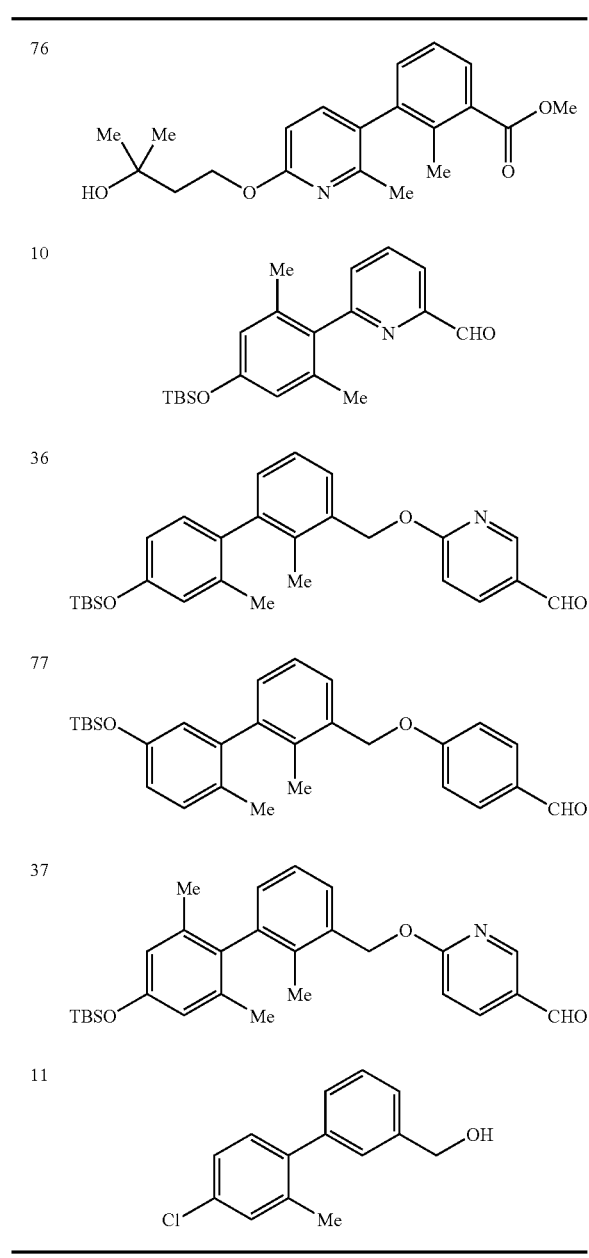
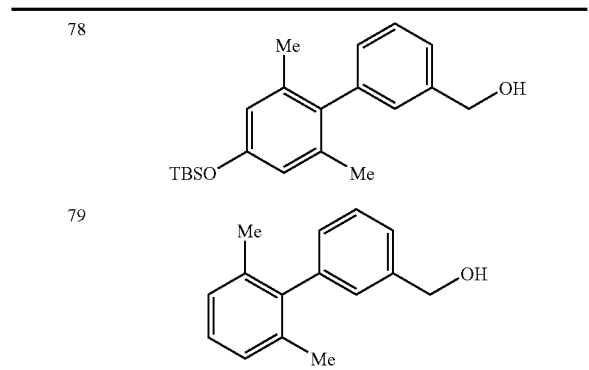
TABLE 11
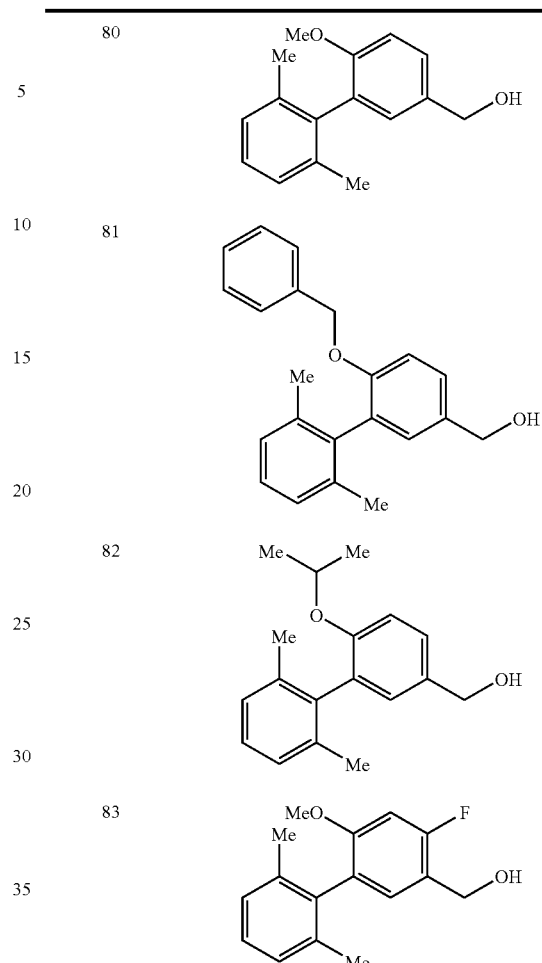
TABLE 12
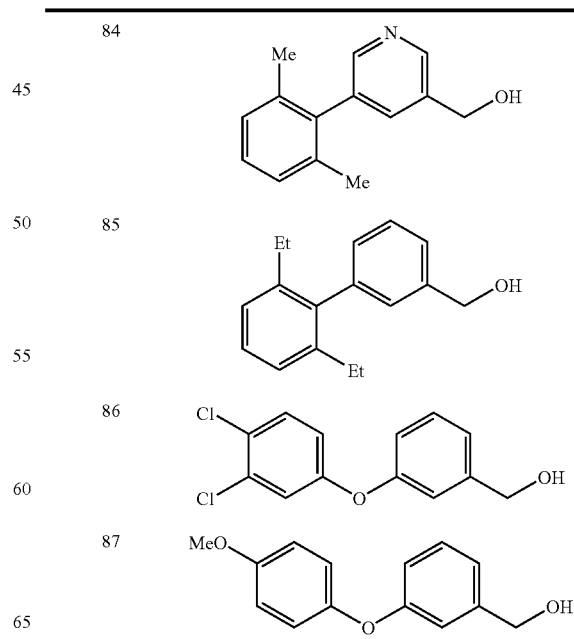

TABLE 12-continued
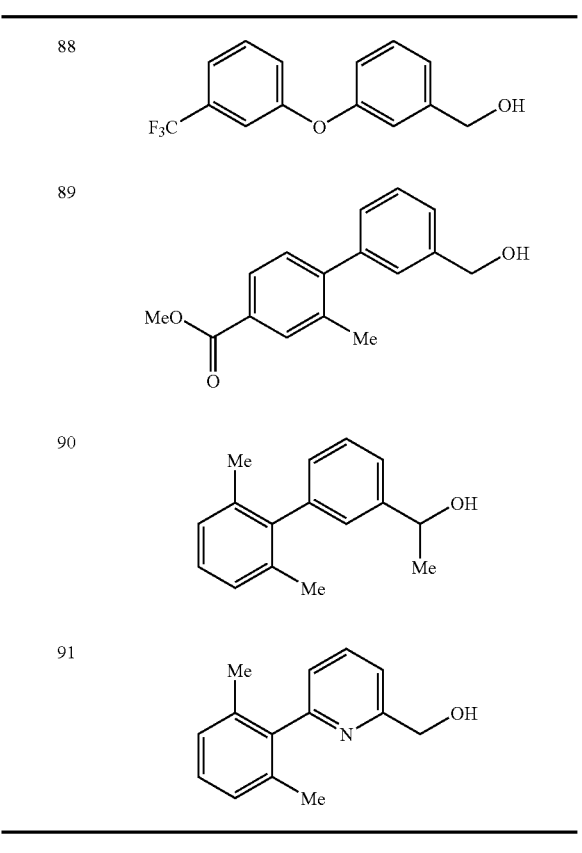
TABLE 13
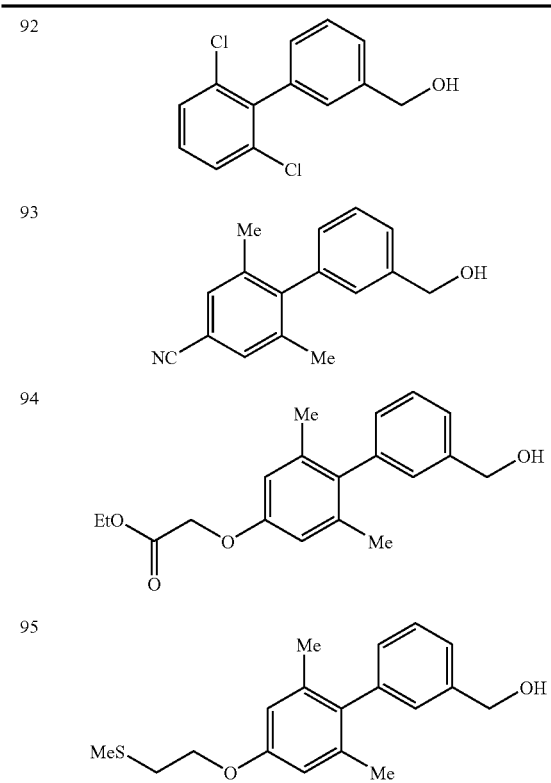
TABLE 13-continued
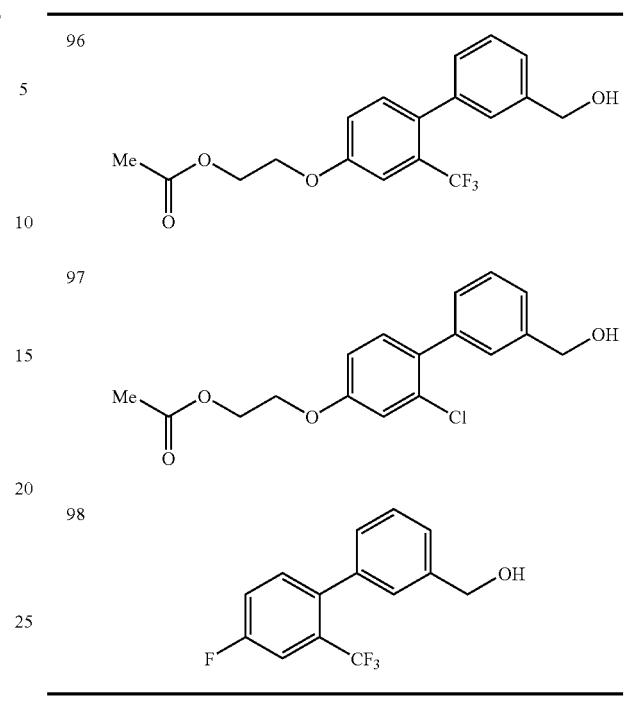
TABLE 14
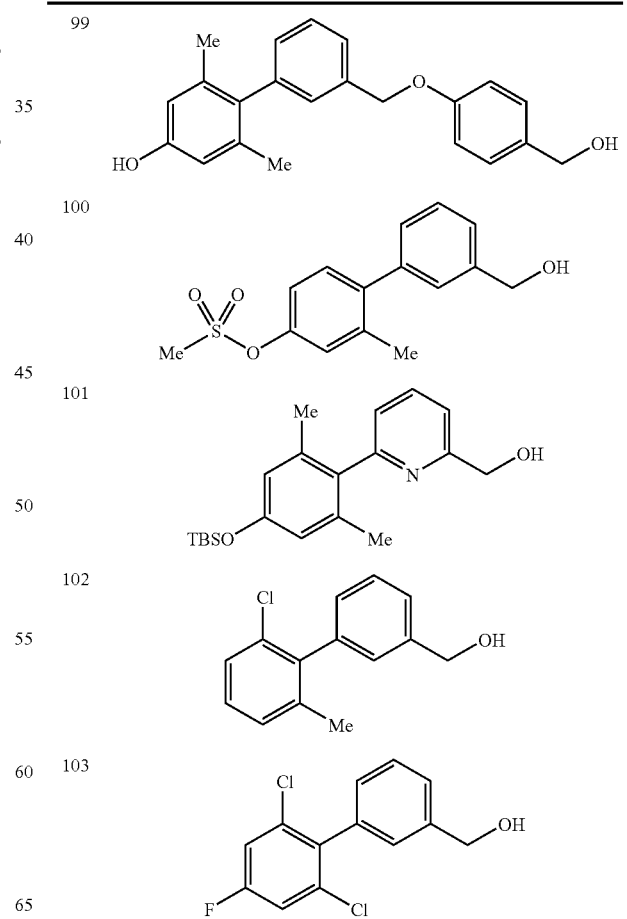

TABLE 14-continued
104 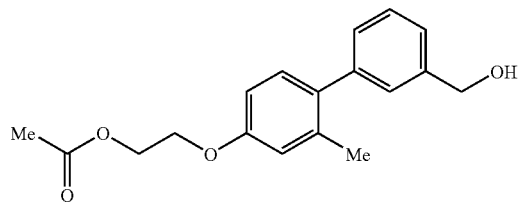
105 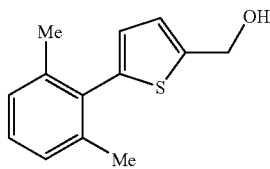
TABLE 15
106 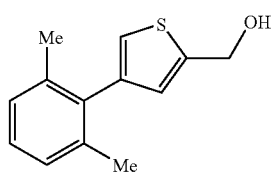
107 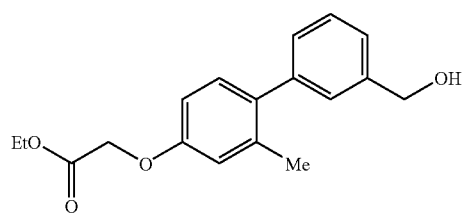
108 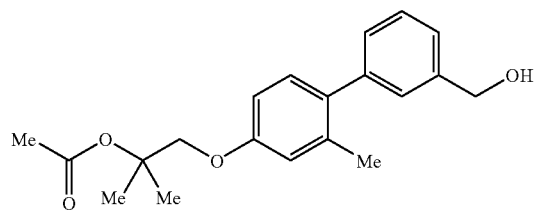
109 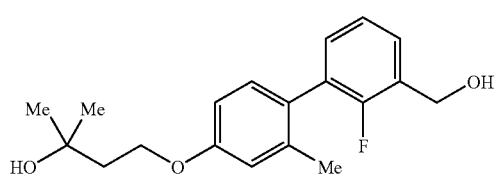
110 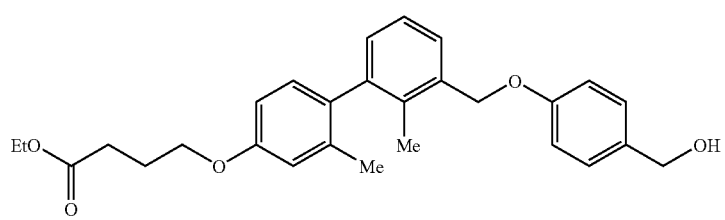
12 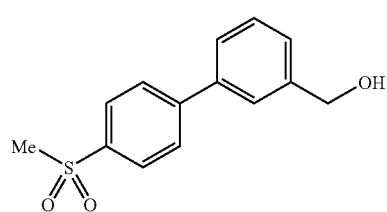

TABLE 15-continued
111 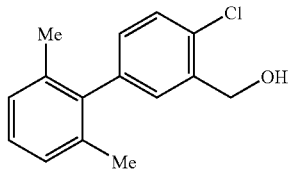
TABLE 16
112 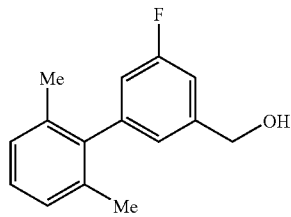
113 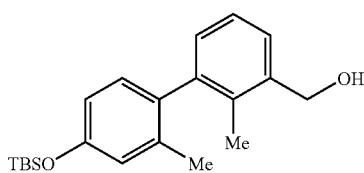
114 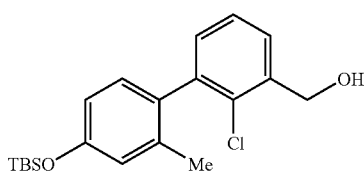
115 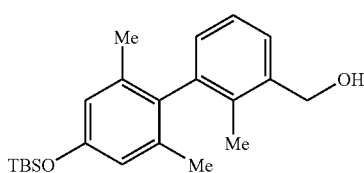
116 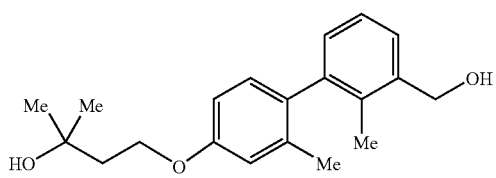
117 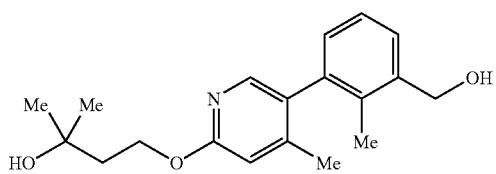
118 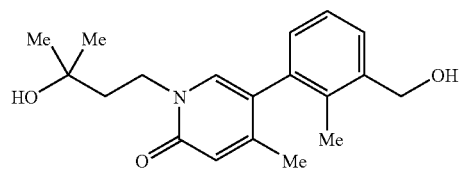
TABLE 16-continued
119 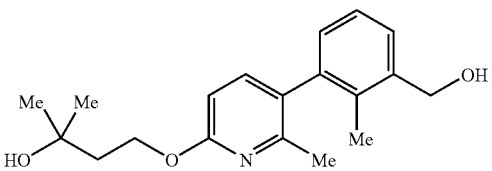
TABLE 17
120 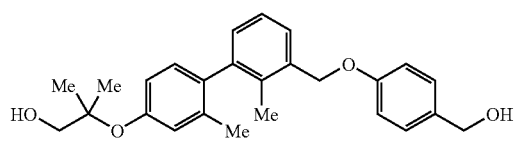
121 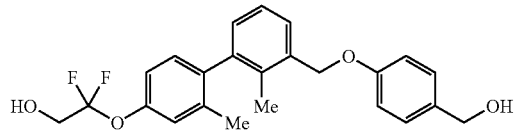
13 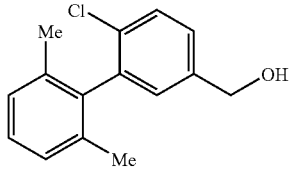
122 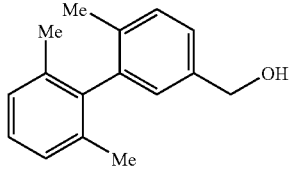
123 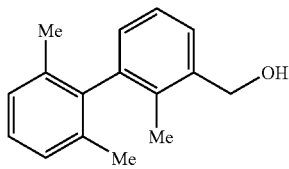
14 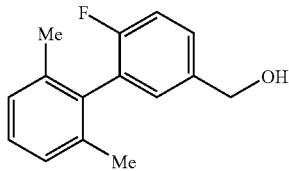

TABLE 17-continued
| 124 | 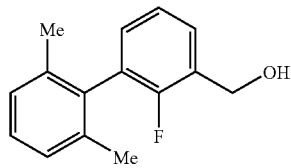 |
| --- | --- |
| 125 | 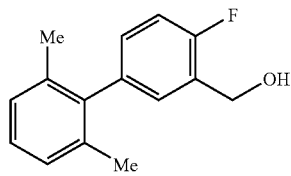 |
TABLE 18
| 34 | 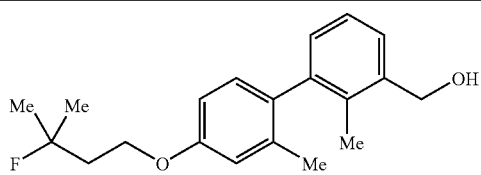 |
| --- | --- |
| 15 | 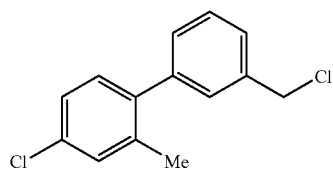 |
| 16 | 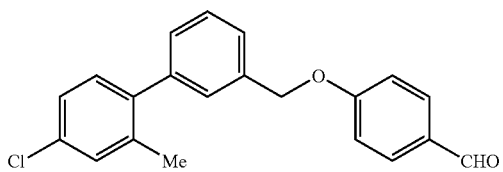 |
TABLE 18-continued
| 126 | 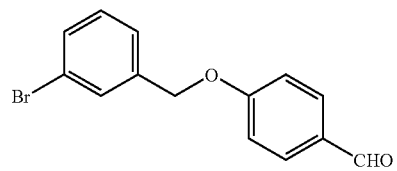 |
| --- | --- |
| 127 | 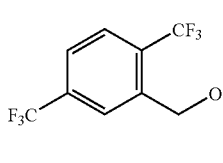 |
| 128 | 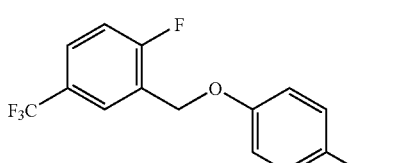 |
| 129 | 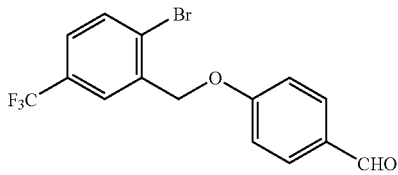 |
| 130 | 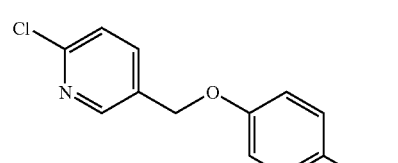 |
TABLE 19
| 17 | 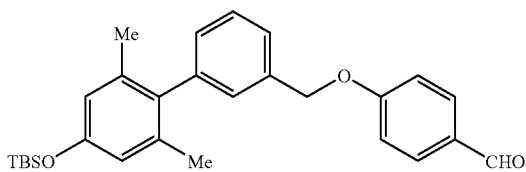 |
| --- | --- |
| 131 | 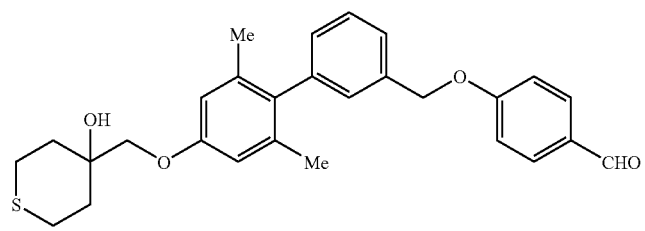 |
| 132 | 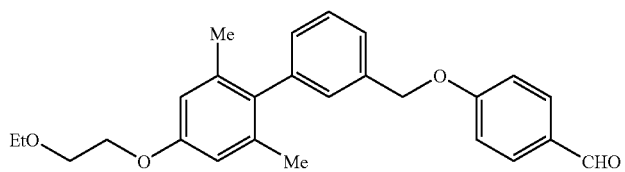 |

TABLE 19-continued
| | |
|---|---|
| 133 | 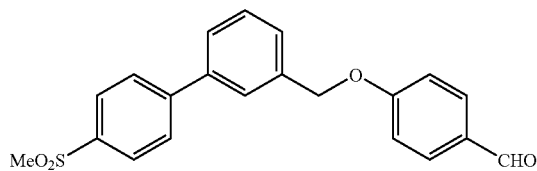 |
| 134 | 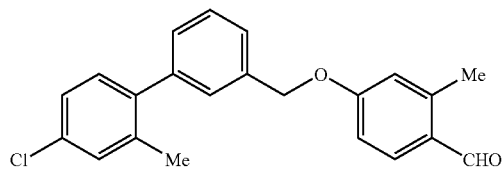 |
| 135 | 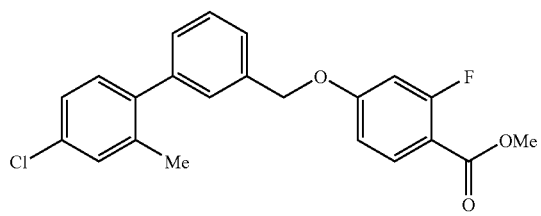 |
| 136 | 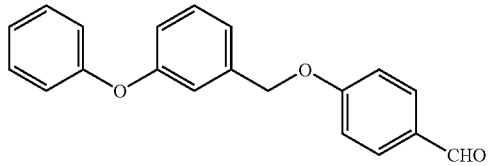 |
TABLE 20
| | |
|---|---|
| 137 | 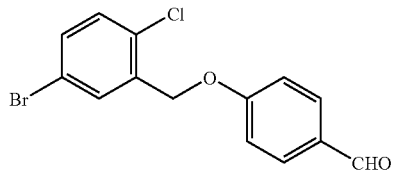 |
| 138 | 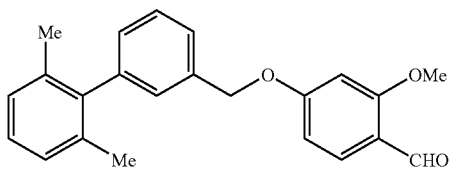 |
| 139 | 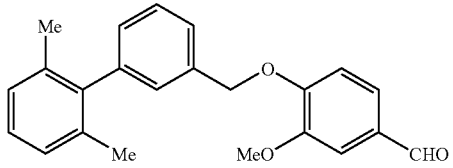 |
| 140 | 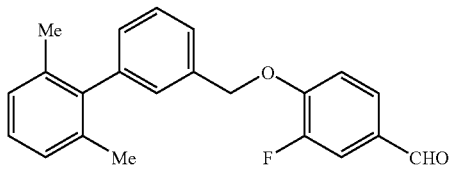 |
TABLE 20-continued
| | |
|---|---|
| 141 | 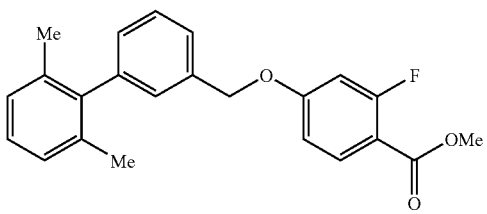 |
| 142 | 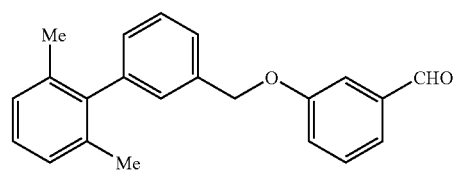 |
| 143 | 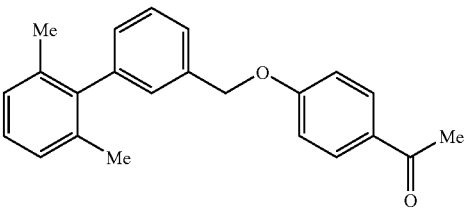 |

TABLE 21
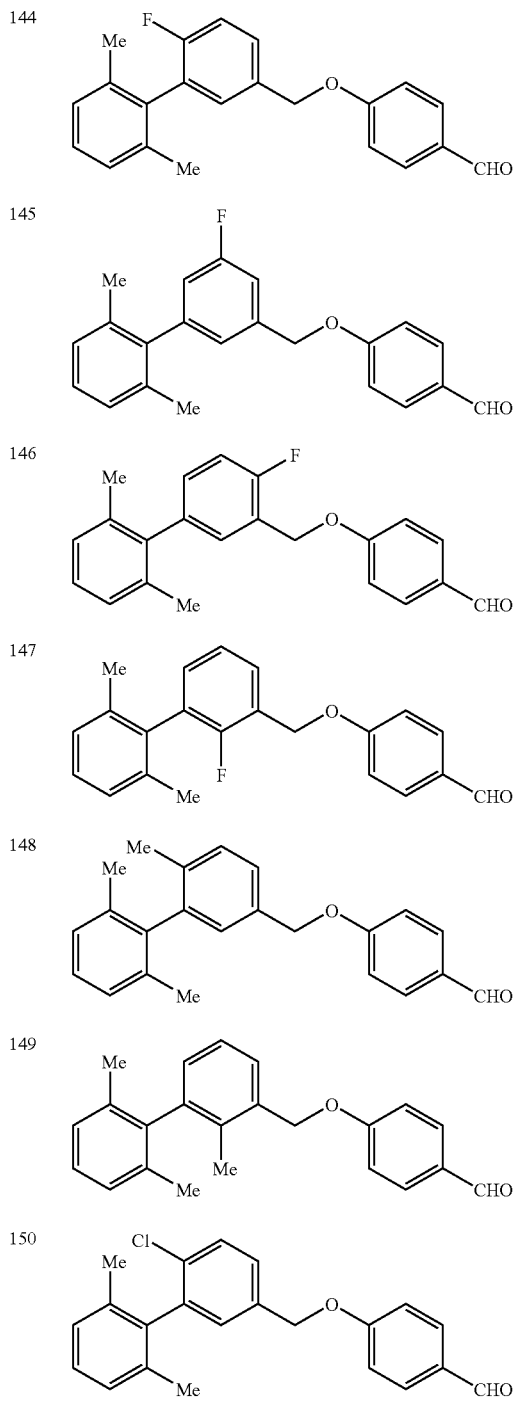
TABLE 22
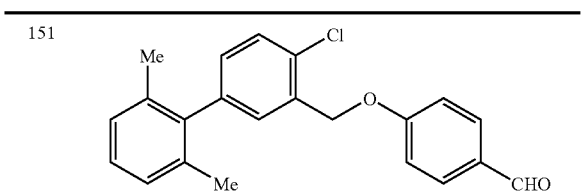
TABLE 22-continued
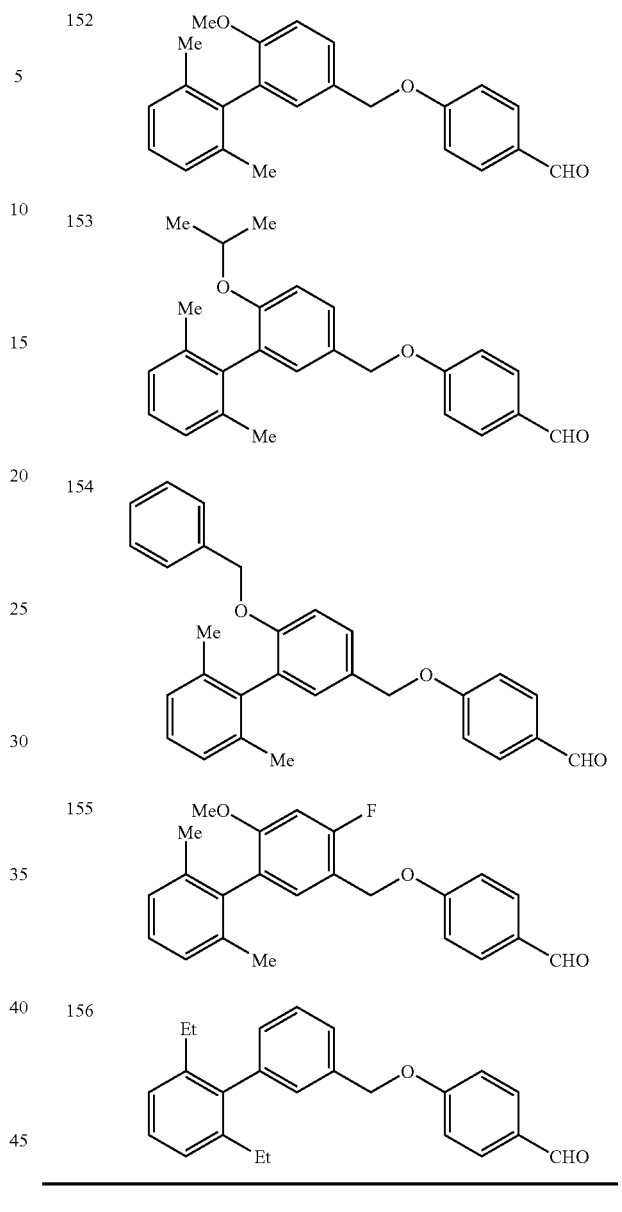
TABLE 23
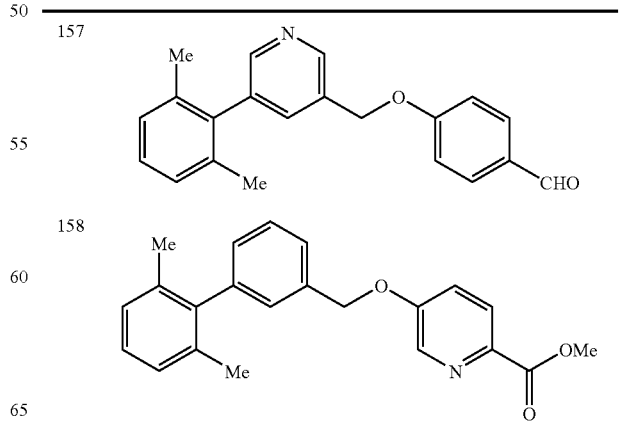

TABLE 23-continued
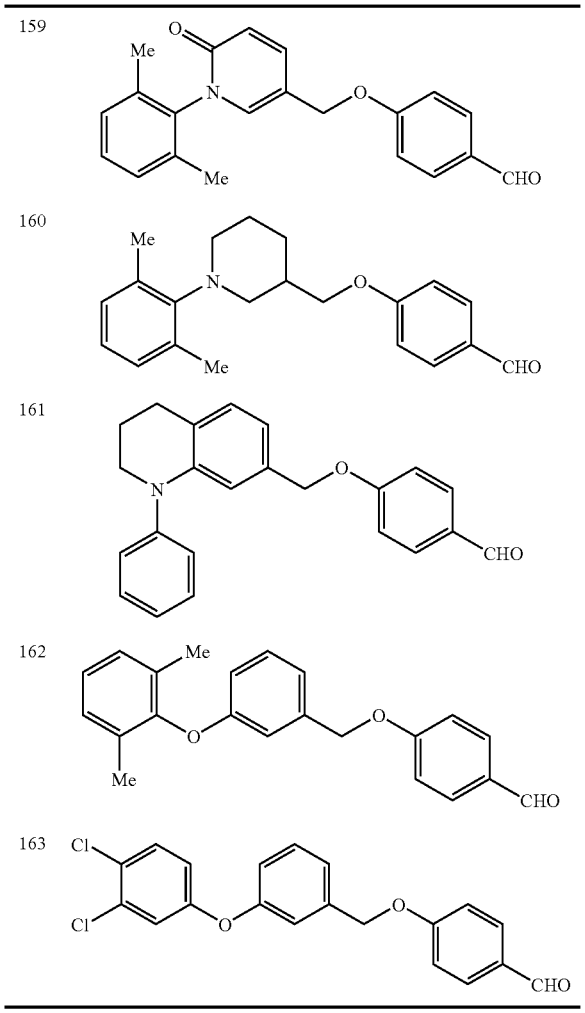
TABLE 24
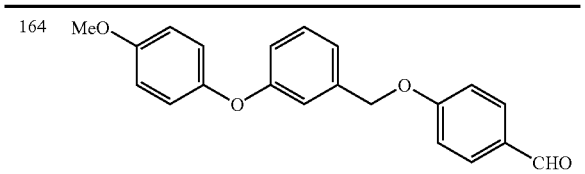
TABLE 24-continued
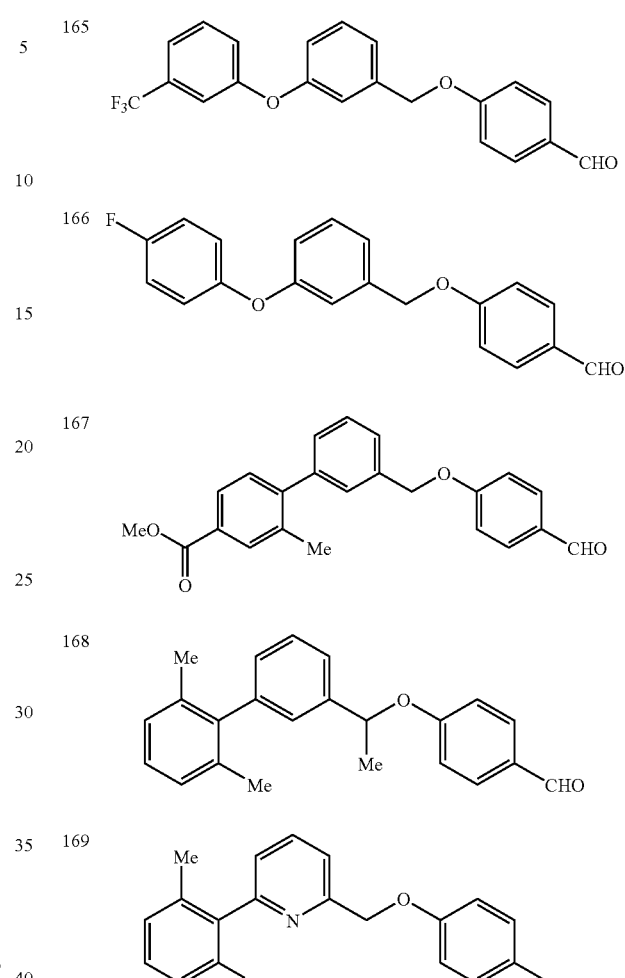
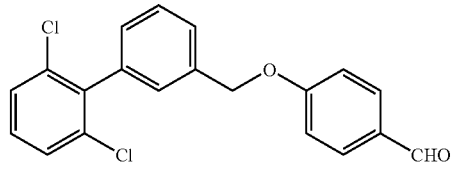
TABLE 25
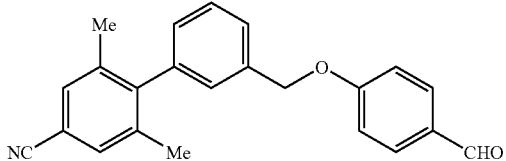
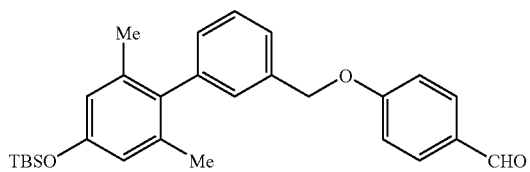

TABLE 25-continued
173
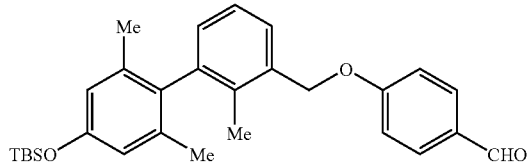
174
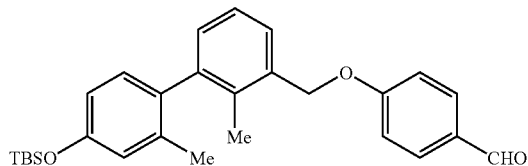
175
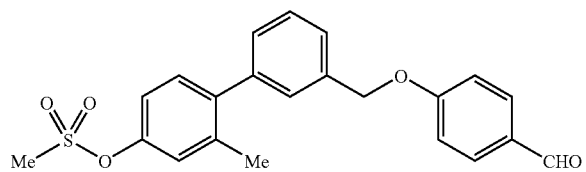
176
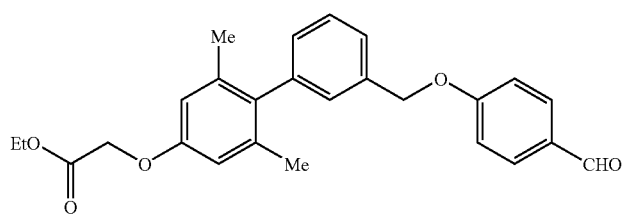
177
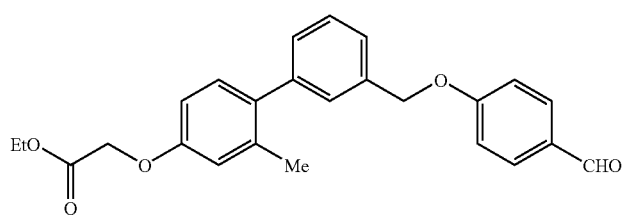
TABLE 26
178
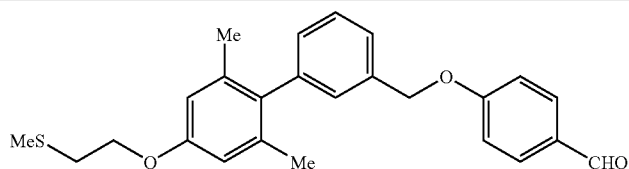
179
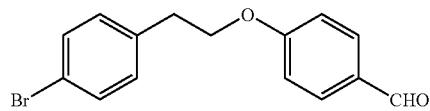
180
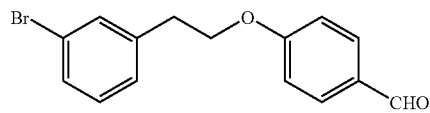

TABLE 26-continued
| | |
|---|---|
| 181 | 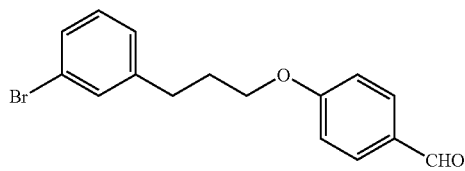 |
| 182 | 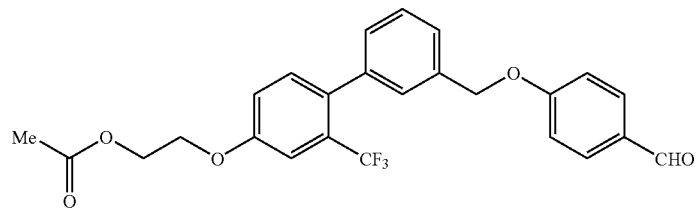 |
| 183 | 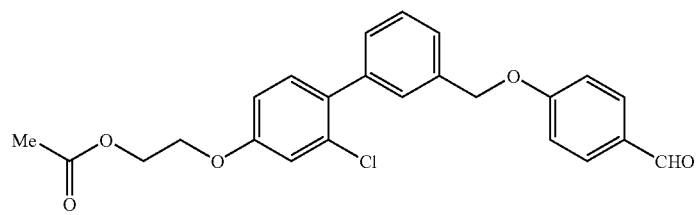 |
| 184 | 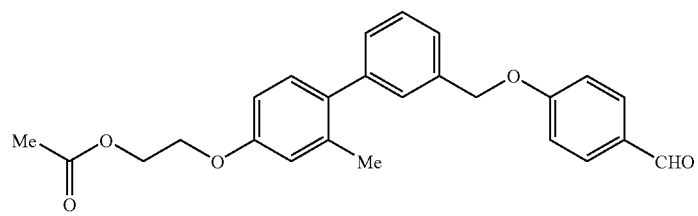 |
| 185 | 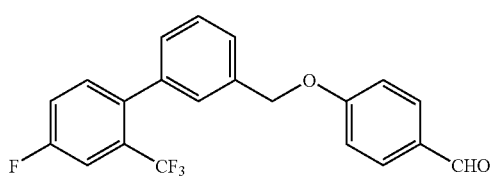 |
TABLE 27
| | |
|---|---|
| 186 | 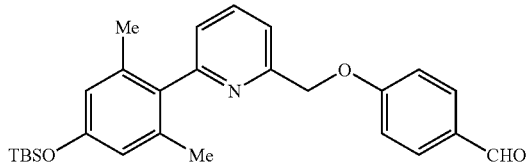 |
| 187 | 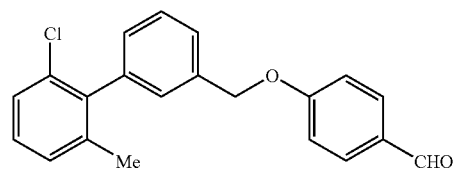 |
| 188 | 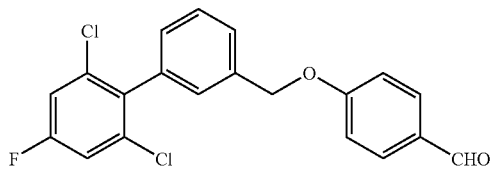 |

TABLE 27-continued
| 189 | 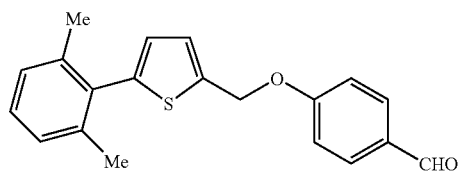 |
| --- | --- |
| 190 | 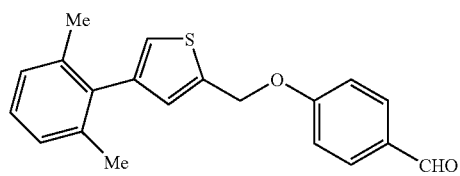 |
| 191 | 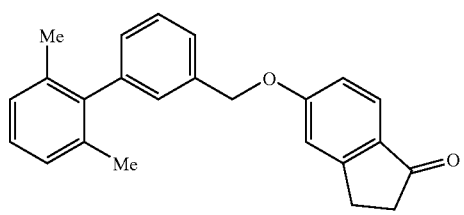 |
| 192 | 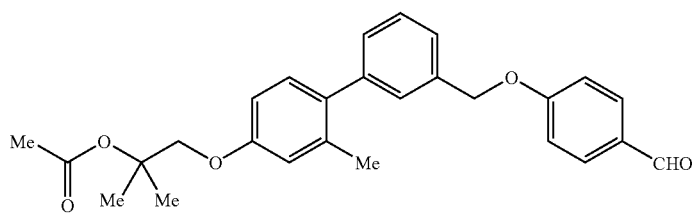 |
TABLE 28
| 193 | 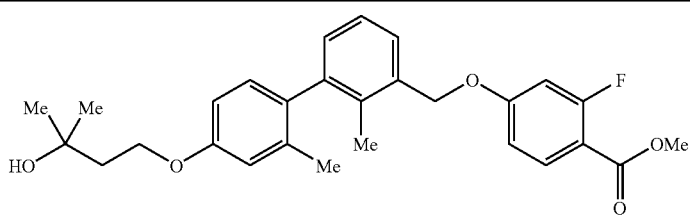 |
| --- | --- |
| 194 | 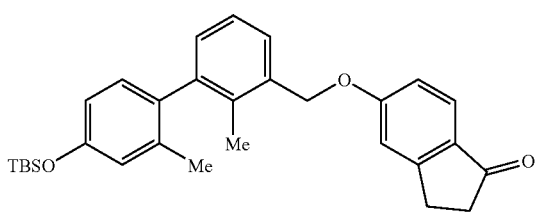 |
| 195 | 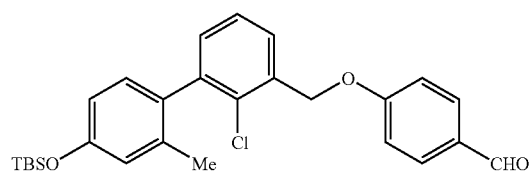 |

TABLE 28-continued
196
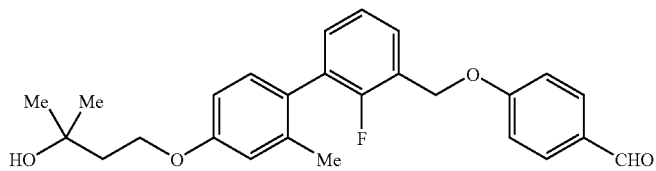
197
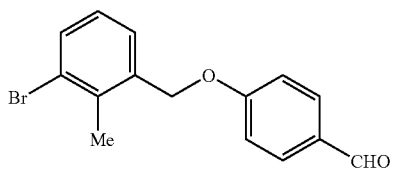
198
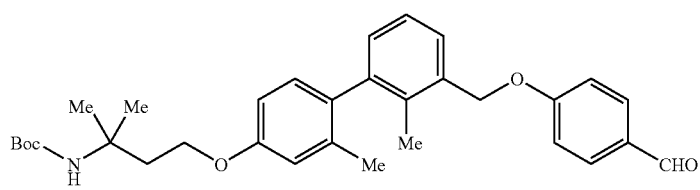
199
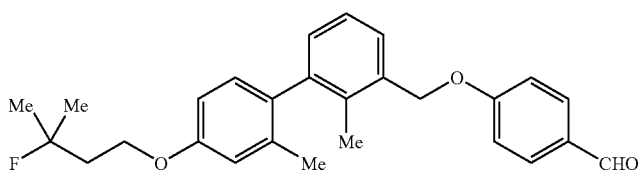
TABLE 29
200
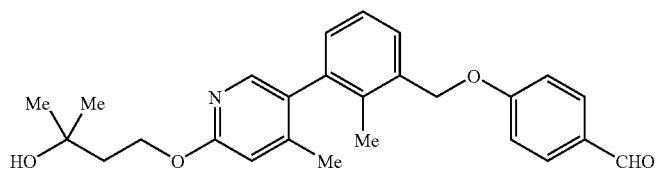
201
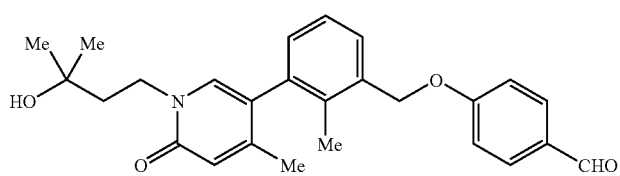
202
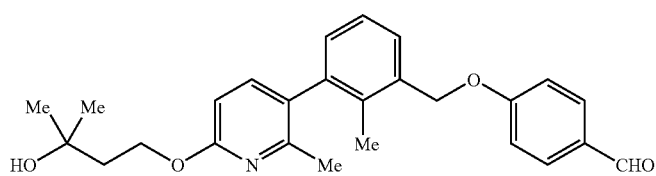
18
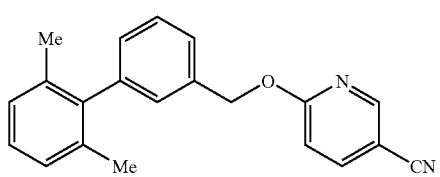

TABLE 29-continued
203 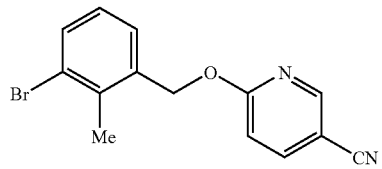
19 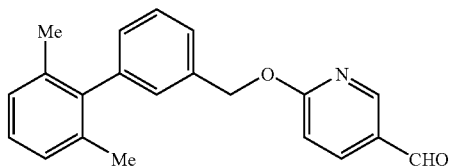
204 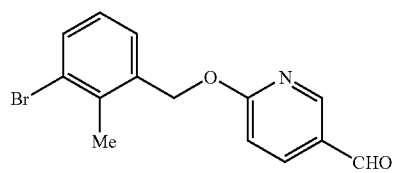
20 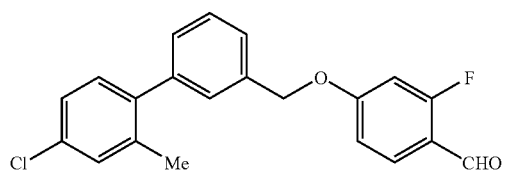
TABLE 30
205 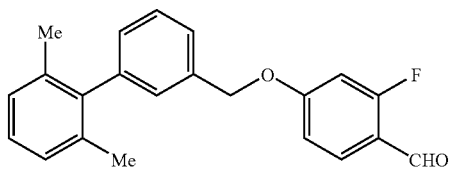
206 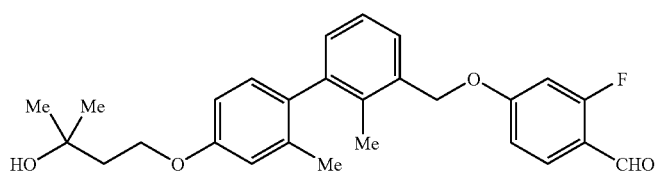
21 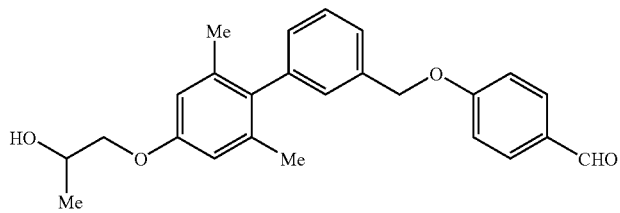
207 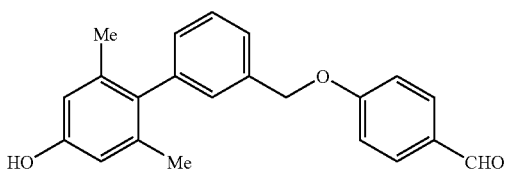

TABLE 30-continued
208 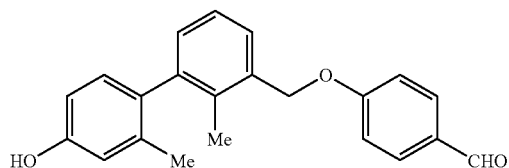
209 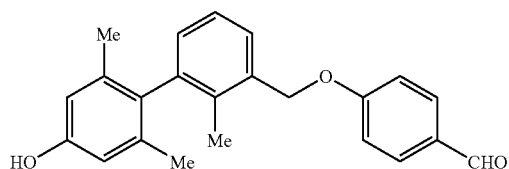
210 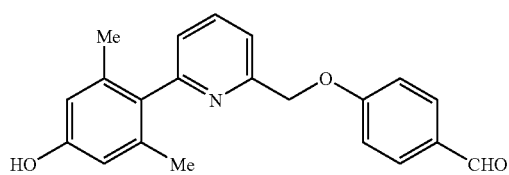
TABLE 31
211 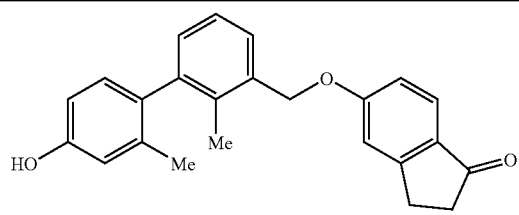
212 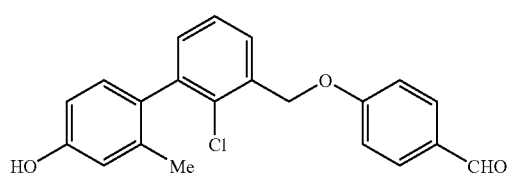
213 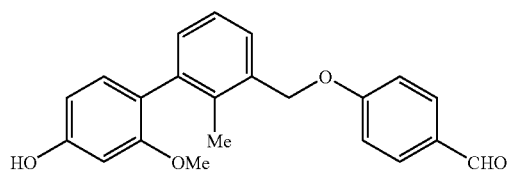
214 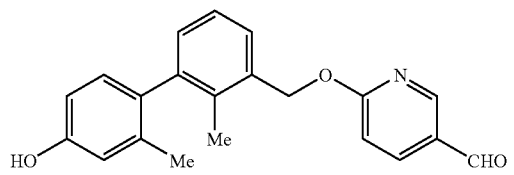
TABLE 31-continued
215 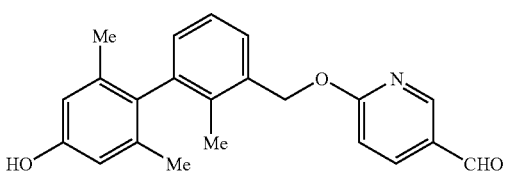
216 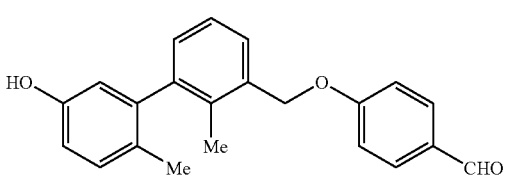
22 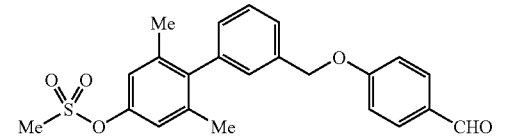
TABLE 32
217 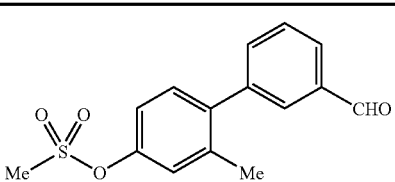

TABLE 32-continued
23
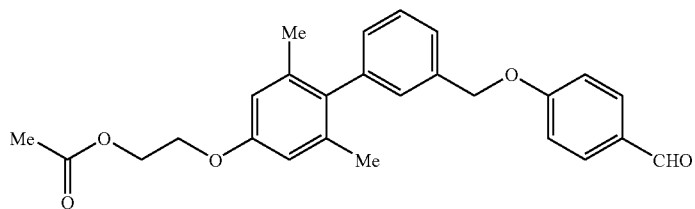
218
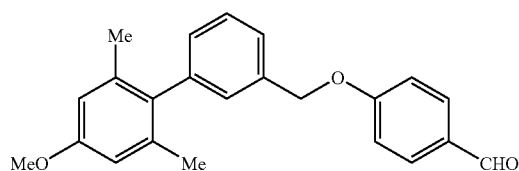
219
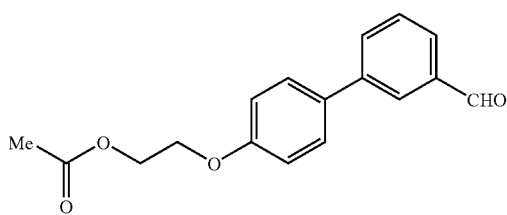
220
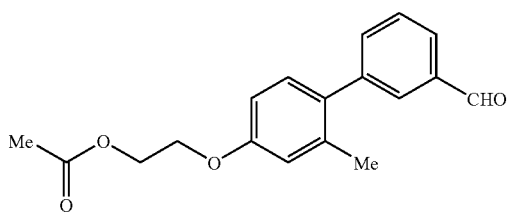
221
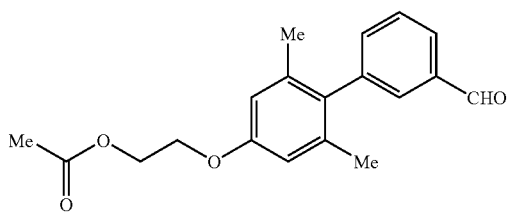
222
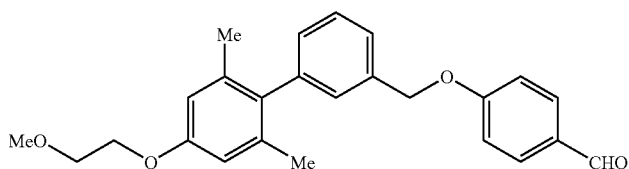
TABLE 33
223
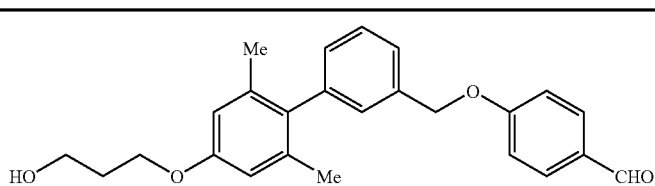

TABLE 33-continued
| 224 | 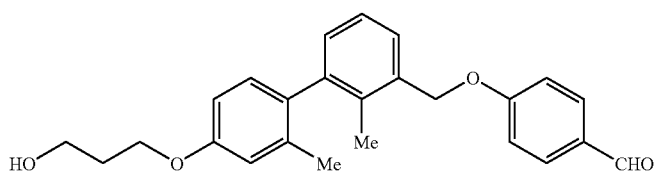 |
| --- | --- |
| 225 | 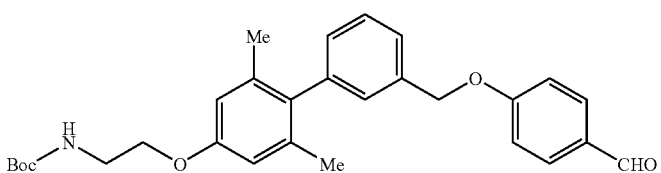 |
| 226 | 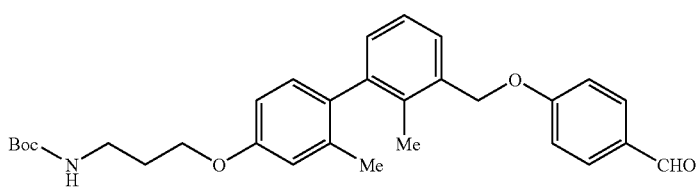 |
| 227 | 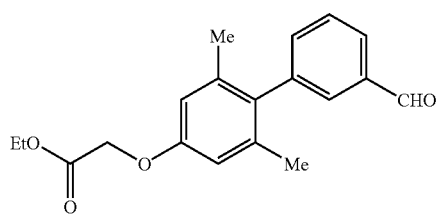 |
| 228 | 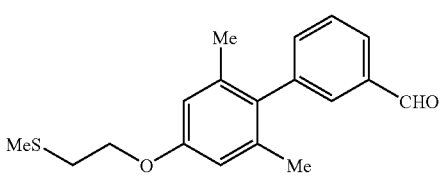 |
| 229 | 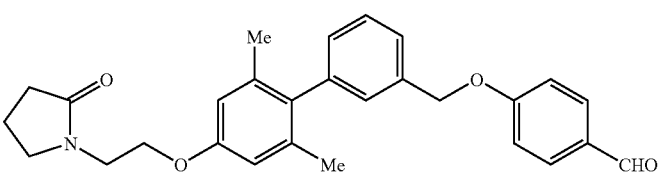 |
| 230 | 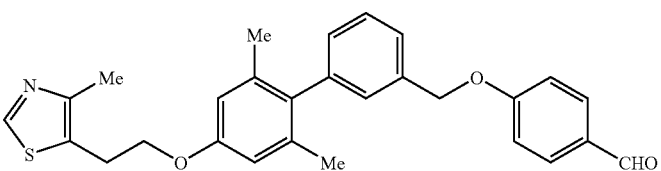 |
TABLE 34
| 231 | 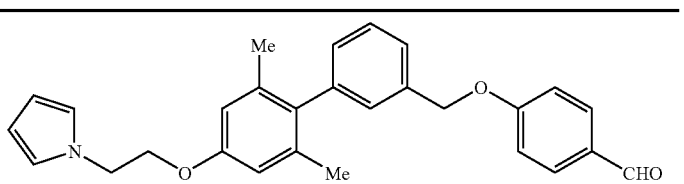 |
| --- | --- |

TABLE 34-continued
232 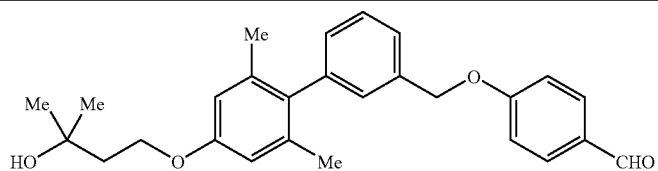
233 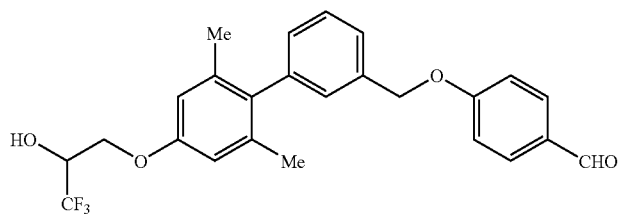
234 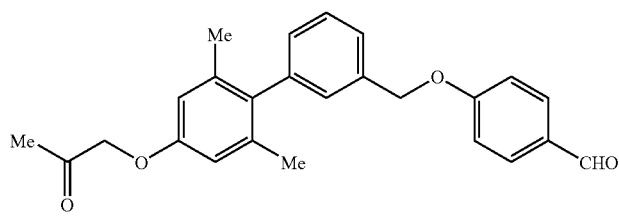
235 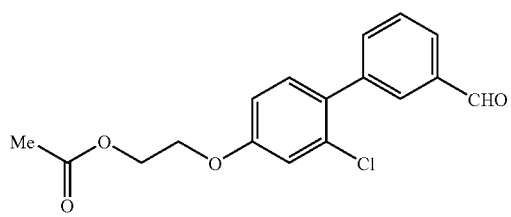
236 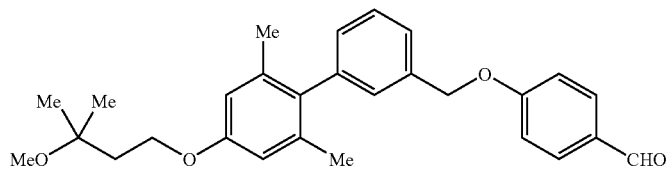
237 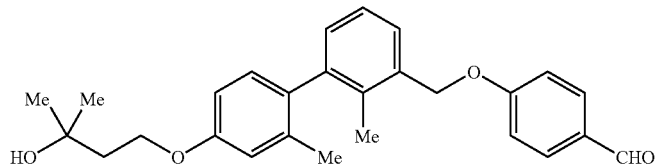
238 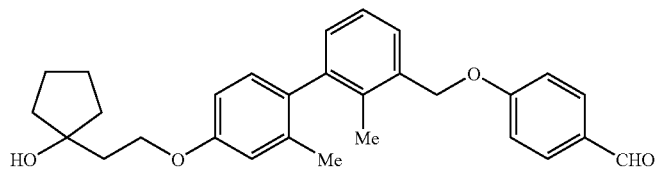
TABLE 35
239 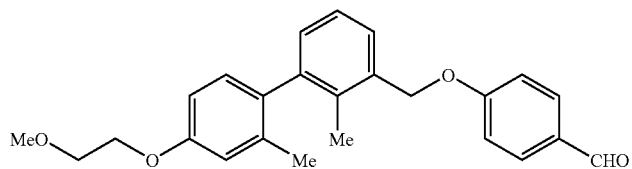

TABLE 35-continued
240
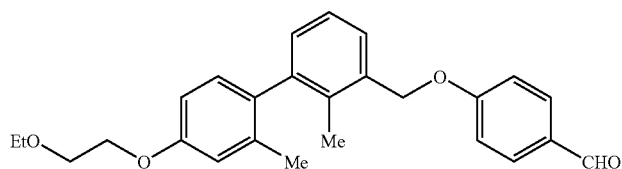
241
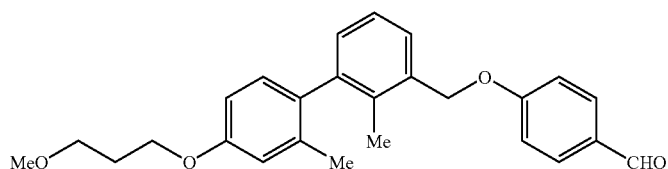
242
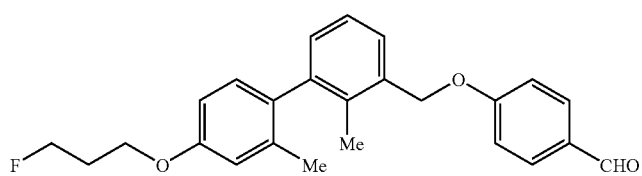
243
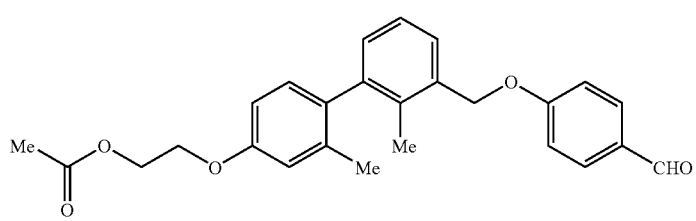
244
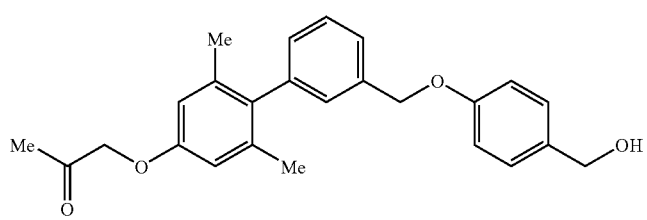
245
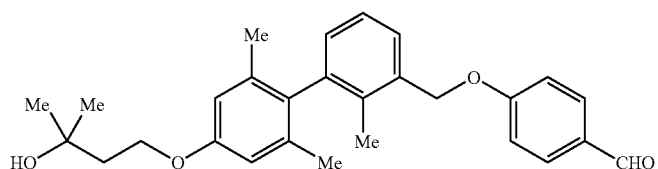
TABLE 36
246
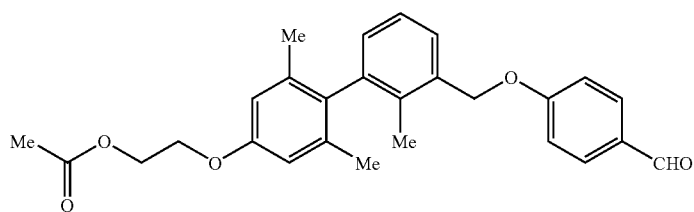

TABLE 36-continued
| 247 | 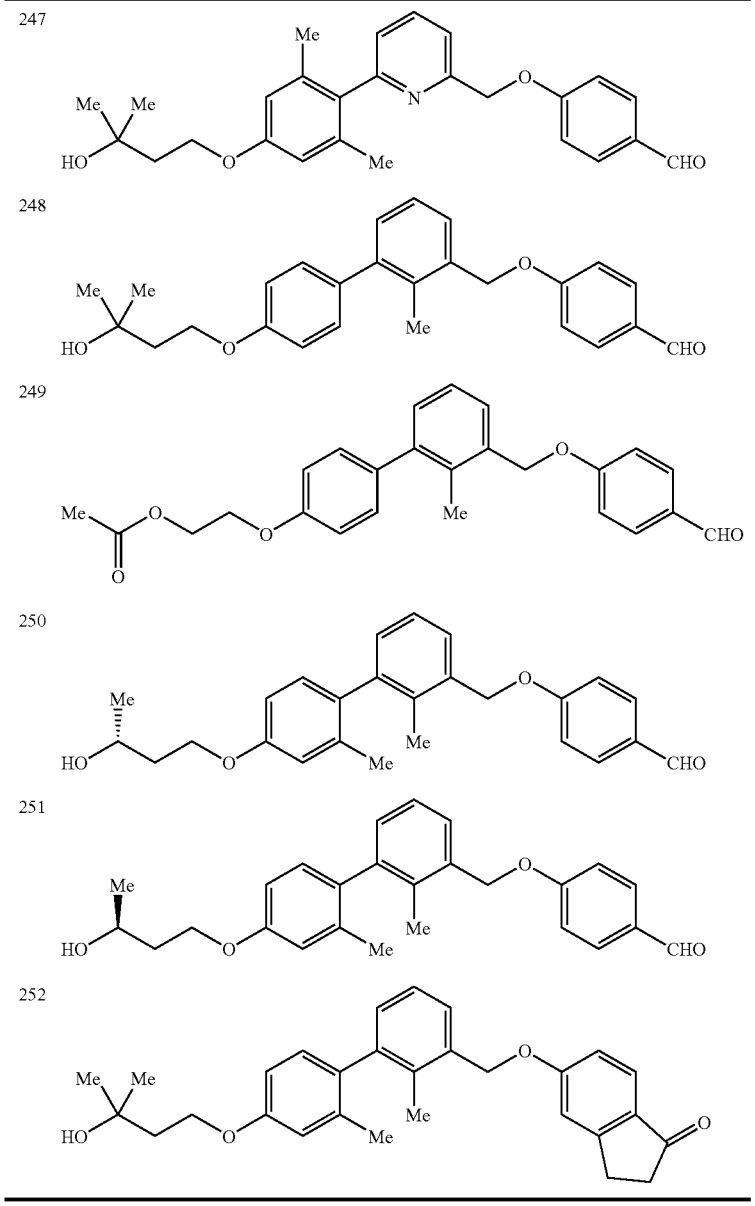 |
| 248 | |
| 249 | |
| 250 | |
| 251 | |
| 252 | |
TABLE 37
| 253 | 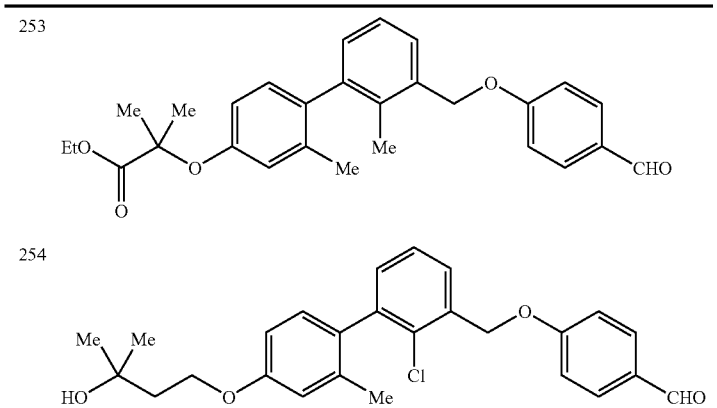 |
| 254 | |

TABLE 37-continued
| | |
|---|---|
| 255 | 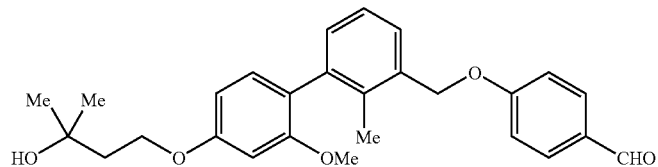 |
| 256 | 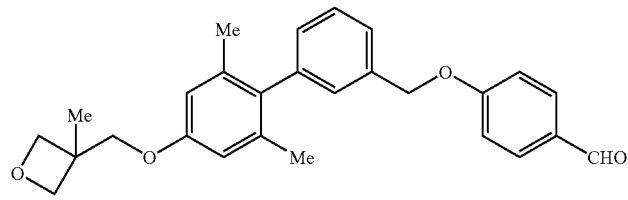 |
| 257 | 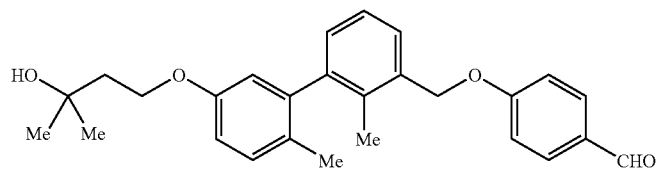 |
| 258 | 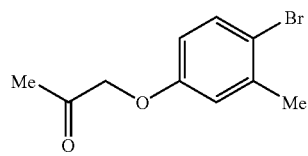 |
| 259 | 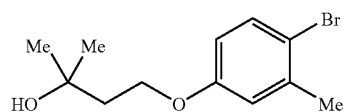 |
| 35 | 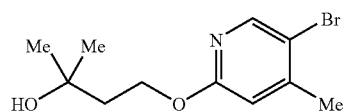 |
TABLE 38
| | |
|---|---|
| 260 | 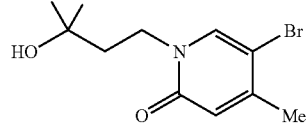 |
| 261 | 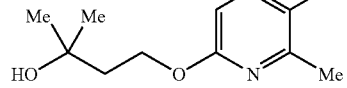 |
| 24 | 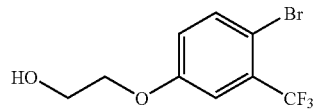 |
| 33 | 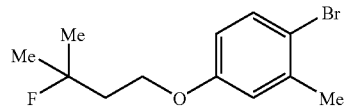 |

TABLE 38-continued
| | |
|---|---|
| 25 | 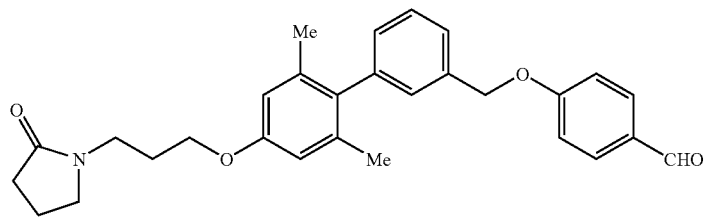 |
| 262 | 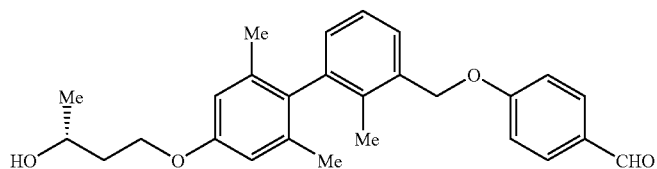 |
| 263 | 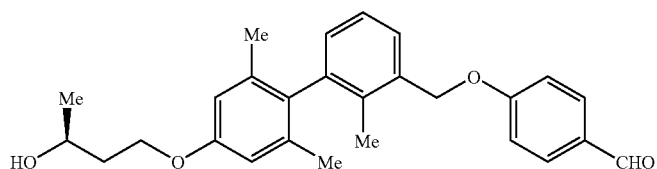 |
| 264 | 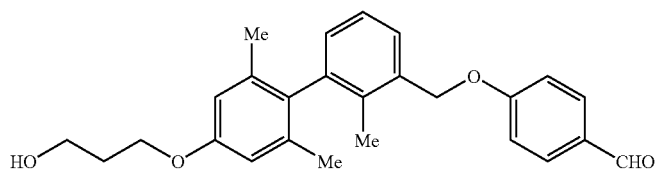 |
| 265 | 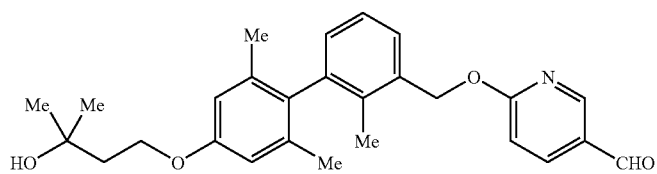 |
TABLE 39
| | |
|---|---|
| 266 | 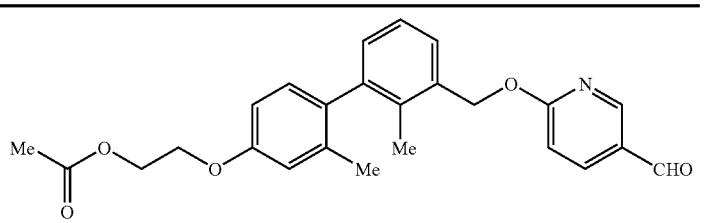 |
| 267 | 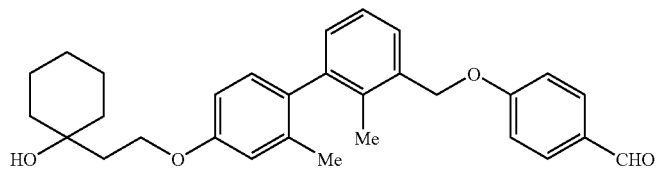 |
| 268 | 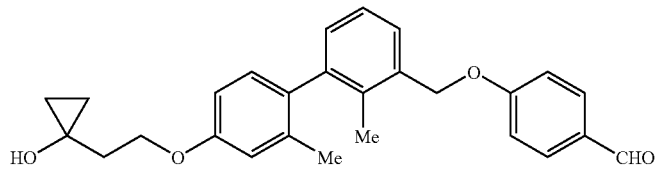 |

TABLE 39-continued
269 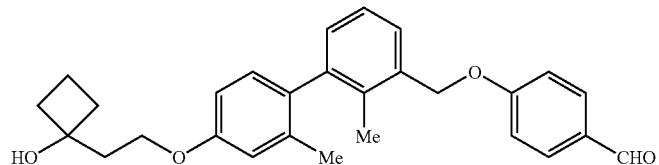
270 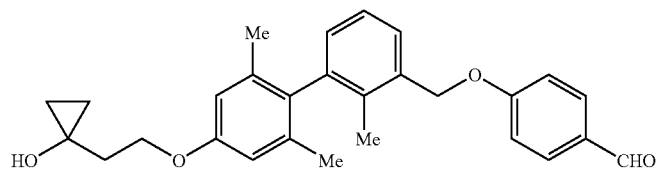
271 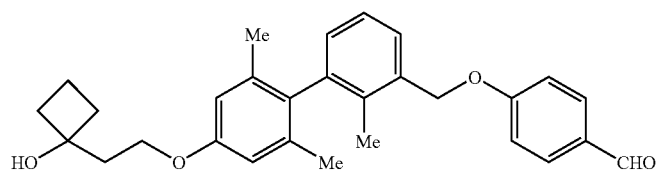
272 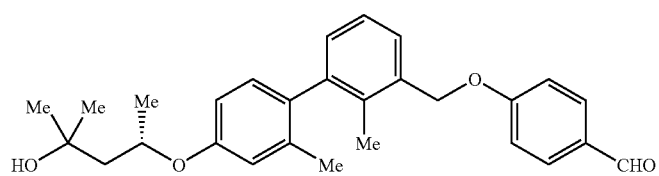
273 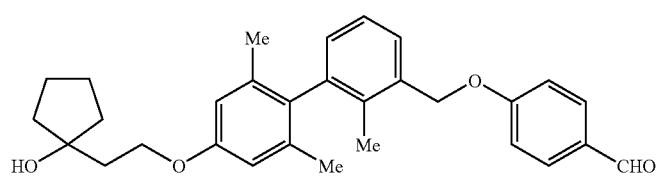
TABLE 40
274 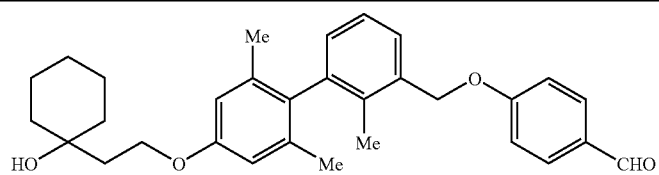
275 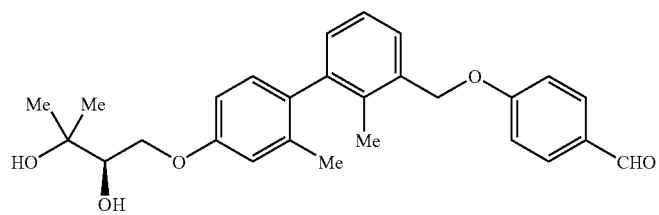
276 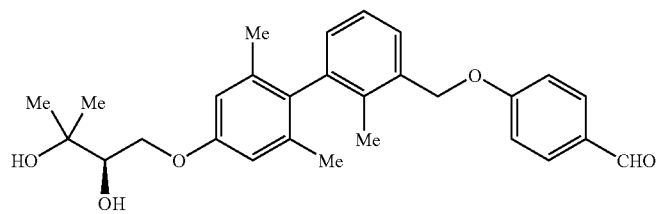

TABLE 40-continued
277 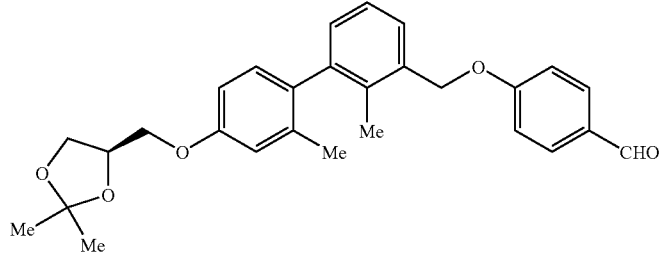
278 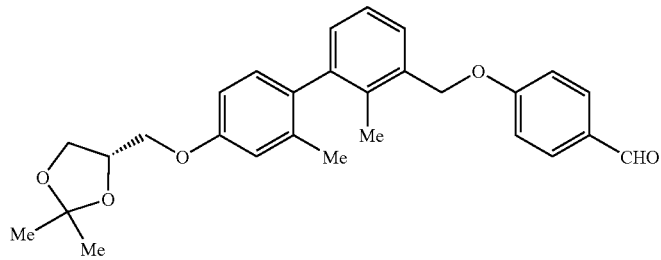
279 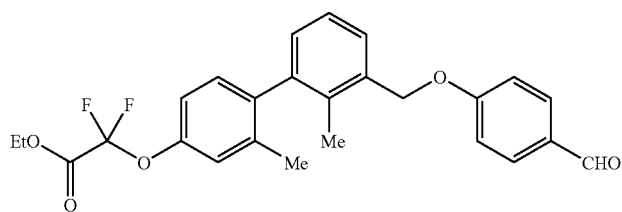
280 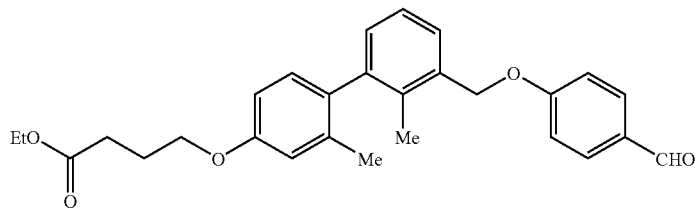
TABLE 41
281 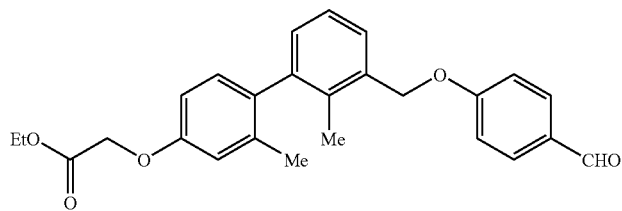
282 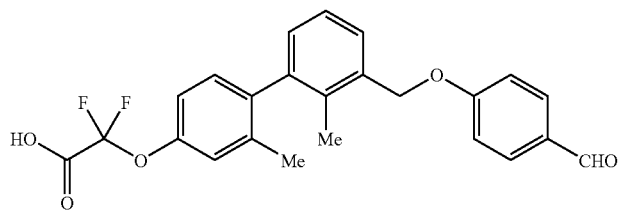

TABLE 41-continued
283 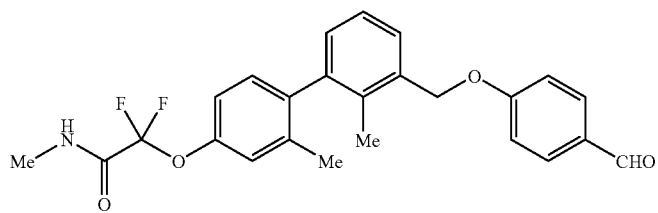
300 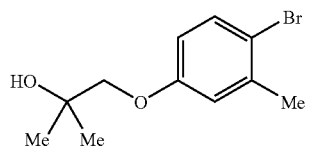
284 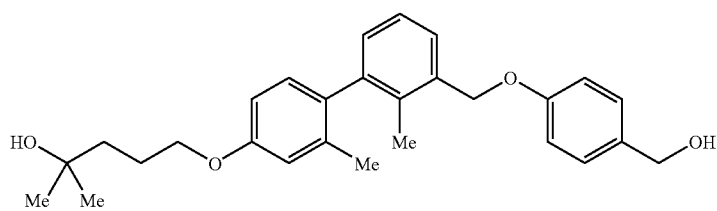
27 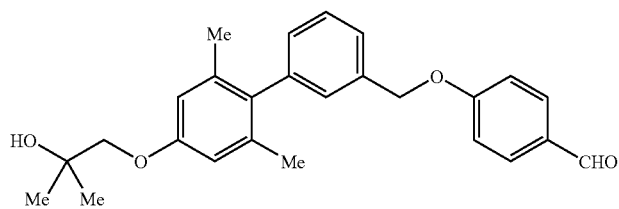
285 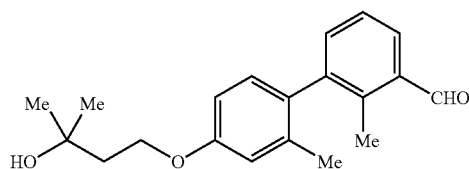
TABLE 42
286 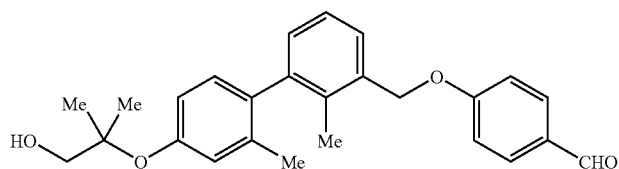
287 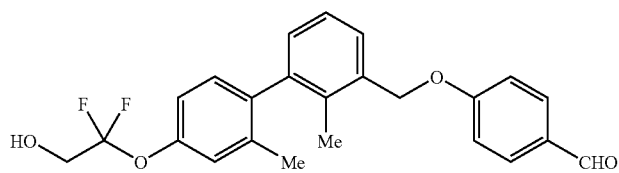
288 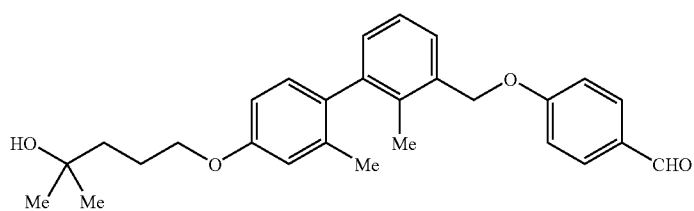

TABLE 42-continued
28
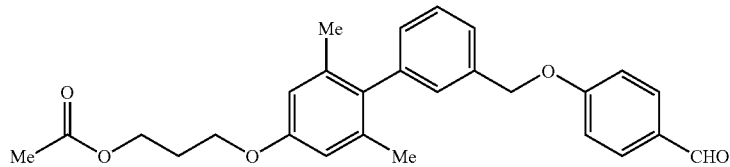
29
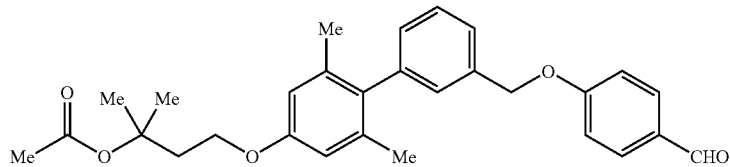
289
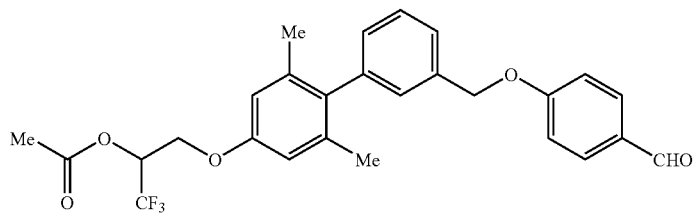
290
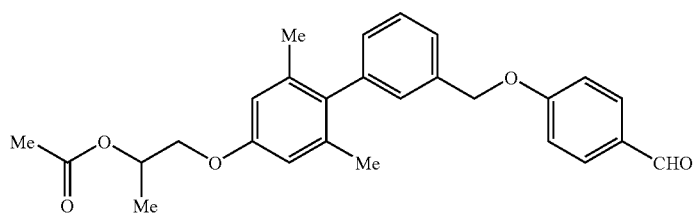
291
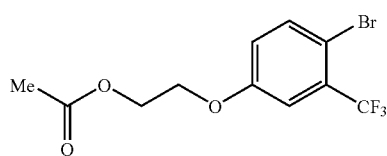
TABLE 43
292
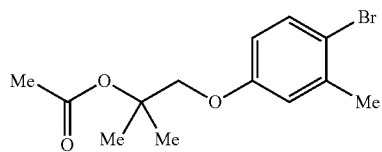
293
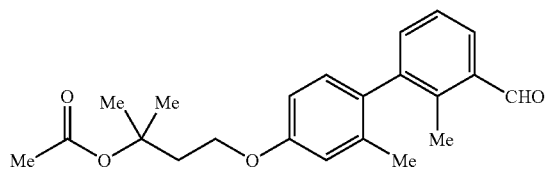
30
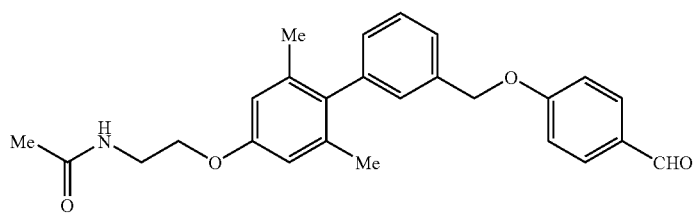

TABLE 43-continued
| | |
|---|---|
| 31 | 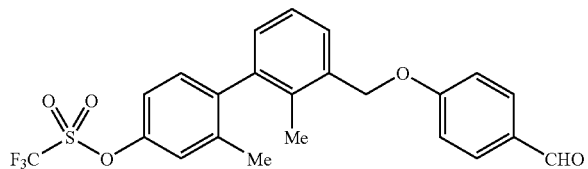 |
| 32 | 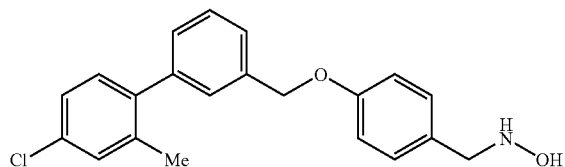 |
| 294 | 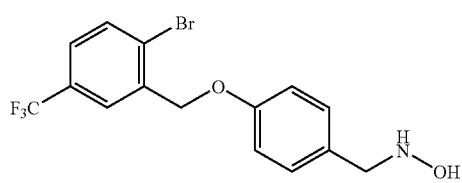 |
| 295 | 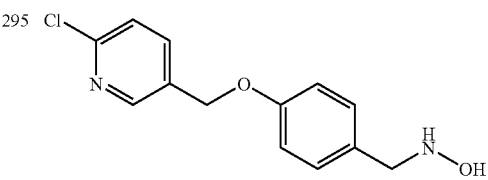 |
TABLE 44
| | |
|---|---|
| 296 | 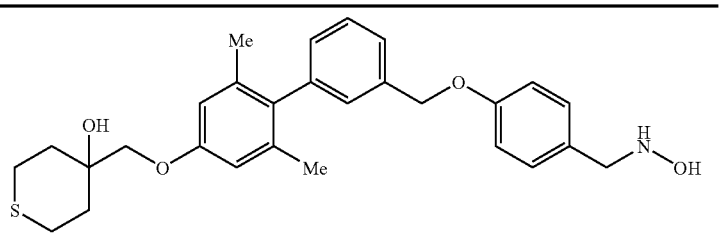 |
| 297 | 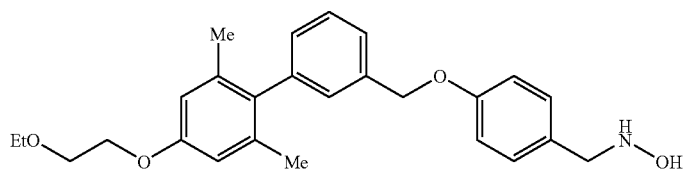 |
| 298 | 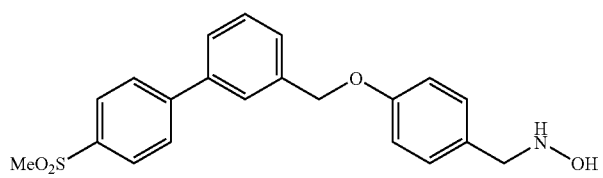 |
| 299 | 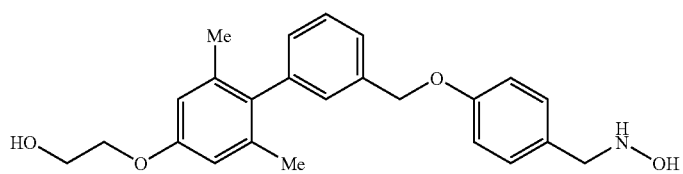 |

TABLE 44-continued

| 38 | 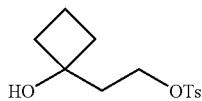 |
|---|---|

TABLE 45

| REx | Syn | Dat |
|---|---|---|
| 1 | R1 | ESI: 230 |
| 2 | R2 | ESI: 220 |
| 3 | R3 | ESI: 341 |
| 39 | R3 | EI: 301, 303 |
| 40 | R3 | ESI: 385 |
| 41 | R3 | EI: 300 |
| 4 | R4 | NMR2: 0.23(6H, s), 0.99(9H, s), 3.87(3H, s), 5.69 (2H, s), 6.40(1H, d, J = 2.1 Hz), 6.50(1H, dd, J = 2.1, 8.0 Hz), 7.68(1H, d, J = 8.0 Hz) |
| 42 | R4 | NMR2: 0.21(6H, s), 1.01(9H, s), 2.75(3H, s), 6.93(1H, dd, J = 2.7, 8.1 Hz), 7.13(1H, d, J = 8.1 Hz), 7.68(1H, d, J = 2.7 Hz) |
| 5 | R5 | ESI: 277 |
| 43 | 4 | ESI: 291 |
| 44 | 4 | EI: 288 |
| 45 | 4 | EI: 272 |
| 46 | 4 | EI: 211 |
| 47 | 4 | FAB: 317 |
| 48 | 4 | FAB: 269 |
| 49 | 4 | EI: 258 |
| 50 | 4 | ESI: 225 |
| 51 | 4 | ESI: 371 |
| 52 | 4 | EI: 390 |
| 53 | 4 | FAB: 462(M) |
| 54 | 4 | ESI-N: 317 |
| 55 | 4 | FAB: 217 |
| 56 | 4 | EI: 216 |
| 57 | 4 | ESI: 331 |
| 58 | 4 | ESI: 331 |
| 59 | 4 | FAB: 345 |
| 60 | 4 | ESI-N: 433(-TBS) |
| 6 | R6 | ESI-N: 225 |
| 7 | R7 | EI: 240 |
| 61 | R7 | EI: 238 |
| 62 | R7 | ESI-N: 211 |
| 63 | R7 | ESI: 255 |
| 64 | R7 | ESI: 251, 253, 255 |
| 65 | R7 | FAB: 353 |
| 66 | R7 | ESI-N: 231 |
| 67 | R7 | EI: 268 |

TABLE 46

| 68 | R7 | NMR1: 2.05(3H, s), 7.27-7.45(4H, m), 7.56-7.61(1H, m), 7.69-7.78(2H, m), 7.94-7.98(1H, m), 10.07(1H, s) |
|---|---|---|
| 69 | R7 | EI: 298 |
| 70 | R7 | ESI: 327 |
| 71 | R7 | EI: 316 |
| 8 | R8 | ESI: 236 |
| 72 | R8 | ESI: 268 |
| 9 | R9 | ESI: 271 |
| 73 | R9 | FAB: 342(M) |
| 74 | R9 | FAB: 344 |
| 75 | R9 | CI: 344 |
| 76 | R9 | CI: 344 |
| 10 | R10 | ESI: 342 |
| 36 | R36 | EI: 447 |
| 77 | R36 | ESI: 447 |
| 37 | R37 | ESI-N: 460 |
| 11 | R11 | EI: 232 |
| 78 | R11 | ESI: 343 |
| 79 | R11 | EI: 212 |
| 80 | R11 | EI: 242 |
| 81 | R11 | FAB: 318 |
| 82 | R11 | EI: 270 |
| 83 | R11 | FAB: 260 |

TABLE 46-continued

| 84 | R11 | FAB: 214 |
|---|---|---|
| 85 | R11 | EI: 240 |
| 86 | R11 | EI: 268, 270 |
| 87 | R11 | EI: 230 |
| 88 | R11 | EI: 268 |
| 89 | R11 | FAB: 257 |
| 90 | R11 | EI: 226 |
| 91 | R11 | ESI: 214 |
| 92 | R11 | EI: 253, 255, 257 |
| 93 | R11 | ESI: 238 |
| 94 | R11 | ESI: 315 |
| 95 | R11 | ESI: 303 |
| 96 | R11 | ESI: 355 |
| 97 | R11 | EI: 320, 322 |
| 98 | R11 | EI: 270 |
| 99 | R11 | ESI-N: 333 |
| 100 | R11 | ESI: 293 |
| 101 | R11 | ESI: 344 |

TABLE 47

| 102 | R11 | ESI-N: 232 |
|---|---|---|
| 103 | R11 | ESI-N: 270 |
| 104 | R11 | NMR1: 2.06(3H, s), 2.21(3H, s), 4.18-4.23(2H, m), 4.31-4.37(2H, m), 4.51-4.56(2H, m), 5.17-5.24(1H, m), 6.78-6.94(2H, m), 7.07-7.18(2H, m), 7.22-7.30(2H, m), 7.33-7.39(1H, m) |
| 105 | R11 | ESI-N: 217 |
| 106 | R11 | ESI: 219 |
| 107 | R11 | EI: 300 |
| 108 | R11 | ESI-N: 328 |
| 109 | R11 | FAB: 318(M) |
| 110 | R11 | NMR2: 1.28(3H, t, J = 7.1, 7.2 Hz), 1.55-1.57(1H, m), 2.04(3H, s), 2.07(3H, s), 2.10-2.18(2H, m), 2.53-2.57(2H, m), 4.03-4.05(2H, m), 4.17(2H, q, J = 7.1, 7.2 Hz), 4.64-4.65(2H, m), 5.09(2H, s), 6.75-6.78(1H, m), 6.81-6.82(1H, m), 7.00-7.04(3H, m), 7.10-7.12(1H, m), 7.22-7.26(1H, m), 7.31-7.34(2H, m), 7.41-7.43(1H, m) |
| 12 | R12 | FAB: 263 |
| 111 | R12 | FAB: 246 |
| 112 | R12 | FAB: 230 |
| 113 | R12 | EI: 342 |
| 114 | R12 | EI: 362 |
| 115 | R12 | EI: 356 |
| 116 | R12 | FAB: 314(M) |
| 117 | R12 | CI: 316 |
| 118 | R12 | CI: 316 |
| 119 | R12 | CI: 316 |
| 120 | R12 | FAB: 406(M) |
| 121 | R12 | FAB: 414(M) |
| 13 | R13 | EI: 246 |
| 122 | R13 | EI: 226 |
| 123 | R13 | EI: 226 |
| 14 | R14 | EI: 230 |
| 124 | R14 | EI: 230 |
| 125 | R14 | EI: 230 |
| 34 | R34 | EI: 316 |
| 15 | R15 | ESI: 250, 252 |
| 16 | R16 | ESI: 337 |
| 126 | R16 | EI: 290, 292 |
| 127 | R16 | ESI: 349 |
| 128 | R16 | ESI: 299 |
| 129 | R16 | ESI: 360 |
| 130 | R16 | ESI: 248 |

TABLE 48

| | | |
|---|---|---|
| 17 | R17 | ESI: 447 |
| 131 | R17 | FAB: 462 |
| 132 | R17 | ESI: 405 |
| 133 | R17 | ESI: 367 |
| 134 | R17 | FAB: 351 |
| 135 | R17 | FAB: 385 |
| 136 | R17 | FAB: 305 |
| 137 | R17 | ESI: 326 |
| 138 | R17 | ESI: 347 |
| 139 | R17 | ESI: 347 |
| 140 | R17 | FAB: 335 |
| 141 | R17 | FAB: 365 |
| 142 | R17 | FAB: 317 |
| 143 | R17 | FAB: 331 |
| 144 | R17 | FAB: 335 |
| 145 | R17 | EI: 334 |
| 146 | R17 | FAB: 335 |
| 147 | R17 | FAB: 335 |
| 148 | R17 | ESI-N: 329 |
| 149 | R17 | FAB: 331 |
| 150 | R17 | FAB: 351 |
| 151 | R17 | FAB: 351 |
| 152 | R17 | ESI-N: 345 |
| 153 | R17 | ESI-N: 373 |
| 154 | R17 | ESI-N: 421 |
| 155 | R17 | ESI-N: 363 |
| 156 | R17 | FAB: 345 |
| 157 | R17 | FAB: 318 |
| 158 | R17 | FAB: 348 |
| 159 | R17 | ESI: 334 |
| 160 | R17 | EI: 323 |
| 161 | R17 | ESI-N: 342 |
| 162 | R17 | EI: 332 |
| 163 | R17 | EI: 372, 374 |
| 164 | R17 | EI: 334 |
| 165 | R17 | EI: 372 |
| 166 | R17 | FAB: 323 |
| 167 | R17 | ESI: 361 |
| 168 | R17 | ESI: 331 |
| 169 | R17 | ESI: 318 |
| 170 | R17 | ESI: 357 |

TABLE 49

| | | |
|---|---|---|
| 171 | R17 | ESI: 342 |
| 172 | R17 | FAB: 447 |
| 173 | R17 | ESI-N: 459 |
| 174 | R17 | ESI: 447 |
| 175 | R17 | ESI: 397 |
| 176 | R17 | ESI: 419 |
| 177 | R17 | FAB: 405 |
| 178 | R17 | ESI-N: 405 |
| 179 | R17 | ESI: 305 |
| 180 | R17 | ESI: 305 |
| 181 | R17 | ESI: 321 |
| 182 | R17 | ESI-N: 457 |
| 183 | R17 | FAB: 425 |
| 184 | R17 | ESI-N: 403 |
| 185 | R17 | ESI: 375 |
| 186 | R17 | ESI: 448 |
| 187 | R17 | ESI-N: 335 |
| 188 | R17 | ESI-N: 374 |
| 189 | R17 | ESI-N: 321 |
| 190 | R17 | EI: 323 |
| 191 | R17 | ESI: 343 |
| 192 | R17 | ESI-N: 431 |
| 193 | R17 | FAB: 466(M) |
| 194 | R17 | FAB: 473 |
| 195 | R17 | ESI: 467 |
| 196 | R17 | FAB: 422(M) |
| 197 | R17 | EI: 306, 304 |
| 198 | R17 | ESI-N: 516 |
| 199 | R17 | FAB: 420(M) |
| 200 | R17 | ESI: 420 |
| 201 | R17 | ESI: 420 |
| 202 | R17 | ESI: 420 |
| 18 | R18 | FAB: 315 |

TABLE 49-continued

| | | |
|---|---|---|
| 203 | R18 | EI: 303, 305 |
| 19 | R19 | FAB: 318 |
| 204 | R19 | ESI-N: 304 |
| 20 | R20 | FAB: 355 |
| 205 | R20 | FAB: 335 |
| 206 | R20 | FAB: 436(M) |
| 21 | R21 | ESI: 391 |
| 207 | 8 | ESI: 333 |

TABLE 50

| | | |
|---|---|---|
| 208 | 8 | ESI-N: 331 |
| 209 | 8 | ESI-N: 345 |
| 210 | 8 | ESI: 334 |
| 211 | 8 | FAB: 359 |
| 212 | 8 | CI: 353 |
| 213 | 8 | EI: 348 |
| 214 | 8 | ESI-N: 332 |
| 215 | 8 | ESI-N: 346 |
| 216 | 8 | EI: 332 |
| 22 | R22 | ESI: 411 |
| 217 | R22 | ESI: 291 |
| 23 | R23 | ESI: 419 |
| 218 | R23 | ESI: 347 |
| 219 | R23 | FAB: 285 |
| 220 | R23 | ESI: 299 |
| 221 | R23 | ESI: 313 |
| 222 | R23 | ESI: 391 |
| 223 | R23 | ESI: 391 |
| 224 | R23 | ESI-N: 389 |
| 225 | R23 | ESI: 476 |
| 226 | R23 | ESI-N: 488 |
| 227 | R23 | ESI: 313 |
| 228 | R23 | EI: 300 |
| 229 | R23 | ESI: 444 |
| 230 | R23 | ESI: 458 |
| 231 | R23 | ESI: 426 |
| 232 | R23 | ESI-N: 417 |
| 233 | R23 | ESI: 445 |
| 234 | R23 | ESI-N: 387 |
| 235 | R23 | EI: 318, 320 |
| 236 | R23 | ESI-N: 431 |
| 237 | R23 | ESI-N: 417 |
| 238 | R23 | ESI-N: 443 |
| 239 | R23 | ESI-N: 389 |
| 240 | R23 | ESI-N: 403 |
| 241 | R23 | ESI-N: 403 |
| 242 | R23 | ESI: 392 |
| 243 | R23 | ESI-N: 417 |
| 244 | R23 | ESI-N: 389 |
| 245 | R23 | ESI-N: 431 |
| 246 | R23 | ESI-N: 431 |

TABLE 51

| | | |
|---|---|---|
| 247 | R23 | ESI-N: 418 |
| 248 | R23 | ESI-N: 403 |
| 249 | R23 | ESI-N: 403 |
| 250 | R23 | ESI-N: 403 |
| 251 | R23 | ESI-N: 403 |
| 252 | R23 | FAB: 445 |
| 253 | R23 | FAB: 447 |
| 254 | R23 | FAB: 438(M) |
| 255 | R23 | FAB: 434(M) |
| 256 | R23 | ESI: 417 |
| 257 | R23 | FAB: 418(M) |
| 258 | R23 | FAB: 244 |
| 259 | R23 | EI: 272 |
| 35 | R35 | CI: 274 |
| 260 | R35 | EI: 273 |
| 261 | R35 | EI: 273 |
| 24 | R24 | ESI: 285 |
| 33 | R33 | EI: 274 |
| 25 | R25 | ESI: 458 |
| 262 | R23 | ESI-N: 417 |

TABLE 51-continued
| | | |
|---|---|---|
| 263 | R23 | ESI-N: 417 |
| 264 | R23 | ESI-N: 403 |
| 265 | R23 | ESI-N: 432 |
| 266 | R23 | FAB: 420 |
| 267 | R23 | ESI-N: 457 |
| 268 | R23 | ESI-N: 415 |
| 269 | P23 | ESI: 430(M) |
| 270 | R23 | ESI: 431 |
| 271 | R23 | FAB: 444(M) |
| 272 | R23 | CI: 432 |
| 273 | R23 | FAB: 458(M) |
| 274 | R23 | FAB: 472(M) |
| 275 | R23 | ESI-N: 433 |
| 276 | R23 | ESI-N: 447 |
| 277 | R23 | FAB: 447 |
| 278 | R23 | FAB: 447 |
| 279 | R23 | ESI-N: 454 |
| 280 | R23 | ESI: 447 |
| 281 | R23 | ESI-N: 417 |
| 282 | 5 | FAB: 427 |
| 283 | 17 | FAB: 440 |
TABLE 52
| | | |
|---|---|---|
| 300 | R26 | NMR1: 1.18(6H, s), 2.30(3H, s), 3.68(2H, s), 4.63 (1H, s), 6.73(1H, dd, J = 8.8, 3.0 Hz), 6.97(1H, d, J = 3.0 Hz), 7.43(1H, d, J = 8.7 Hz) |
| 284 | R26 | ESI-N: 433 |
| 27 | R27 | ESI-N: 403 |
| 285 | R27 | FAB: 313 |
| 286 | R27 | FAB: 404(M) |
| 287 | R27 | FAB: 413 |
| 288 | R27 | ESI: 433 |
| 28 | R28 | ESI: 433 |
| 29 | R29 | ESI-N: 459 |
| 289 | R29 | ESI: 487 |
| 290 | R29 | ESI-N: 431 |
| 291 | R29 | ESI: 327 |
| 292 | R29 | EI: 300 |
| 293 | R29 | FAB: 354(M) |
| 30 | R30 | ESI: 418 |
| 31 | R31 | ESI-N: 463 |
| 32 | R32 | FAB: 352 |
| 294 | R32 | ESI: 377 |
| 295 | R32 | FAB: 265 |
| 296 | R32 | ESI: 480 |
| 297 | R32 | FAB: 422 |
| 298 | R32 | FAB: 384 |
| 299 | R32 | FAB: 394 |
| 38 | R38 | ESI-N: 270(M) |
TABLE 53
| Ex | Str |
|---|---|
| 1 | |
| 2 | |
| 3 | |
| 9 | |
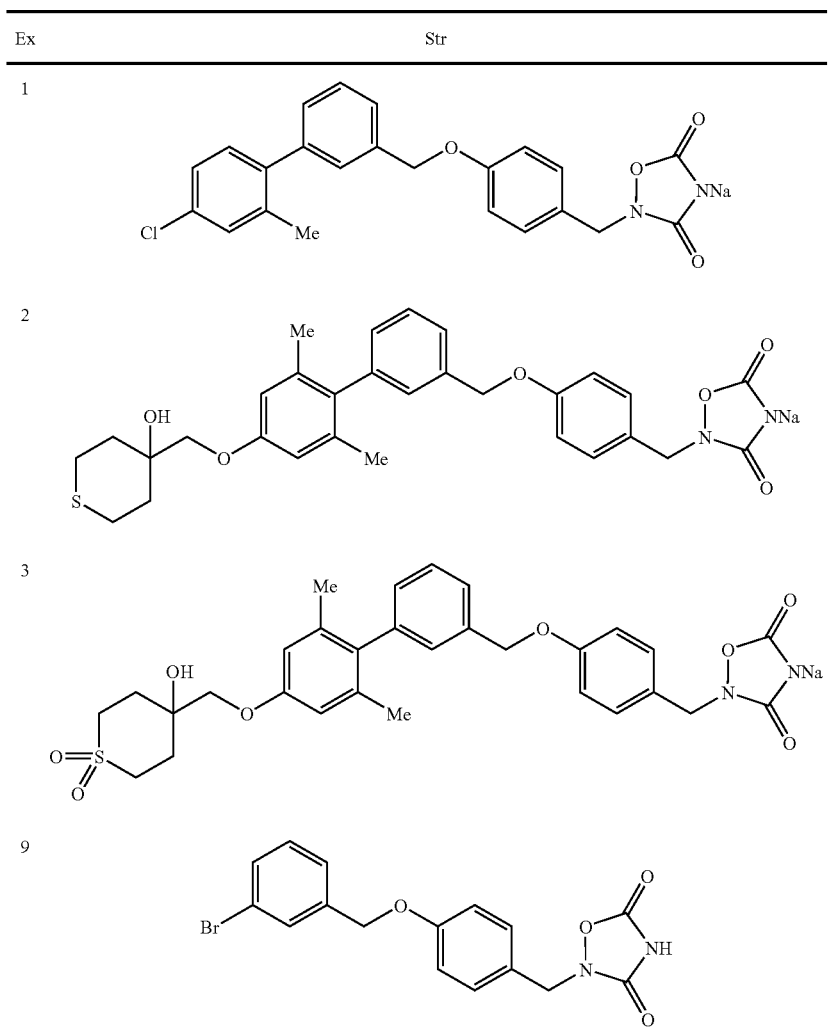

TABLE 53-continued
| Ex | Str |
|---|---|
| 4 | 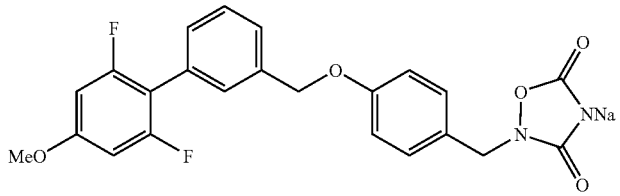 |
| 28 | 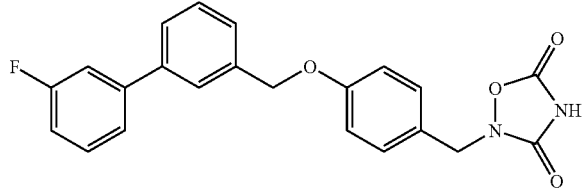 |
TABLE 54
| | |
|---|---|
| 29 | 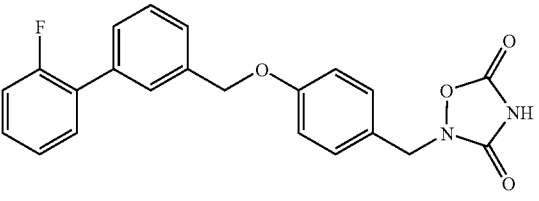 |
| 30 | 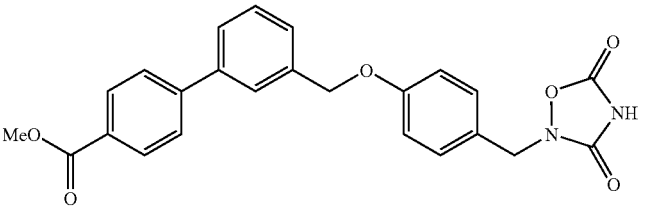 |
| 5 | 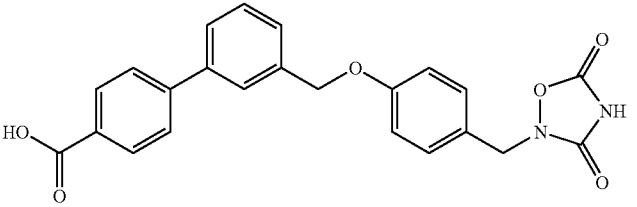 |
| 31 | 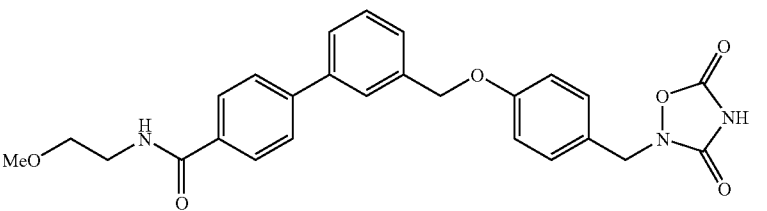 |
| 6 | 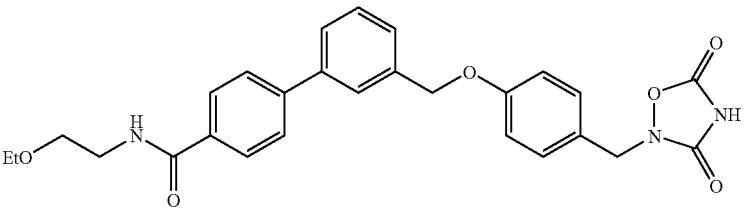 |

TABLE 54-continued
| 32 | 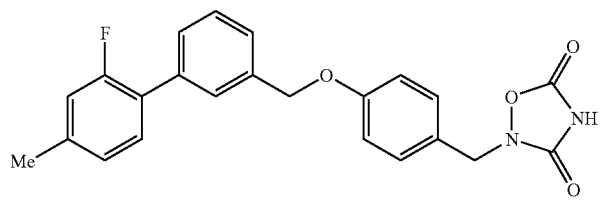 |
| --- | --- |
| 33 | 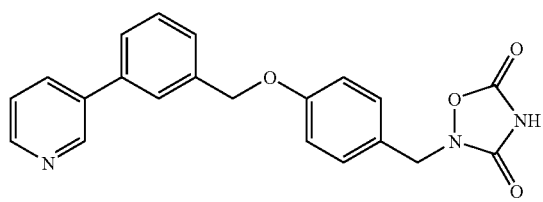 |
TABLE 55
| 8 | 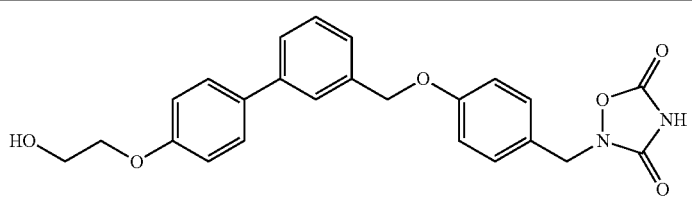 |
| --- | --- |
| 34 | 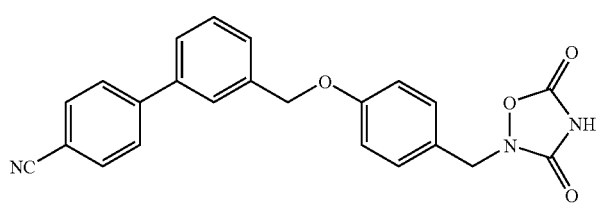 |
| 35 | 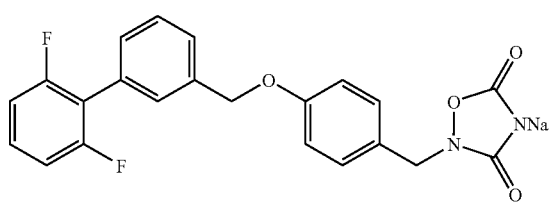 |
| 36 | 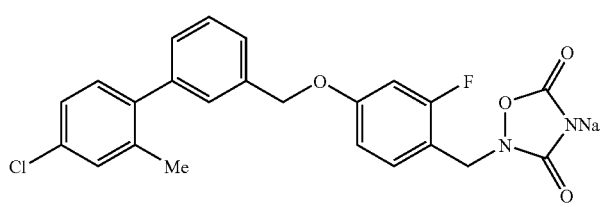 |
| 37 | 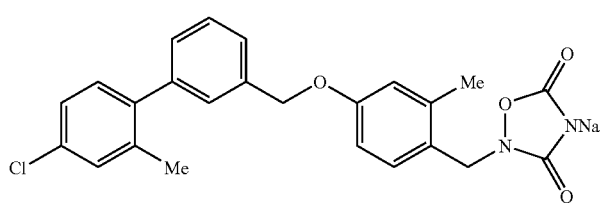 |

TABLE 55-continued
38 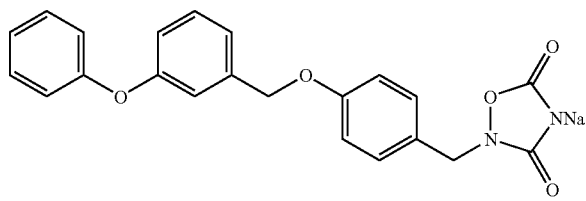
39 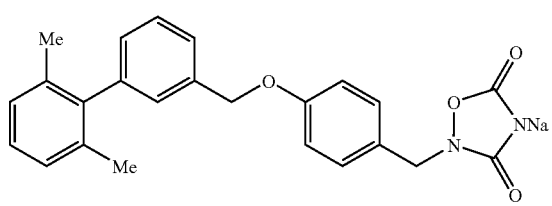
TABLE 56
40 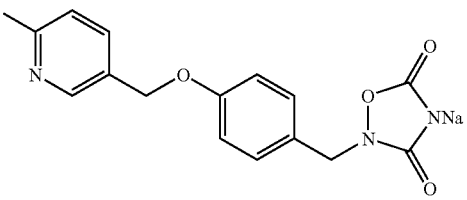
7 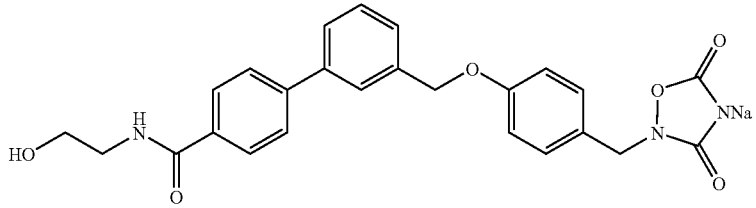
41 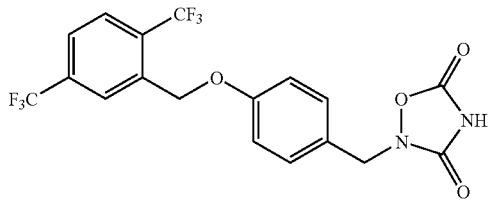
42 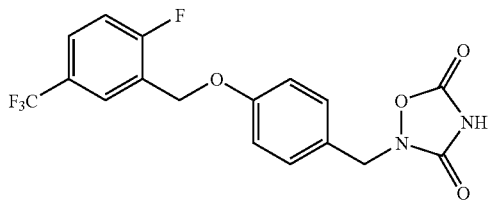
43 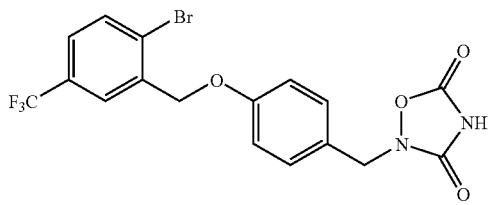

TABLE 56-continued
| 44 | 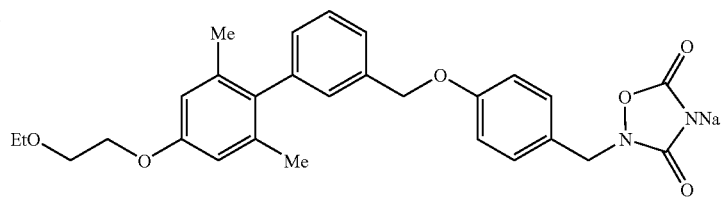 |
| 45 | 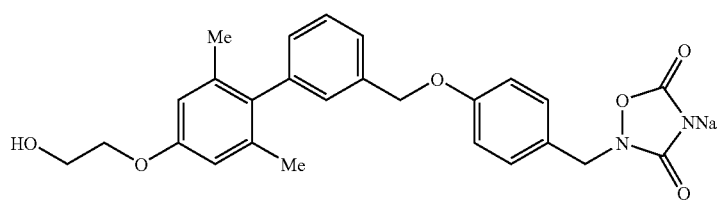 |
TABLE 57
| 46 | 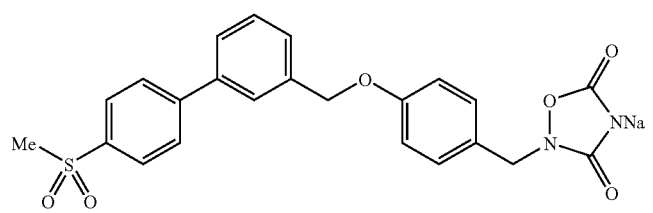 |
| 47 | 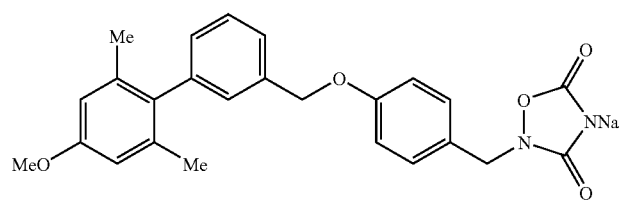 |
| 48 | 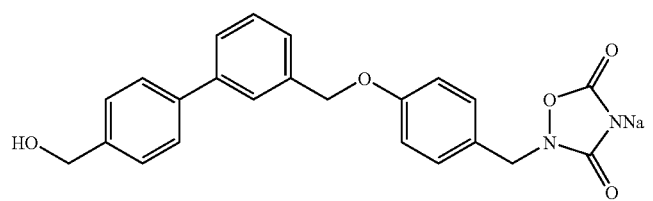 |
| 49 | 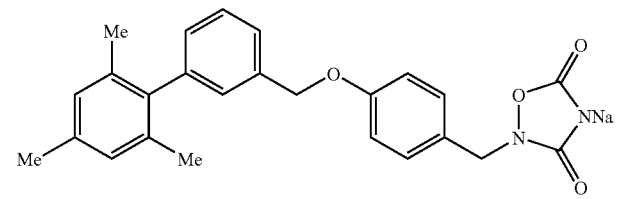 |
| 50 | 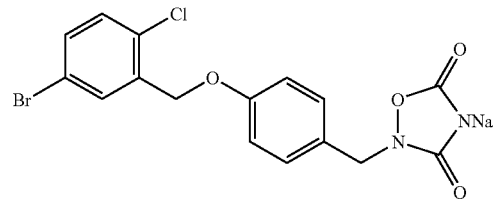 |

TABLE 57-continued
51 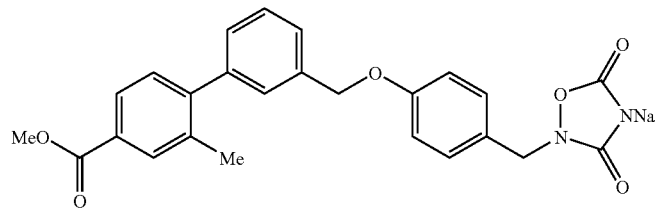
52 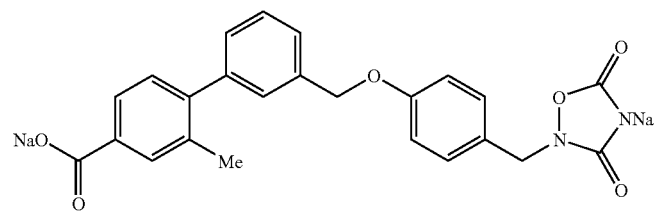
TABLE 58
10 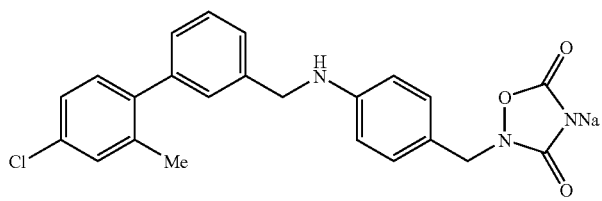
53 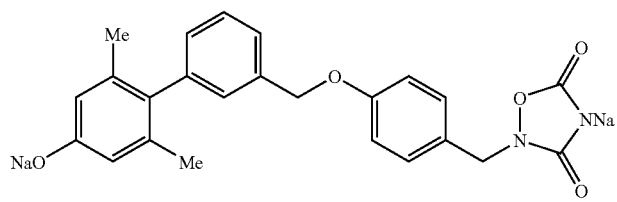
54 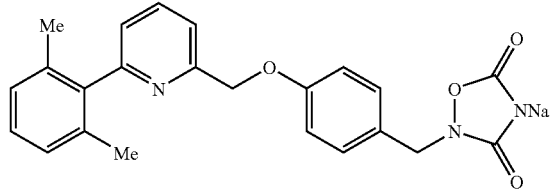
55 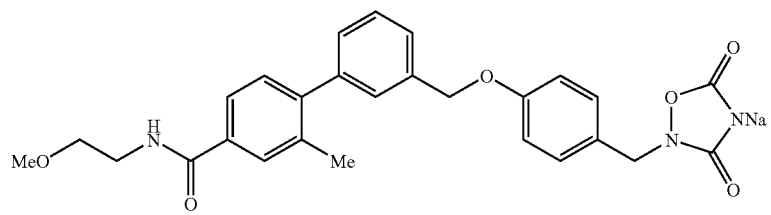
56 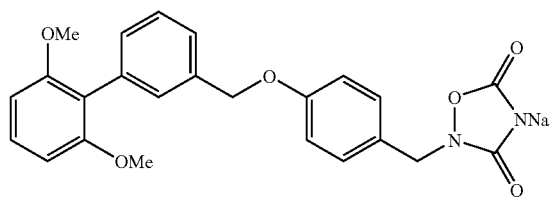

TABLE 58-continued
57 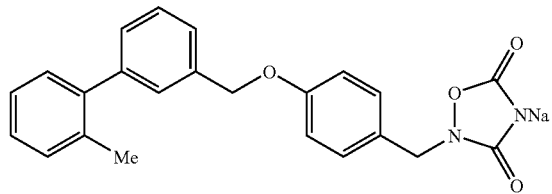
11 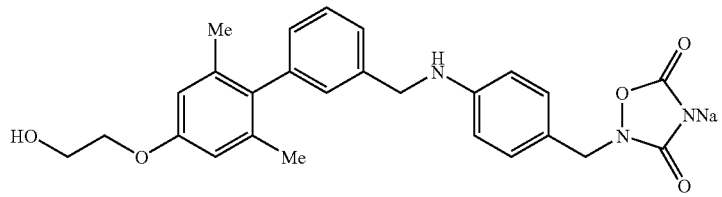
TABLE 59
58 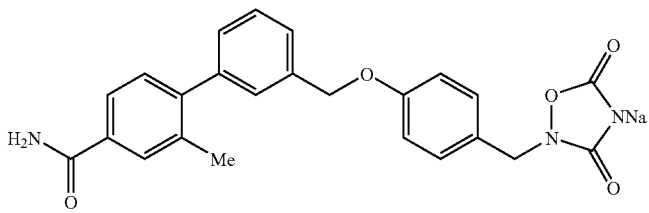
59 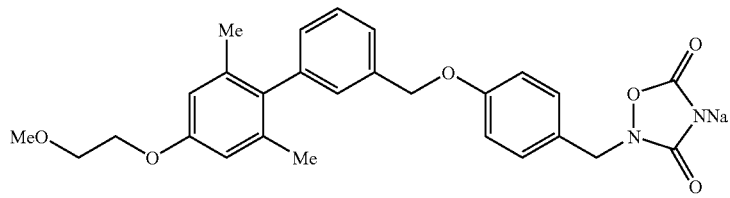
60 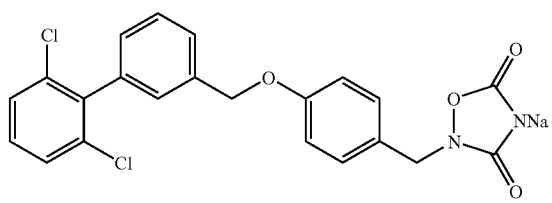
61 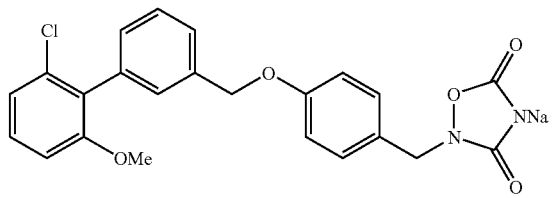
62 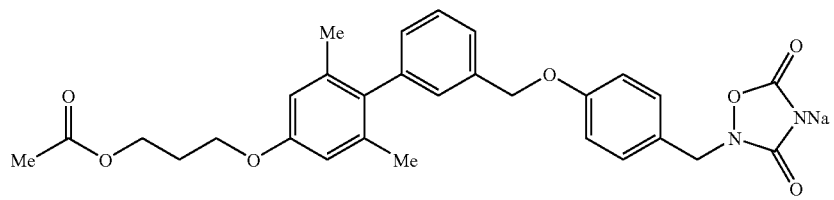

TABLE 59-continued
13 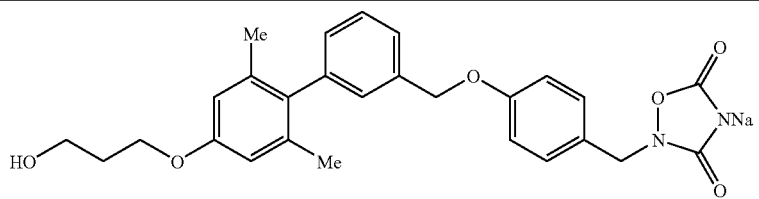
63 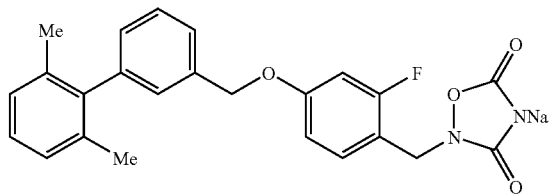
TABLE 60
64 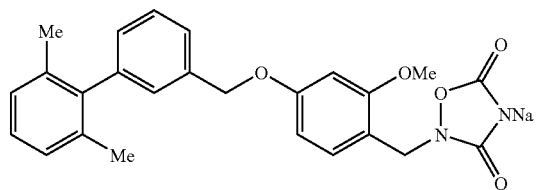
65 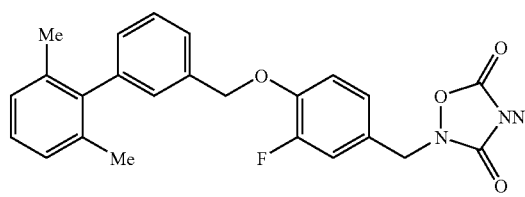
66 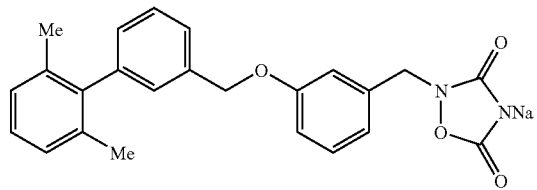
67 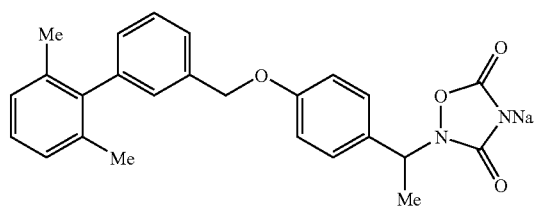
68 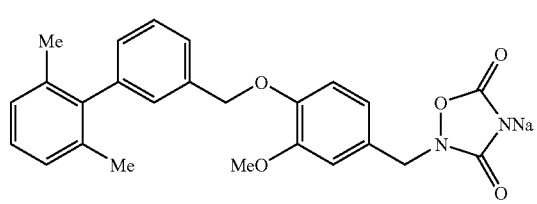
TABLE 60-continued
69 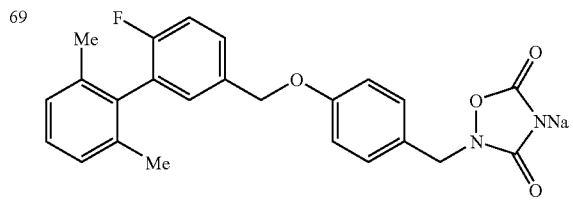
70 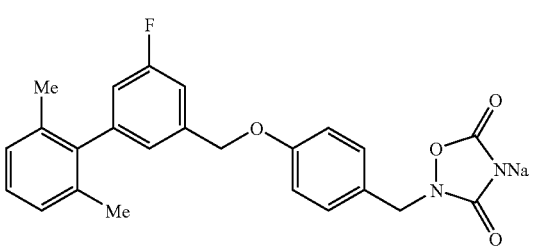
TABLE 61
71 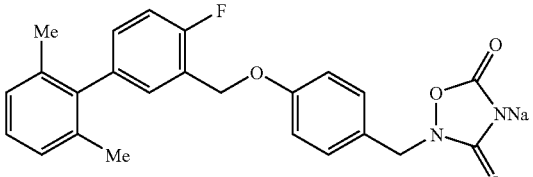
72 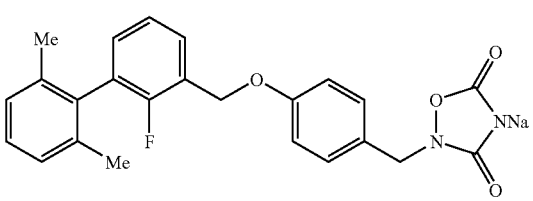
73 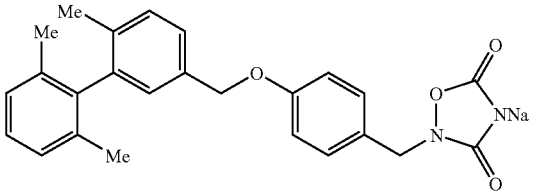

TABLE 61-continued
74 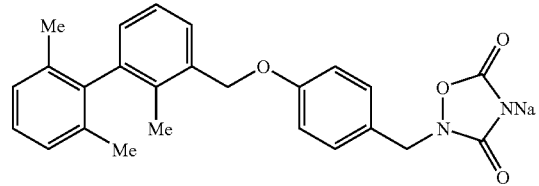
75 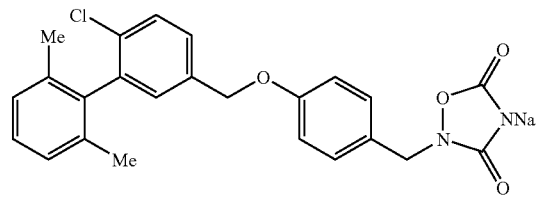
76 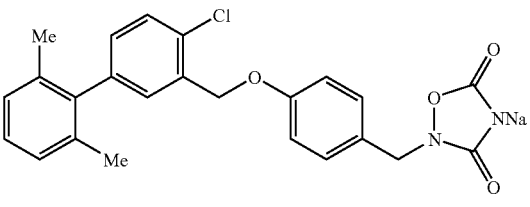
77 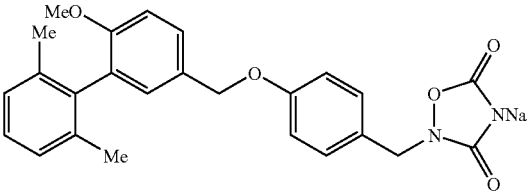
TABLE 62
78 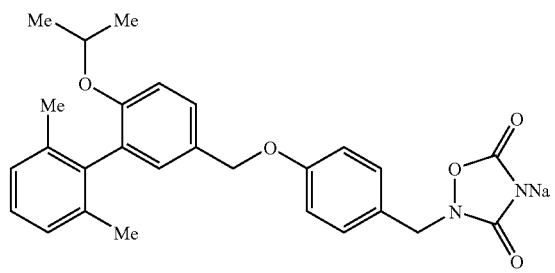
79 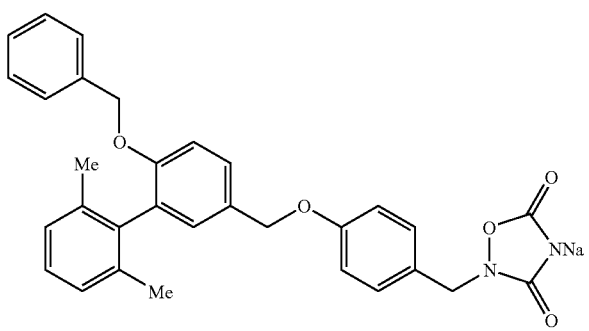
80 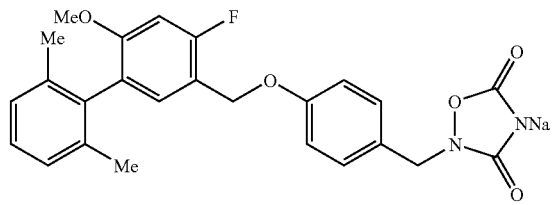
81 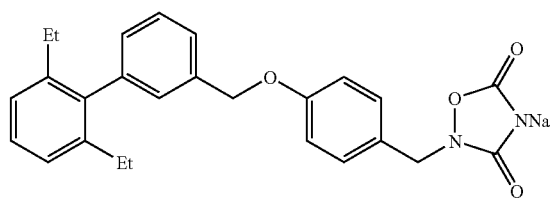

TABLE 62-continued
82
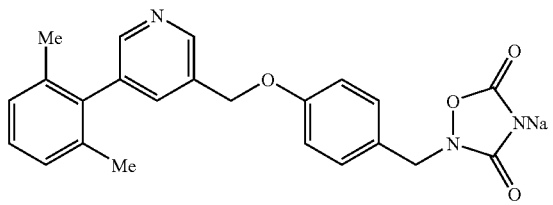
83
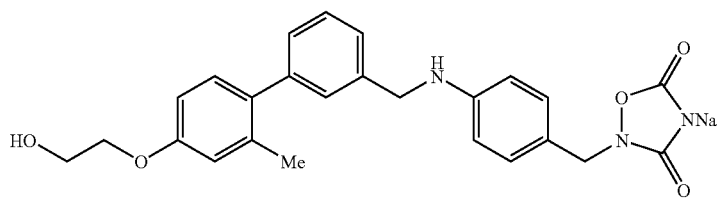
TABLE 63
84
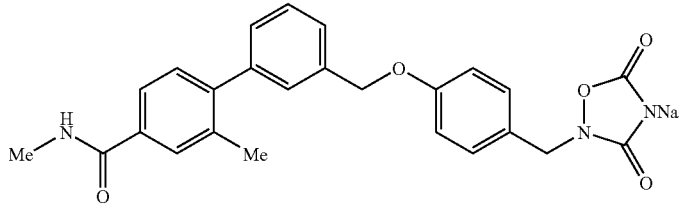
85
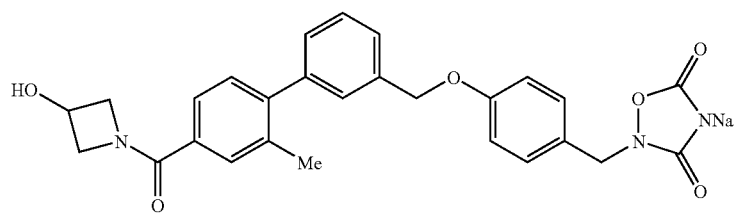
86
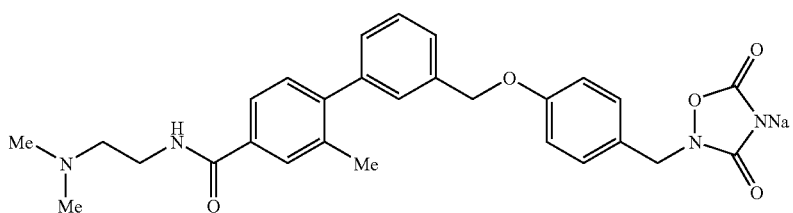
87
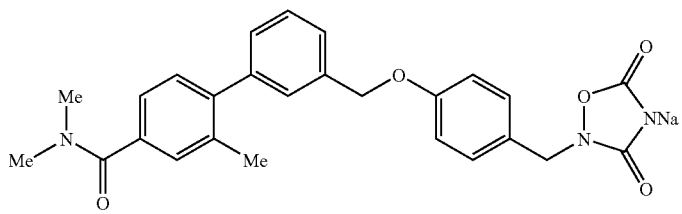
88
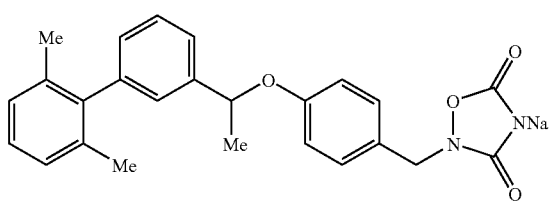

TABLE 63-continued
89 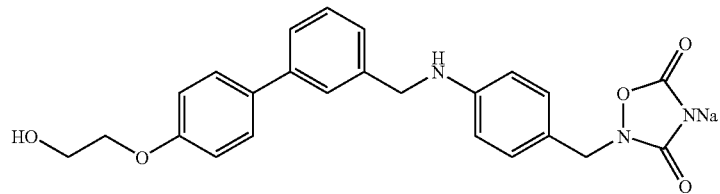
90 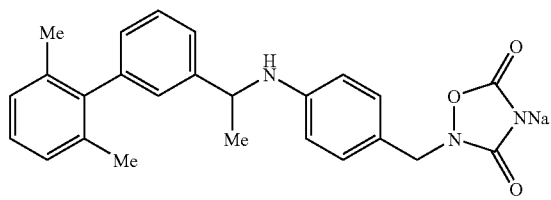
TABLE 64
91 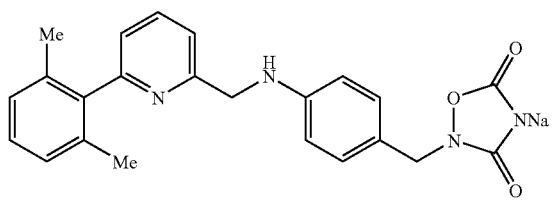
92 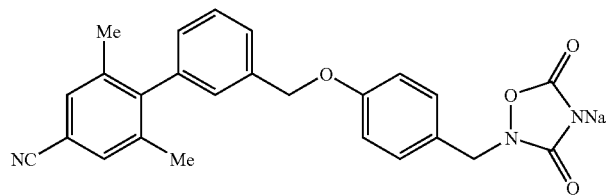
20 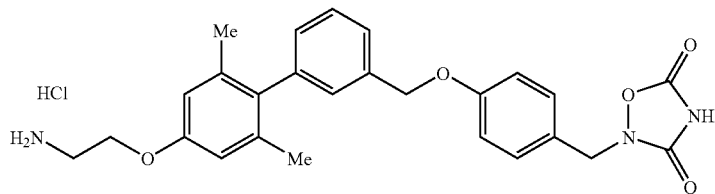
93 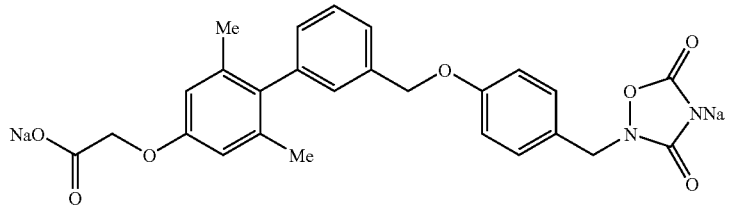
94 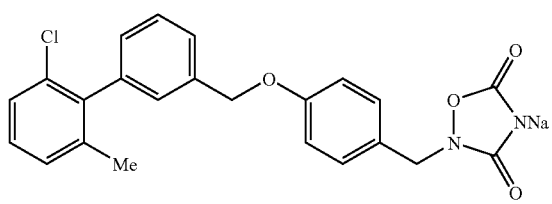

TABLE 64-continued
95
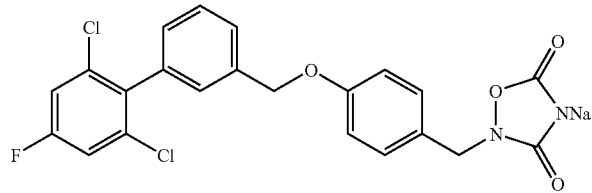
96
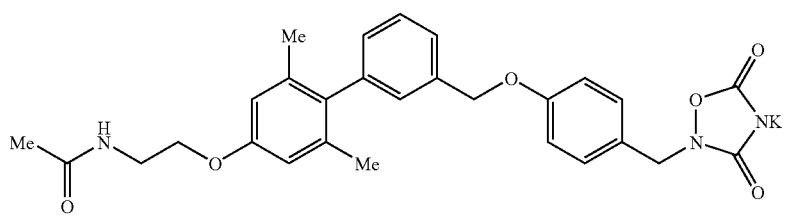
TABLE 65
15
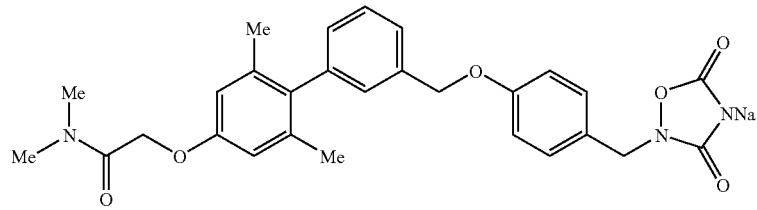
97
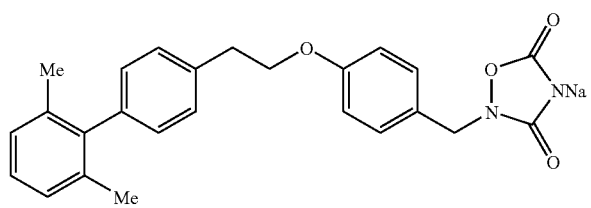
98
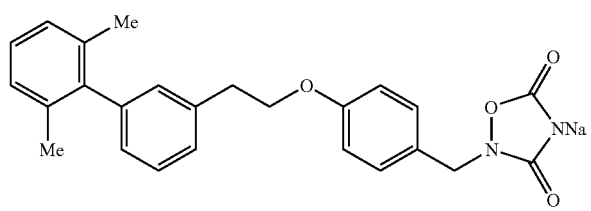
99
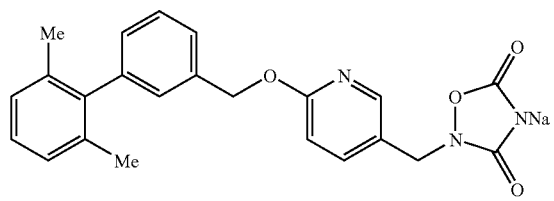
100
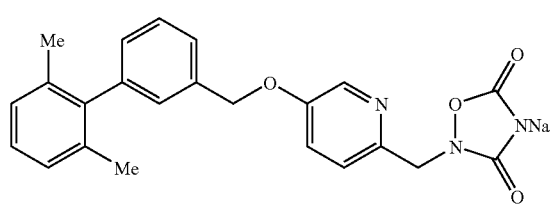

TABLE 65-continued
| | |
|---|---|
| 101 | 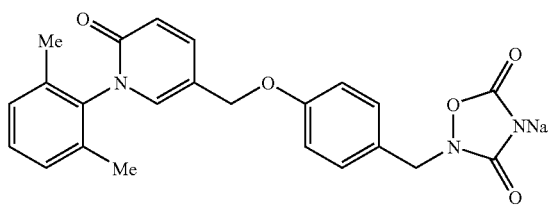 |
TABLE 66
| | |
|---|---|
| 102 | 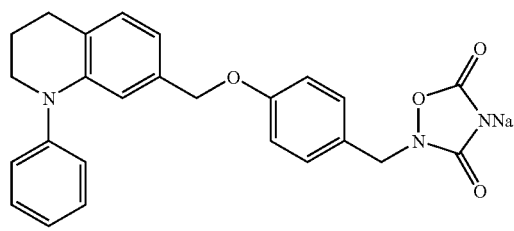 |
| 103 | 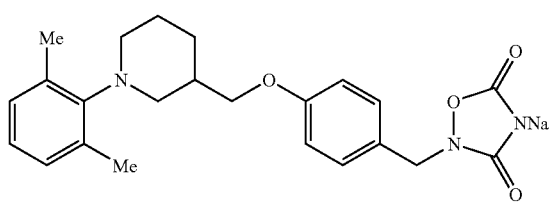 |
| 16 | 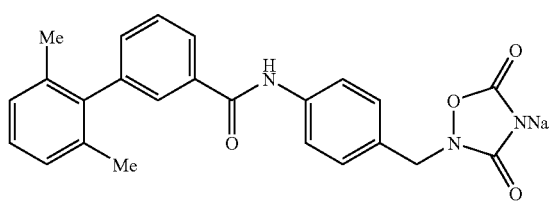 |
| 104 | 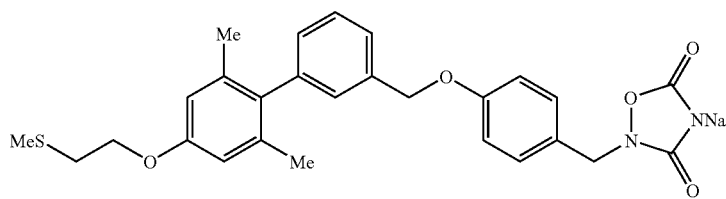 |
| 105 | 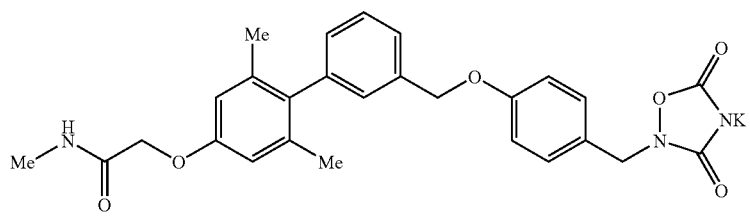 |
| 14 | 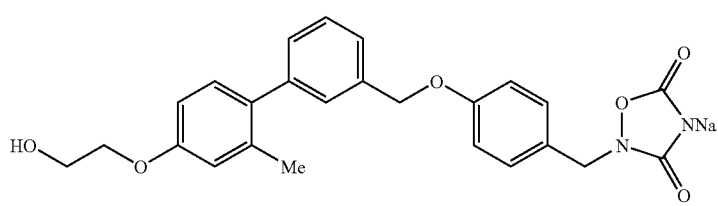 |

TABLE 66-continued
| 106 | 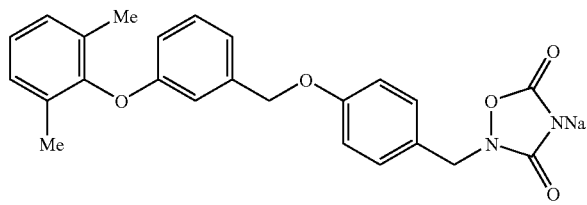 |
TABLE 67
| 107 | 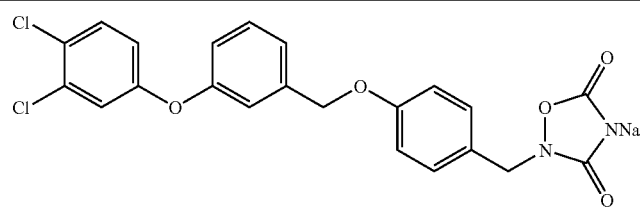 |
| 108 | 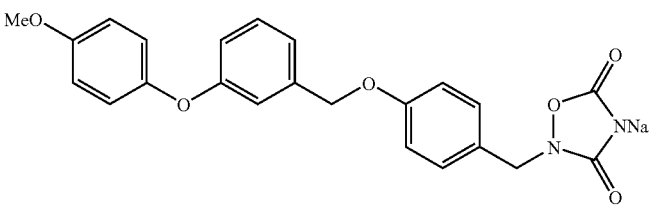 |
| 109 | 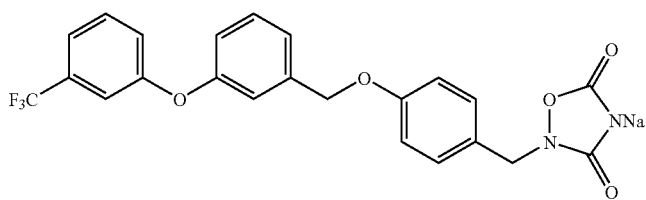 |
| 110 | 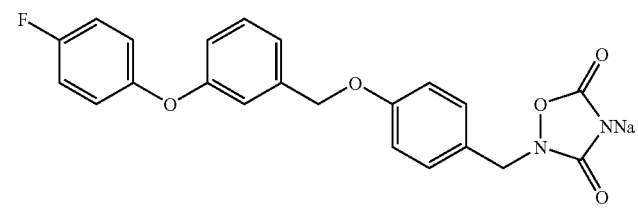 |
| 111 | 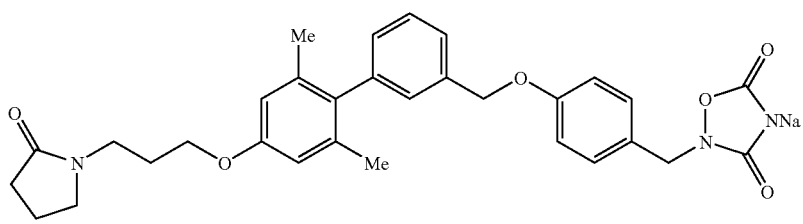 |
| 112 | 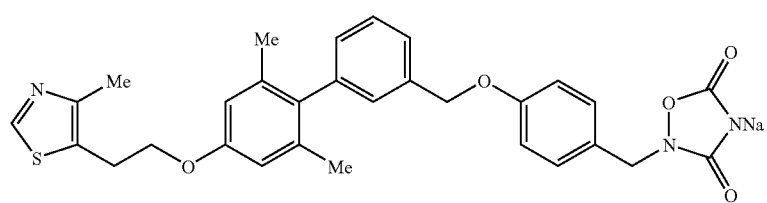 |

TABLE 67-continued
113
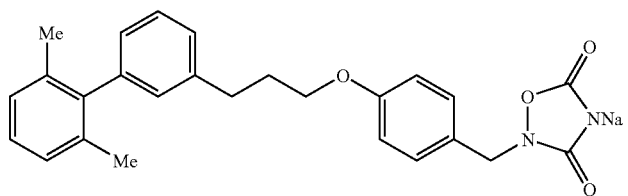
TABLE 68
114
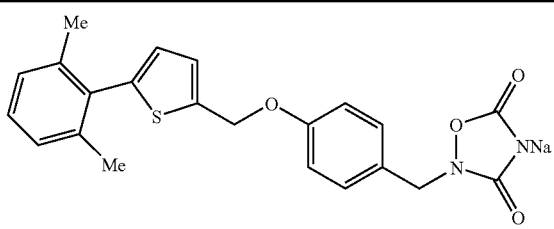
115
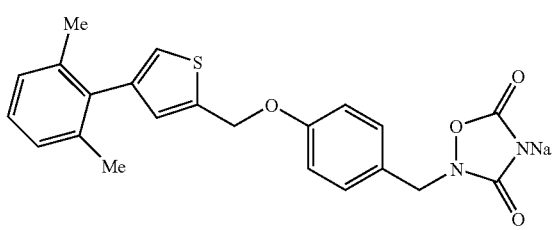
116
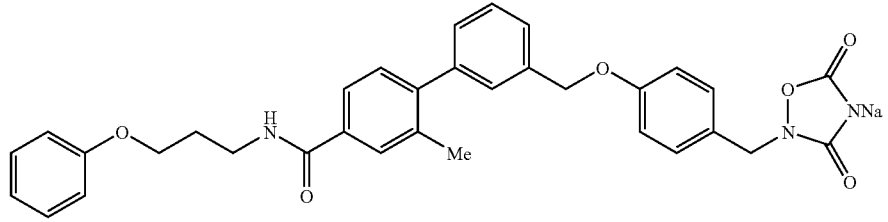
117
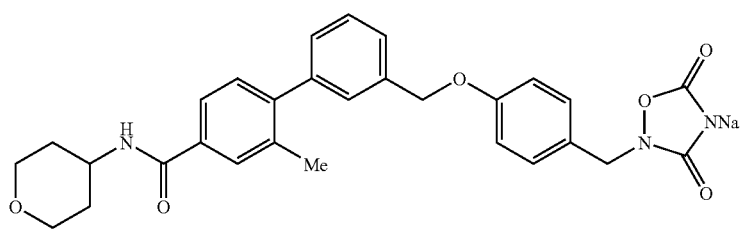
118
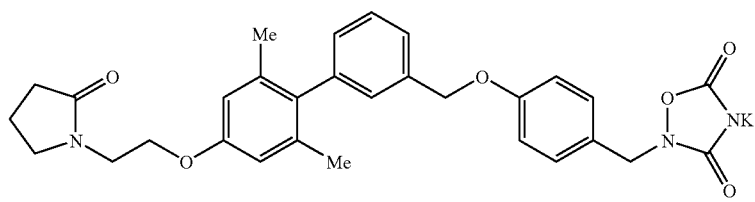
119
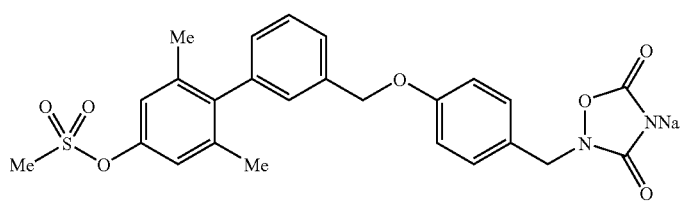

TABLE 68-continued
120 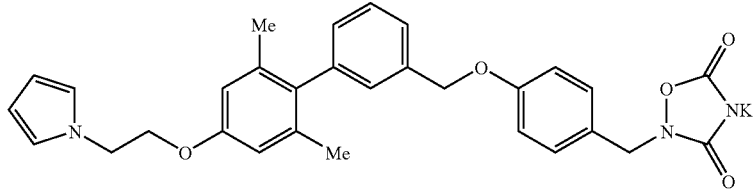
TABLE 69
121 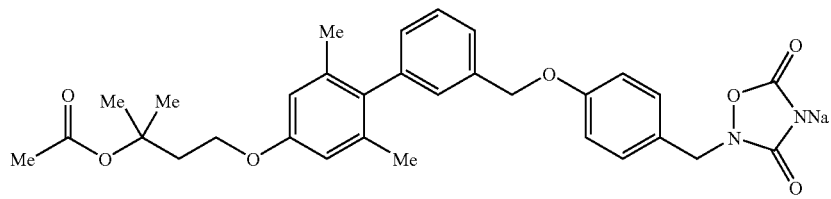
122 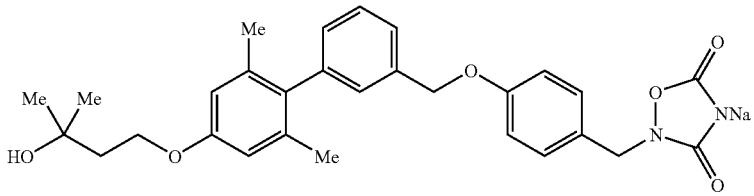
123 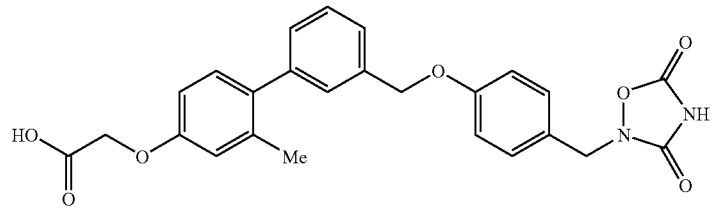
124 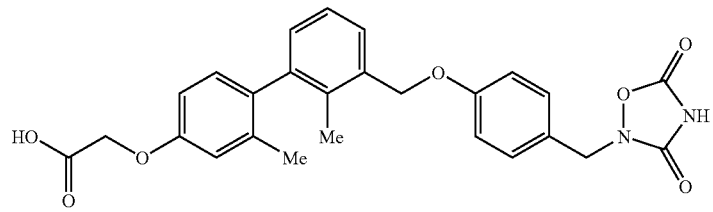
17 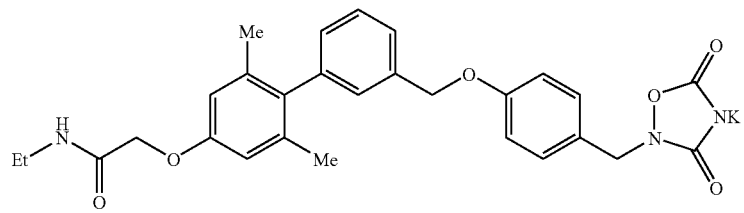
125 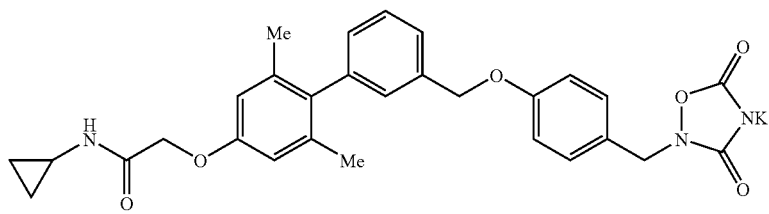

TABLE 69-continued
| 126 | 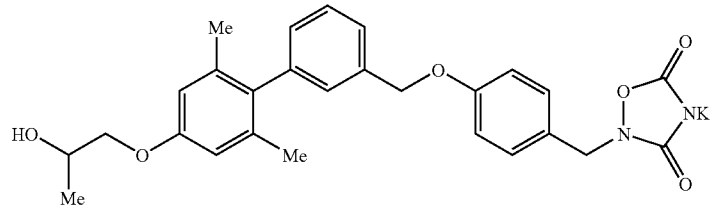 |
TABLE 70
| 127 | 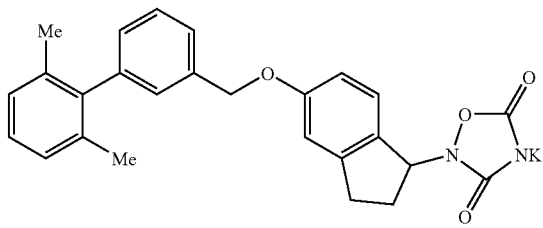 |
| 128 | 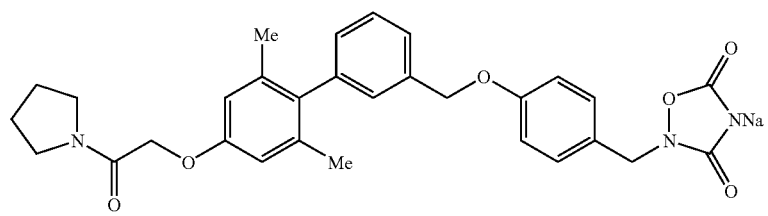 |
| 129 | 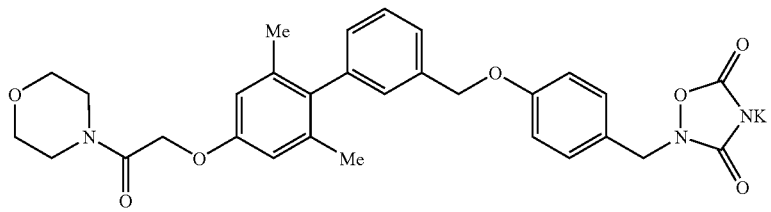 |
| 130 | 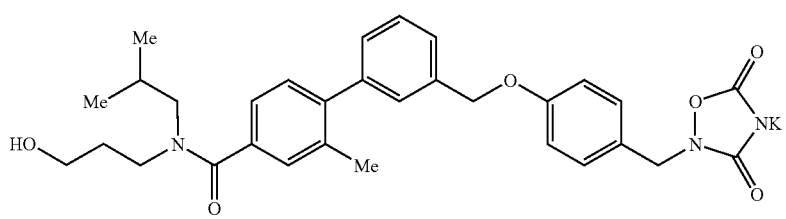 |
| 131 | 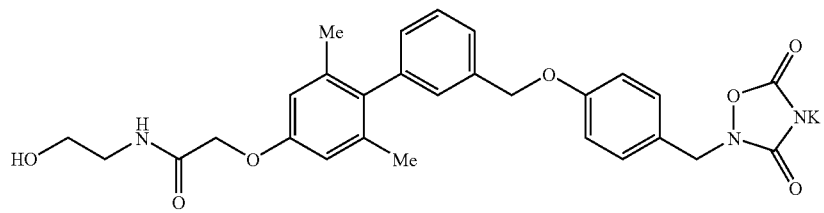 |
| 132 | 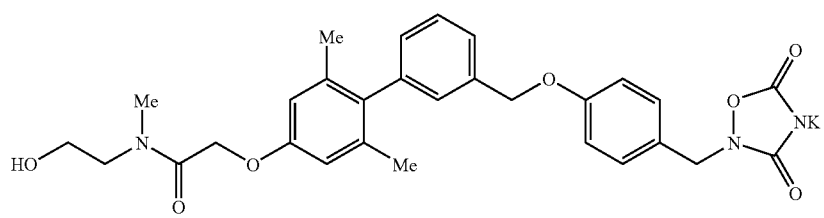 |

TABLE 70-continued
18
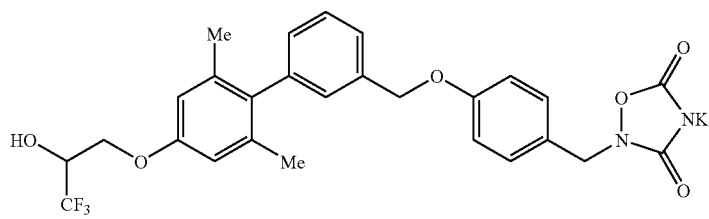
TABLE 71
133
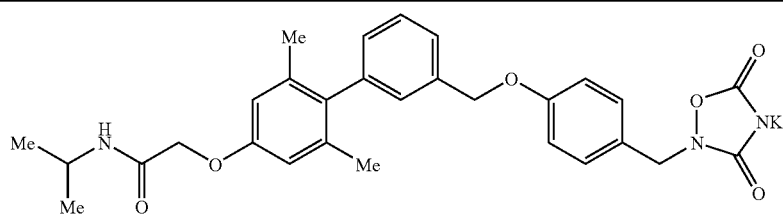
134
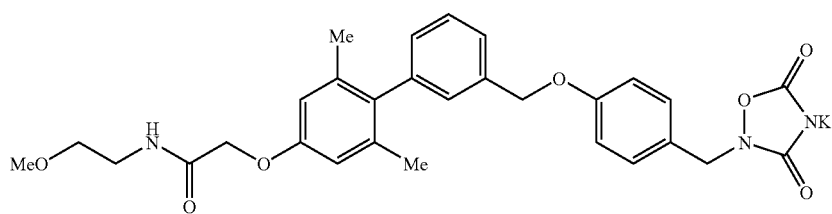
135
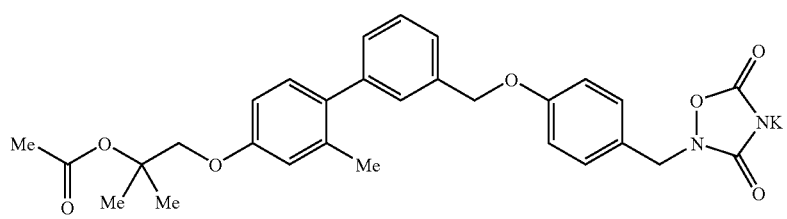
136
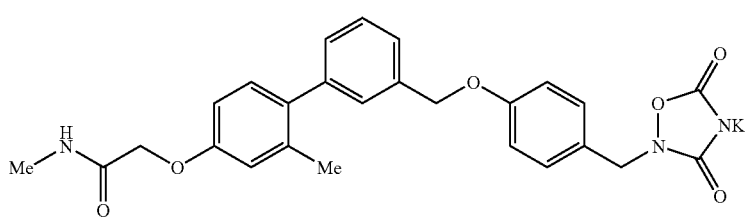
137
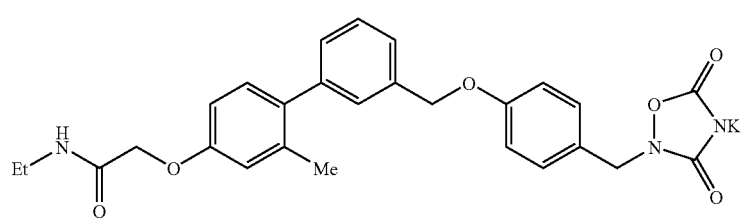
138
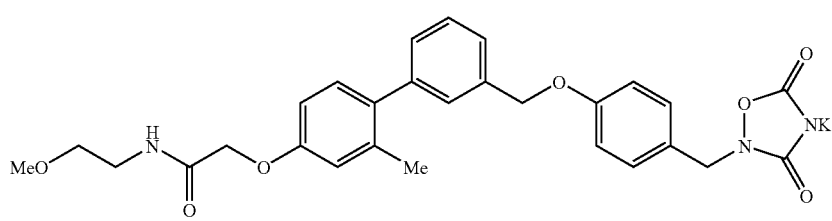

TABLE 71-continued
139
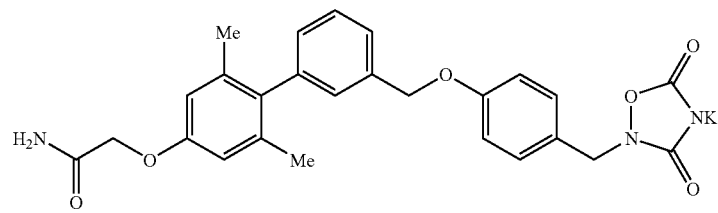
TABLE 72
140
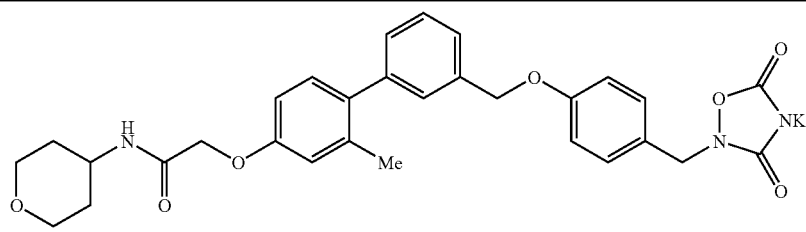
141
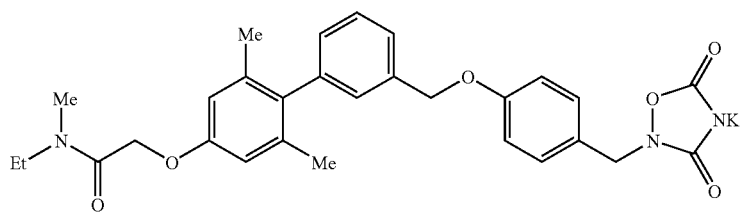
142
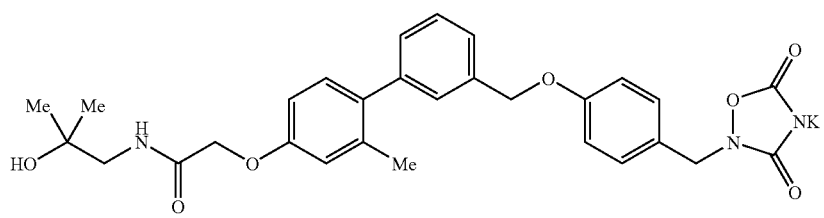
143
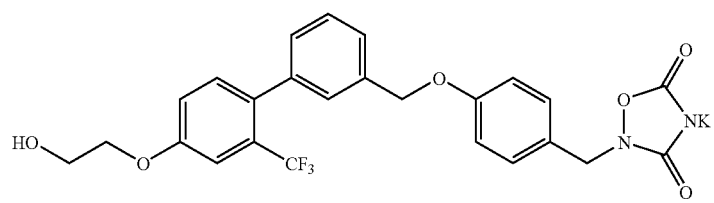
144
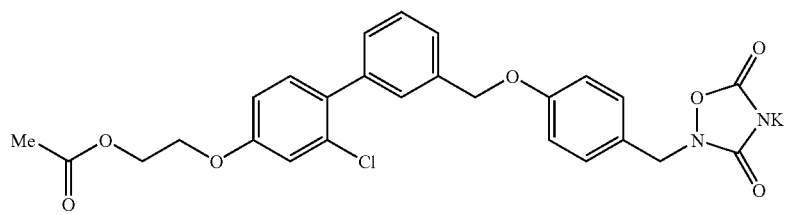
145
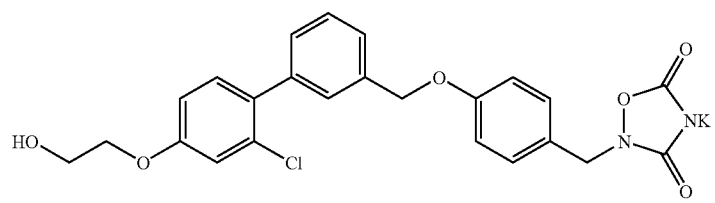

TABLE 72-continued
146
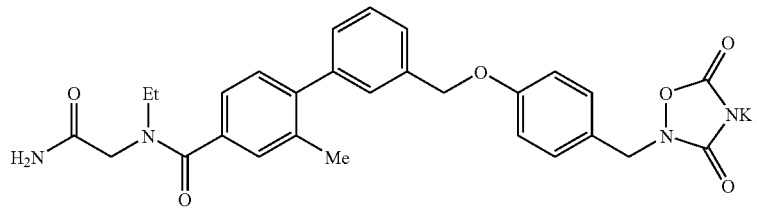
147
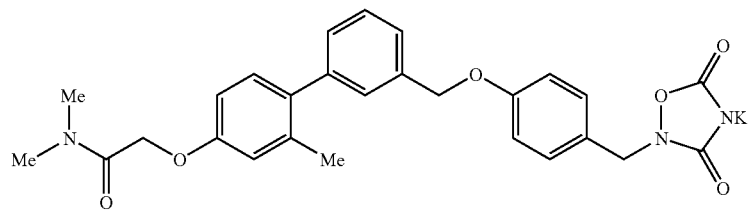
TABLE 73
148
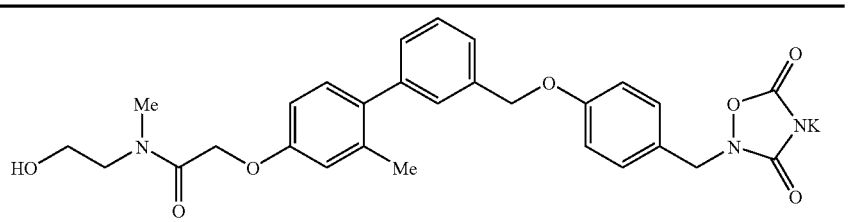
149
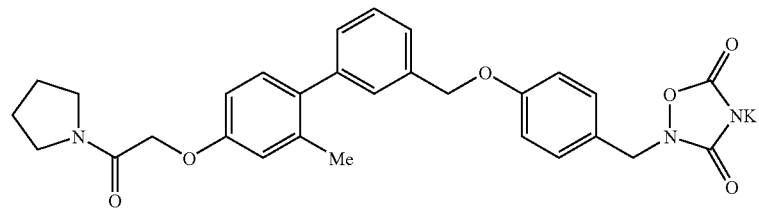
150
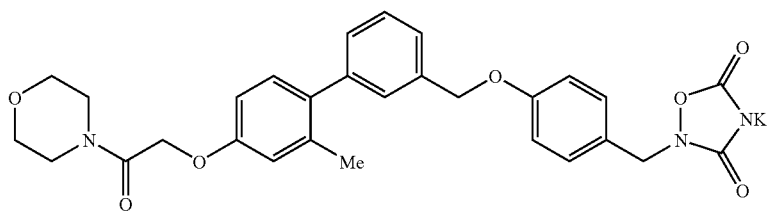
151
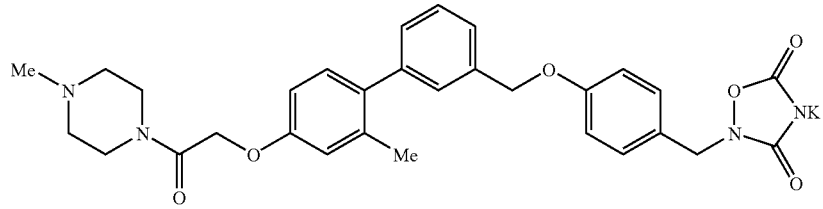
152
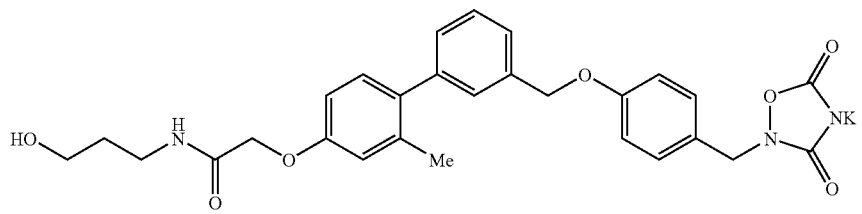

TABLE 73-continued
153 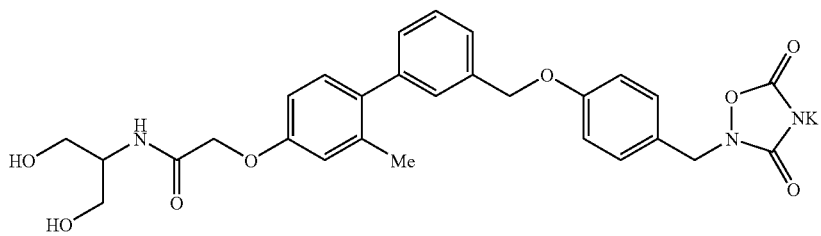
154 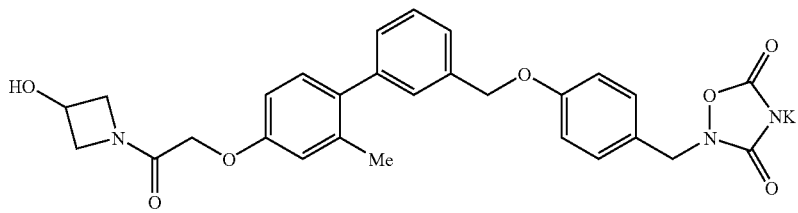
155 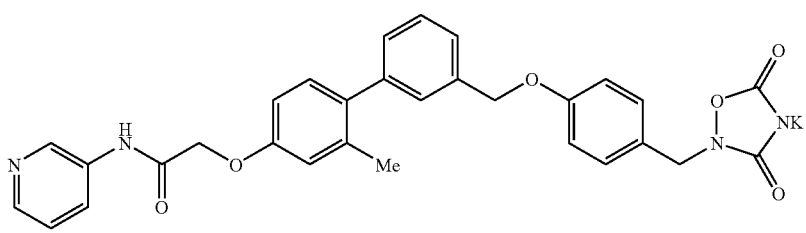
TABLE 74
156 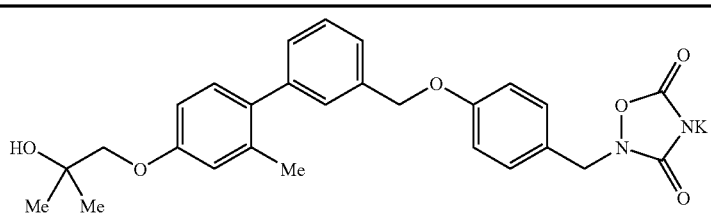
157 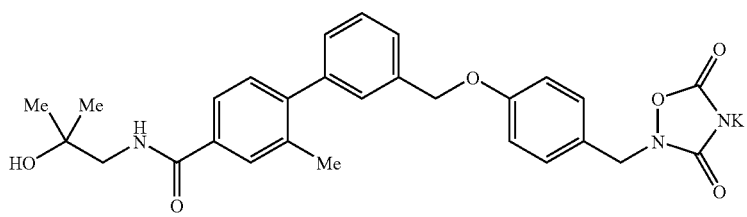
19 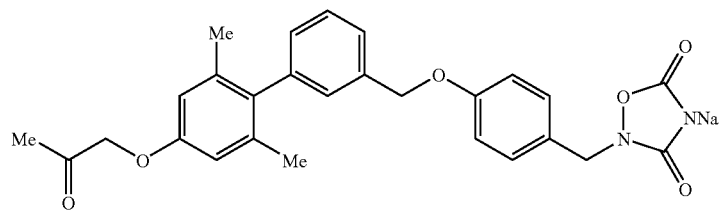
158 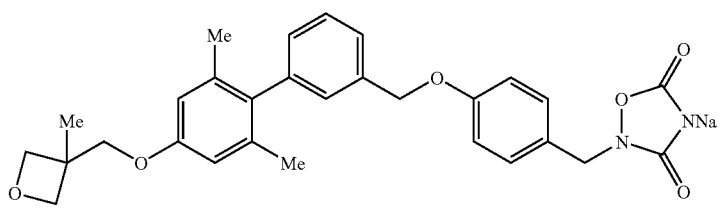

TABLE 74-continued
159 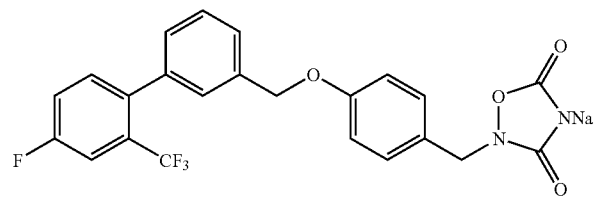
160 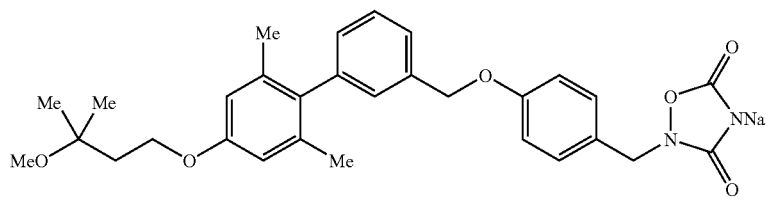
161 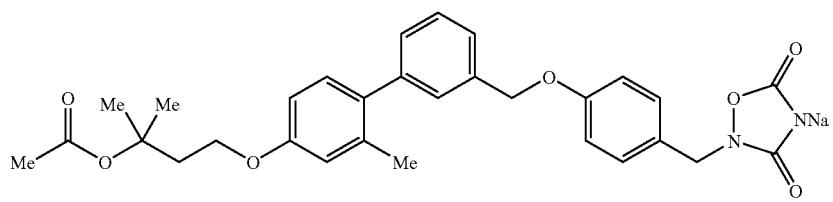
162 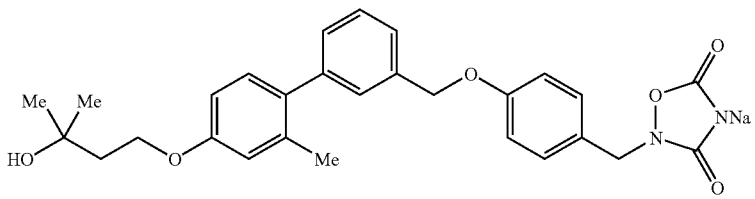
TABLE 75
163 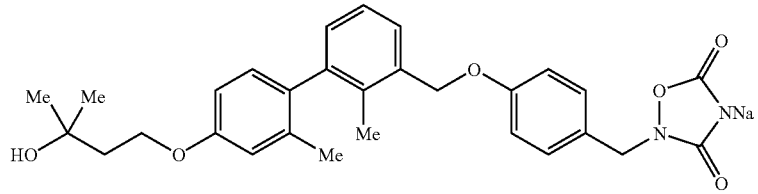
164 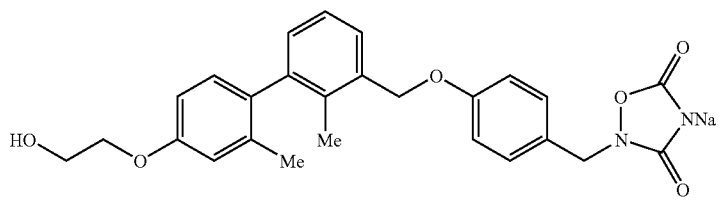
165 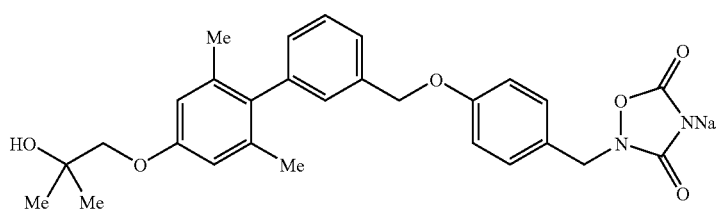

TABLE 75-continued
166
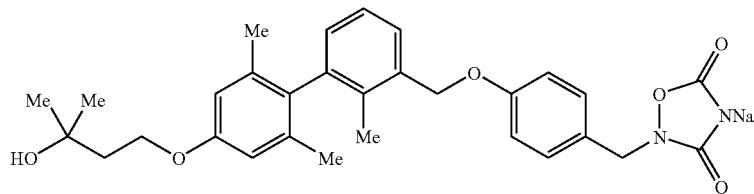
167
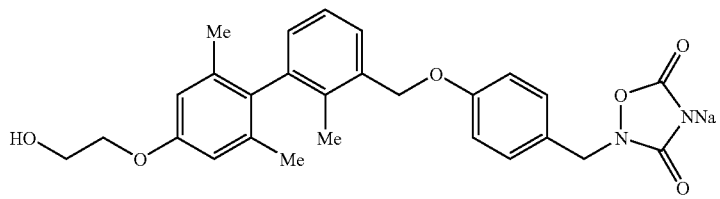
168
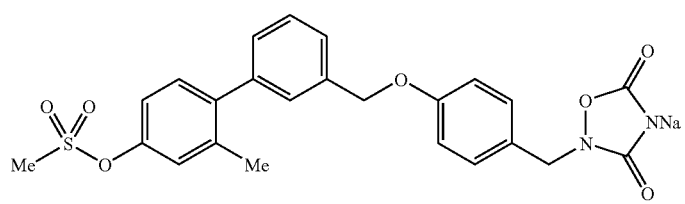
169
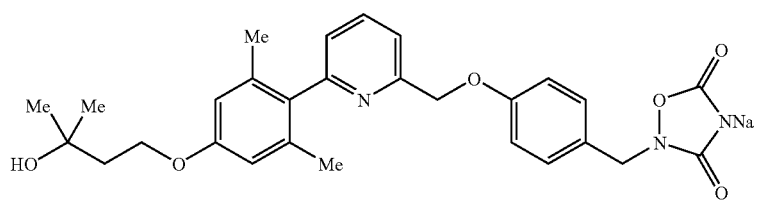
170
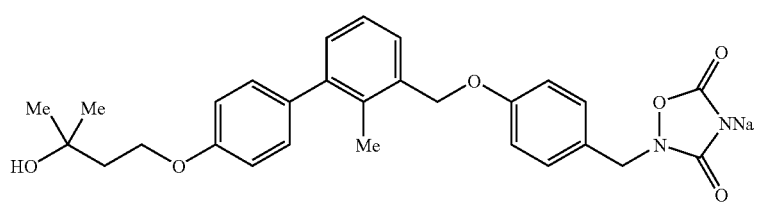
TABLE 76
171
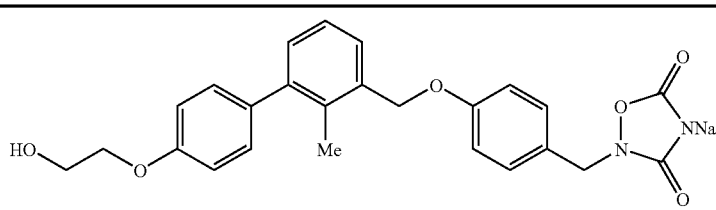
172
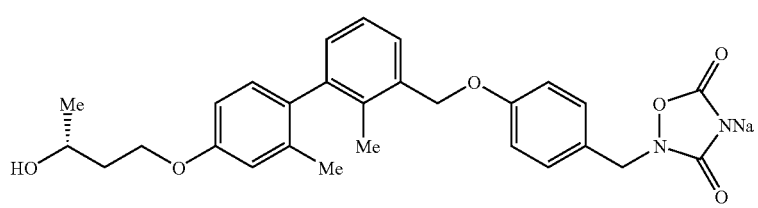

TABLE 76-continued
173 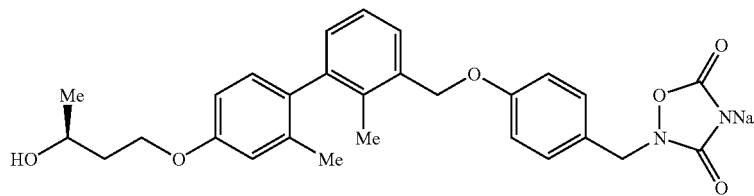
174 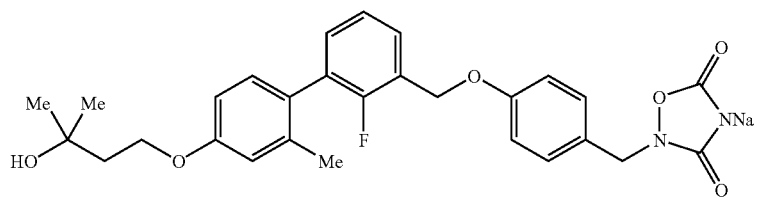
12 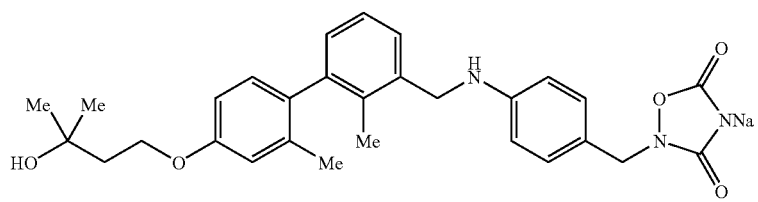
175 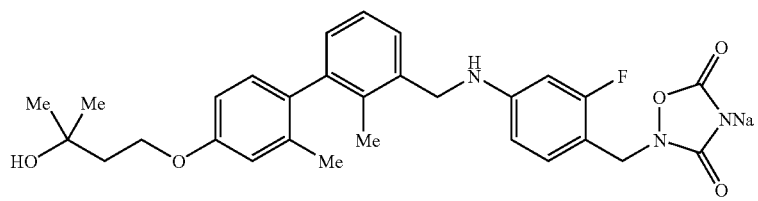
176 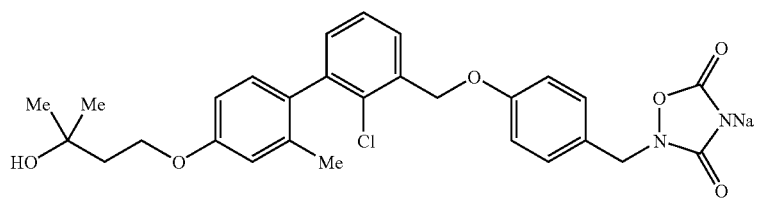
TABLE 77
177 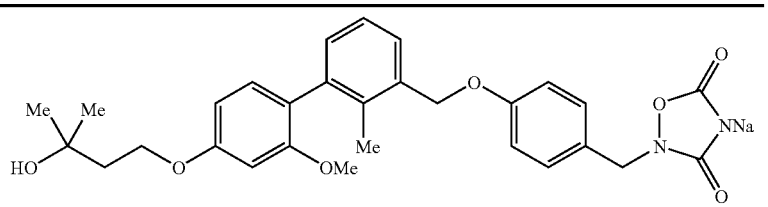
178 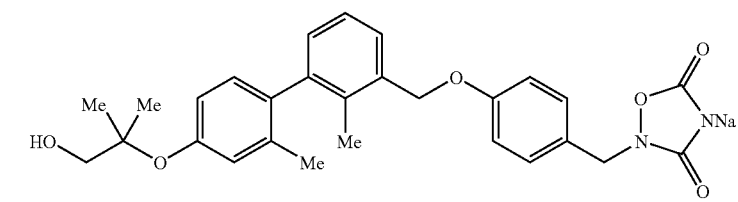

TABLE 77-continued
| | |
|---|---|
| 179 | 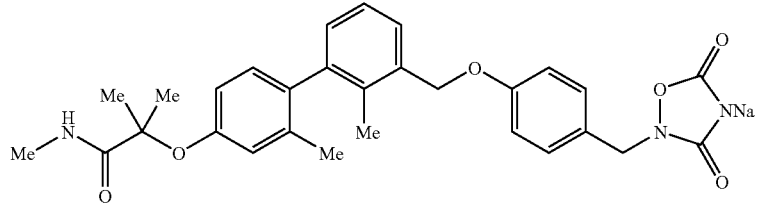 |
| 21 | 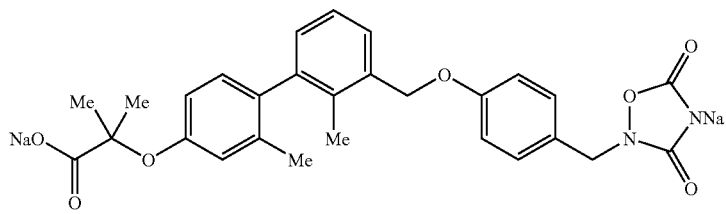 |
| 180 | 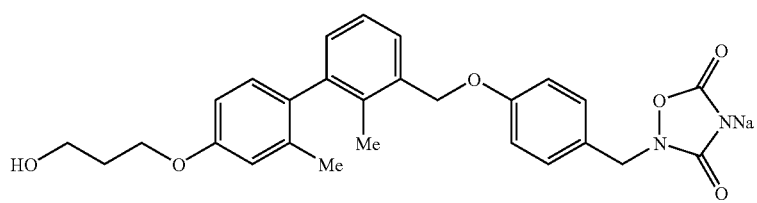 |
| 181 | 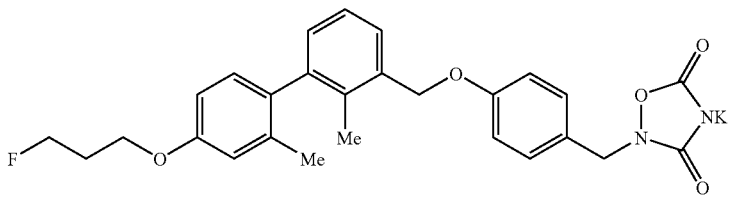 |
| 182 | 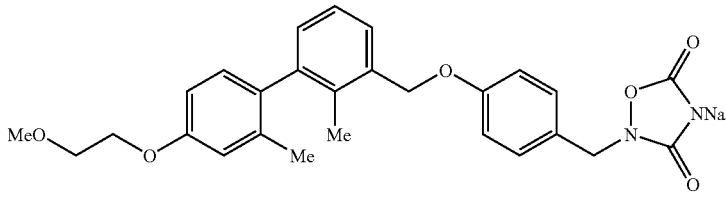 |
TABLE 78
| | |
|---|---|
| 183 | 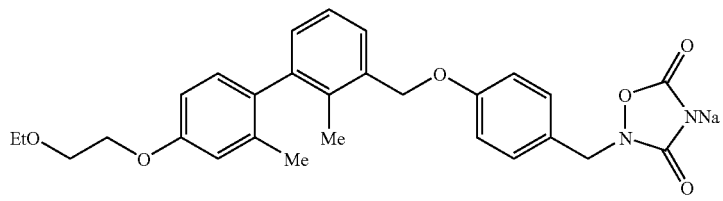 |
| 184 | 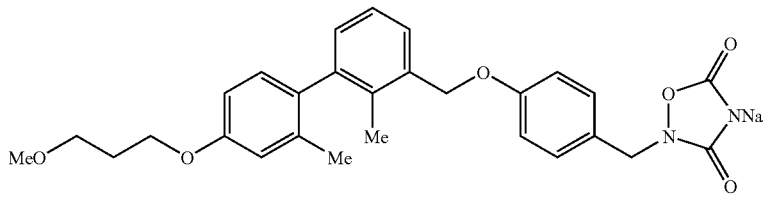 |

TABLE 78-continued
185
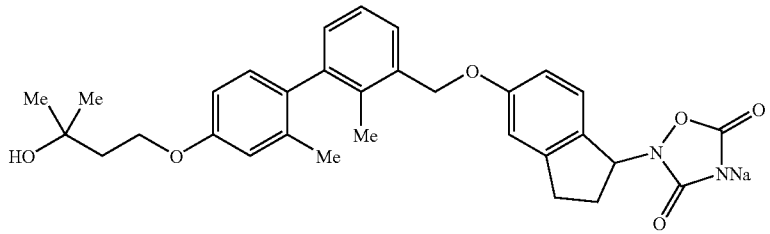
186
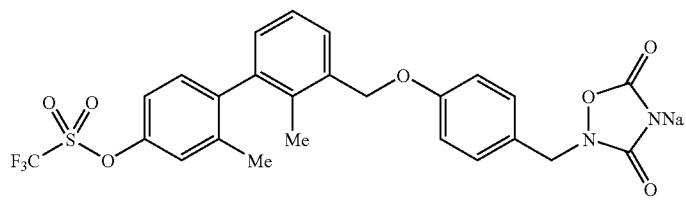
187
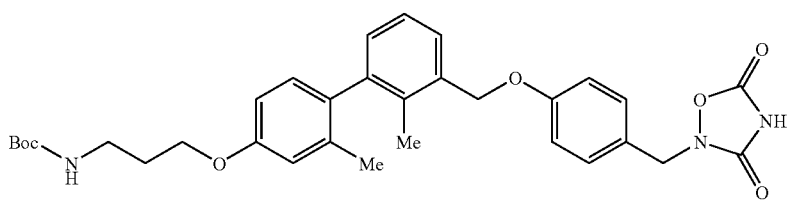
22
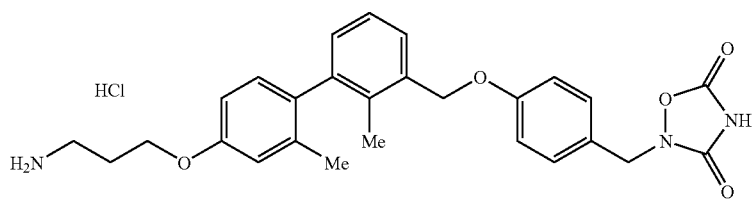
188
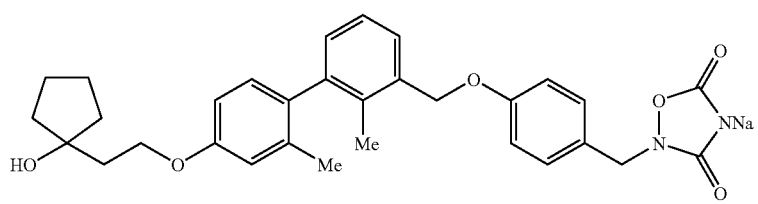
TABLE 79
189
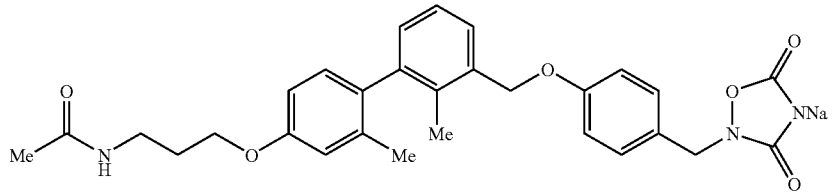
190
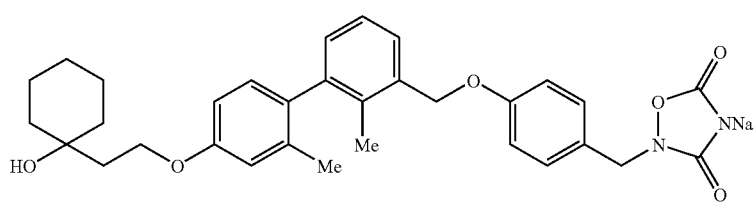

TABLE 79-continued
| | |
|---|---|
| 191 | 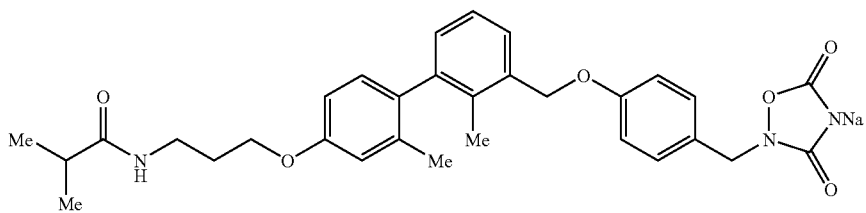 |
| 192 | 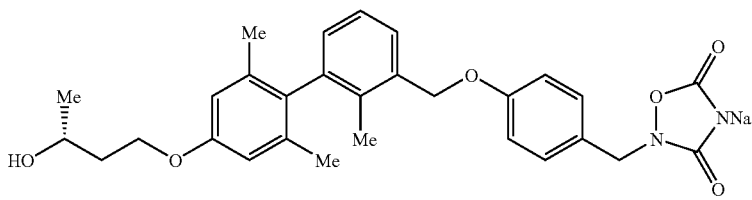 |
| 193 | 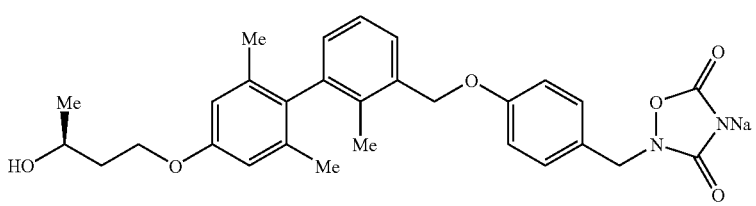 |
| 194 | 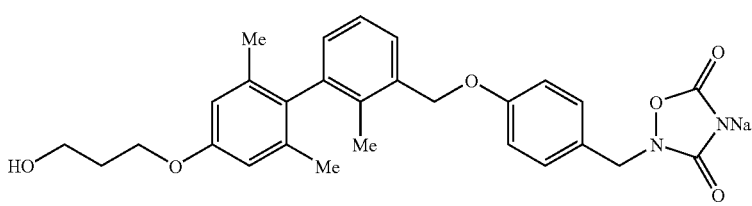 |
| 195 | 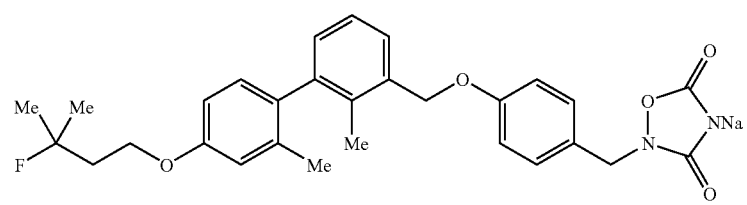 |
TABLE 80
| | |
|---|---|
| 196 | 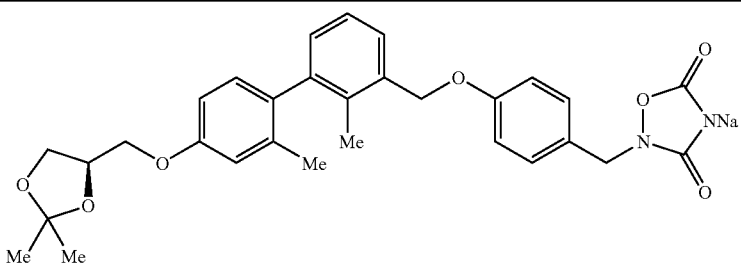 |
| 23 | 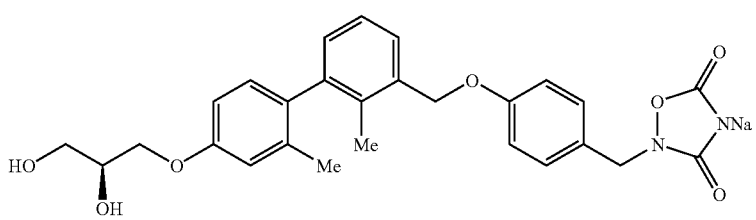 |

TABLE 80-continued
| | |
|---|---|
| 197 | 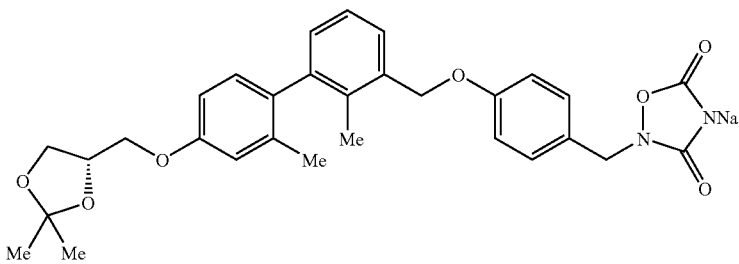 |
| 198 | 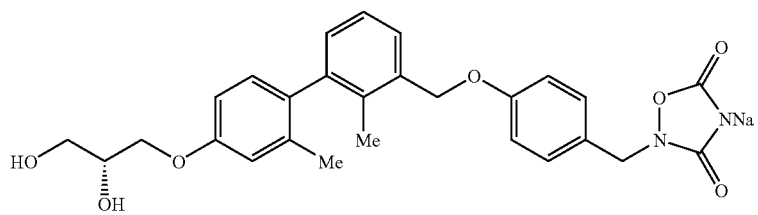 |
| 199 | 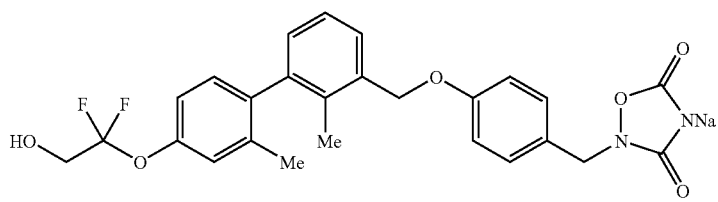 |
| 200 | 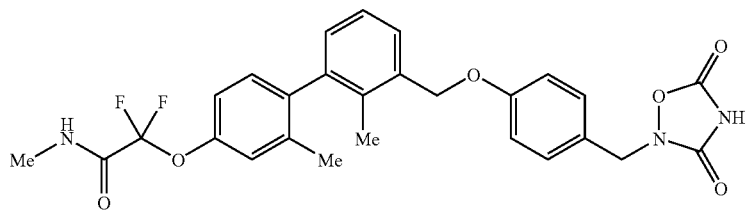 |
| 24 | 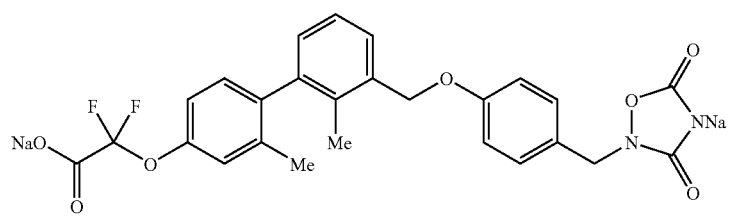 |
TABLE 81
| | |
|---|---|
| 201 | 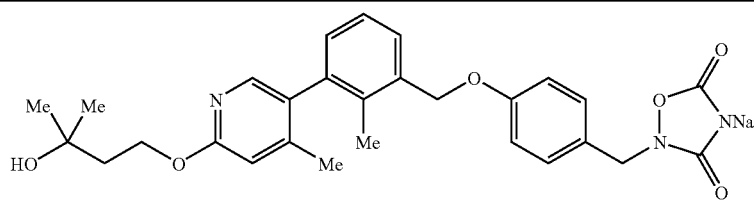 |
| 202 | 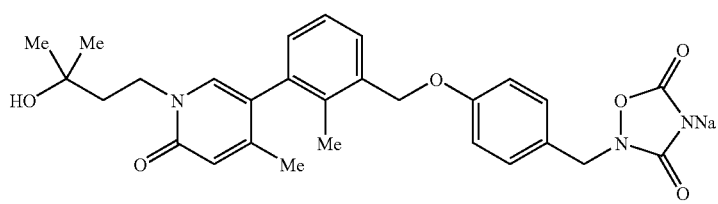 |

TABLE 81-continued
| | |
|---|---|
| 203 | 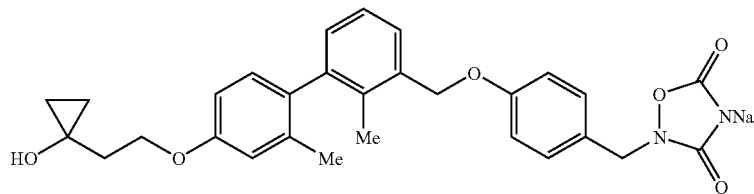 |
| 204 | 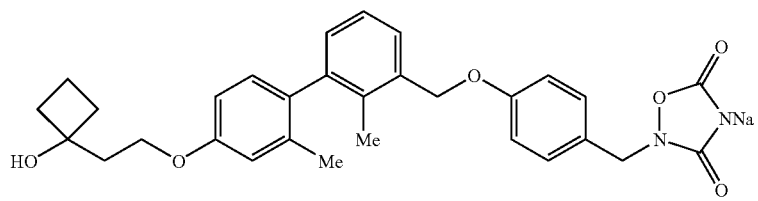 |
| 205 | 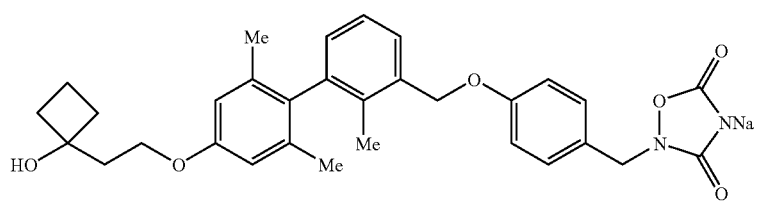 |
| 206 | 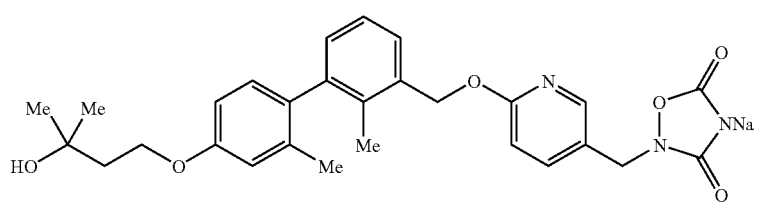 |
| 207 | 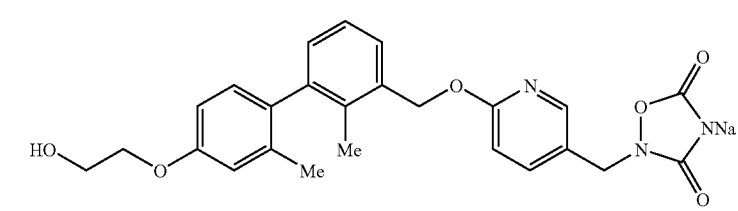 |
TABLE 82
| | |
|---|---|
| 208 | 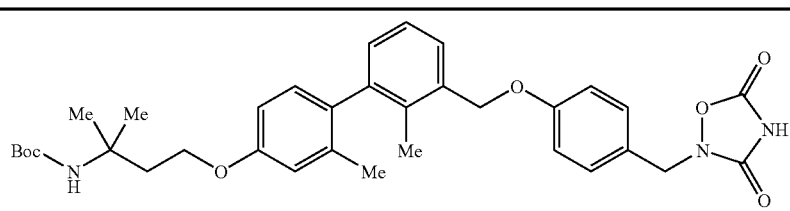 |
| 209 | 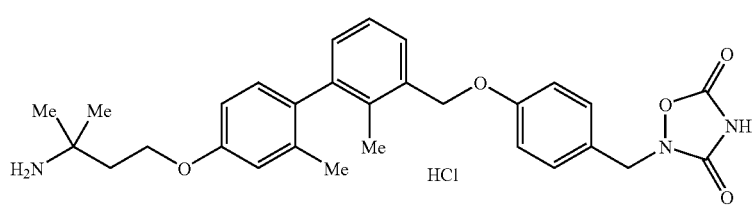 |

TABLE 82-continued
210
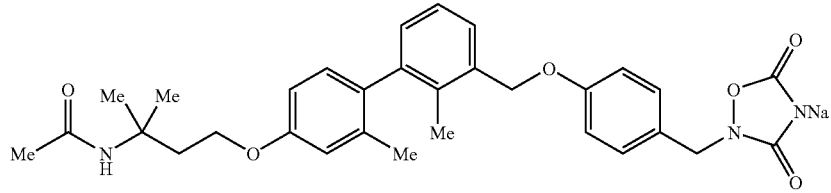
211
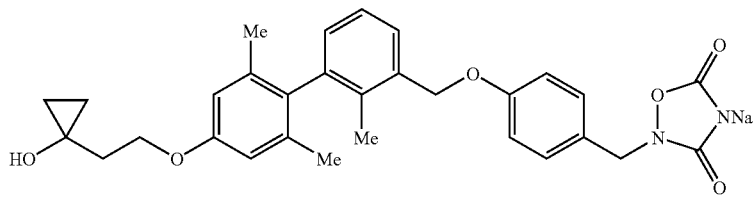
212
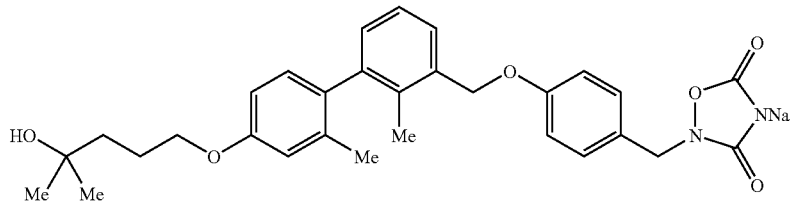
213
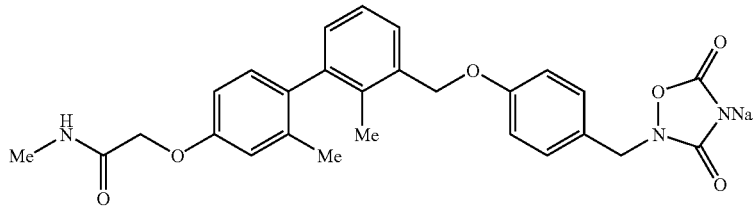
214
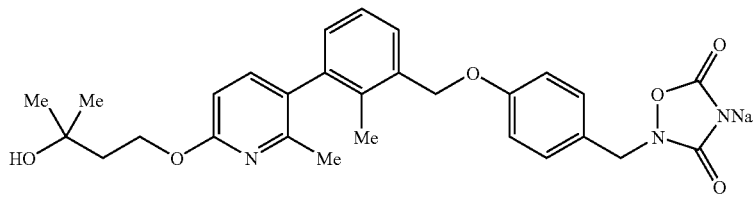
TABLE 83
215
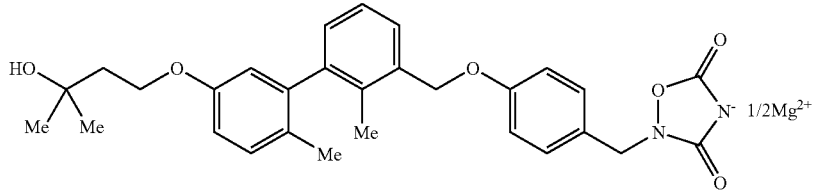
216
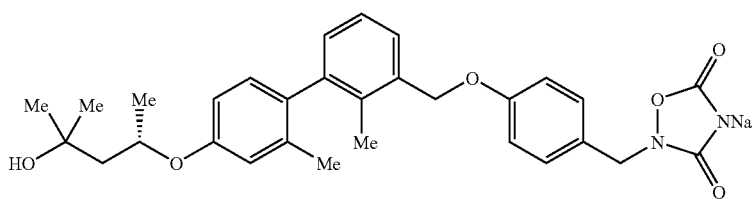

TABLE 83-continued
217 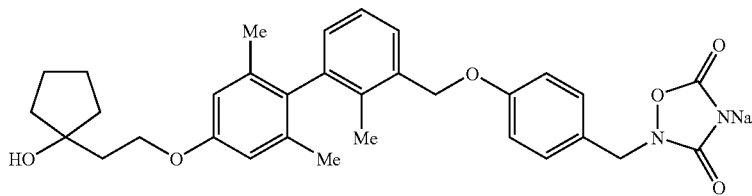
218 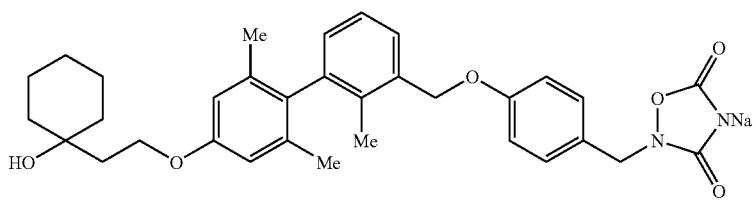
219 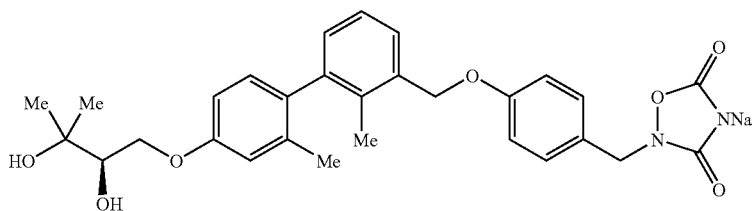
220 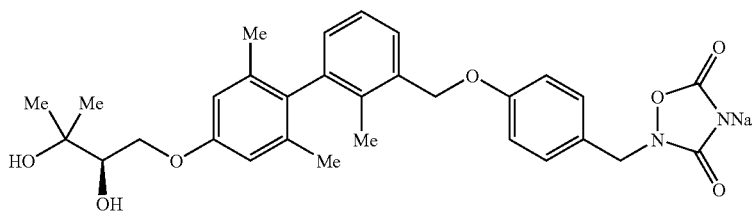
221 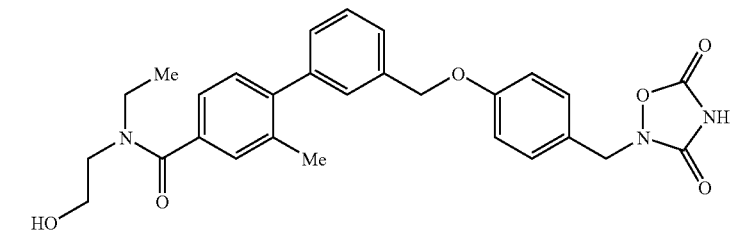
TABLE 84
222 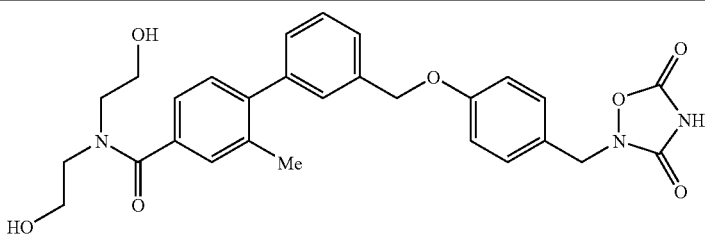

TABLE 84-continued
223 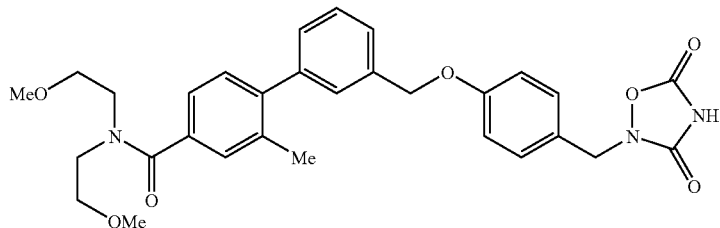
224 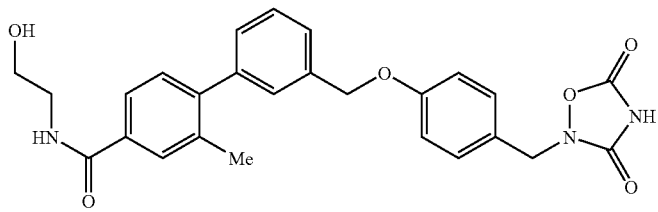
225 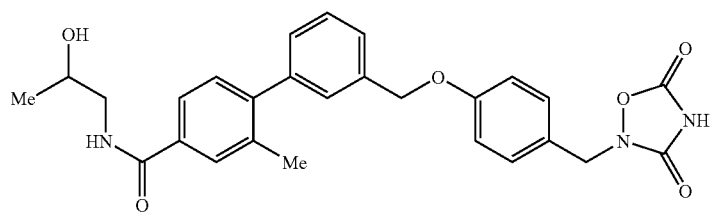
226 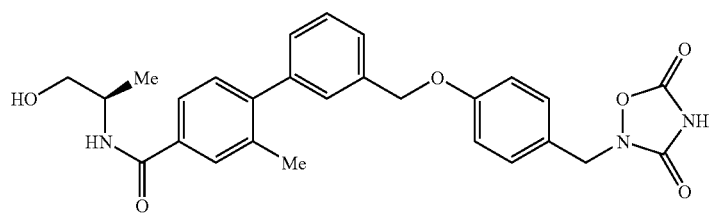
227 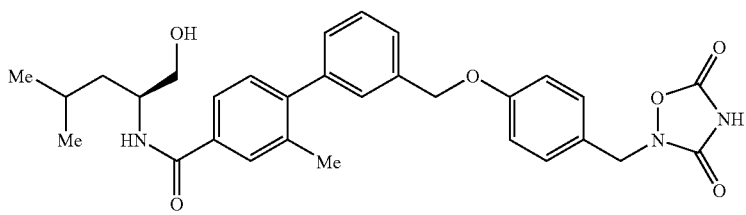
TABLE 85
228 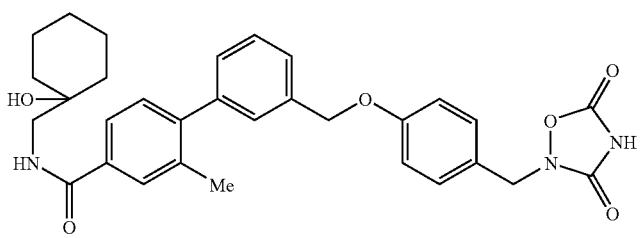

TABLE 85-continued
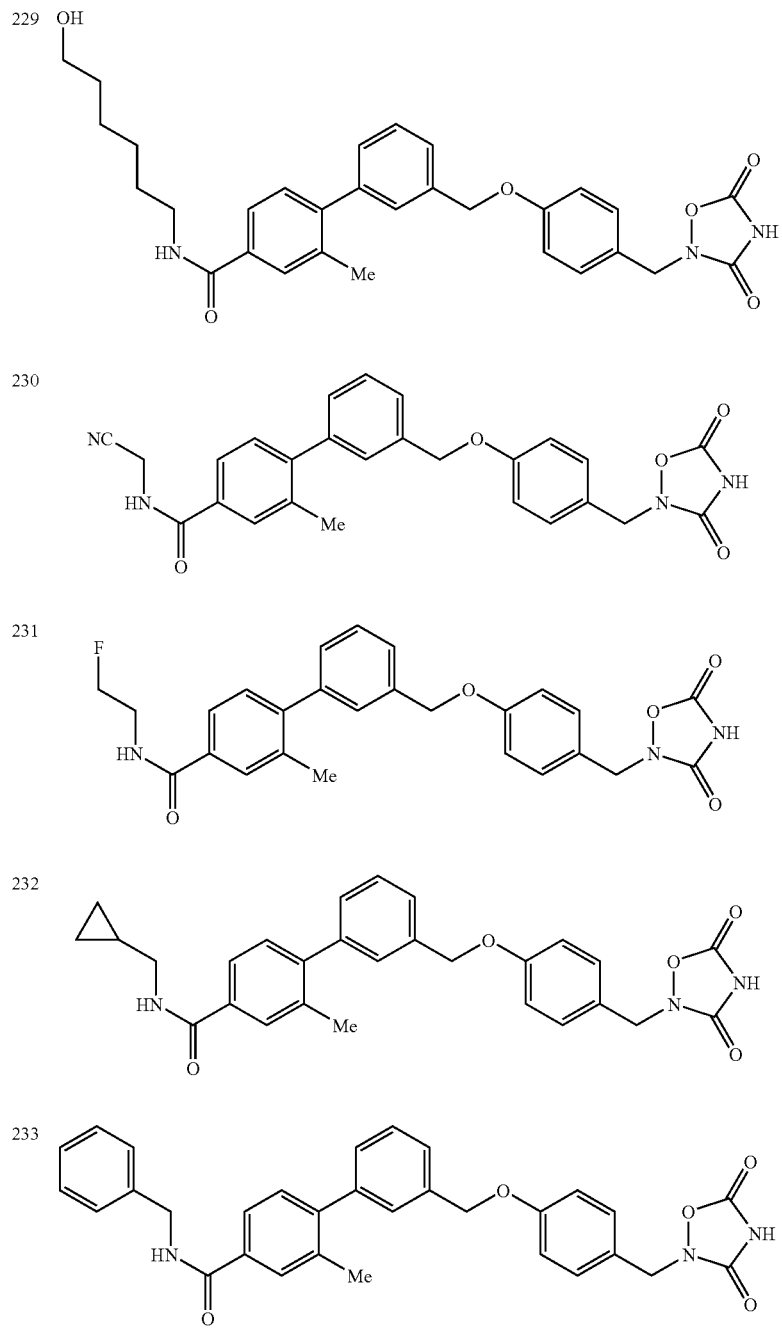
TABLE 86
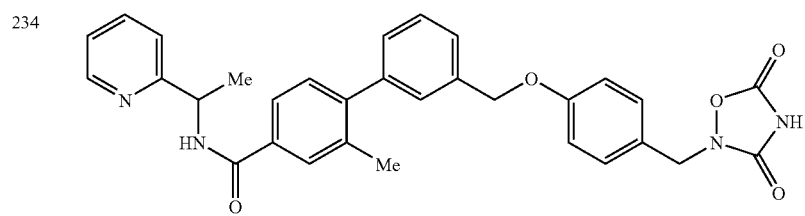

TABLE 86-continued
235 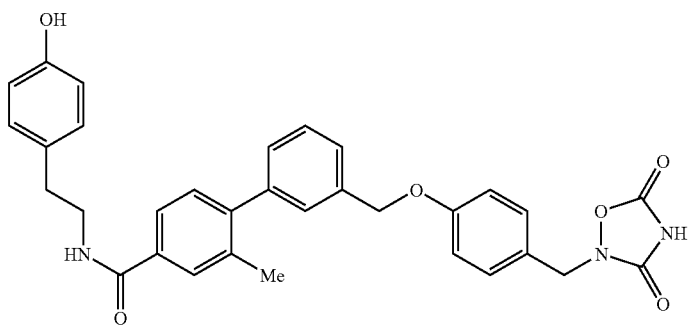
236 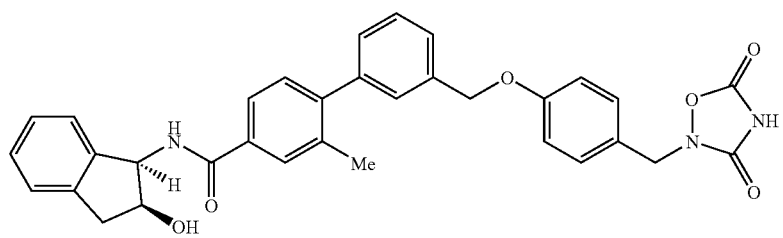
237 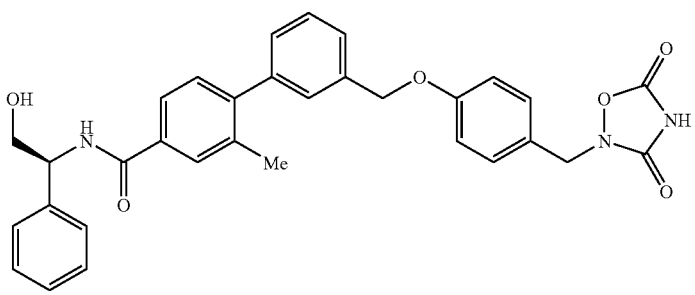
238 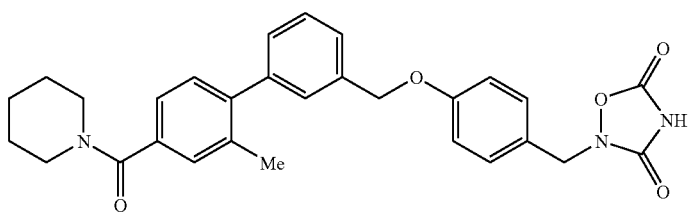
239 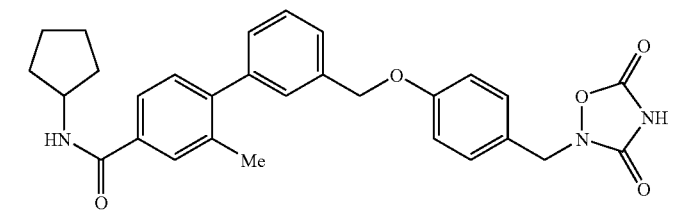
TABLE 87
240 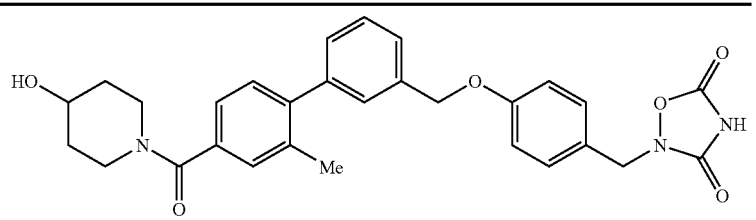

TABLE 87-continued
241 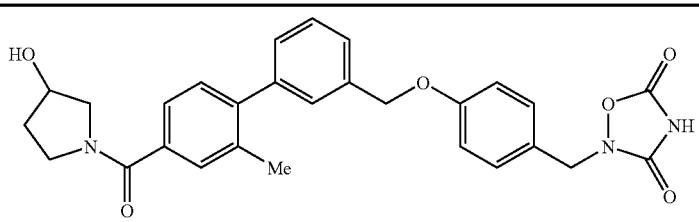
242 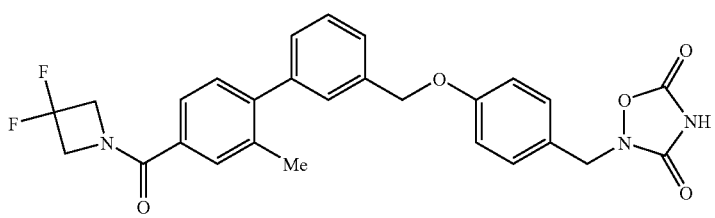
243 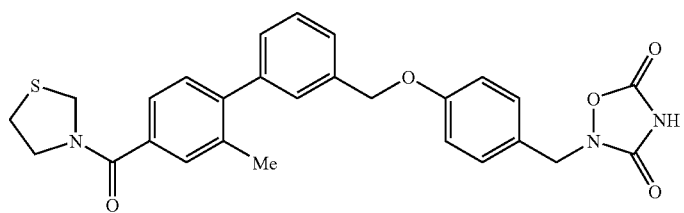
25 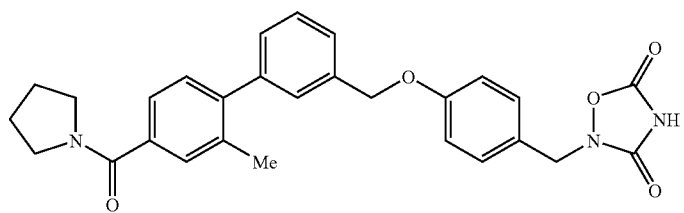
244 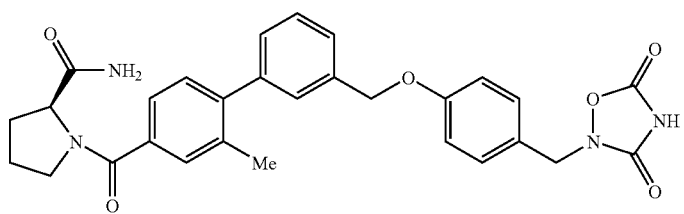
245 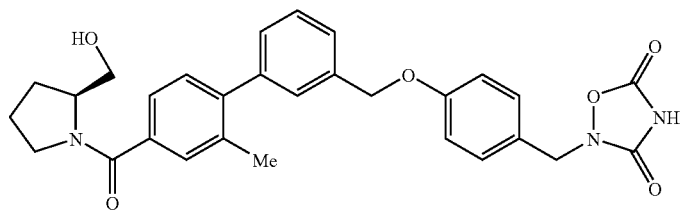
TABLE 88
246 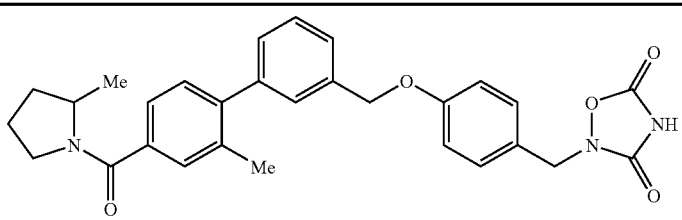

TABLE 88-continued
247 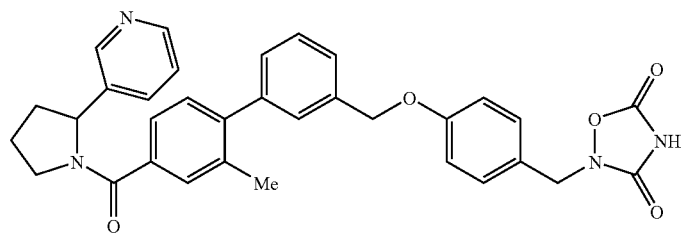
248 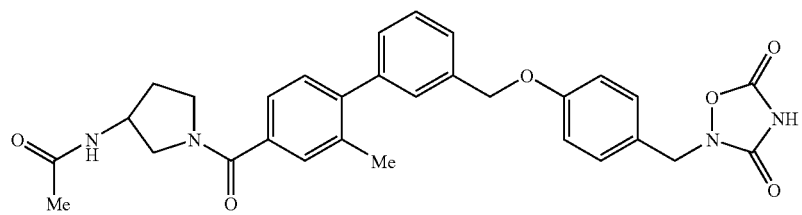
249 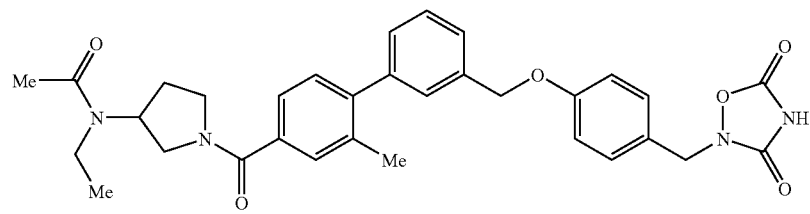
250 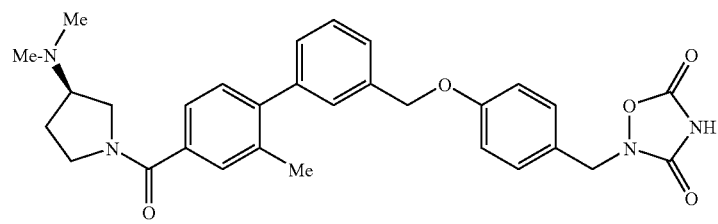
251 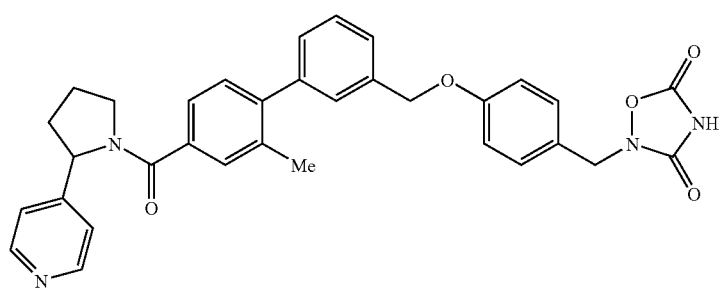
252 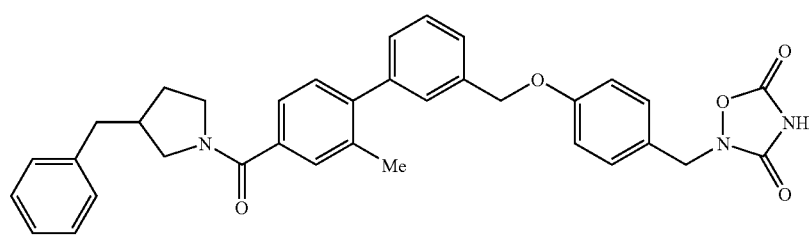

TABLE 89
253 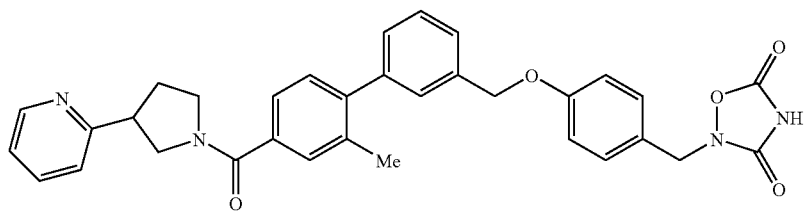
254 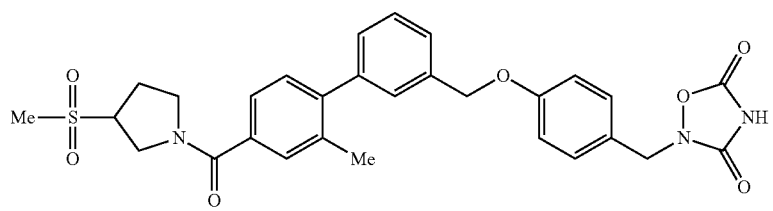
255 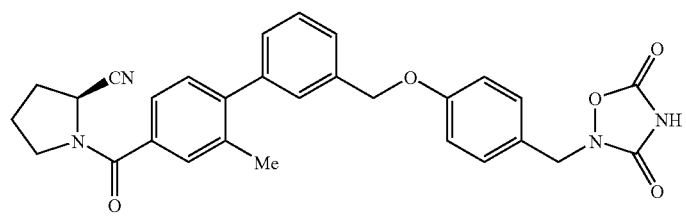
256 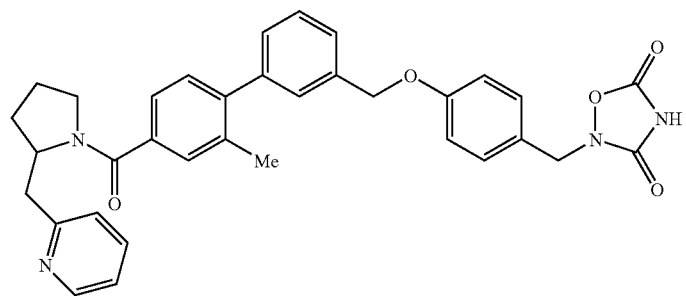
257 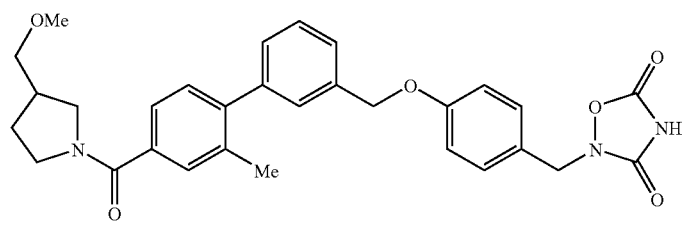
258 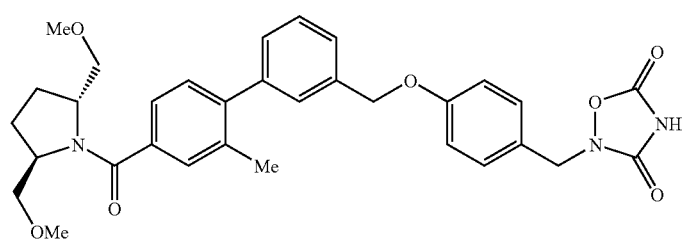

TABLE 90
259 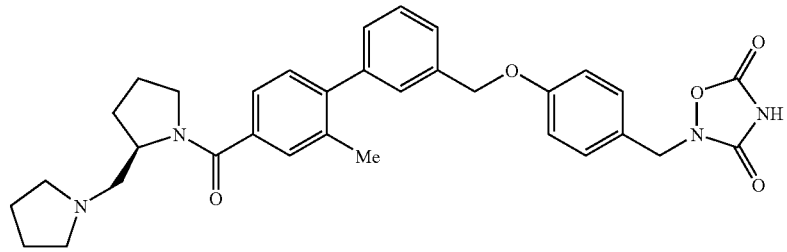
260 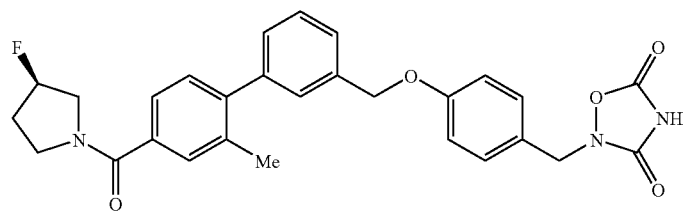
261 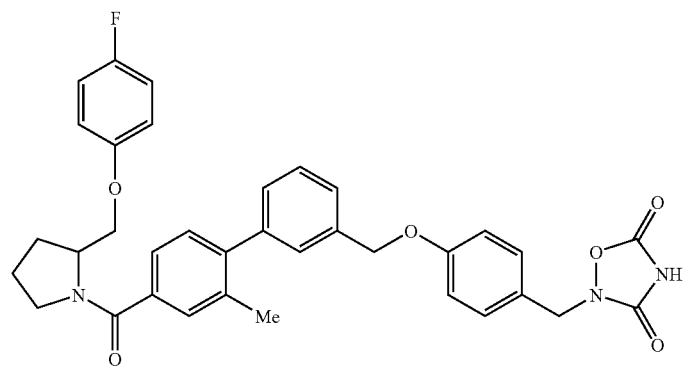
262 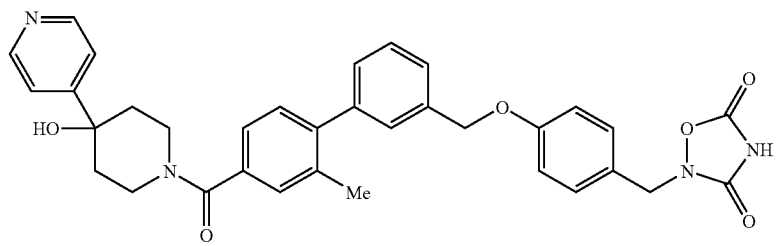
263 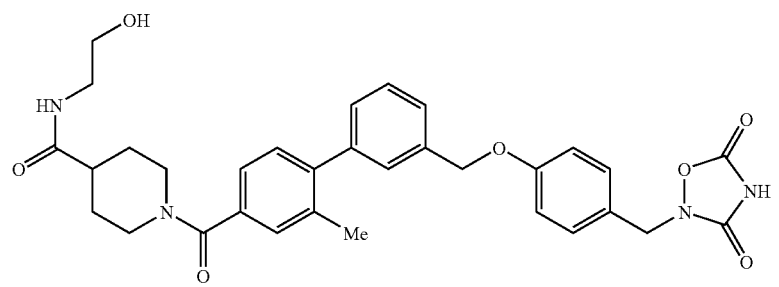

TABLE 90-continued
264 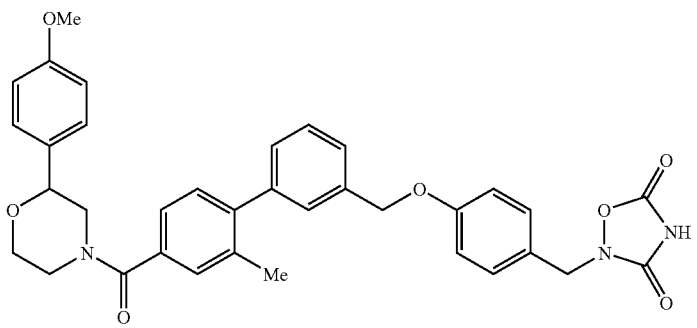
TABLE 91
265 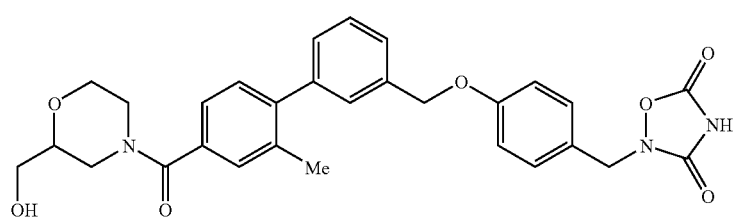
266 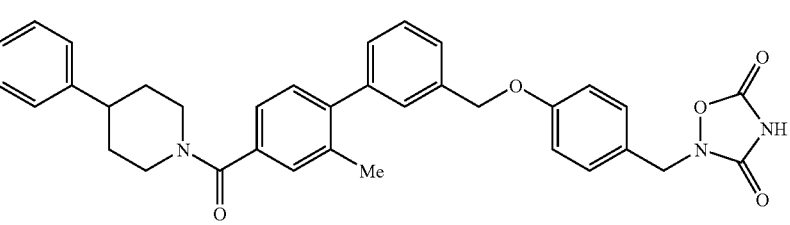
267 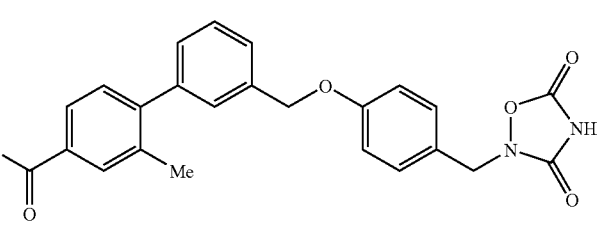
268 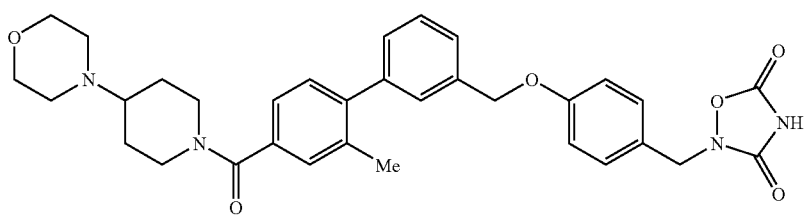
269 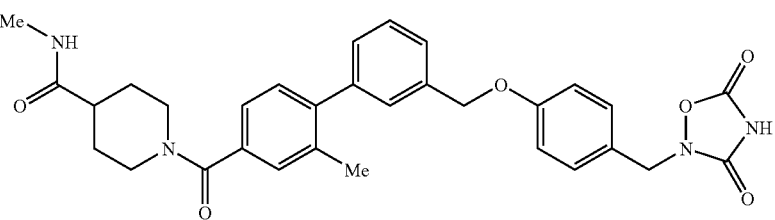

TABLE 91-continued
270 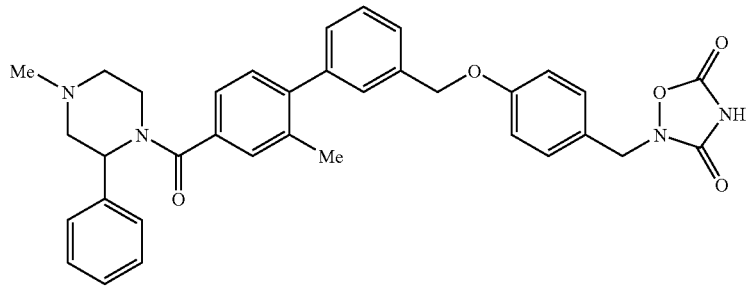
271 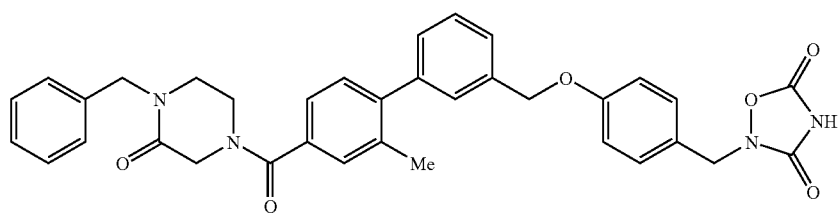
TABLE 92
272 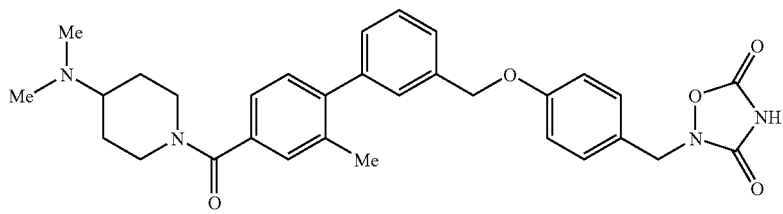
273 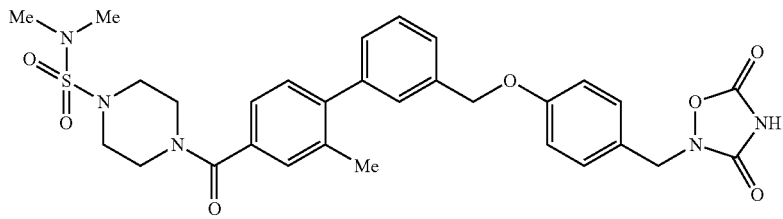
274 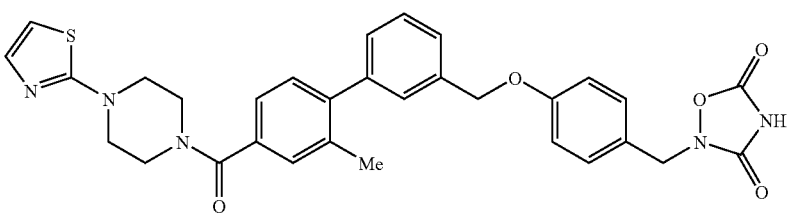
275 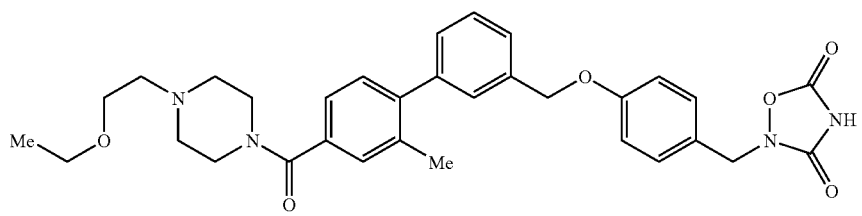

TABLE 92-continued
| 276 | 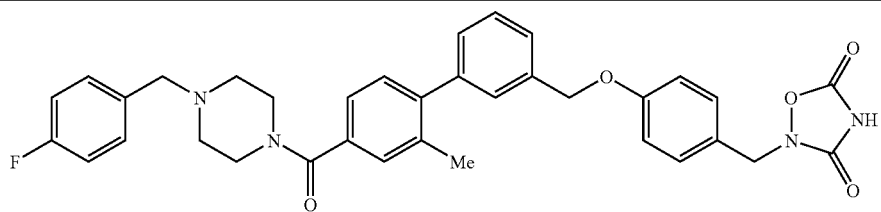 |
| 277 | 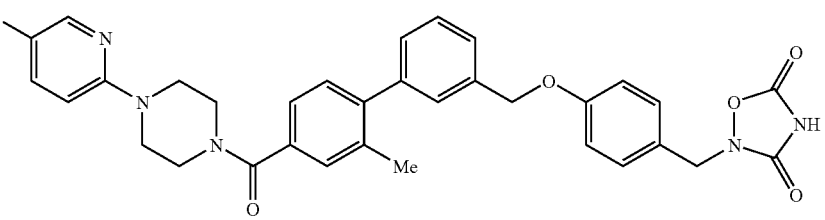 |
| 278 | 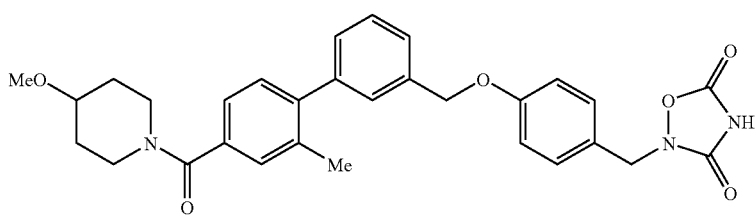 |
TABLE 93
| 279 | 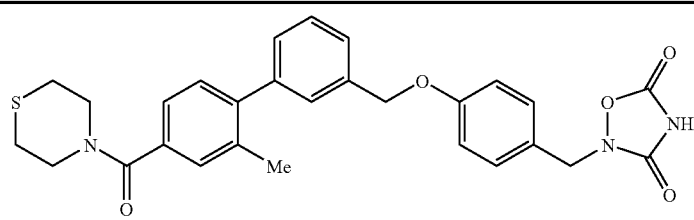 |
| 280 | 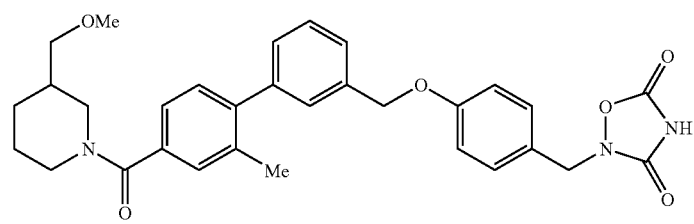 |
| 26 | 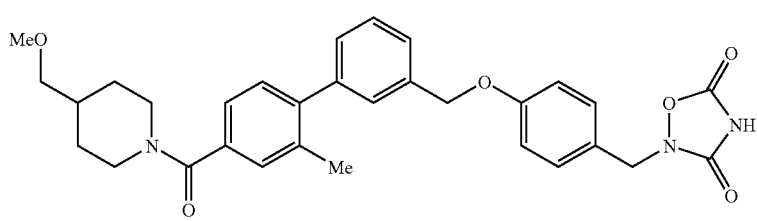 |
| 281 | 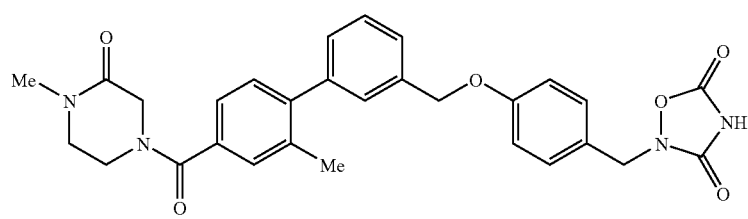 |

TABLE 93-continued
| 282 | 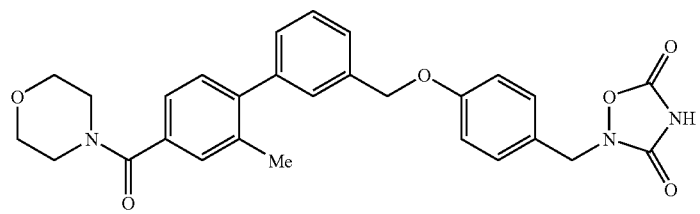 |
| 283 | 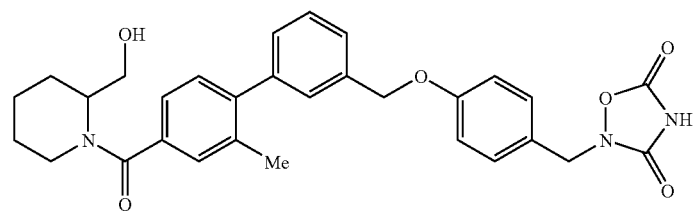 |
| 284 | 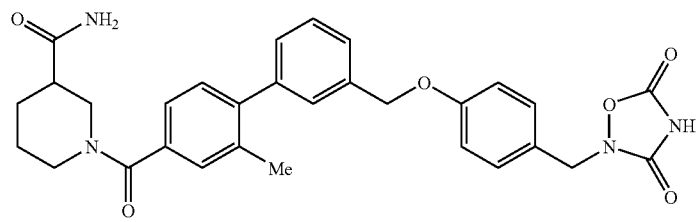 |
TABLE 94
| 285 | 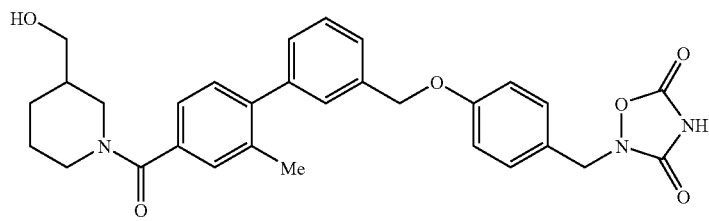 |
| 286 | 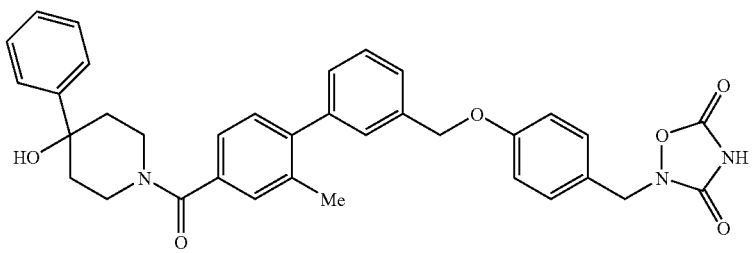 |
| 287 | 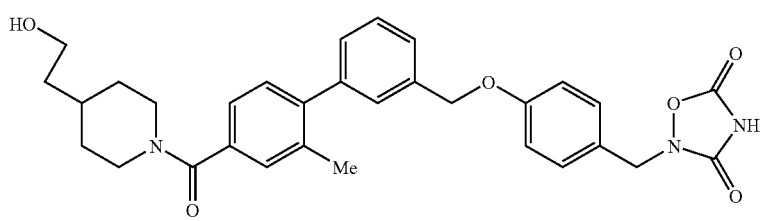 |

TABLE 94-continued
288 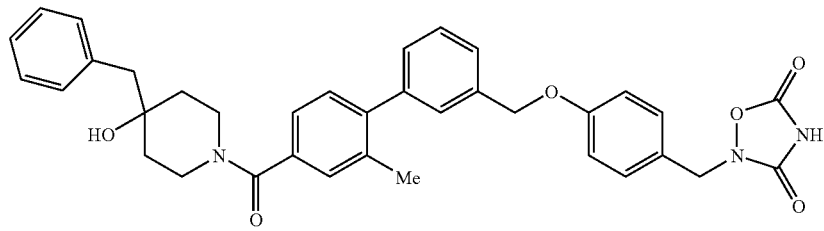
289 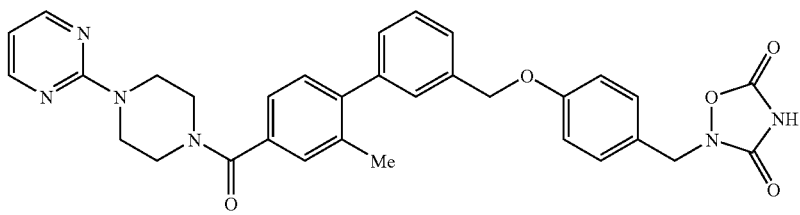
290 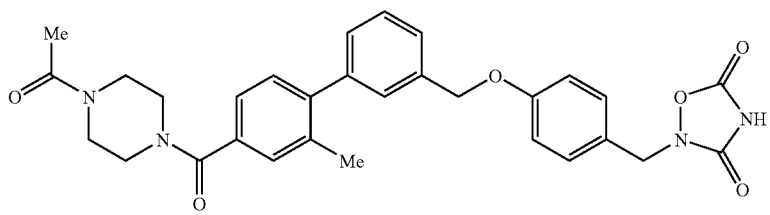
291 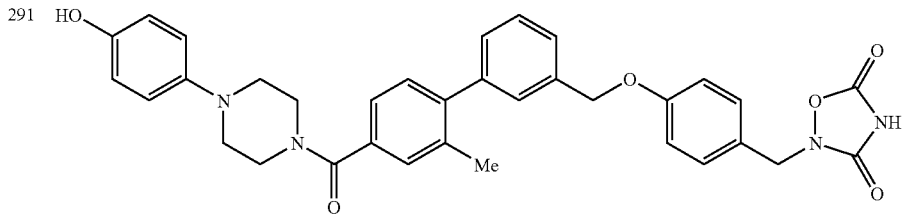
TABLE 95
292 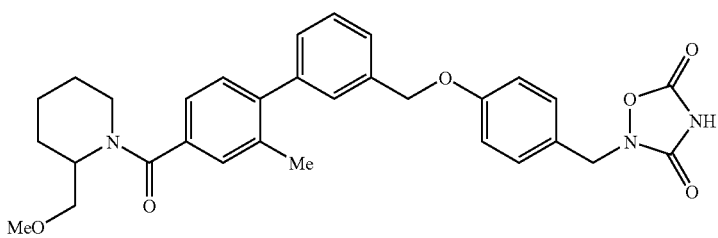
293 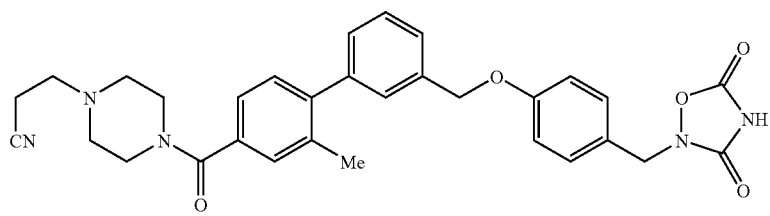

TABLE 95-continued
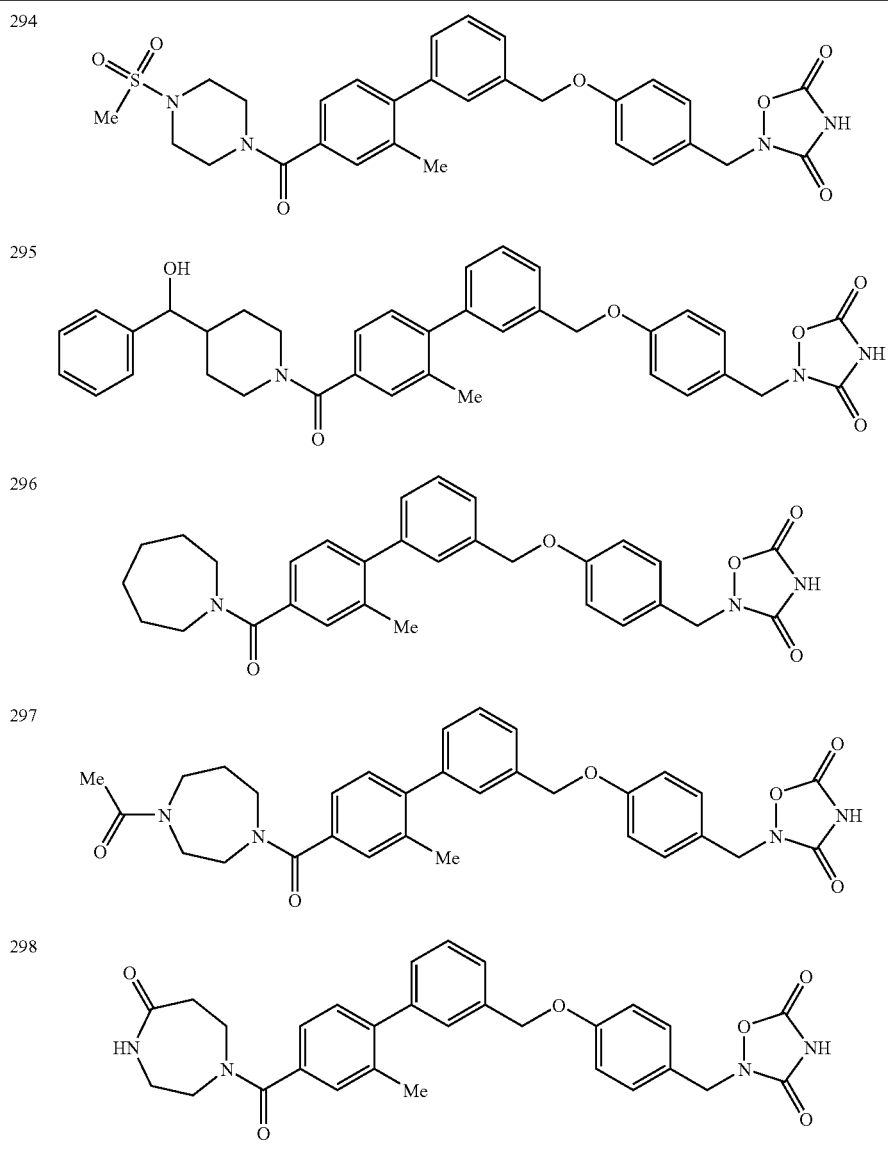
TABLE 96
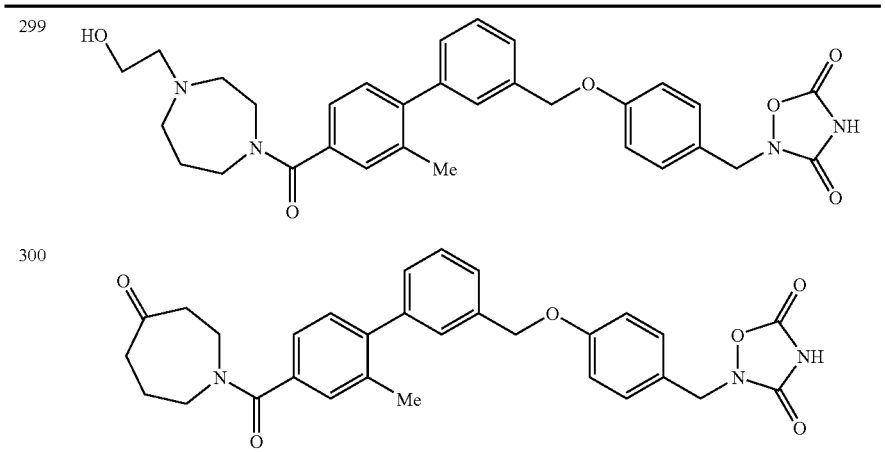

TABLE 96-continued
301 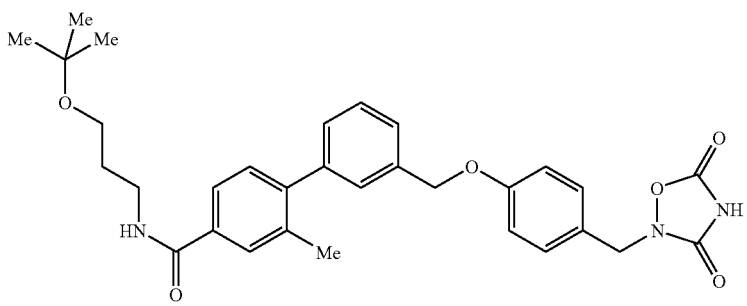
302 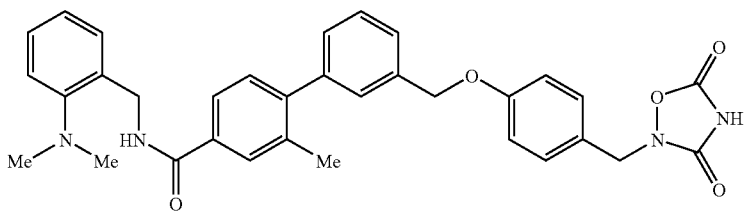
303 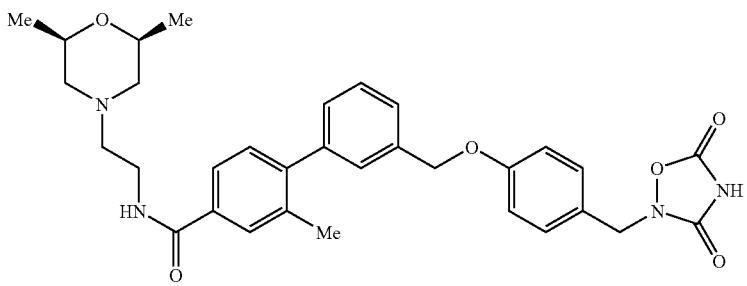
304 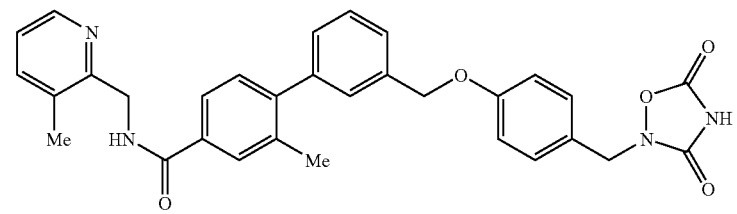
305 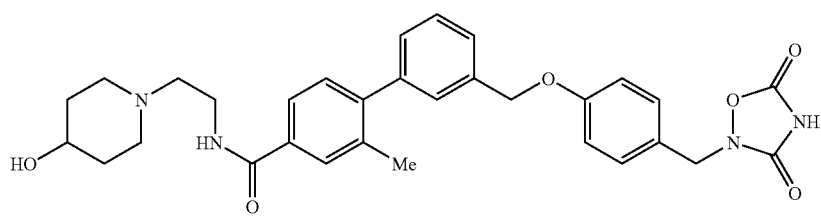
TABLE 97
306 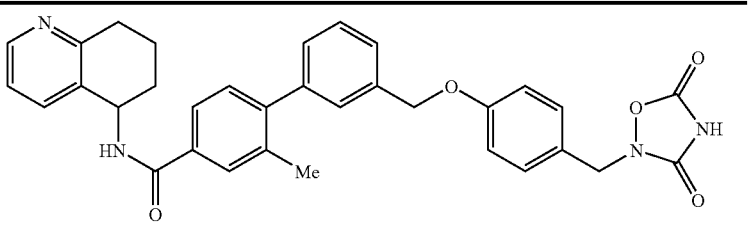

TABLE 97-continued
307 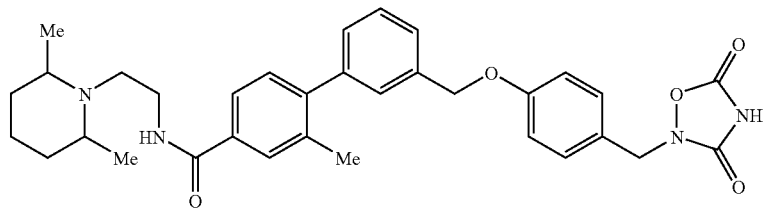
308 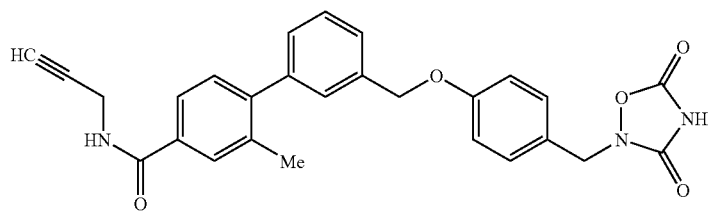
309 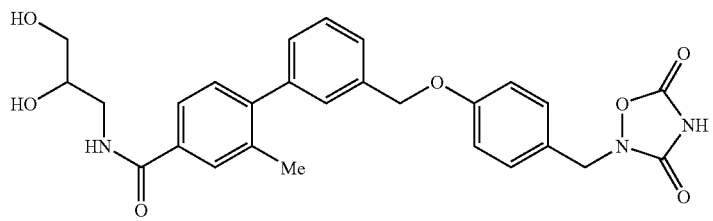
310 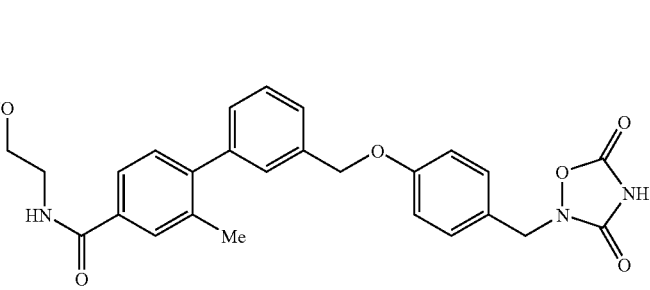
311 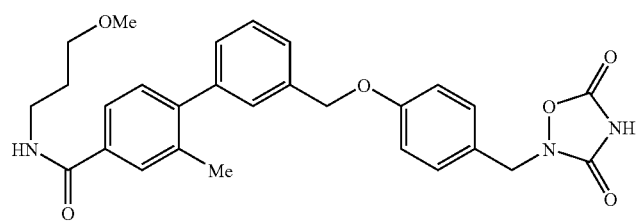
TABLE 98
312 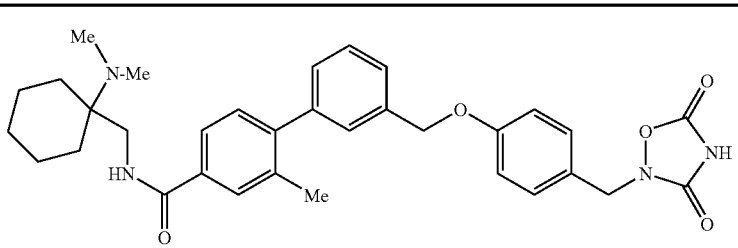

TABLE 98-continued
313 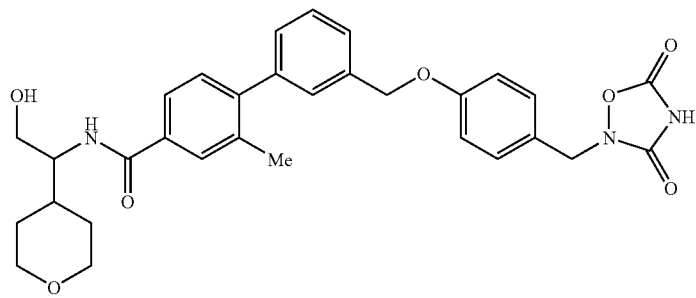
314 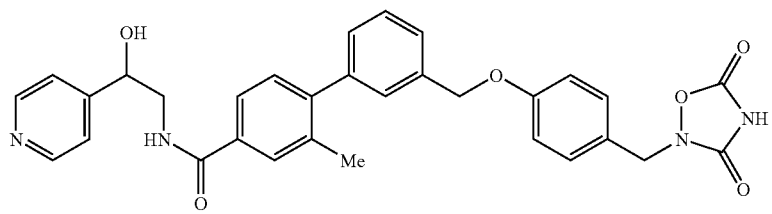
315 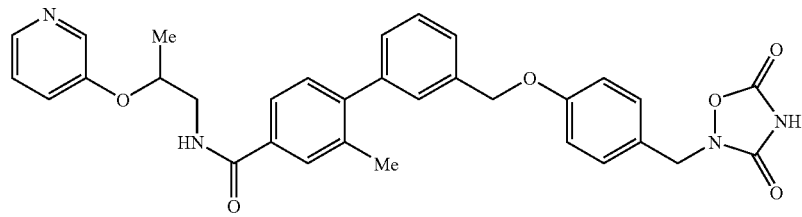
316 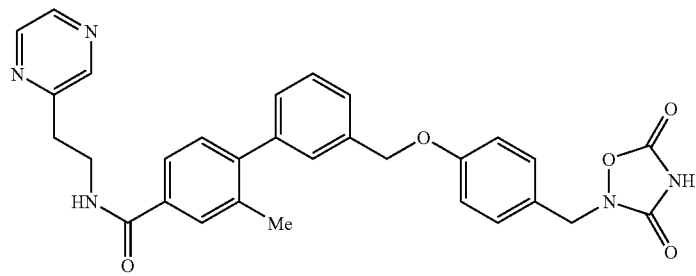
27 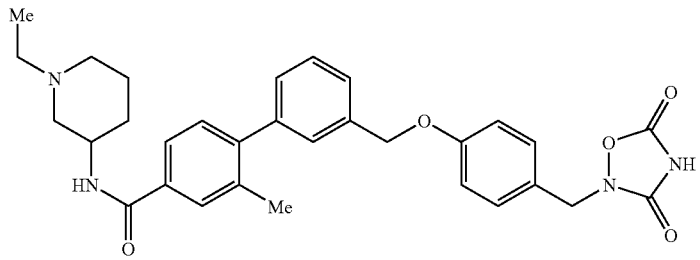

TABLE 99
317 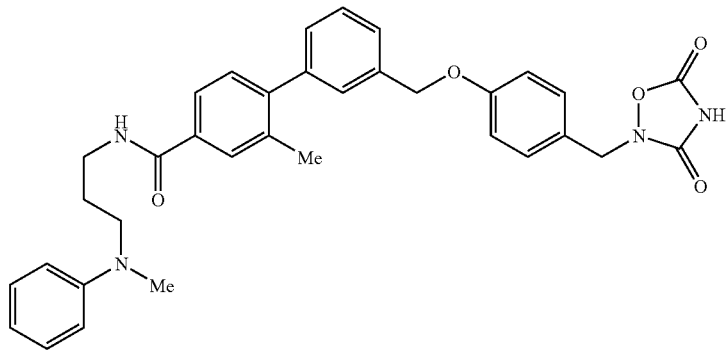
318 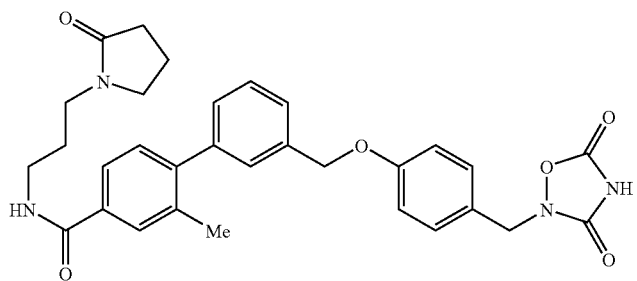
319 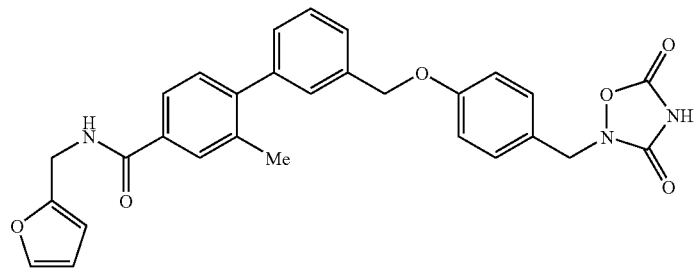
320 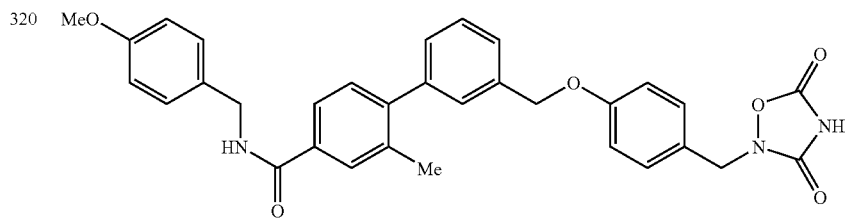
321 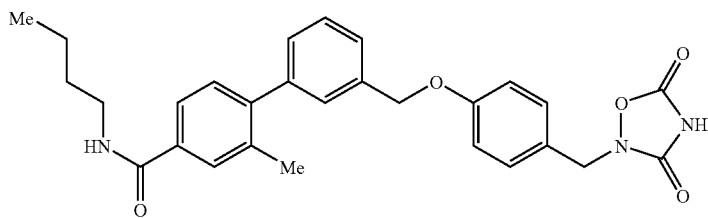

TABLE 99-continued
322
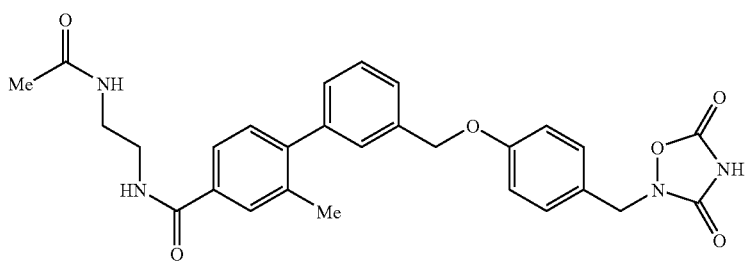
TABLE 100
323
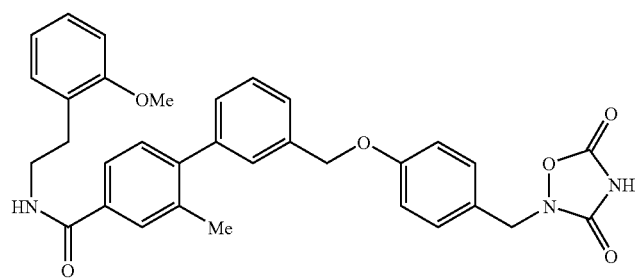
324
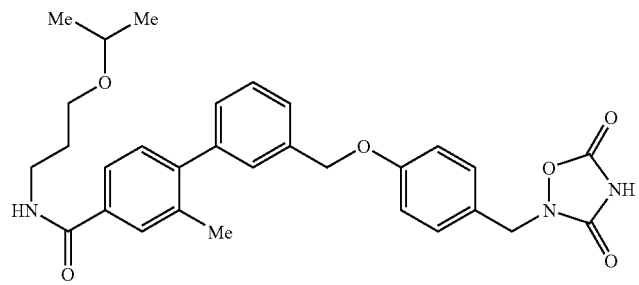
325
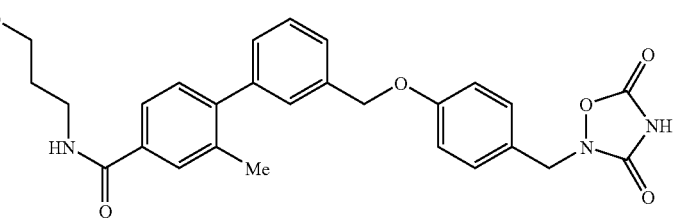
326
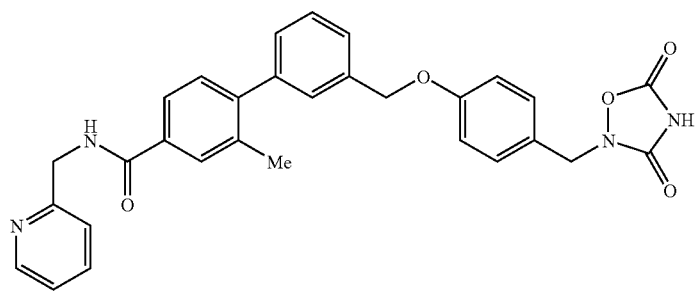

TABLE 100-continued
327
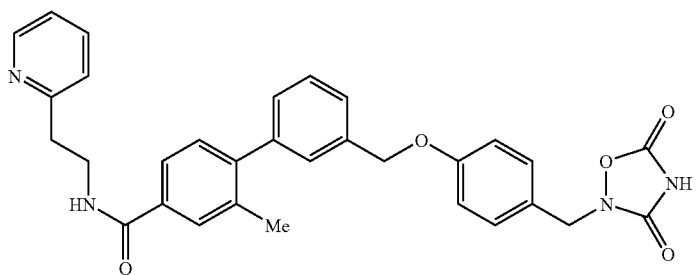
328
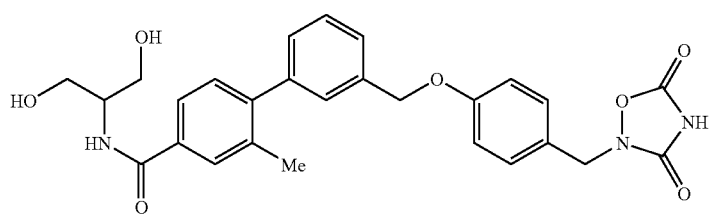
TABLE 101
329
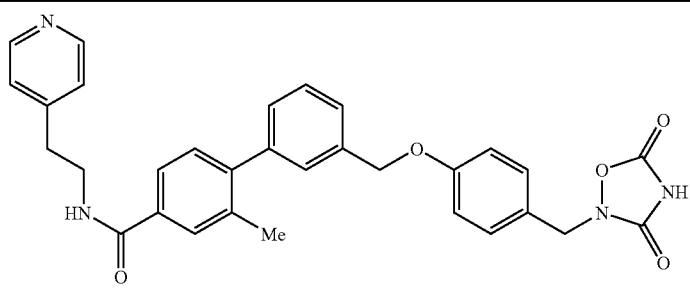
330
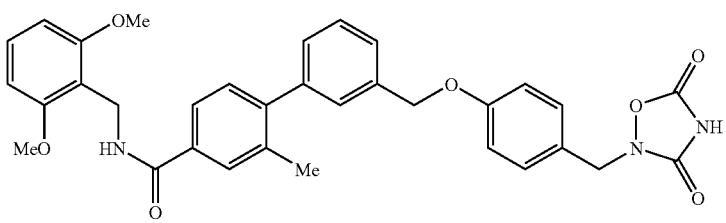
331
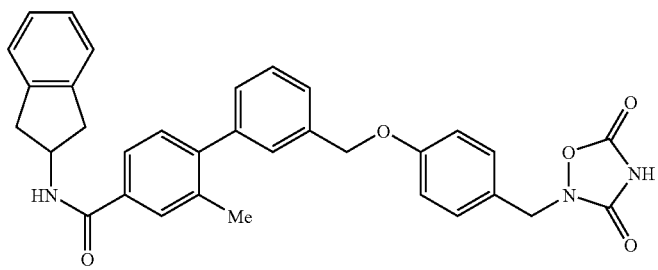
332
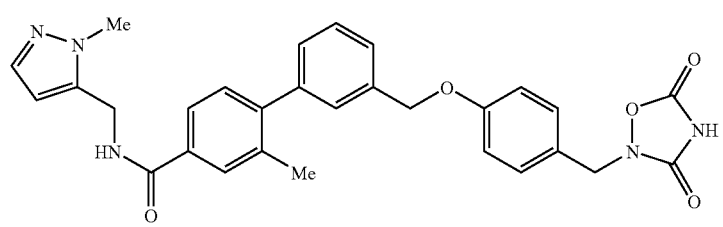

TABLE 101-continued
| 333 | 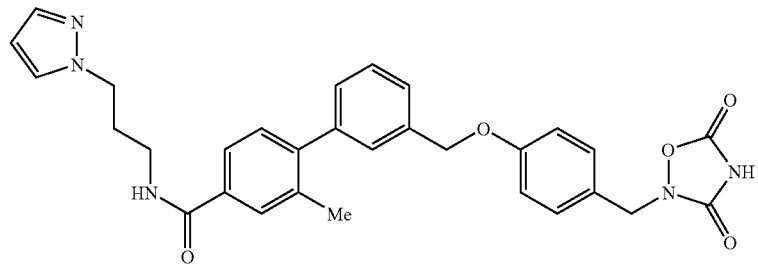 |
| 334 | 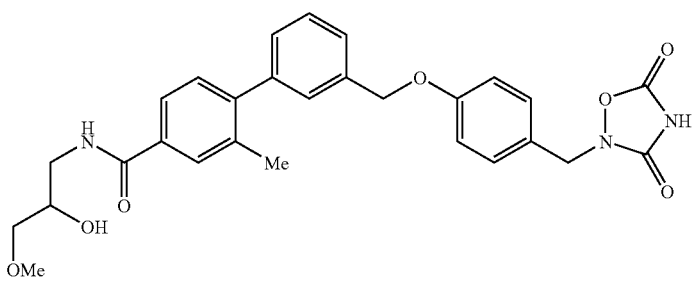 |
TABLE 102
| 335 | 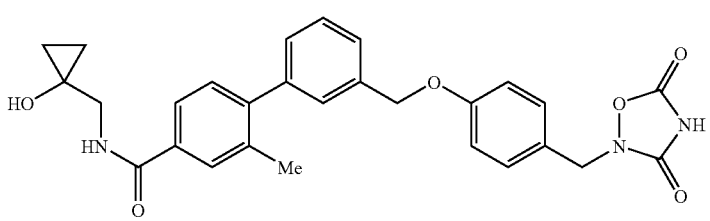 |
| 336 | 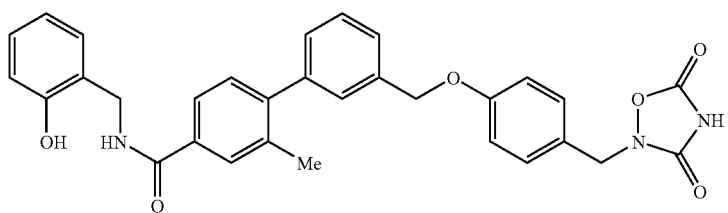 |
| 337 | 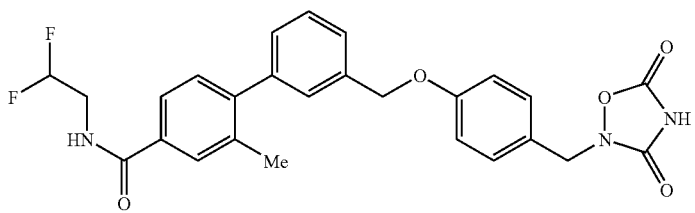 |
| 338 | 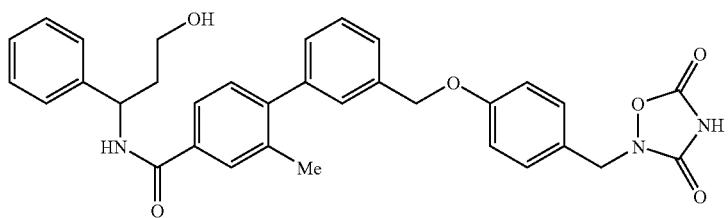 |

TABLE 102-continued
339 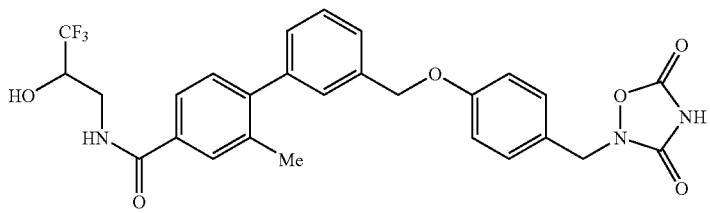
340 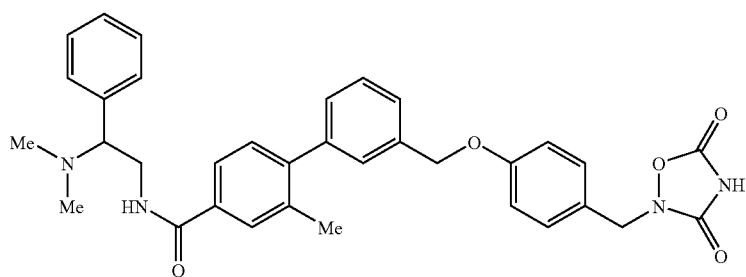
341 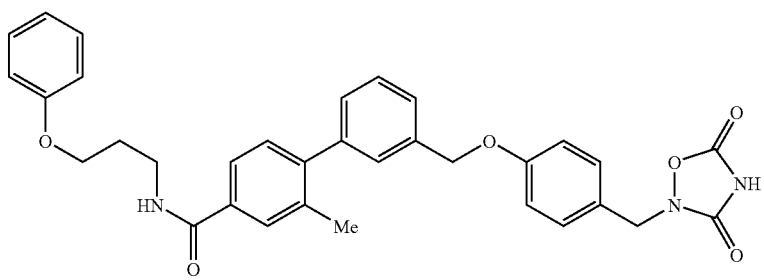
TABLE 103
342 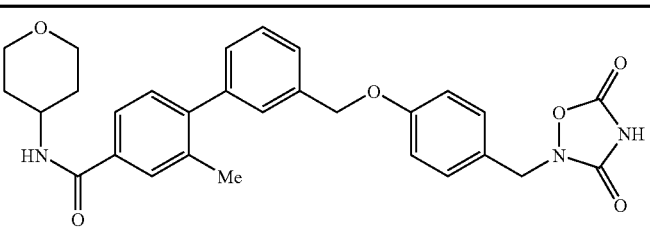
343 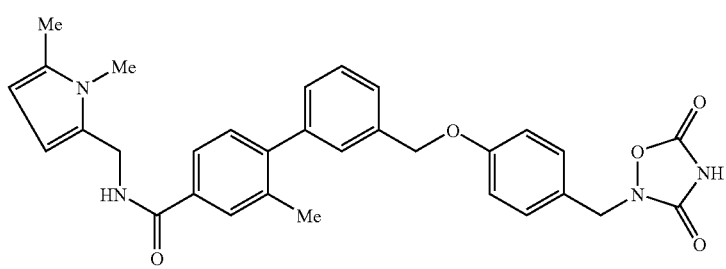
344 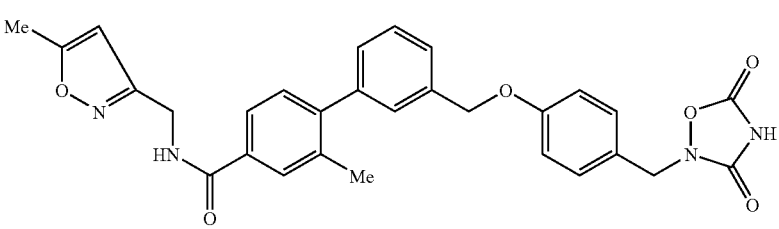

TABLE 103-continued
345 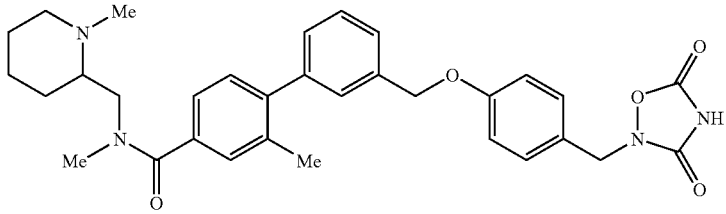
346 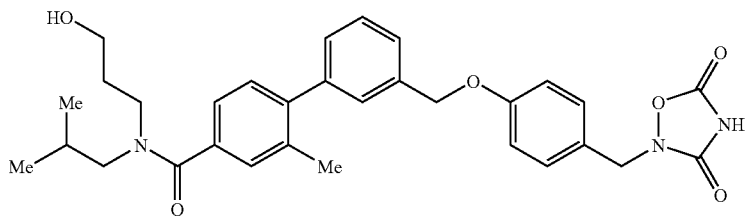
347 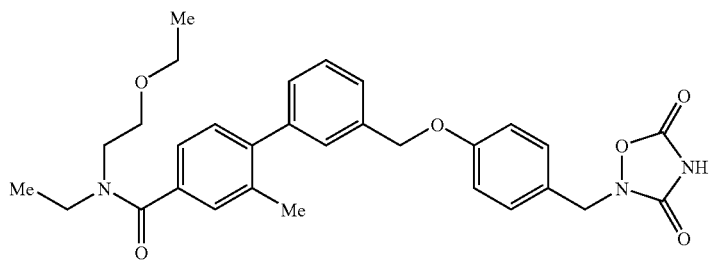
348 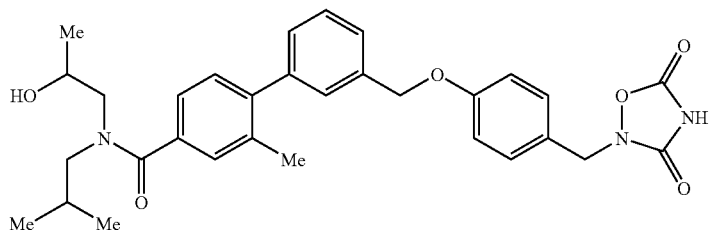
TABLE 104
349 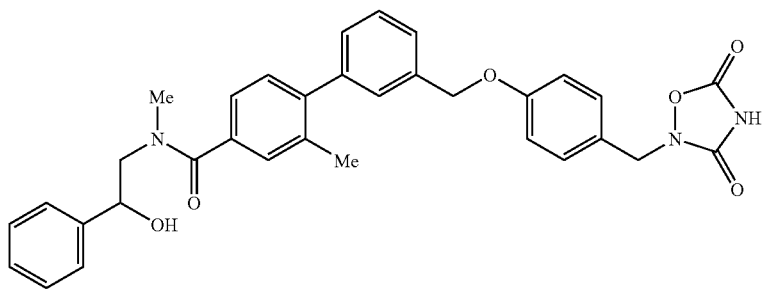
350 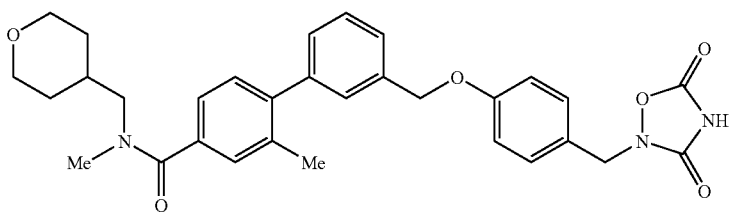

TABLE 104-continued
351 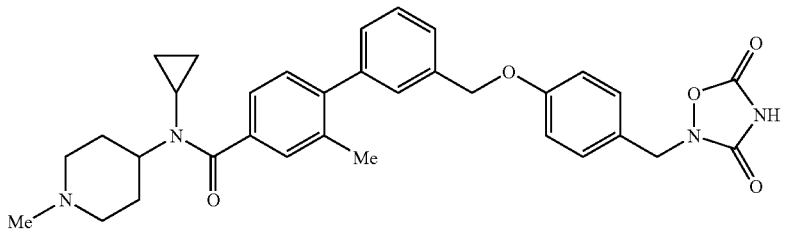
352 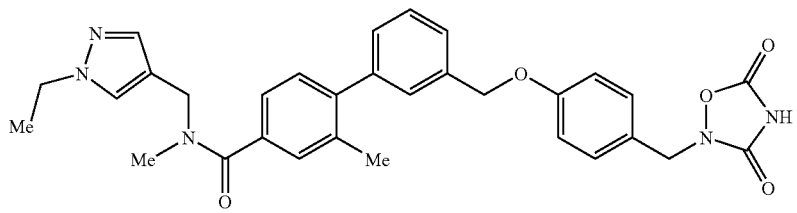
353 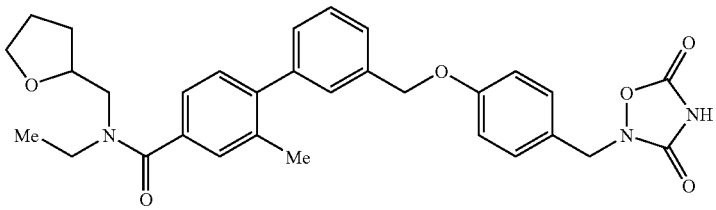
354 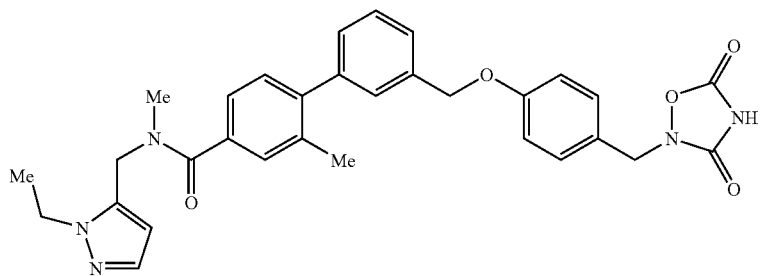
355 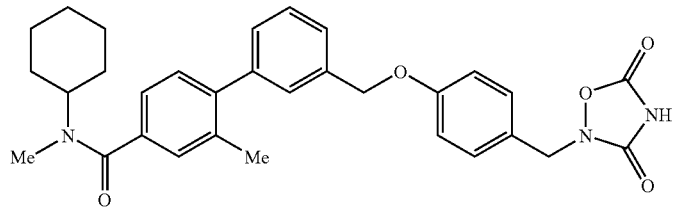
TABLE 105
356 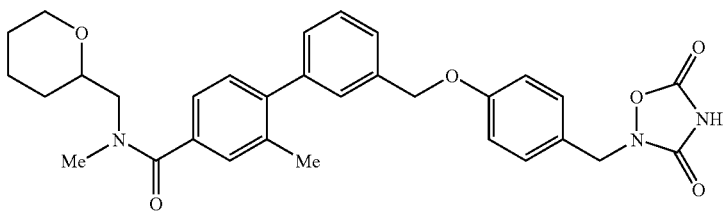

TABLE 105-continued
357 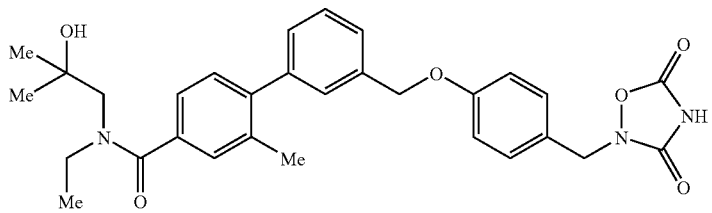
358 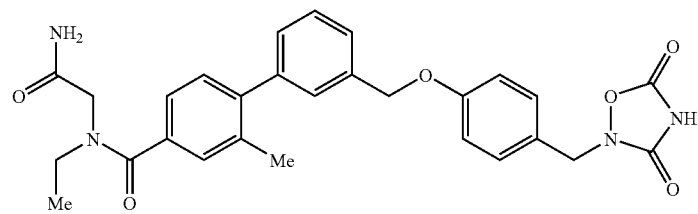
359 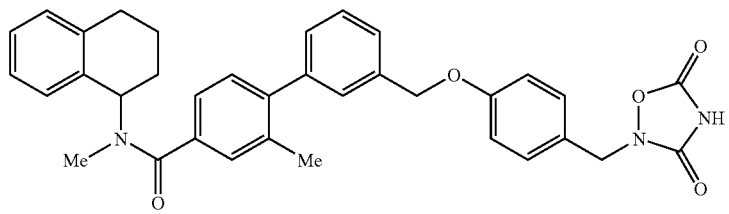
360 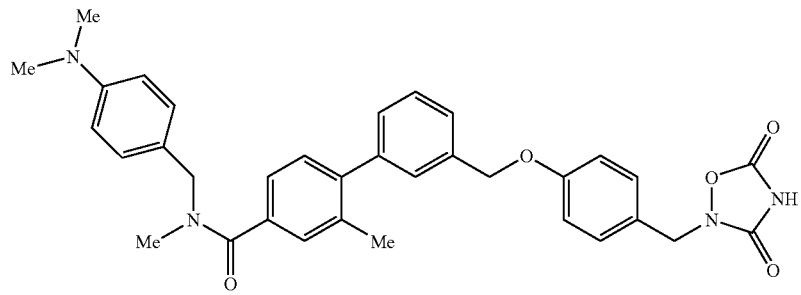
361 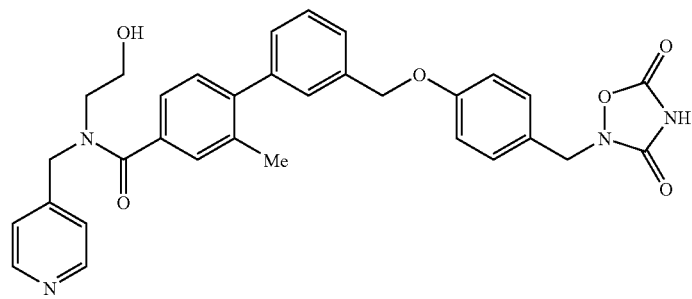
TABLE 106
362 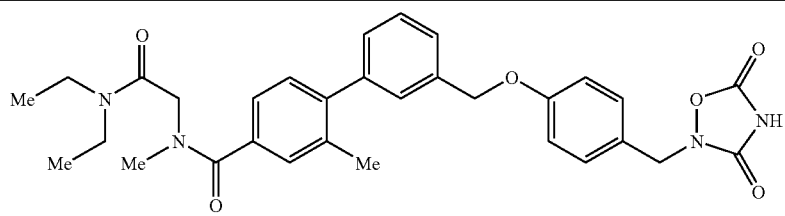

TABLE 106-continued
363 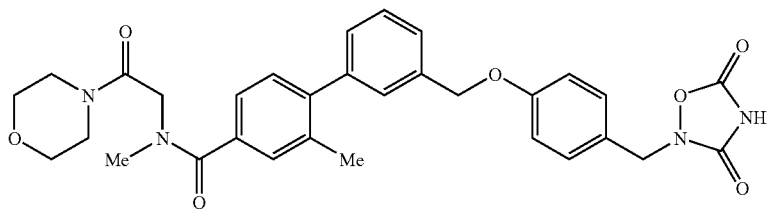
364 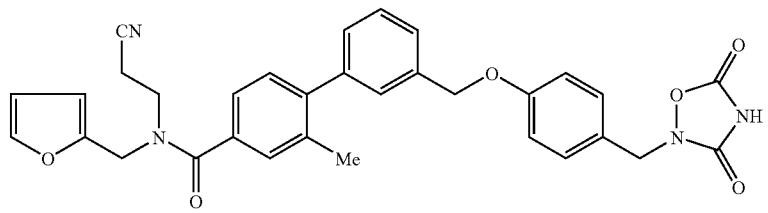
365 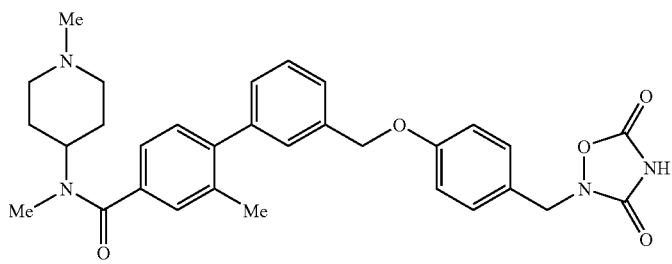
366 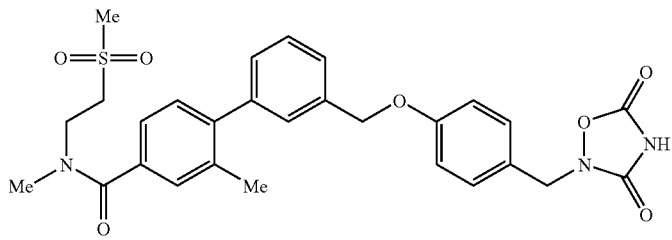
367 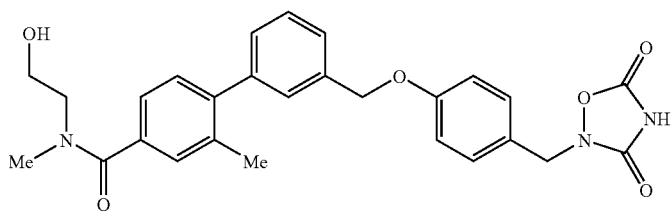
368 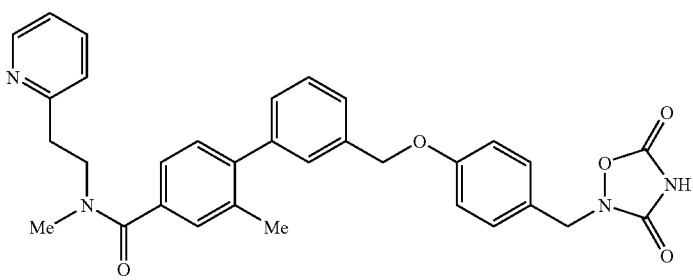

TABLE 107
369 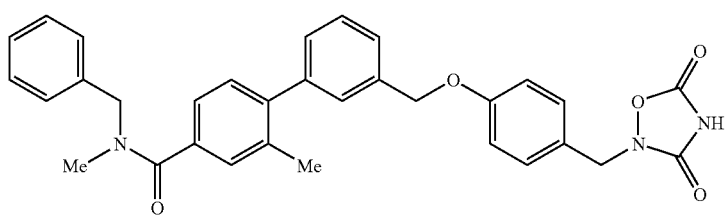
370 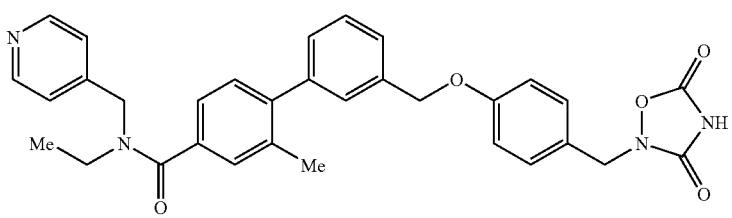
371 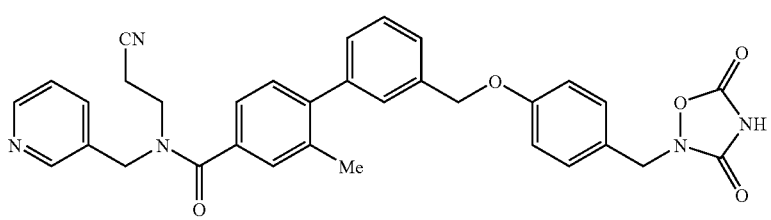
372 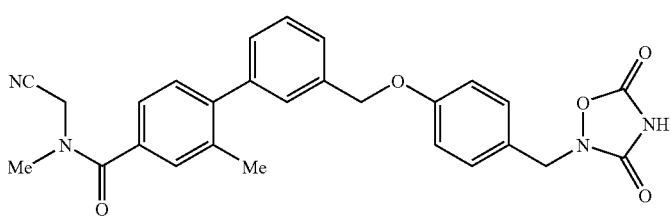
373 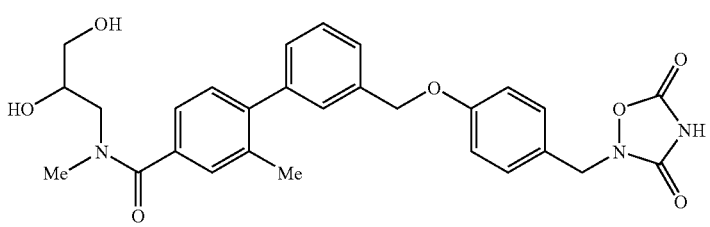
374 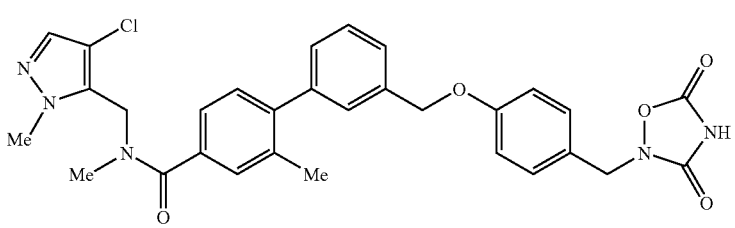
375 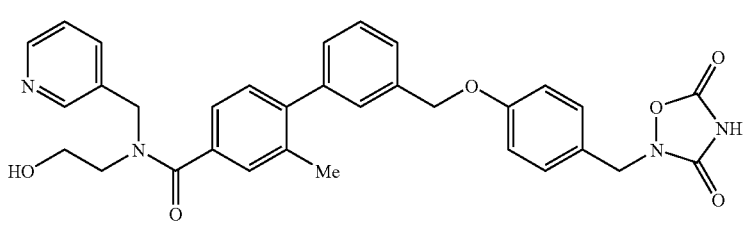

TABLE 108
376 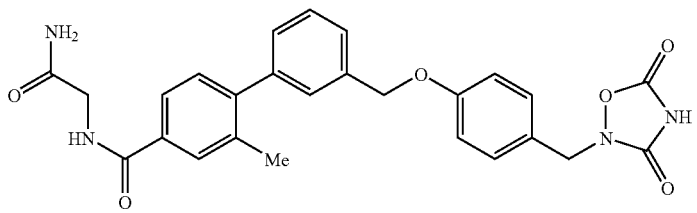
377 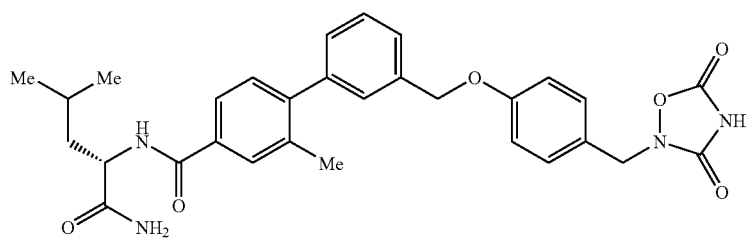
378 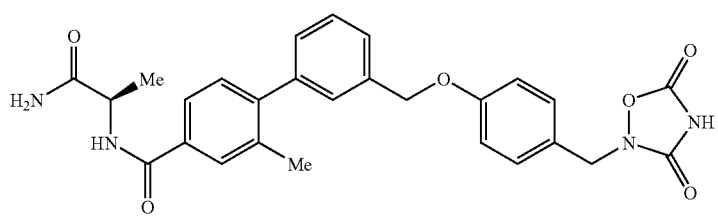
379 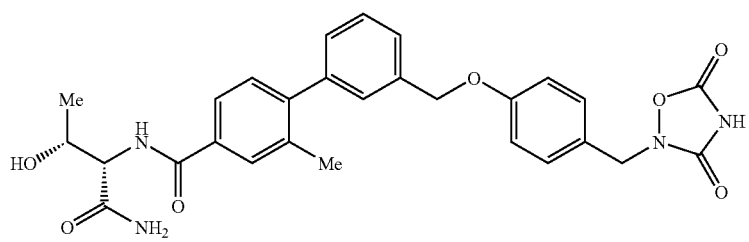
380 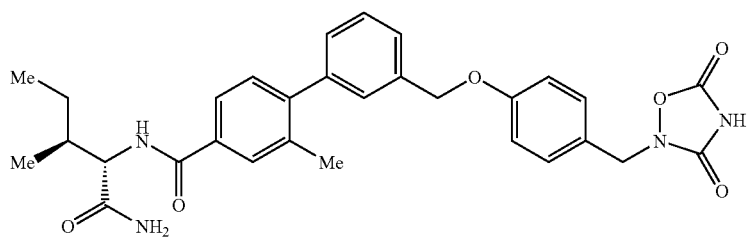
381 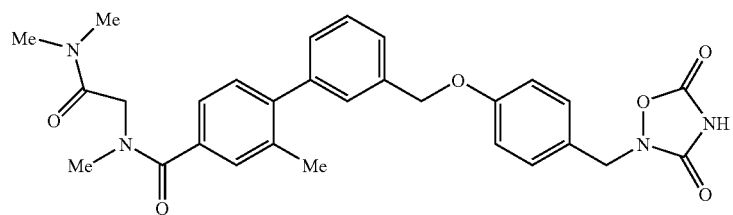

TABLE 109
382 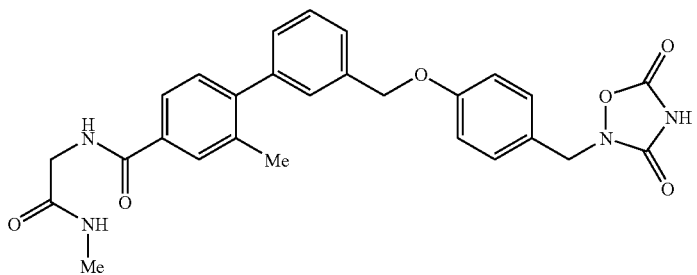
383 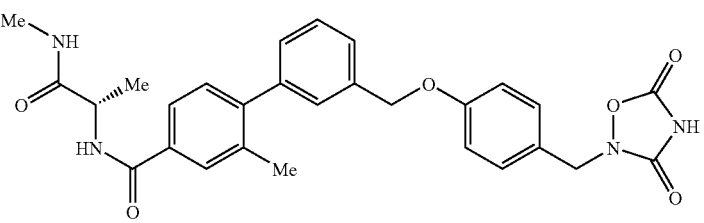
384 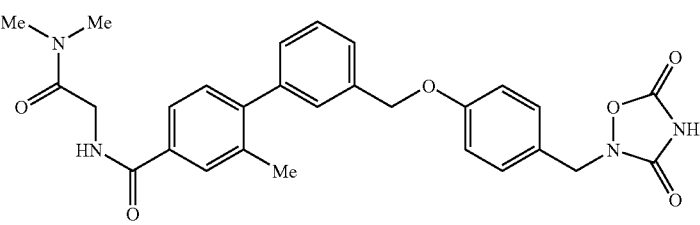
385 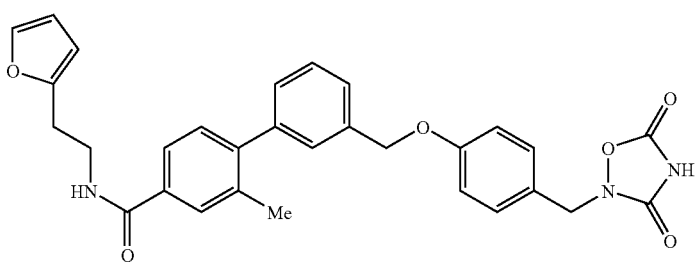
386 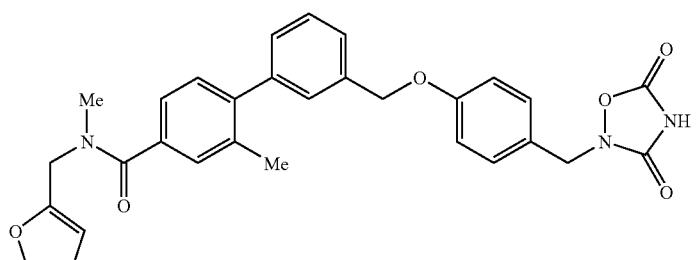
387 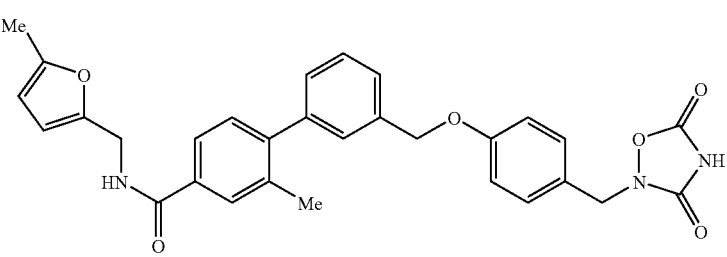

TABLE 110
388 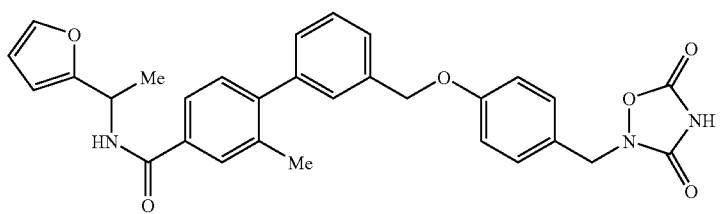
389 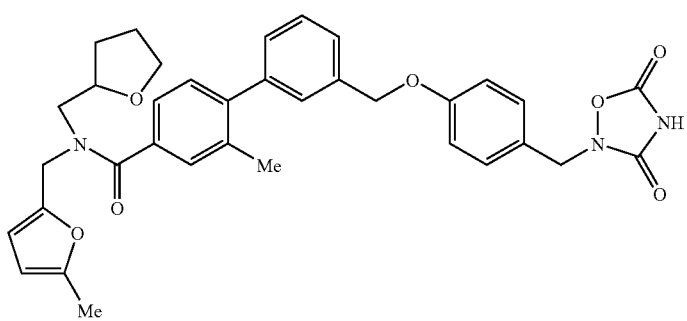
390 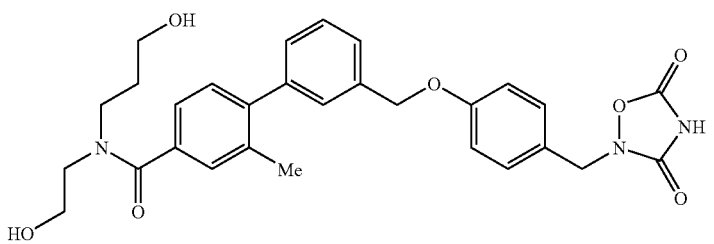
391 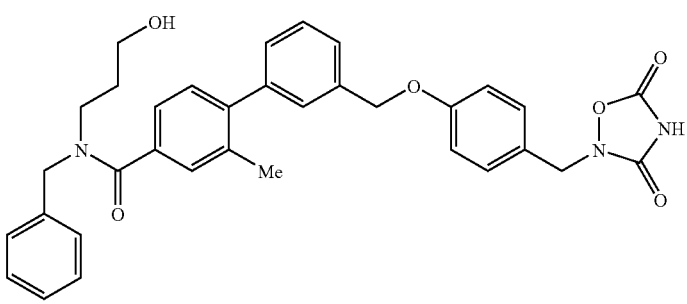
392 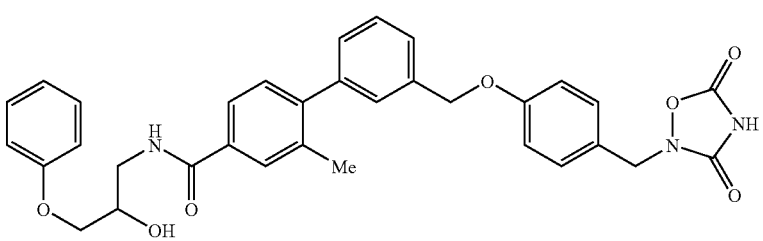

TABLE 111
393
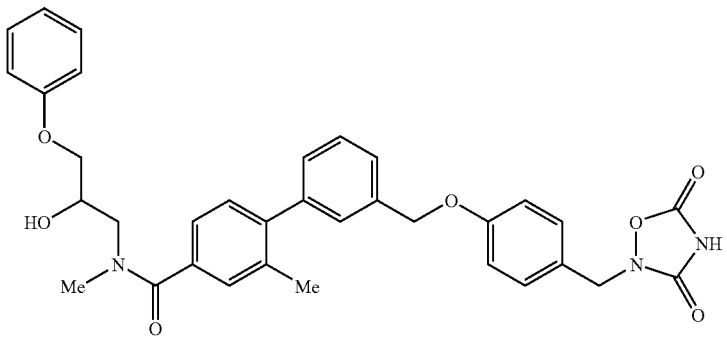
394
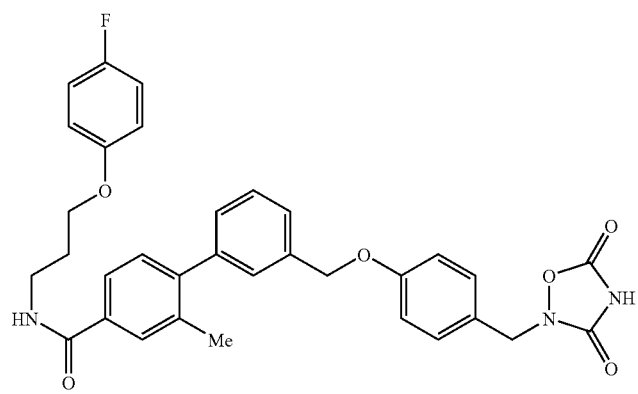
395
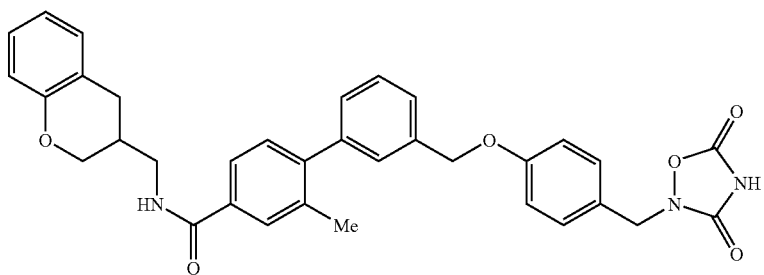
396
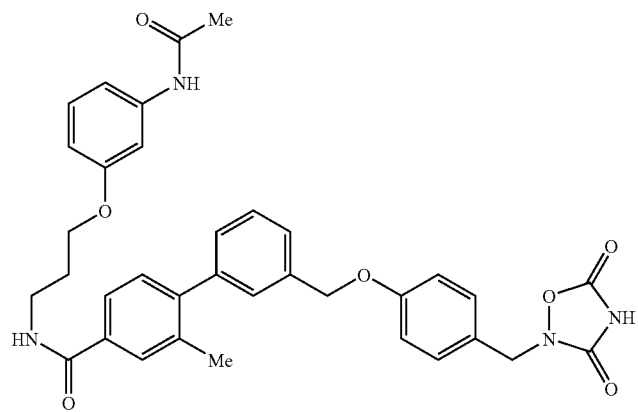

TABLE 111-continued
397 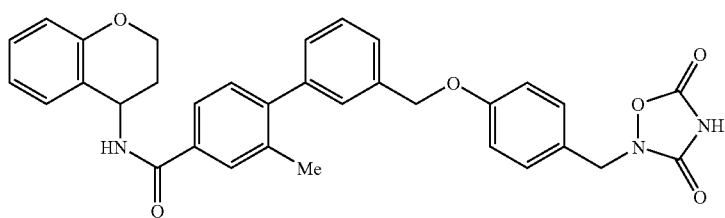
TABLE 112
398 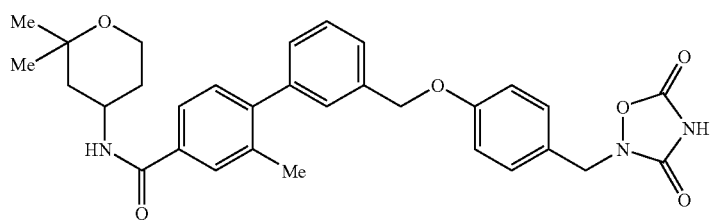
399 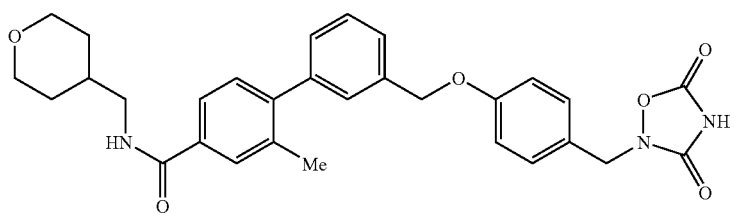
400 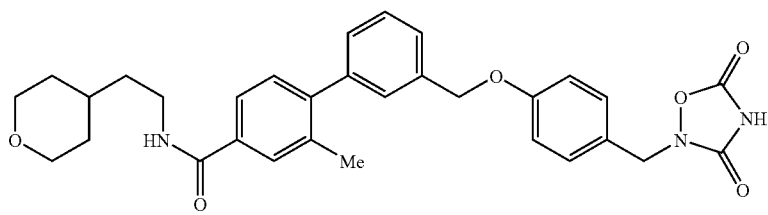
401 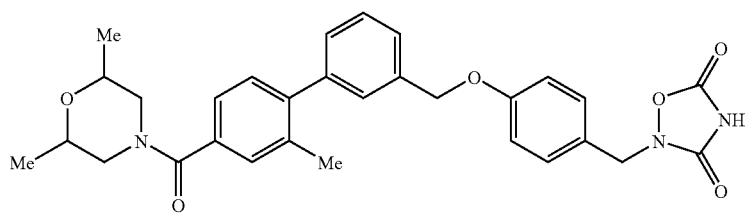
402 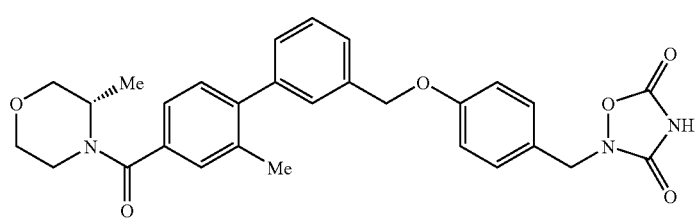

TABLE 112-continued
403
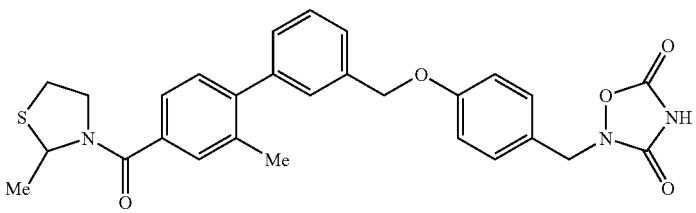
TABLE 113
404
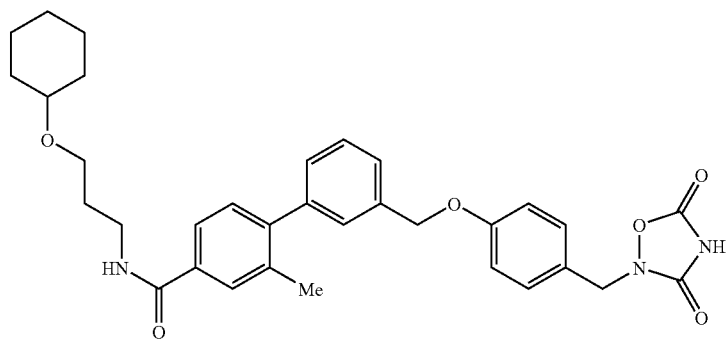
405
406
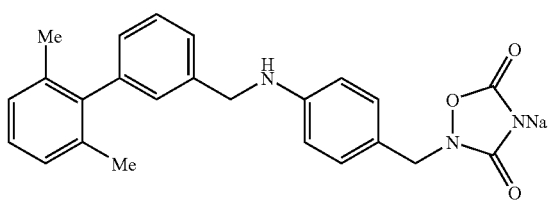
407
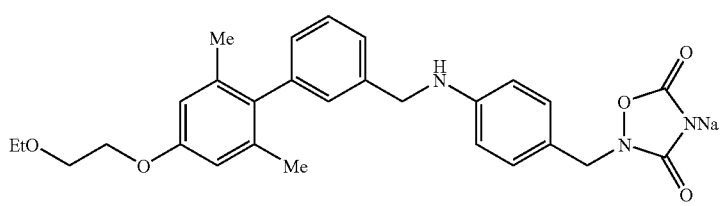
| TABLE 114 | | |
|---|---|---|
| Ex | Syn | Dat |
| 1 | 1 | NMR1: 2.21(3H, s), 4.33(2H, s), 5.14(2H, s), 6.96(2H, d), 7.15-7.25(3H, m), 7.25-7.35(2H, m), 7.36-7.43(2H, m), 7.43-7.51(2H, m); FAB-N: 421 |
| 2 | 2 | FAB-N: 547 |
| 3 | 3 | NMR1: 1.92(6H, s), 1.96-2.09(2H, m), 2.09-2.24(2H, m), 2.93-3.10(2H, m), 3.18-3.40(2H, m), 3.85(2H, s), 4.31(2H, s), 5.13(2H, s), 5.15-5.40(1H, br), 6.72(2H, s), 6.94(2H, d), 7.05(1H, d), 7.11-7.25(3H, m), 7.35-7.52(2H, m); FAB: 581 |
| TABLE 114-continued | | |
|---|---|---|
| Ex | Syn | Dat |
| 9 | 9 | NMR1: 4.71(2H, s), 5.12(2H, s), 7.03(2H, d), 7.28(2H, d), 7.36(1H, dd), 7.46(1H, d), 7.53(1H, d), 7.66(1H, s), 12.00-12.80(1H, br); FAB-N: 375, 377 |
| 4 | 4 | NMR1: 3.83(3H, s), 4.32(2H, s), 5.13(2H, s), 6.87(2H, d), 6.96(2H, d), 7.20(2H, d), 7.29-7.41(1H, m), 7.41-7.58(3H, m); FAB-N: 439 |
| 28 | 4 | ESI-N: 391 |
| 29 | 4 | ESI-N: 391 |
| 30 | 4 | ESI-N: 431 |

TABLE 114-continued

| Ex | Syn | Dat |
|---|---|---|
| 5 | 5 | NMR1: 4.71(2H, s), 5.20(2H, s), 7.05-7.07(2H, m), 7.23-7.28(2H, m), 7.49-7.55(2H, m), 7.69-7.72(1H, m), 7.80-7.81(3H, m), 8.03-8.04(2H, m), 12.42(1H, bs), 12.99(1H, s); FAB-N: 417 |
| 31 | 6 | FAB: 476 |
| 6 | 6 | NMR1: 1.10-1.14(3H, m), 3.41-3.53(6H, m), 4.44(2H, s), 5.18(2H, s), 7.00(2H, d, J = 8.4 Hz), 7.23(2H, d, J = 8.8 Hz), 7.47-7.53(2H, m), 7.69-7.70(1H, m), 7.78(2H, d, J = 8.8 Hz), 7.81(1H, s), 7.95(2H, d, J = 8.4 Hz), 8.58-8.61(1H, m); FAB: 490 |
| 32 | 4 | NMR1: 2.36(3H, s), 4.34(2H, s), 5.14(2H, s), 6.96-6.98(2H, m), 7.11-7.48(8H, m), 7.59(1H, s); ESI-N: 405 |
| 33 | 4 | ESI: 376; ESI-N: 374 |
| 8 | 8 | NMR1: 3.73(2H, t, J = 4.8 Hz, 5.2 Hz), 4.03(2H, t, J = 4.8 Hz), 4.72(2H, s), 4.89(1H, bs), 5.17(2H, s), 7.01-7.07(4H, m), 7.26-7.28(2H, m), 7.37-7.47(2H, m), 7.57-7.62(3H, m), 7.69(1H, s), 12.41(1H, bs); ESI-N: 433 |
| 34 | 4 | ESI-N: 398 |
| 35 | 4 | NMR1: 4.32(2H, s), 5.14(2H, s), 6.97(2H, d), 7.12-729(4H, m), 7.36-7.59(5H, m); FAB-N: 409 |
| 36 | 9 | NMR1: 2.21(3H, s), 4.36(2H, s), 5.17(2H, s), 6.78-6.94(2H, m), 7.18-7.36(4H, m), 7.37-7.43(2H, m), 7.43-7.53(2H, m); ESI-N: 439 |
| 37 | 9 | ESI-N: 435 |

TABLE 115

| Ex | Syn | Dat |
|---|---|---|
| 38 | 9 | NMR1: 4.31(2H, s), 5.08(2H, s), 6.86-6.97(3H, m), 7.02(2H, d), 7.06-7.11(1H, m), 7.11-7.27(4H, m), 7.34-7.46(3H, m); ESI-N: 389 |
| 39 | 4 | NMR1: 1.95(6H, s), 4.31(2H, s), 5.14(2H, s), 6.94-6.96(2H, m), 7.08-7.20(7H, m), 7.42-7.49(2H, m); ESI-N: 401 |
| 40 | 1 | ESI: 334 |
| 7 | 7 | NMR1: 3.30-3.41(2H, m), 3.51-3.55(2H, m), 4.33(2H, s), 4.74-4.77(1H, m), 5.17(2H, s), 6.98(2H, d, J = 8.8 Hz), 7.21(2H, d, J = 8 Hz), 7.47-7.53(2H, m), 7.68-7.70(1H, m), 7.78(2H, d, J = 8.8 Hz), 7.81(1H, s), 7.95(2H, d, J = 8.4 Hz), 8.49-8.51(1H, m); ESI: 462 |
| 41 | 9 | ESI-N: 433 |
| 42 | 9 | NMR1: 4.73(2H, s), 5.23(2H, s), 7.08(2H, d, J = 8.8 Hz), 7.29(2H, d, J = 8.4 Hz), 7.50-7.55(1H, m), 7.84-7.85(1H, m), 7.98-7.99(1H, m), 12.42(1H, bs); ESI-N: 383 |
| 43 | 1 | ESI-N: 444 |
| 44 | 1 | NMR1: 1.14(3H, t, J = 6.8 Hz, 7.6 Hz), 1.92(6H, s), 3.51(2H, q, J = 6.8 Hz, 7.2 Hz), 3.69(2H, t, J = 4.4 Hz, 4.8 Hz), 4.08(2H, t, J = 4.4 Hz, 4.8 Hz), 4.33(2H, s), 5.13(2H, s), 6.70(2H, s), 6.93-6.96(2H, m), 7.05-7.07(1H, m), 7.17-7.20(3H, m), 7.40-7.47(2H, m); ESI: 491 |
| 45 | 2 | NMR1: 1.92(6H, s), 3.69-3.75(2H, m), 3.97-4.00(2H, m), 4.32(2H, s), 4.84-4.87(1H, m), 5.13(2H, s), 6.66(2H, s), 6.94-6.96(2H, m), 7.05-7.07(1H, m), 7.17-7.20(3H, m), 7.40-7.47(2H, m); FAB: 463 |
| 46 | 1 | NMR1: 3.26(3H, s), 4.33(2H, s), 5.18(2H, s), 6.98(2H, d, J = 8.8 Hz), 7.21(2H, d, J = 8.8 Hz), 7.53-7.57(2H, m), 7.71-7.73(1H, m), 7.84(1H, m), 7.95-8.02(4H, m); ESI-N: 451 |
| 47 | 9 | NMR1: 1.93(6H, s), 3.75(3H, s), 4.32(2H, s), 5.13(2H, s), 6.69(2H, s), 6.94-6.96(2H, m), 7.05-7.07(1H, m), 7.17-7.20(3H, m), 7.40-7.47(2H, m); FAB-N: 431 |
| 48 | 4 | FAB-N: 403 |
| 49 | 4 | NMR1: 1.88(6H, s), 2.24(3H, s), 4.31(2H, s), 5.11(2H, s), 6.87-6.95(4H, m), 7.01-7.05(1H, m), 7.12-7.19(3H, m), 7.37-7.46(2H, m); ESI-N: 415 |
| 50 | 9 | NMR1: 4.30(2H, s), 5.10(2H, s), 6.96(2H, d), 7.21(2H, d), 7.44-7.46(1H, m), 7.56-7.60(1H, m), 7.77-7.78(1H, m); FAB-N: 411 |
| 51 | 1 | ESI-N: 445 |
| 52 | 5 | FAB-N: 431 |
| 10 | 10 | NMR1: 2.17(3H, s), 4.19(2H, s), 4.29-4.31(2H, m), 6.20-6.23(1H, m), 6.50-6.52(2H, m), 6.94-6.96(2H, m), 7.16-7.20(2H, m), 7.28-7.31(2H, m), 7.35-7.41(3H, m) ESI: 422, 424 |

TABLE 116

| Ex | Syn | Dat |
|---|---|---|
| 53 | 2 | NMR1: 1.76(6H, s), 4.33(2H, s), 5.09(2H, s), 6.00(2H, s), 6.95(2H, d, J = 8.7 Hz), 7.00-7.02(1H, m), 7.13(1H, s), 7.19(2H, d, J = 8.7 Hz), 7.26-7.28(1H, m), 7.32-7.36(1H, m) FAB-N: 417 |
| 54 | 1 | NMR1: 1.97(6H, s), 4.32(2H, s), 5.20(2H, s), 6.95-6.97(2H, m), 7.11-7.13(2H, m), 7.19-7.21(2H, m), 7.22-7.26(2H, m), 7.48-7.50(1H, m), 7.89-7.93(1H, m) FAB: 404 |
| 55 | 7 | FAB: 490 |
| 56 | 4 | NMR1: 3.64(6H, s), 4.34(2H, s), 5.08(2H, s), 6.72-6.74(2H, m), 6.96(2H, d, J = 8.5 Hz), 7.14-7.16(1H, m), 7.20(2H, d, J = 8.5 Hz), 7.26-7.39(4H, m) FAB-N: 433 |
| 57 | 4 | NMR1: 2.21(3H, s), 4.33(2H, s), 5.15(2H, s), 6.96(2H, d, J = 8.6 Hz), 7.20(2H, d, J = 8.6 Hz), 7.26-7.30(5H, m), 7.40-7.48(3H, m) FAB-N: 387 |
| 11 | 11 | NMR1: 1.89(6H, s), 3.68-3.72(2H, m), 3.95-3.98(2H, m), 4.20(2H, s), 4.28-4.30(2H, m), 4.84(1H, bs), 6.18-6.21(1H, m), 6.50(2H, d, J = 8.5 Hz), 6.66(2H, s), 6.94(2H, d, J = 8.5 Hz), 6.93-6.95(1H, m), 7.06(1H, m), 7.29-7.31(1H, m), 7.34-7.38(1H, m) ESI: 462 |
| 58 | 7 | FAB-N: 430 |
| 59 | 1 | NMR1: 1.92(6H, s), 3.32(3H, s), 3.65(2H, t, J = 4.5, 4.7 Hz), 4.09(2H, t, J = 4.5, 4.7 Hz), 4.32(2H, s), 5.13(2H, s), 6.70(2H, s), 6.93-6.95(2H, m), 7.05-7.07(1H, m), 7.17-7.20(3H, m), 7.40-7.47(2H, m) ESI-N: 475 |
| 60 | 1 | NMR1: 4.33(2H, s), 5.14(2H, s), 6.97(2H, d, J = 8.6 Hz), 7.20(2H, d, J = 8.6 Hz), 7.22-7.24(1H, m), 7.35(1H, s), 7.42-7.46(1H, m), 7.51-7.52(2H, m), 7.58-7.60(2H, m) FAB-N: 441 |
| 61 | 4 | FAB-N: 437 |
| 62 | 1 | FAB-N: 475(-COMe) |
| 13 | 13 | NMR1: 1.82-1.89(2H, m), 1.92(6H, s), 3.53-3.58(2H, m), 4.01-4.04(2H, m), 4.32(2H, s), 4.53-4.55(1H, m), 5.13(2H, s), 6.68(2H, s), 6.94(2H, d, J = 8.8 Hz), 7.05-7.07(1H, m), 7.16-7.19(1H, m), 7.17(2H, d, J = 8.8 Hz), 7.39-7.46(2H, m) FAB-N: 475 |
| 63 | 1 | NMR1: 1.95(6H, s), 4.35(2H, s), 5.17(2H, s), 6.75-6.93(2H, m), 7.04-7.32(6H, m), 7.38-7.54(2H, m) FAB-N: 419 |
| 64 | 1 | FAB-N: 431 |

TABLE 117

| Ex | Syn | Dat |
|---|---|---|
| 65 | 1 | NMR1: 1.94(6H, s), 4.33(2H, s), 5.22(2H, s), 6.94-7.30(8H, m), 7.38-7.58(2H, m) FAB-N: 419 |
| 66 | 1 | FAB-N: 401 |
| 67 | 1 | FAB-N: 415 |
| 68 | 1 | FAB-N: 431 |
| 69 | 1 | FAB-N: 419 |
| 70 | 1 | FAB-N: 419 |
| 71 | 1 | FAB-N: 419 |
| 72 | 1 | FAB-N: 419 |
| 73 | 1 | NMR1: 1.86(6H, s), 1.90(3H, s), 4.32(2H, s), 5.08(2H, s), 6.93(2H, d, J = 8.5 Hz), 7.04(1H, s), 7.09-7.24(5H, m), 7.32-7.36(2H, m) FAB-N: 415 |
| 74 | 1 | NMR1: 1.88(6H, s), 1.92(3H, s), 4.34(2H, s), 5.12(2H, s), 6.90-7.05(3H, m), 7.08-7.20(3H, m), 7.22(2H, d, J = 8.6 Hz), 7.29(1H, t, J = 7.3 Hz), 7.45(1H, d, J = 7.3 Hz) FAB-N: 415 |
| 75 | 1 | FAB-N: 435 |
| 76 | 1 | FAB-N: 435 |
| 77 | 1 | FAB-N: 431 |
| 78 | 1 | FAB-N: 459 |
| 79 | 1 | FAB-N: 507 |
| 80 | 1 | FAB-N: 449 |
| 81 | 1 | FAB-N: 429 |
| 82 | 1 | FAB: 404 |
| 83 | 11 | NMR1: 2.16(3H, s), 3.69-3.73(2H, m), 3.98-4.00(2H, m), 4.20(2H, s), 4.28-4.30(2H, m), 4.85-4.88(1H, m), 6.18-6.21(1H, m), 6.52(2H, d, J = 8.4 Hz), 6.80-6.85(2H, m), 6.95(2H, d, J = 8.4 Hz), 7.07-7.10(1H, m), 7.13-7.15(1H, m), 7.27-7.37(3H, m) ESI-N: 446 |
| 84 | 7 | NMR1: 2.26(3H, s), 2.79-2.80(3H, m), 4.33(2H, s), 5.15(2H, s), 6.96(2H, d, J = 8.6 Hz), 7.20(2H, d, J = 8.6 Hz), 7.28-7.32(2H, m), 7.43-7.48(3H, m), 7.70-7.72(1H, m), 7.77(1H, s), 8.44-8.45(1H, m) ESI-N: 444 |
| 85 | 7 | ESI: 488 |
| 86 | 7 | ESI: 503 |
| 87 | 7 | NMR1: 2.24(3H, s), 2.98(6H, s), 4.32(2H, s), 5.15(2H, s), 6.95-6.97(2H, m), 7.19-7.21(2H, m), 7.24-7.33(4H, m), 7.43-7.50 (3H, m) FAB: 460 |

TABLE 118

| | | |
|---|---|---|
| 88 | 1 | FAB-N: 415 |
| 89 | 11 | ESI: 434 |
| 90 | 10 | ESI-N: 414 |
| 91 | 10 | ESI: 403 |
| 92 | 1 | ESI-N: 426 |
| 20 | 20 | FAB: 462 |
| 93 | 5 | ESI-N: 475 |
| 94 | 1 | NMR1: 2.01(3H, s), 4.33(2H, s), 5.14(2H, s), 6.92-7.00(2H, m), 7.10-7.34(6H, m), 7.35-7.42(1H, m), 7.44-7.54(2H, m) FAB-N: 421 |
| 95 | 1 | NMR1: 4.32(2H, s), 5.14(2H, s), 6.92-7.00(2H, m), 7.16-7.26(4H, m), 7.32-7.36(1H, m), 7.48-7.57(3H, m) FAB-N: 459 |
| 96 | 1 | NMR1: 1.84(3H, s), 1.92(6H, s), 3.38-3.42(2H, m), 3.96-3.99(2H, m), 4.32(2H, s), 5.13(2H, s), 6.70(2H, s), 6.94(2H, d, J = 8.5 Hz), 7.05-7.06(1H, m), 7.16-7.20(1H, m), 7.19(2H, d, J = 8.5 Hz), 7.40-7.47(2H, m), 8.08-8.10(1H, m) FAB: 504 |
| 15 | 15 | NMR1: 1.91(6H, s), 2.86(3H, s), 3.01(3H, s), 4.31(2H, s), 4.77(2H, s), 5.13(2H, s), 6.68(2H, s), 6.93-6.95(2H, m), 7.05-7.07(1H, m), 7.17-7.20(3H, m), 7.40-7.47(2H, m) FAB: 504 |
| 97 | 1 | FAB-N: 415 |
| 98 | 1 | FAB-N: 415 |
| 99 | 1 | ESI-N: 402 |
| 100 | 1 | FAB: 420(M + NH$_3$) |
| 101 | 1 | NMR1: 1.96(6H, s), 4.33(2H, s), 4.86(2H, s), 6.57(1H, d, J = 9.3 Hz), 6.94(2H, d, J = 8.5 Hz), 7.13-7.35(5H, m), 7.55-7.73(2H, m) FAB: 420 |
| 102 | 1 | NMR1: 1.85-2.02(2H, m), 2.77(2H, t, J = 6.4 Hz), 3.50-3.62(2H, m), 4.31(2H, s), 4.85(2H, s), 6.64-6.75(2H, m), 6.81(2H, d, J = 8.5 Hz), 7.01(1H, d, J = 7.6 Hz), 7.08(1H, t, J = 7.3 Hz), 7.12-7.23(4H, m), 7.28-7.40(2H, m) ESI: 430 |
| 103 | 1 | ESI: 410 |
| 16 | 16 | NMR1: 2.00(6H, s), 4.36(2H, s), 7.12-7.23(3H, m), 7.25(2H, d, J = 8.4 Hz), 7.34-7.44(1H, m), 7.58-7.66(1H, m), 7.71(2H, d, J = 8.4 Hz), 7.78-7.84(1H, m), 7.89-8.06(1H, m), 10.20(1H, s) ESI: 416 |

TABLE 119

| | | |
|---|---|---|
| 104 | 1 | NMR1: 1.92(6H, s), 2.17(3H, s), 2.84(2H, t, J = 6.5, 6.6 Hz), 4.15(2H, t, J = 6.5, 6.6 Hz), 4.32(2H, s), 5.13(2H, s), 6.71(2H, s), 6.94(2H, d, J = 8.6 Hz), 7.05-7.07(1H, m), 7.17-7.20(1H, m), 7.19(2H, d, J = 8.6 Hz), 7.40-7.47(2H, m) FAB-N: 491 |
| 105 | 7 | NMR1: 1.94(6H, s), 2.66-2.67(3H, m), 4.32(2H, s), 4.45(2H, s), 5.13(2H, s), 6.73(2H, s), 6.93-6.95(2H, m), 7.05-7.07(1H, m), 7.17-7.20(3H, m), 7.40-7.47(2H, m), 7.99-8.07(1H, m) ESI-N: 488 |
| 14 | 14 | NMR1: 2.20(3H, s), 3.73(2H, q, J = 5.2 Hz), 4.01(2H, t, J = 5.0 Hz), 4.34(2H, s), 4.89(1H, t, J = 5.6 Hz), 5.13(2H, s), 6.81-6.89(2H, m), 6.96(2H, d, J = 8.8 Hz), 7.12(1H, d, J = 8.4 Hz), 7.21(2H, d, J = 8.7 Hz), 7.24-7.28(1H, m), 7.35-7.46(3H, m) FAB-N: 447 |
| 106 | 1 | NMR1: 2.04(6H, s), 4.34(2H, s), 5.04(2H, s), 6.65(1H, dd, J = 2.2, 8.2 Hz), 6.82(1H, d, J = 2.2 Hz), 6.89(2H, d, J = 8.7 Hz), 7.02-7.13(2H, m), 7.13-7.24(4H, m), 7.30(1H, t, J = 7.9 Hz) FAB-N: 417 |
| 107 | 1 | FAB-N: 457, 459 |
| 108 | 1 | FAB-N: 419 |
| 109 | 1 | FAB-N: 457 |
| 110 | 1 | FAB-N: 407 |
| 111 | 1 | NMR1: 1.87-1.97(4H, m), 1.92(6H, s), 2.19-2.24(2H, m), 3.32-3.39(4H, m), 3.94-3.97(2H, m), 4.33(2H, s), 5.13(2H, s), 6.68(2H, s), 6.95(2H, d, J = 8.7 Hz), 7.05-7.07(1H, m), 7.17-7.20(1H, m), 7.19(2H, d, J = 8.7 Hz), 7.40-7.47(2H, m) FAB: 544 |
| 112 | 1 | ESI: 544 |
| 113 | 1 | FAB-N: 429 |
| 114 | 1 | NMR1: 2.10(6H, s), 4.33(2H, s), 5.27(2H, s), 6.80(1H, d, J = 3.4 Hz), 6.96-7.01(2H, m), 7.11-7.15(2H, m), 7.17-7.25(4H, m) FAB-N: 407 |
| 115 | 1 | FAB-N: 407 |
| 116 | 7 | ESI: 566 |
| 117 | 7 | NMR1: 1.53-1.66(2H, m), 1.73-1.81(2H, m), 2.26(3H, m), 3.32-3.45(2H, m), 3.85-3.92(2H, m), 3.96-4.06(1H, m), 4.32(2H, s), 5.16(2H, s), 6.96(2H, d, J = 8.6 Hz), 7.20(2H, d, J = 8.7 Hz), 7.26-7.34(2H, m), 7.40-7.43(1H, m), 7.45-7.50(2H, m), 7.70-7.75(1H, m), 7.76-7.80(1H, m), 8.28-8.34(1H, m) FAB: 516 |
| 118 | 1 | ESI-N: 528 |

TABLE 120

| | | |
|---|---|---|
| 119 | 1 | NMR1: 1.98(6H, s), 3.41(3H, s), 4.32(2H, s), 5.15(2H, s), 6.94-6.96(2H, m), 7.10-7.13(3H, m), 7.18-7.22(3H, m), 7.45-7.51(2H, m) ESI-N: 495 |
| 120 | 1 | ESI: 512 |
| 121 | 1 | ESI-N: 545 |
| 122 | 13 | NMR1: 1.17(6H, s), 1.84(2H, t, J = 7.0, 7.2 Hz), 1.92(6H, s), 4.07(2H, t, J = 7.0, 7.2 Hz), 4.32(2H, s), 4.37(1H, s), 5.13(2H, s), 6.68(2H, s), 6.93-6.96(2H, m), 7.05-7.07(1H, m), 7.17-7.20(3H, m), 7.40-7.46(2H, m) FAB-N: 503 |
| 123 | 5 | NMR1: 2.18(3H, s), 4.69(2H, s), 4.72(2H, s), 5.16(2H, s), 6.80(1H, dd, J = 2.5, 8.4 Hz), 6.86(1H, d, J = 2.5 Hz), 7.04(2H, d, J = 8.6 Hz), 7.12(1H, d, J = 8.4 Hz), 7.20-7.32(3H, m), 7.34-7.49(3H, m), 11.80-13.50(2H, m) ESI-N: 461 |
| 124 | 21 | ESI-N: 475 |
| 17 | 17 | NMR1: 1.04-1.07(3H, m), 1.93(6H, s), 3.14-3.21(2H, m), 4.32(2H, s), 4.44(2H, s), 5.13(2H, s), 6.73(2H, s), 6.94(2H, d, J = 8.7 Hz), 7.05-7.07(1H, m), 7.17-7.20(1H, m), 7.19(2H, d, J = 8.7 Hz), 7.40-7.47(2H, m), 8.09-8.11(1H, m) ESI-N: 502 |
| 125 | 17 | FAB-N: 514 |
| 126 | 13 | ESI-N: 475 |
| 127 | 1 | NMR1: 1.86-2.00(1H, m), 1.95(6H, s), 2.13-2.24(1H, m), 2.64-2.77(1H, m), 2.81-2.93(1H, m), 5.13(2H, s), 5.17-5.25(1H, m), 6.77-6.82(1H, m), 6.84-6.88(1H, m), 7.03-7.21(6H, m), 7.39-7.50(2H, m) FAB-N: 427 |
| 128 | 17 | ESI: 530 |
| 129 | 17 | NMR1: 1.92(6H, s), 3.42-3.54(4H, m), 3.54-3.67(4H, m), 4.32(2H, s), 4.79(2H, s), 5.13(2H, s), 6.70(2H, s), 6.91-6.97(2H, m), 7.03-7.09(1H, m), 7.15-7.21(3H, m), 7.38-7.48(2H, m) FAB: 546 |
| 130 | 7 | FAB: 546 |
| 131 | 17 | ESI: 520 |
| 132 | 17 | ESI: 534 |
| 18 | 18 | NMR1: 1.93(6H, s), 4.05-4.09(1H, m), 4.16-4.19(1H, m), 4.31(2H, s), 4.36-4.40(1H, m), 5.13(2H, s), 6.71(1H, bs), 6.74(2H, s), 6.94(2H, d, J = 8.6 Hz), 7.05-7.07(1H, m), 7.17-7.20(1H, m), 7.18(2H, d, J = 8.6 Hz), 7.40-7.47(2H, m) ESI-N: 529 |

TABLE 121

| | | |
|---|---|---|
| 133 | 17 | ESI-N: 516 |
| 134 | 17 | ESI-N: 532 |
| 135 | 1 | ESI-N: 517 |
| 136 | 17 | NMR1: 2.20(3H, s), 2.66-2.67(3H, s), 4.32(2H, s), 4.48(2H, s), 5.13(2H, s), 6.84-6.86(1H, s), 6.90-6.91(1H, m), 6.96(2H, d, J = 8.7 Hz), 7.13-7.15(1H, m), 7.20(2H, d, J = 8.7 Hz), 7.24-7.26(1H, m), 7.36(1H, s), 7.40-7.45(2H, m), 8.02-8.04(1H, m) ESI: 476 |
| 137 | 17 | NMR1: 1.04-1.07(3H, m), 2.20(3H, s), 3.14-3.20(2H, m), 4.32(2H, s), 4.46(2H, s), 5.13(2H, s), 6.84-6.86(1H, m), 6.91-6.92(1H, m), 6.96(2H, d, J = 8.7 Hz), 7.13-7.15(1H, m), 7.20(2H, d, J = 8.7 Hz), 7.25-7.26(1H, m), 7.36-7.45(3H, m), 8.09-8.11(1H, m) ESI: 490 |
| 138 | 17 | FAB-N: 518 |
| 139 | 17 | ESI-N: 474 |
| 140 | 17 | ESI-N: 544 |
| 141 | 17 | FAB-N: 516 |
| 142 | 17 | NMR1: 1.05(6H, s), 2.19(3H, s), 3.12(2H, d, J = 6.0 Hz), 4.33(2H, s), 4.45-4.56(3H, m), 5.13(2H, s), 6.84-6.87(1H, m), 6.90-6.91(1H, m), 6.96(2H, d, J = 8.6 Hz), 7.13-7.15(1H, m), 7.20(2H, d, J = 8.6 Hz), 7.24-7.26(1H, m), 7.36(1H, m), 7.40-7.45(2H, m), 7.77(1H, t, J = 6.0 Hz) FAB-N: 532 |
| 143 | 13 | NMR1: 3.73-3.77(2H, m), 4.11-4.13(2H, m), 4.32(2H, s), 4.91-4.94(1H, m), 5.12(2H, s), 6.95(2H, d, J = 8.5 Hz), 7.20 |

TABLE 121-continued

| | | |
|---|---|---|
| | | (2H, d, J = 8.5 Hz), 7.23-7.25(1H, m), 7.28-7.36(4H, m), 7.42-7.49(2H, m) FAB-N: 501 |
| 144 | 1 | FAB-N: 509 |
| 145 | 13 | NMR1: 3.71-3.73(2H, m), 4.05-4.07(2H, m), 4.32(2H, s), 4.90-4.92(1H, m), 5.14(2H, s), 6.95-6.97(2H, m), 7.00-7.01 (1H, m), 7.13-7.14(1H, m), 7.19-7.21(2H, m), 7.32-7.35(2H, m), 7.45-7.46(3H, m) ESI-N: 467 |
| 146 | 7 | NMR1: 1.01-1.20(3H, m), 2.16-2.32(3H, m), 3.32-3.46(2H, m), 3.75-4.08(2H, m), 4.32(2H, s), 5.15(2H, s), 6.96(2H, d, J = 8.7 Hz), 7.04-7.51(9H, m) FAB: 517 |
| 147 | 17 | NMR1: 2.16(3H, s), 2.86(3H, s), 3.01(3H, s), 4.32(2H, s), 4.81(2H, s), 5.13(2H, s), 6.80(1H, dd, J = 8.4, 2.6 Hz), 6.86 (1H, d, J = 2.6 Hz), 6.93-6.98(2H, m), 7.11(1H, d, J = 8.4 Hz), 7.17-7.22(2H, m), 7.23-7.27(1H, m), 7.36(1H, bs), 7.38-7.46(2H, m) ESI: 490 |

TABLE 122

| | | |
|---|---|---|
| 148 | 17 | ESI: 520 |
| 149 | 17 | ESI: 516 |
| 150 | 17 | ESI: 532 |
| 151 | 17 | ESI: 545 |
| 152 | 17 | ESI: 520 |
| 153 | 17 | ESI-N: 534 |
| 154 | 17 | ESI: 518 |
| 155 | 17 | ESI-N: 537 |
| 156 | 14 | NMR1: 1.21(6H, s), 2.20(3H, s), 3.73(2H, s), 4.32(2H, s), 4.62(2H, s), 5.13(2H, s), 6.82(1H dd, J = 8.4, 2.6 Hz), 6.87 (1H, d, J = 2.5 Hz), 6.93-6.98(2H, m), 7.12(1H, d, J = 8.4 Hz), 7.17-7.22(2H, m), 7.23-7.27(1H, m), 7.36(1H, bs), 7.38-7.46(2H, m) FAB-N: 475 |
| 157 | 17 | NMR1: 1.12(6, Hs), 2.27(3H, s), 3.27(2H, d, J = 6.1 Hz), 4.33(2H, s), 4.61(1H, bs), 5.16(2H, s), 6.96-6.98(2H, m), 7.19-7.21(2H, m), 7.29-7.33(2H, m), 7.43(1H, s), 7.47-7.51(2H, m), 7.74-7.76(1H, m), 7.81(1H, s), 8.27(1H, t, J = 6.1 Hz) ESI: 504 |
| 19 | 19 | FAB-N: 473 |
| 158 | 18 | NMR1: 1.37(3H, s), 1.93(6H, s), 4.05(2H, s), 4.30-4.32 (4H, m), 4.49-4.50(2H, m), 5.13(2H, s), 6.75(2H, s), 6.93-6.96(2H, m), 7.05-7.07(1H, m), 7.17-7.20(3H, m), 7.40-7.47(2H, m) FAB-N: 501 |
| 159 | 1 | ESI-N: 459 |
| 160 | 1 | NMR1: 1.18(6H, s), 1.90-1.93(2H, m), 1.92(6H, s), 3.12 (3H, s), 4.00-4.04(2H, m), 4.32(2H, s), 5.13(2H, s), 6.68 (2H, s), 6.94(2H, d, J = 8.6 Hz), 7.05-7.07(1H, m), 7.17-7.20(1H, m), 7.19(2H, d, J = 8.6 Hz), 7.39-7.46(2H, m) FAB-N: 517 |
| 161 | 1 | ESI-N: 531 |
| 162 | 13 | NMR1: 1.18(6H, s), 1.85(2H, t, J = 7.1, 7.2 Hz), 2.20(3H, s), 4.10(2H, t, J = 7.1, 7.2 Hz), 4.33(2H, s), 4.40(1H, s), 5.13(2H, s), 6.81-6.86(2H, m), 6.96(2H, d, J = 8.6 Hz), 7.11-7.13(1H, m), 7.20(2H, d, J = 8.6 Hz), 7.24-7.26(1H, m), 7.36-7.45(3H, m) FAB-N: 489 |
| 163 | 18 | NMR1: 1.18(6H, s), 1.86(2H, t, J = 7.1, 7.2 Hz), 1.97(3H, s), 2.00(3H, s), 4.10(2H, t, J = 7.1, 7.2 Hz), 4.35(2H, s), 4.39(1H, s), 5.11(2H, s), 6.79-6.81(1H, m), 6.86-6.87(1H, m), 6.96-7.06(4H, m), 7.21-7.25(3H, m), 7.41-7.43(1H, m) ESI-N: 503 |

TABLE 123

| | | |
|---|---|---|
| 164 | 14 | NMR1: 1.97(3H, s), 2.00(3H, s), 3.71-3.75(2H, m), 4.00-4.03(2H, m), 4.34(2H, s), 4.85-4.88(1H, m), 5.11(2H, s), 6.80-6.82(1H, m), 6.87-6.88(1H, m), 6.97-7.05(4H, m), 7.21-7.26(3H, m), 7.42-7.43(1H, m) ESI-N: 461 |
| 165 | 18 | NMR1: 1.21(6H, s), 1.92(6H, s), 3.70(2H, s), 4.32(2H, s), 4.60(1H, bs), 5.13(2H, s), 6.69(2H, s), 6.94(2H, d, J = 8.5 Hz), 7.05-7.06(1H, m), 7.16-7.20(1H, m), 7.19(2H, d, J = 8.5 Hz), 7.39-7.47(2H, m) ESI-N: 489 |
| 166 | 18 | NMR1: 1.18(6H, s), 1.83-1.87(2H, m), 1.85(6H, s), 1.92 (3H, s), 4.06-4.10(2H, m), 4.34(2H, s), 4.37(6H, s), 5.11 (2H, s), 6.71(2H, s), 6.95-7.00(3H, m), 7.21-7.28(3H, m), 7.41-7.43(1H, m) FAB-N: 517 |
| 167 | 14 | NMR1: 1.85(6H, s), 1.92(3H, s), 3.71-3.73(2H, m), 3.98-4.00(2H, m), 4.34(2H, s), 4.85(1H, bs), 5.11(2H, s), |

TABLE 123-continued

| | | |
|---|---|---|
| | | 6.72(2H, s), 6.95-7.00(3H, m), 7.21-7.28(3H, m), 7.41-7.43 (1H, m) FAB-N: 475 |
| 168 | 18 | NMR1: 2.24(3H, s), 3.42(3H, s), 4.33(2H, s), 5.15(2H, s), 6.96(2H, d, J = 8.7 Hz), 7.20(2H, d, J = 8.7 Hz), 7.24-7.33 (4H, m), 7.42-7.50(3H, m) ESI-N: 481 |
| 169 | 18 | NMR1: 1.18(6H, s), 1.83-1.87(2H, m), 1.96(6H, s), 4.07-4.11(2H, m), 4.32(2H, s), 4.38(1H, s), 5.19(2H, s), 6.69(2H, s), 6.95-6.97(2H, m), 7.18-7.22(3H, m), 7.44-7.46 (1H, m), 7.86-7.90(1H, m) FAB: 506 |
| 170 | 18 | NMR1: 1.18(6H, s), 1.85-1.89(2H, m), 2.20(3H, s), 4.11-4.15(2H, m), 4.34(2H, s), 4.39(1H, s), 5.11(2H, s), 6.98-7.00(4H, m), 7.16-7.26(6H, m), 7.41-7.42(1H, m) FAB-N: 489 |
| 171 | 14 | NMR1: 2.20(3H, s), 3.72-3.76(2H, m), 4.02-4.05(2H, m), 4.34(2H, s), 4.88-4.91(1H, m), 5.11(2H, s), 6.98-7.02(4H, m), 7.15-7.26(6H, m), 7.41-7.42(1H, m) FAB-N: 447 |
| 172 | 18 | NMR1: 1.13-1.14(3H, m), 1.72-1.83(2H, m), 1.96(3H, s), 2.00(3H, s), 3.80-3.85(1H, m), 4.01-4.10(2H, m), 4.34(2H, s), 4.57-4.58(1H, m), 5.10(2H, s), 6.79-6.81(1H, m), 6.86-6.87(1H, m), 6.96-7.05(4H, m), 7.21-7.25(3H, m), 7.42-7.43 (1H, m) FAB-N: 489 |

TABLE 124

| | | |
|---|---|---|
| 173 | 18 | NMR1: 1.13-1.14(3H, m), 1.71-1.82(2H, m), 1.96(3H, s), 2.00(3H, s), 3.80-3.86(1H, m), 4.01-4.10(2H, m), 4.34(2H, s), 4.56-4.57(1H, m), 5.10(2H, s), 6.78-6.81(1H, m), 6.86-6.87(1H, m), 6.96-7.05(4H, m), 7.21-7.25(3H, m), 7.41-7.43 (1H, m) ESI-N: 489 |
| 174 | 18 | NMR1: 1.18(6H, s), 1.86(2H, t, J = 7.1 Hz), 2.11(3H, s), 4.11(2H, t, J = 7.1 Hz), 4.33(2H, s), 4.39(1H, s), 5.16(2H, s), 6.83(1H, dd, J = 2.5, 8.4 Hz), 6.89(1H, d, J = 2.5 Hz), 6.98(2H, d, J = 8.7 Hz), 7.12(1H, d, J = 8.4 Hz), 7.21(2H, d, J = 8.7 Hz), 7.24-7.31(2H, m), 7.50-7.59(1H, m) ESI-N: 507 |
| 12 | 12 | NMR1: 1.18(6H, s), 1.86(2H, t, J = 7.2 Hz), 1.97(3H, s), 1.99(3H, s), 4.10(2H, t, J = 7.2 Hz), 4.17-4.26(4H, m), 4.39 (1H, s), 6.01(1H, t, J = 5.6 Hz), 6.54(2H, d, J = 8.4 Hz), 6.79 (1H, dd, J = 2.6, 8.3 Hz), 6.86(1H, d, J = 2.6 Hz), 6.91-7.01 (4H, m), 7.16(1H, t, J = 7.5 Hz), 7.28(1H, t, J = 7.5 Hz) ESI-N: 502 |
| 175 | 18 | NMR1: 1.18(6H, s), 1.86(2H, t, J = 7.1 Hz), 1.96(3H, s), 2.00(3H, s), 4.10(2H, t, J = 7.1 Hz), 4.33-4.41(3H, m), 5.13 (2H, s), 6.80(1H, dd, J = 2.4, 8.3 Hz), 6.84-6.89(2H, m), 6.93 (1H, dd, J = 2.4, 12.1 Hz), 6.97(1H, d, J = 8.3 Hz), 7.06(1H, d, J = 7.8 Hz), 7.24(1H, t, J = 7.6 Hz), 7.29(1H, t, J = 8.7 Hz), 7.42(1H, t, J = 7.6 Hz) ESI-N: 521 |
| 176 | 18 | NMR1: 1.18(6H, s), 1.86(2H, t, J = 7.1 Hz), 2.03(3H, s), 4.11(2H, t, J = 7.1 Hz), 4.34(2H, s), 4.40(1H, s), 5.19(2H, s), 6.82(1H, dd, J = 2.5, 8.4 Hz), 6.88(1H, d, J = 2.5 Hz), 6.99(2H, d, J = 8.7 Hz), 7.03(1H, d, J = 8.4 Hz), 7.20-7.28(3H, m), 7.42(1H, t, J = 7.6 Hz), 7.60(1H, dd, J = ESI-N: 523 |
| 177 | 18 | NMR1: 1.19(6H, s), 1.87(2H, t, J = 7.2 Hz), 2.03(3H, s), 3.70(3H, s), 4.13(2H, t, J = 7.2 Hz), 4.33(2H, s), 4.38(1H, s), 5.08(2H, s), 6.58(1H, dd, J = 2.2, 8.2 Hz), 6.62(1H, d, J = 2.2 Hz), 6.95-7.01(3H, m), 7.06(1H, dd, J = 1.2, 7.6 Hz), 7.19(1H, t, J = 7.4 Hz), 7.22(2H, d, J = 8.7 Hz), 7.38(1H, dd, J = 1.2, 7.8 Hz) ESI-N: 519 |
| 178 | 18 | NMR1: 1.24(6H, s), 1.96(3H, s), 2.00(3H, s), 3.41(2H, d, J = 5.7 Hz), 4.34(2H, s), 4.89(1H, t, J = 5.7 Hz), 5.11(2H, s), 6.89(1H, dd, J = 2.3, 8.1 Hz), 6.92-7.02(4H, m), 7.07(1H, d, J = 7.5 Hz), 7.18-7.28(3H, m), 7.43(1H, d, J = 7.5 Hz) ESI-N: 489 |

TABLE 125

| | | |
|---|---|---|
| 179 | 17 | NMR1: 1.44(6H, s), 1.95(3H, s), 1.99(3H, s), 2.65(3H, d, J = 4.6 Hz), 4.34(2H, s), 5.10(2H, s), 6.73(1H, d, J = 2.4, 8.3 Hz), 6.84(1H, d, J = 2.4 Hz), 6.93-7.02(3H, m), 7.05(1H, d, J = 7.6 Hz), 7.18-7.27(3H, m), 7.43(1H, d, J = 7.4 Hz), 8.05 (1H, q, J = 4.6 Hz) ESI-N: 516 |
| 21 | 21 | NMR1: 1.41(6H, s), 1.90(3H, s), 2.00(3H, s), 4.33(2H, s), 5.10(2H, s), 6.70(1H, dd, J = 2.4, 8.3 Hz), 6.74(1H, d, J = 2.4 Hz), 6.82(1H, d, J = 8.3 Hz), 6.99(2H, d, J = 8.5 Hz), |

TABLE 125-continued

| | | |
|---|---|---|
| | | 7.03(1H, d, J = 7.5 Hz), 7.18-7.25(3H, m), 7.40(1H, d, J = 7.6 Hz) ESI-N: 503 |
| 180 | 18 | NMR1: 1.84-1.91(2H, m), 1.96(3H, s), 2.00(3H, s), 3.55-3.60(2H, m), 4.04-4.07(2H, m), 4.34(2H, s), 4.55-4.57(1H, m), 5.10(2H, s), 6.79-6.81(1H, m), 6.87-6.88(1H, m), 6.96-7.00(3H, m), 7.03-7.05(1H, m), 7.21-7.23(3H, m), 7.41-7.43(1H, m) ESI-N: 475 |
| 181 | 9 | NMR1: 1.97(3H, s). 2.00(3H, s), 2.06-2.19(2H, m), 4.10(2H, t, J = 6.3 Hz), 4.33(2H, s), 4.57-4.71(2H, m), 5.11(2H, s), 6.80-6.84(1H, m), 6.89-6.91(1H, m), 6.96-7.01(3H, m), 7.02-7.06(1H, m), 7.19-7.27(3H, m), 7.41-7.45(1H, m) ESI-N: 477 |
| 182 | 9 | NMR1: 1.96(3H, s), 2.00(3H, s), 3.33(3H, s), 3.67(2H, t, J = 4.4 Hz), 4.12(2H, t, J = 4.4 Hz), 4.34(2H, s), 5.11(2H, s), 6.76-6.84(1H, m), 6.87-6.91(1H, m), 6.95-7.07(4H, m), 7.16-7.29(3H, m), 7.38-7.46(1H, m); FAB-N: 475 |
| 183 | 9 | NMR1: 1.14(3H, t, J = 7.2 Hz), 1.96(3H, s), 2.00(3H, s), 3.52(2H, q, J = 7.2 Hz), 3.71(2H, t, J = 4.8 Hz), 4.11(2H, t, J = 4.8 Hz), 4.33(2H, s), 5.27(2H, s), 6.76-6.84(1H, m), 6.86-6.92(1H, m), 6.95-7.08(4H, m), 7.15-7.29(3H, m), 7.38-7.47(1H, m); FAB-N: 489 |
| 184 | 9 | NMR1: 1.91-2.03(8H, m), 3.26(3H, s), 3.49(2H, t, J = 6.4 Hz), 4.04(2H, t, J = 6.4 Hz), 4.24(2H, s), 5.11(2H, s), 6.78-6.83(1H, m), 6.86-6.89(1H, m), 6.94-7.07(4H, m), 7.19-7.28(3H, m), 7.40-7.46(1H, m); FAB-N: 489 |

TABLE 126

| | | |
|---|---|---|
| 185 | 18 | NMR1: 1.18(6H, s), 1.86(2H, t, J = 7.1 Hz), 1.90-2.1(1H, m), 1.97(3H, s), 1.99(3H, s), 2.16-2.28(1H, m), 2.69-2.80(1H, m), 2.85-2.97(1H, m), 4.10(2H, t, J = 7.1 Hz), 4.38(1H, s), 5.09(2H, s), 5.23(1H, dd, J = 5.8, 8.3 Hz), 6.80(1H, dd, J = 2.5, 8.4 Hz), 6.84(1H, dd, J = 2.2, 8.4 Hz), 6.87(1H, d, J = 2.5 Hz), 6.92(1H, d, J = 2.2 Hz), 6.97(1H, d J = 8.4 Hz), 7.04(1H, d, J = 7.6 Hz), 7.09(1H, d, J = 8.4 Hz), 7.24(1H, t, J = 7.6 Hz), 7.42(1H, d, J = 7.6 Hz) ESI-N: 529 |
| 186 | 9 | NMR1: 1.99(3H, s), 2.05(3H, s), 4.34(2H, s), 5.13(2H, s), 6.98-7.01(2H, m), 7.08-7.11(1H, m), 7.21-7.23(2H, m), 7.27-7.31(2H, m), 7.35-7.38(1H, m), 7.48-7.50(2H, m) ESI-N: 549 |
| 187 | 9 | ESI-N: 574 |
| 22 | 22 | NMR1: 1.97(3H, s), 2.00(3H, s), 2.02-2.10(2H, m), 2.95-3.00(2H, m), 4.08-4.11(2H, m), 4.73(2H, s), 5.13(2H, s), 6.81-6.84(1H, m), 6.89-6.90(1H, m), 6.98-7.00(1H, m), 7.03-7.06(1H, m), 7.07(2H, d, J = 8.6 Hz), 7.22-7.26(1H, m), 7.29(2H, d, J = 8.6 Hz), 7.42-7.44(1H, m), 8.00-8.10(3H, m), 12.48(1H, bs) ESI: 476 |
| 188 | 18 | NMR1: 1.48-1.77(8H, m), 1.92-1.95(5H, m), 2.00(3H, s), 4.14(2H, t, J = 6.8 Hz), 4.23(1H, s), 4.34(2H, s), 5.11(2H, s), 6.75-6.82(1H, m), 6.85-6.88(1H, m), 6.95-7.02(3H, m), 7.03-7.07(1H, m), 7.19-7.27(3H, m), 7.40-7.45(1H, m) FAB-N: 529 |
| 189 | 17 | NMR1: 1.81(3H, s), 1.82-1.89(2H, m), 1.97(3H, s), 2.00(3H, s), 3.17-3.23(2H, m), 3.99-4.02(2H, m), 4.34(2H, s), 5.10(2H, s), 6.78-6.81(1H, m), 6.87-6.88(1H, m), 6.97-7.00(3H, m), 7.03-7.05(1H, m), 7.20-7.26(3H, m), 7.41-7.43(1H, m), 7.92-7.95(1H, m) ESI-N: 516 |
| 190 | 18 | FAB-N: 543 |
| 191 | 17 | FAB-N: 544 |
| 192 | 18 | NMR1: 1.12-1.14(3H, m), 1.71-1.80(2H, m), 1.85(6H, s), 1.92(3H, s), 3.79-3.87(1H, m), 3.99-4.09(2H, m), 4.33(2H, s), 4.54-4.56(1H, m), 5.11(2H, s), 6.70(2H, s), 6.94-6.96(1H, m), 6.99(2H, d, J = 8.6 Hz), 7.21(2H, d, J = 8.6 Hz), 7.24-7.28(1H, m), 7.41-7.43(1H, m) FAB-N: 503 |

TABLE 127

| | | |
|---|---|---|
| 193 | 18 | NMR1: 1.12-1.14(3H, m), 1.71-1.80(2H, m), 1.85(6H, s), 1.92(3H, s), 3.79-3.87(1H, m), 3.98-4.09(2H, m), 4.33(2H, s), 4.54-4.56(1H, m), 5.11(2H, s), 6.71(2H, s), 6.94-6.96(1H, m), 6.99(2H, d, J = 8.5 Hz), 7.21(2H, d, J = 8.5 Hz), 7.24-7.28(1H, m), 7.41-7.43(1H, m) FAB-N: 503 |

TABLE 127-continued

| | | |
|---|---|---|
| 194 | 18 | NMR1: 1.85(6H, s), 1.83-1.90(2H, m), 1.92(3H, s), 3.55-3.59(2H, m), 4.02-4.05(2H, m), 4.33(2H, s), 4.5404.56(1H, m), 5.11(2H, s), 6.71(2H, s), 6.94-6.96(1H, m), 6.99(2H, d, J = 8.5 Hz), 7.21(2H, d, J = 8.5 Hz), 7.24-7.28(1H, m), 7.41-7.43(1H, m) FAB-N: 489 |
| 195 | 18 | FAB-N: 505 |
| 196 | 18 | NMR1: 1.32(3H, s), 1.38(3H, s), 1.97(3H, s), 2.00(3H, s), 3.78(1H, dd, J = 6.3, 8.3 Hz), 3.98-4.07(2H, m), 4.11(1H, dd, J = 6.8, 8.3 Hz), 4.34(2H, s), 4.38-4.47(1H, m), 5.11(2H, s), 6.83(1H, dd, J = 2.5, 8.3 Hz), 6.91(1H, d, J = 2.5 Hz), 6.95-7.07(4H, m), 7.18-7.27(3H, m), 7.40-7.46(1H, m) FAB-N: 531 |
| 23 | 23 | NMR1: 1.97(3H, s), 2.00(3H, s), 3.41-3.51(2H, m), 3.76-3.84(1H, m), 3.89(1H, dd, J = 6.0, 9.8 Hz), 4.02(1H, dd, 4.3, 9.8 Hz), 4.34(2H, s), 4.62-4.76(1H, m), 4.89-5.03(1H, m), 5.11(2H, s), 6.81(1H, d, J = 2.5, 8.2 Hz), 6.88(1H, d, J = 2.5 Hz), 6.98(1H, d, J = 8.2 Hz), 6.99(2H, d, J = 8.6 Hz), 7.05(1H, d, J = 7.5 Hz), 7.22(2H, d, J = 8.6 Hz), 7.24(1H, t, J = 7.5 Hz), 7.42(1H, d, J = 7.5 Hz) ESI-N: 491 |
| 197 | 18 | NMR1: 1.32(3H, s), 1.38(3H, s), 1.97(3H, s), 2.00(3H, s), 3.78(1H, dd, J = 6.3, 8.4 Hz), 3.98-4.07(2H, m), 4.11(1H, dd, J = 6.8, 8.3 Hz), 4.34(2H, s), 4.38-4.46(1H, m), 5.11(2H, s), 6.83(1H, dd, J = 2.5, 8.3 Hz), 6.91(1H, d, J = 2.5 Hz), 6.95-7.02(3H, m), 7.04(1H, dd, J = 1.0, 7.5 Hz), 7.22(2H, d, J = 8.6 Hz), 7.24(1H, t, J = 7.5 Hz), 7.43(1H, d, J = 7.5 Hz) FAB-N: 531 |

TABLE 128

| | | |
|---|---|---|
| 198 | 23 | NMR1: 1.97(3H, s), 2.00(3H, s), 3.42-3.50(2H, m), 3.76-3.85(1H, m), 3.89(1H, dd, J = 6.0, 9.8 Hz), 4.02(1H, dd, 4.2, 9.8 Hz), 4.33(2H, s), 4.66(1H, t, J = 5.7 Hz), 4.94(1H, d, J = 5.1 Hz), 5.11(2H, s), 6.81(1H, dd, J = 2.5, 8.2 Hz), 6.88(1H, d, J = 2.5 Hz), 6.98(1H, d, J = 8.2 Hz), 6.99(2H, d, J = 8.4 Hz), 7.05(1H, d, J = 7.6 Hz), 7.22(2H, d, J = 8.4 Hz), 7.24(1H, t, J = 7.6 Hz), 7.43(1H, d, J = 7.6 Hz) ESI-N: 491 |
| 199 | 18 | NMR1: 2.00(3H, s), 2.01(3H, s), 3.86(2H, t, J = 10.1 Hz), 4.33(2H, s), 5.12(2H, s), 5.91(1H, bs), 7.00(2H, d, J = 8.7 Hz), 7.05-7.17(4H, m), 7.22(2H, d, J = 8.7 Hz), 7.27(1H, t, J = 7.6 Hz), 7.46(1H, d, J = 7.6 Hz) ESI-N: 497 |
| 200 | 24 | NMR1: 1.99(3H, s), 2.01(3H, s), 2.74(3H, d, J = 4.7 Hz), 4.72(2H, s), 5.15(2H, s), 7.04-7.18(5H, m), 7.20-7.32(4H, m), 7.47(1H, d, J = 7.3 Hz), 9.06(1H, q, J = 4.7 Hz), 12.42(1H, bs) ESI-N: 524 |
| 24 | 24 | ESI-N: 511 |
| 201 | 18 | NMR1: 1.17(6H, s), 1.85(2H, t, J = 7.3 Hz), 1.97(3H, s), 2.02(3H, s), 4.33(2H, s), 4.37(1H, s), 4.37(2H, t, J = 7.3 Hz), 5.12(2H, s), 6.75(2H, s), 7.00(2H, d, J = 8.7 Hz), 7.10(1H, dd, J = 1.1, 7.6 Hz), 7.22(2H, d, J = 8.7 Hz), 7.28(1H, J = 7.6 Hz), 7.48(1H, dd, J = 1.1, 7.6 Hz), 7.84(1H, s) ESI: 506 |
| 202 | 18 | ESI: 506 |
| 203 | 18 | NMR1: 0.44-0.49(2H, m), 0.55-0.62(2H, m), 1.93(2H, t, J = 7.0 Hz), 1.97(3H, s), 2.00(3H, s), 3.17(1H, s), 4.18(2H, t, J = 7.0 Hz), 4.33(2H, s), 5.10(2H, s), 6.77-6.83(1H, m), 6.85-6.89(1H, m), 6.95-7.08(4H, m), 7.18-7.28(3H, m), 7.40-7.45(1H, m). ESI: 501 |
| 204 | 18 | NMR1: 1.46-1.71(2H, m), 1.92-2.11(12H, m), 4.10(2H, t, J = 7.2 Hz), 4.33(2H, s), 5.02(1H, s), 5.11(2H, s), 6.76-6.82(1H, m), 6.85-6.88(1H, m), 6.94-7.07(4H, m), 7.18-7.27(3H, m), 7.40-7.45(1H, m) FAB-N: 515 |

TABLE 129

| | | |
|---|---|---|
| 205 | 18 | NMR1: 1.45-1.58(1H, m), 1.59-1.71(1H, m), 1.85(6H, s), 1.92(3H, s), 1.94-2.11(6H, m), 4.08(2H, t, J = 7.0 Hz), 4.34(2H, s), 5.02(1H, s), 5.11(2H, s), 6.70(2H, s), 6.92-7.02(3H, m), 7.18-7.31(3H, m), 7.39-7.49(1H, m) FAB-N: 529 |
| 206 | 18 | NMR1: 1.18(6H, s), 1.82-1.87(2H, m), 1.85(6H, s), 1.92(3H, s), 4.06-4.10(2H, m), 4.36(2H, s), 4.37(1H, s), 5.37(2H, s), 6.70(2H, s), 6.84-6.87(1H, m), 6.94-6.96(1H, m), |

TABLE 129-continued

| | | |
|---|---|---|
| | | 7.23-7.27(1H, m), 7.40-7.42(1H, m), 7.62-7.64(1H, m), 8.07-8.08(1H, m) ESI: 520 |
| 207 | 14 | NMR1: 1.97(3H, s), 2.00(3H, s), 3.70-3.75(2H, m), 3.99-4.04(2H, m), 4.36(2H, s), 4.84-4.87(1H, m), 5.37(2H, s), 6.79-6.88(3H, m), 6.96-6.99(1H, m), 7.02-7.04(1H, m), 7.20-7.24(1H, m), 7.40-7.42(1H, m), 7.61-7.64(1H, m), 8.07-8.08(1H, m) ESI: 464 |
| 208 | 9 | ESI: 504(-Boc) |
| 209 | 22 | ESI: 504 |
| 210 | 17 | ESI: 546 |
| 211 | 18 | NMR1: 0.44-0.49(2H, m), 0.56-0.60(2H, m), 1.85(6H, s), 1.90-1.96(5H, m), 4.16(2H, t, J = 6.4 Hz), 4.33(2H, s), 5.11(2H, s), 5.21(1H, s), 6.71(2H, s), 6.93-7.02(3H, m), 7.19-7.29(3H, m), 7.39-7.45(1H, m) FAB-N: 515 |
| 212 | 18 | NMR1: 1.12(6H, s), 1.46-1.54(2H, m), 1.72-1.83(2H, m), 1.96(3H, s), 2.00(3H, s), 3.96-3.99(2H, m), 4.21(1H, s), 4.33(2H, s), 5.11(2H, s), 6.77-6.82(1H, m), 6.85-6.88(1H, m), 6.95-7.07(4H, m), 7.19-7.27(3H, m), 7.40-7.44(1H, m) FAB-N: 517 |
| 213 | 17 | NMR1: 1.97(3H, s), 2.00(3H, s), 2.67-2.68(3H, m), 4.33(2H, s), 4.48(2H, s), 5.11(2H, s), 6.81-6.86(1H, m), 6.91-6.94(1H, m), 6.97-7.06(4H, m), 7.19-7.27(3H, m), 7.41-7.45(1H, m), 8.03-8.09(1H, m) ESI-N: 488 |

TABLE 130

| | | |
|---|---|---|
| 214 | 18 | NMR1: 1.18(6H, s), 1.86(2H, t, J = 7.3 Hz), 2.02(3H, s), 2.12(3H, s), 4.33(2H, s), 4.37(1H, s), 4.38(2H, t, J = 7.3 Hz), 5.12(2H, s), 6.66(1H, d, J = 8.3 Hz), 6.99(2H, d, J = 8.6 Hz), 7.10(1H, d, J = 7.6 Hz), 7.22(2H, d, J = 8.6 Hz), 7.27(1H, t, J = 7.6 Hz), 7.40(1H, d, J = 8.3 Hz), 7.46(1H, d, J = 7.6 Hz) FAB-N: 504 |
| 215 | 18 | NMR1: 1.15(6H, s), 1.82(2H, t, J = 7.2 Hz), 1.90(3H, s), 2.01(3H, s), 4.04(2H, t, J = 7.2 Hz), 4.34(2H, s), 4.35(1H, s), 5.11(2H, s), 6.62(1H, d, J = 2.7 Hz), 6.84(1H, dd, J = 2.7, 8.4 Hz), 7.00(2H, d, J = 8.7 Hz), 7.07(1H, dd, J = 1.1, 7.5 Hz), 7.19(1H, d, J = 8.4 Hz), 7.22(2H, d, J = 8.7 Hz), 7.26(1H, t, J = 7.5 Hz), 7.44(1H, dd, J = 1.1, 7.5 Hz) ESI-N: 503 |
| 216 | 18 | NMR1: 1.14(3H, s), 1.16(3H, s), 1.28(3H, d, J = 6.0 Hz), 1.63(1H, dd, J = 3.6, 14.3 Hz), 1.87(1H, dd, J = 7.2, 14.3 Hz), 1.96(3H, s), 2.00(3H, s), 4.32(1H, s), 4.34(2H, s), 4.68(1H, ddd, J = 3.6, 6.0, 7.2 Hz), 5.10(2H, s), 6.76-6.87(2H, m), 6.94-7.02(3H, m), 7.03-7.08(1H, m), 7.18-7.27(3H, m), 7.39-7.45(1H, m) ESI-N: 517 |
| 217 | 18 | NMR1: 1.48-1.76(8H, m), 1.85(6H, s), 1.90-2.00(5H, m), 3.30-3.34(1H, m), 4.12(2H, t, J = 6.9 Hz), 4.34(2H, s), 5.11(2H, s), 6.70(2H, s), 6.93-7.02(3H, m), 7.18-7.31(3H, m), 7.40-7.46(1H, m) ESI-N: 543 |
| 218 | 18 | NMR1: 1.19-1.66(10H, m), 1.83(2H, t, J = 7.1 Hz), 1.85(6H, s), 1.92(3H, s), 4.10(2H, t, J = 7.1 Hz), 4.15(1H, s), 4.33(2H, s), 5.11(2H, s), 6.70(2H, s), 6.93-7.02(3H, m), 7.19-7.29(3H, m), 7.40-7.44(1H, m) ESI-N: 557 |
| 219 | 18 | NMR1: 1.10(3H, s), 1.16(3H, s), 1.98(3H, s), 2.00(3H, s), 3.53-3.59(1H, m), 3.79-3.86(1H, m), 4.22-4.28(1H, m), 4.33(2H, s), 4.42(1H, s), 4.97-5.04(1H, m), 5.11(2H, s), 6.79-6.85(1H, m), 6.87-6.91(1H, m), 6.95-7.02(3H, m), 7.03-7.08(1H, m), 7.19-7.27(3H, m), 7.40-7.46(1H, m) ESI-N: 519 |
| 220 | 18 | NMR1: 1.09(3H, s), 1.15(3H, s), 1.85(6H, s), 1.92(3H, s), 3.52-3.58(1H, m), 3.77-3.83(1H, m), 4.20-4.26(1H, m), 4.33(2H, s), 4.39-4.43(1H, m), 4.94-5.01(1H, m), 5.11(2H, s), 6.72(2H, s), 6.93-7.02(3H, m), 7.19-7.31(3H, m), 7.40-7.47(1H, m) ESI-N: 533 |

TABLE 131

| | | |
|---|---|---|
| 221 | 25 | ESI: 526(M + Na) |
| 222 | 25 | ESI: 520 |
| 223 | 25 | ESI: 548 |
| 224 | 25 | ESI: 476 |
| 225 | 25 | ESI: 512(M + Na) |
| 226 | 25 | ESI: 512(M + Na) |
| 227 | 25 | ESI: 532 |
| 228 | 26 | ESI: 566(M + Na) |

TABLE 131-continued

| | | |
|---|---|---|
| 229 | 25 | ESI: 532 |
| 230 | 26 | ESI: 493(M + Na) |
| 231 | 26 | ESI: 500(M + Na) |
| 232 | 25 | ESI: 508(M + Na) |
| 233 | 25 | ESI: 522 |
| 234 | 27 | ESI: 537 |
| 235 | 25 | ESI: 574(M + Na) |
| 236 | 25 | ESI: 564 |
| 237 | 25 | ESI: 552 |
| 238 | 25 | ESI: 500 |
| 239 | 25 | ESI: 500 |
| 240 | 25 | ESI: 516 |
| 241 | 25 | ESI: 502 |
| 242 | 26 | ESI: 508 |
| 243 | 25 | ESI: 504 |
| 25 | 25 | ESI: 486 |
| 244 | 25 | ESI: 529 |
| 245 | 25 | ESI: 516 |
| 246 | 25 | ESI: 500 |
| 247 | 27 | ESI: 563 |
| 248 | 25 | ESI: 543 |
| 249 | 25 | ESI: 571 |
| 250 | 27 | ESI: 529 |
| 251 | 27 | ESI: 563 |
| 252 | 25 | ESI: 576 |
| 253 | 27 | ESI: 563 |
| 254 | 25 | ESI: 564 |
| 255 | 25 | ESI: 511 |
| 256 | 27 | ESI: 577 |
| 257 | 25 | ESI: 530 |
| 258 | 25 | ESI: 574 |
| 259 | 27 | ESI: 569 |
| 260 | 26 | ESI: 504 |

TABLE 132

| | | |
|---|---|---|
| 261 | 25 | ESI: 610 |
| 262 | 27 | ESI: 593 |
| 263 | 25 | ESI: 587 |
| 264 | 25 | ESI: 608 |
| 265 | 25 | ESI: 532 |
| 266 | 25 | ESI: 594 |
| 267 | 27 | ESI: 597 |
| 268 | 27 | ESI: 585 |
| 269 | 25 | ESI: 557 |
| 270 | 27 | ESI: 591 |
| 271 | 25 | ESI: 605 |
| 272 | 27 | ESI: 543 |
| 273 | 25 | ESI: 608 |
| 274 | 27 | ESI: 584 |
| 275 | 27 | ESI: 573 |
| 276 | 27 | ESI: 609 |
| 277 | 27 | ESI: 603 |
| 278 | 26 | ESI: 530 |
| 279 | 25 | ESI: 518 |
| 280 | 26 | ESI: 544 |
| 26 | 26 | ESI: 544 |
| 281 | 25 | ESI: 529 |
| 282 | 25 | ESI: 502 |
| 283 | 25 | ESI: 530 |
| 284 | 25 | ESI: 543 |
| 285 | 25 | ESI: 530 |
| 286 | 25 | ESI: 592 |
| 287 | 25 | ESI: 544 |
| 288 | 25 | ESI: 606 |
| 289 | 27 | ESI: 579 |
| 290 | 25 | ESI: 543 |
| 291 | 27 | ESI: 593 |
| 292 | 25 | ESI: 544 |
| 293 | 25 | ESI: 554 |
| 294 | 25 | ESI: 579 |
| 295 | 25 | ESI: 606 |
| 296 | 25 | ESI: 514 |
| 297 | 25 | ESI: 557 |
| 298 | 25 | ESI: 529 |
| 299 | 27 | ESI: 559 |
| 300 | 26 | ESI: 528 |

TABLE 133

| | | |
|---|---|---|
| 301 | 26 | ESI: 546 |
| 302 | 27 | ESI: 565 |
| 303 | 27 | ESI: 573 |
| 304 | 27 | ESI: 537 |
| 305 | 27 | ESI: 559 |
| 306 | 27 | ESI: 563 |
| 307 | 27 | ESI: 571 |
| 308 | 25 | ESI: 470 |
| 309 | 25 | ESI: 506 |
| 310 | 25 | ESI: 520 |
| 311 | 25 | ESI: 504 |
| 312 | 27 | ESI: 571 |
| 313 | 25 | ESI: 560 |
| 314 | 27 | ESI: 553 |
| 315 | 27 | ESI: 567 |
| 316 | 27 | ESI: 538 |
| 27 | 27 | ESI: 543 |
| 317 | 27 | ESI: 579 |
| 318 | 25 | ESI: 557 |
| 319 | 25 | ESI: 512 |
| 320 | 25 | ESI: 552 |
| 321 | 25 | ESI: 488 |
| 322 | 25 | ESI: 517 |
| 323 | 25 | ESI: 566 |
| 324 | 25 | ESI: 532 |
| 325 | 25 | ESI: 490 |
| 326 | 27 | ESI: 523 |
| 327 | 27 | ESI: 537 |
| 328 | 26 | ESI: 506 |
| 329 | 27 | ESI: 537 |
| 330 | 25 | ESI: 582 |
| 331 | 25 | ESI: 548 |
| 332 | 27 | ESI: 526 |
| 333 | 27 | ESI: 540 |
| 334 | 26 | ESI: 520 |
| 335 | 25 | ESI: 502 |
| 336 | 25 | ESI: 538 |
| 337 | 25 | ESI: 496 |
| 338 | 25 | ESI: 566 |
| 339 | 25 | ESI: 544 |
| 340 | 27 | ESI: 579 |

TABLE 134

| | | |
|---|---|---|
| 341 | 25 | ESI: 566 |
| 342 | 25 | ESI: 516 |
| 343 | 25 | ESI: 539 |
| 344 | 27 | ESI: 527 |
| 345 | 27 | ESI: 557 |
| 346 | 25 | ESI: 546 |
| 347 | 25 | ESI: 532 |
| 348 | 25 | ESI: 546 |
| 349 | 25 | ESI: 566 |
| 350 | 26 | ESI: 544 |
| 351 | 27 | ESI: 569 |
| 352 | 27 | ESI: 554 |
| 353 | 25 | ESI: 544 |
| 354 | 27 | ESI: 554 |
| 355 | 25 | ESI: 528 |
| 356 | 26 | ESI: 544 |
| 357 | 26 | ESI: 532 |
| 358 | 26 | ESI: 517 |

TABLE 134-continued

| | | |
|---|---|---|
| 359 | 25 | ESI: 576 |
| 360 | 27 | ESI: 579 |
| 361 | 27 | ESI: 567 |
| 362 | 25 | ESI: 559 |
| 363 | 25 | ESI: 573 |
| 364 | 25 | ESI: 565 |
| 365 | 27 | ESI: 543 |
| 366 | 25 | ESI: 552 |
| 367 | 25 | ESI: 490 |
| 368 | 27 | ESI: 551 |
| 369 | 25 | ESI: 536 |
| 370 | 27 | ESI: 551 |
| 371 | 27 | ESI: 576 |
| 372 | 25 | ESI: 485 |
| 373 | 25 | ESI: 520 |
| 374 | 27 | ESI: 574 |
| 375 | 27 | ESI: 567 |
| 376 | 26 | ESI: 511(M + Na) |
| 377 | 26 | ESI: 567(M + Na) |
| 378 | 26 | ESI: 525(M + Na) |
| 379 | 26 | ESI: 555(M + Na) |
| 380 | 26 | ESI: 567(M + Na) |
| 381 | 25 | ESI: 553(M + Na) |

TABLE 135

| | | |
|---|---|---|
| 382 | 26 | ESI: 525(M + Na) |
| 383 | 26 | ESI: 539(M + Na) |
| 384 | 25 | ESI: 539(M + Na) |
| 385 | 25 | ESI: 548(M + Na) |
| 386 | 25 | ESI: 548(M + Na) |
| 387 | 25 | ESI: 548(M + Na) |
| 388 | 25 | ESI: 548(M + Na) |
| 389 | 25 | ESI: 632(M + Na) |
| 390 | 25 | ESI: 556(M + Na) |
| 391 | 25 | ESI: 602(M + Na) |
| 392 | 26 | ESI: 582 |
| 393 | 25 | ESI: 596 |
| 394 | 25 | ESI: 606(M + Na) |
| 395 | 26 | ESI: 600(M + Na) |
| 396 | 25 | ESI: 645(M + Na) |
| 397 | 25 | ESI: 586(M + Na) |
| 398 | 25 | ESI: 566(M + Na) |
| 399 | 26 | ESI: 552(M + Na) |
| 400 | 25 | ESI: 566(M + Na) |
| 401 | 25 | ESI: 552(M + Na) |
| 402 | 25 | ESI: 538(M + Na) |
| 403 | 25 | ESI: 540(M + Na) |
| 404 | 25 | ESI: 594(M + Na) |
| 405 | 25 | ESI: 592(M + Na) |
| 406 | 10 | NMR1: 1.91(6H, s), 4.20(2H, s), 4.29-4.35(2H, m), 6.19-6.22(1H, m), 6.50(2H, d, J = 8.4 Hz), 6.94(2H, d, J = 8.4 Hz), 6.96-6.98(1H, m), 7.06-7.15(4H, m), 7.32-7.40 (2H, m) ESI-N: 400 |
| 407 | 10 | NMR1: 1.14(3H, t, J = 7.0 Hz), 1.89(6H, s), 3.50 (2H, s), 3.67 (2H, q, J = 7.0 Hz), 3.67-3.69(2H, m), 4.05-4.08 (2H, m), 4.19(2H, s), 4.28-4.30(2H, m), 6.18-6.21(1H, m), 6.50(2H, d, J = 8.5 Hz), 6.67(2H, s), 6.94(2H, d, J = 8.5 Hz), 6.93-6.95(1H, m), 7.06(1H, s), 7.29-7.38 (2H, m) ESI: 490 |

TABLE 136

| No | Str |
|---|---|
| 1 | 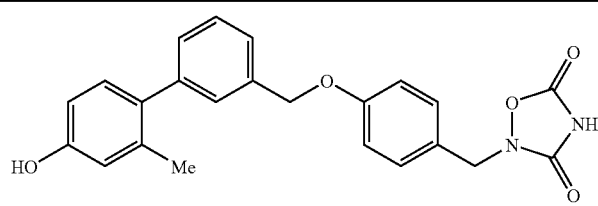 |

TABLE 136-continued

| No | Str |
|---|---|
| 2 | (structure) |
| 3 | (structure) |
| 4 | (structure) |
| 5 | (structure) |
| 6 | (structure) |

TABLE 137

| No | Str |
|---|---|
| 7 | (structure) |
| 8 | (structure) |

TABLE 137-continued

9 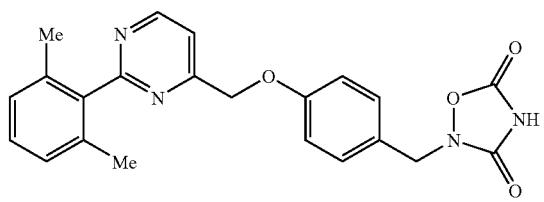

10 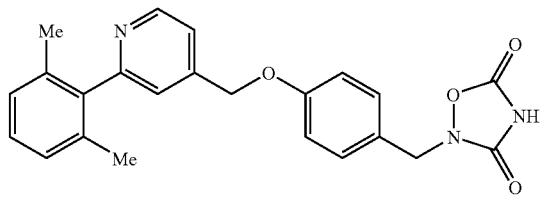

11 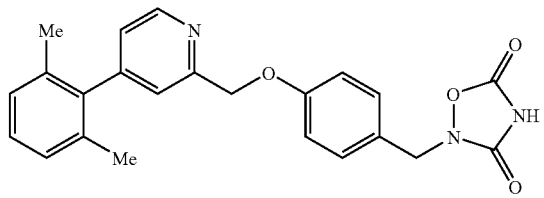

12 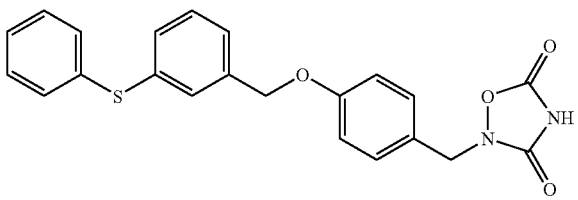

13 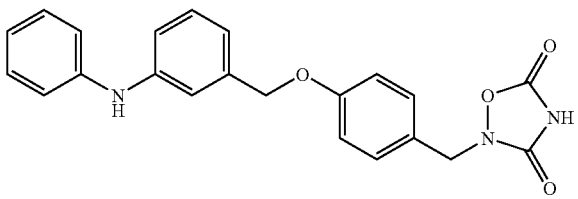

TABLE 138

14 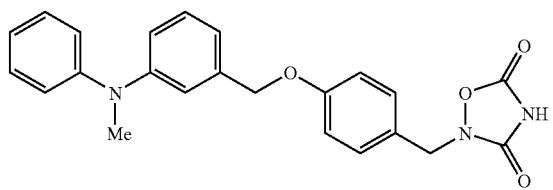

15 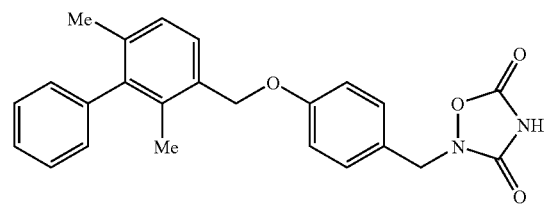

INDUSTRIAL APPLICABILITY

Since the compound of the present invention has excellent GPR40 agonistic action, it is useful as an insulin secretion promoter or an agent for preventing/treating a disease in which GPR40 is concerned, such as diabetes (insulin dependent diabetes mellitus (IDDM), non insulin dependent diabetes mellitus (NIDDM), a border type (abnormal glucose tolerance and fasting blood glucose level) mild case diabetes) and the like.

SEQUENCE LISTING FREE TEXT

An explanation of the "Artificial Sequence" is described in the numeric index <223> of the following SEQUENCE LISTING. Illustratively, the nucleotide sequence represented by SEQ ID NO: 1 of the SEQUENCE LISTING is a nucleotide sequence of an artificially synthesized primer. Also, the nucleotide sequence represented by SEQ ID NO:2 of the SEQUENCE LISTING is a nucleotide sequence of an artificially synthesized primer.

The invention claimed is:

1. An oxadiazolidinedione compound represented by the following formula (I) or a pharmaceutically acceptable salt thereof,

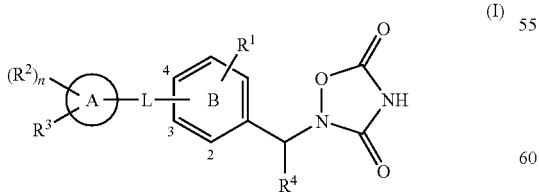

(I)

(symbols in the formula represent the following meanings, $R^1$: —H, halogen, —$R^0$, halogeno-lower alkyl, —O$R^z$, —S—$R^0$ or —O-halogeno-lower alkyl, $R^0$: lower alkyl, $R^z$: the same or different from each other and each represents —H or lower alkyl, L: *-lower alkylene-O—, *-lower alkylene-N($R^z$)— or *-CON($R^z$)—, wherein the * in L represents binding to ring A and the substituting position of L on ring B is the 4-position, ring A: benzene, ring B: benzene, $R^2$: respectively the same or different from one another and each represents -halogen, —$R^0$, halogeno-lower alkyl, —O—$R^z$, —S—$R^0$, —O-halogeno-lower alkyl, —O-lower alkylene-aryl or oxo, n: 0, 1 or 2, $R^3$: phenyl or pyridyl which may respectively be substituted, $R^4$: —H or lower alkyl).

2. The compound described in claim 1, wherein L is *-CH$_2$—O— or *-CH$_2$—NH-(wherein * represents binding to ring A).

3. The compound described in claim 2, wherein $R^4$ is —H.

4. The compound described in claim 3, wherein $R^1$ is —H, halogen or $R^0$.

5. The compound described in claim 4, wherein n is 0, or $R^2$ is halogen or $R^0$.

6. The compound described in claim 5, wherein $R^3$ is phenyl which is substituted with a group selected from the class consisting of —O-lower alkylene-$OR^z$, —O-lower alkylene-$CON(R^z)_2$ and —O-lower alkylene-(cycloalkyl which may be substituted with —$OR^z$), and may be further substituted with 1 or 2 lower alkyl, halogen or —$OR^0$.

7. The compound described in claim 1, which is selected from the group consisting of 2-{[3'-({4-[(3,5-dioxo-1,2,4-oxadiazolidin-2-yl)methyl]phenoxy}methyl)-2,6-dimethylbiphenyl-4-yl]oxy}-N-methylacetamide, 2-(4-{[4'-(2-hydroxyethoxy)-2'-methylbiphenyl-3-yl]methoxy}benzyl)-1,2,4-oxadiazolidine-3,5-dione, 2-(4-{[4'-(3-hydroxy-3-methylbutoxy)-2',6'-dimethylbiphenyl-3-yl]methoxy}benzyl)-1,2,4-oxadiazolidine-3,5-dione, 2-(4-{[4'-(3-hydroxy-3-methylbutoxy)-2,2'-dimethylbiphenyl-3-yl]methoxy}benzyl)-1,2,4-oxadiazolidine-3,5-dione, 2-(4-{[4'-(3-hydroxy-3-methylbutoxy)-2,2',6'-trimethylbiphenyl-3-yl]methoxy}benzyl)-1,2,4-oxadiazolidine-3,5-dione, 2-{4-[(4'-{[(3R)-3-hydroxybutyl]oxy}-2,2'-dimethylbiphenyl-3-yl)methoxy]benzyl}-1,2,4-oxadiazoldine-3,5-dione, 2-{4-[(4'-{[(3S)-3-hydroxybutyl]oxy}-2,2'-dimethylbiphenyl-3-yl)methoxy]benzyl}-1,2,4-oxadiazolidine-3,5-dione, 2-[4-({4'-(3-hydroxy-3-methylbutoxy)-2,2'-dimethylbiphenyl-3-yl]methyl}amino)benzyl]-1,2,4-oxadiazolidine-3,5-dione, 2-(4-{[4'-(3-hydroxy-3-methylbutoxy)-2'-methoxy-2-methylbiphenyl-3-yl]methoxy}benzyl)-1,2,4-oxadiazolidine-3,5-dione, 2-{4-[(4'-{[(3R)-3-hydroxybutyl]oxy}-2,2',6'-trimethylbiphenyl-3-yl)methoxy]benzyl}-1,2,4-oxadiazolidine-3,5-dione, 2-{4-[(4'-{[(3S)-3-hydroxybutyl]oxy}-2,2',6'-trimethylbiphenyl-3-yl)methoxy]benzyl}-1,2,4-oxadiazolidine-3,5-dione, and 2-[4-({4'-[2-(1-hydroxycyclopropyl)ethoxy]-2,2',6'-trimethylbiphenyl-3-yl}methoxy)benzyl]-1,2,4-oxadiazolidine-3,5-dione, or a pharmaceutically acceptable salt thereof.

8. A pharmaceutical composition, which comprises the compound described in claim 1 or a pharmaceutically acceptable salt thereof and a pharmaceutically acceptable carrier.

9. The pharmaceutical composition described in claim 8, wherein the compound or pharmaceutically acceptable salt thereof is a GPR40 agonist.

10. The pharmaceutical composition described in claim 8, wherein the compound or pharmaceutically acceptable salt thereof is an insulin secretion promoter.

11. The pharmaceutical composition described in claim 8, which is an agent for treating diabetes.

12. A method for treating diabetes, which comprises administering an effective amount of the compound described in claim 1 or a salt thereof to a patient.

13. The compound described in claim 1, which is 2-(4-{[4'-(2-hydroxyethoxy)-2'-methylbiphenyl-3-yl]methoxy}benzyl)-1,2,4-oxadiazolidine-3,5-dione, or a pharmaceutically acceptable salt thereof.

14. The compound described in claim 1, which is 2-(4-{[4'-(3-hydroxy-3-methylbutoxy)-2,2',6'-trimethylbiphenyl-3-yl]methoxy}benzyl)-1,2,4-oxadiazolidine-3,5-dione, or a pharmaceutically acceptable salt thereof.

15. The compound described in claim 1, which is 2-{4-[(4'-{[(3S)-3-hydroxybutyl]oxy}-2,2',6'-trimethylbiphenyl-3-yl)methoxy]benzyl}-1,2,4-oxadiazolidine-3,5-dione, or a pharmaceutically acceptable salt thereof.

* * * * *

UNITED STATES PATENT AND TRADEMARK OFFICE
CERTIFICATE OF CORRECTION

PATENT NO. : 7,968,552 B2  Page 1 of 1
APPLICATION NO. : 12/298522
DATED : June 28, 2011
INVENTOR(S) : Kenji Negoro et al.

It is certified that error appears in the above-identified patent and that said Letters Patent is hereby corrected as shown below:

On the Title Page, Item (57), in the Abstract, line 2,
"a insulin" should read --an insulin--; and
"a agent" should read --an agent--.

In claim 7, column 251, lines 28-30,
"2-{4-[(4'-{[(3R)-3-hydroxybutyl]oxy}-2,2'-dimethylbiphenyl-3-yl)methoxy]benzyl}-1,2,4-oxadiazoldine-3,5-dione,"
should read
--2-{4-[(4'-{[(3R)-3-hydroxybutyl]oxy}-2,2'-dimethylbiphenyl-3-yl)methoxy]benzyl}-1,2,4-oxadiazolidine-3,5-dione,--.

Signed and Sealed this
Twenty-seventh Day of September, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artifical Sequence: an
      artificailly synthesized primer sequence

<400> SEQUENCE: 1
ggtctagaat ggacctgccc ccgca                                              25

<210> SEQ ID NO 2
<211> LENGTH: 27
<212> TYPE: DNA
<213> ORGANISM: Artificial Sequence
<220> FEATURE:
<223> OTHER INFORMATION: Description of Artifical Sequence: an
      artificailly synthesized primer sequence

<400> SEQUENCE: 2
ggtctagatt acttctggga cttgccc                                            27

<210> SEQ ID NO 3
<211> LENGTH: 903
<212> TYPE: DNA
<213> ORGANISM: Homo sapiens

<400> SEQUENCE: 3
atggacctgc cccgcagct ctccttcggc tctctatgtgg ccgcctttgc gctgggcttc        60
ccgctcaacg tcctggccat ccgaggcgcg acggcccacg cccggctccg tctcaccct       120 agcctggtct acgccctgaa cctgggctgc tccgacctgc tgctgacagt ctctctgccc      180
ctgaaggcgg tggaggcgct agcctccggg gcctggcctc tgccggcctc gctgtgcccc     240
gtcttcgcgg tggcccactt cttcccactc tatgccggcg ggggcttcct ggccgccctg      300
agtgcaggcc gctacctggg agcagccttc cccttgggct accaagcctt ccggaggccg     360
tgctattcct ggggggtgtg cgcggccatc tgggccctcg tcctgtgtca cctgggtctg      420
gtctttgggt tggaggctcc aggaggctgg ctggaccaca gcaacacctc cctgggcatc      480
aacacaccgg tcaacggctc tccggtctgc ctggaggcct gggacccggc ctctgccggc      540
ccggcccgct tcagcctctc tctcctgctc ttttttctgc ccttggccat cacagccttc      600
tgctacgtgg gctgcctccg ggcactggcc cactccggcc tgacgcacag gcggaagctg      660
cgggccgcct gggtggccgg cggggccctc tcacgctgc tgctctgcgt aggaccctac      720
aacgcctcca acgtggccag cttcctgtac cccaatctag gaggctcctg gcggaagctg      780
gggctcatca cggggtgcctg gagtgtggtg cttaatccgc tggtgaccgg ttacttggga      840
aggggtcctg gcctgaagac agtgtgtgcg gcaagaacgc aagggggcaa gtcccagaag      900
taa                                                                   903

<210> SEQ ID NO 4
<211> LENGTH: 300
<212> TYPE: PRT
<213> ORGANISM: Homo sapiens

<400> SEQUENCE: 4

Met Asp Leu Pro Pro Gln Leu Ser Phe Gly Leu Tyr Val Ala Ala Phe
 1               5                  10                  15

-continued

```
Ala Leu Gly Phe Pro Leu Asn Val Leu Ala Ile Arg Gly Ala Thr Ala
            20              25              30

His Ala Arg Leu Arg Leu Thr Pro Ser Leu Val Tyr Ala Leu Asn Leu
        35              40              45

Gly Cys Ser Asp Leu Leu Leu Thr Val Ser Leu Pro Leu Lys Ala Val
50              55              60

Glu Ala Leu Ala Ser Gly Ala Trp Pro Leu Pro Ala Ser Leu Cys Pro
65              70              75              80

Val Phe Ala Val Ala His Phe Phe Pro Leu Tyr Ala Gly Gly Gly Phe
                85              90              95

Leu Ala Ala Leu Ser Ala Gly Arg Tyr Leu Gly Ala Ala Phe Pro Leu
            100             105             110

Gly Tyr Gln Ala Phe Arg Arg Pro Cys Tyr Ser Trp Gly Val Cys Ala
            115             120             125

Ala Ile Trp Ala Leu Val Leu Cys His Leu Gly Leu Val Phe Gly Leu
        130             135             140

Glu Ala Pro Gly Gly Trp Leu Asp His Ser Asn Thr Ser Leu Gly Ile
145             150             155             160

Asn Thr Pro Val Asn Gly Ser Pro Val Cys Leu Glu Ala Trp Asp Pro
                165             170             175

Ala Ser Ala Gly Pro Ala Arg Phe Ser Leu Ser Leu Leu Leu Phe Phe
            180             185             190

Leu Pro Leu Ala Ile Thr Ala Phe Cys Tyr Val Gly Cys Leu Arg Ala
        195             200             205

Leu Ala His Ser Gly Leu Thr His Arg Arg Lys Leu Arg Ala Ala Trp
        210             215             220

Val Ala Gly Gly Ala Leu Leu Thr Leu Leu Leu Cys Val Gly Pro Tyr
225             230             235             240

Asn Ala Ser Asn Val Ala Ser Phe Leu Tyr Pro Asn Leu Gly Gly Ser
            245             250             255

Trp Arg Lys Leu Gly Leu Ile Thr Gly Ala Trp Ser Val Val Leu Asn
            260             265             270

Pro Leu Val Thr Gly Tyr Leu Gly Arg Gly Pro Gly Leu Lys Thr Val
        275             280             285

Cys Ala Ala Arg Thr Gln Gly Gly Lys Ser Gln Lys
290             295             300
```